US012767656B2

(12) United States Patent
Li et al.

(10) Patent No.: US 12,767,656 B2
(45) Date of Patent: Oct. 20, 2026

(54) TRICYCLIC COMPOUND AND USE THEREOF

(71) Applicant: NANJING ZAIMING PHARMACEUTICAL CO., LTD., Nanjing (CN)

(72) Inventors: Zhen Li, Shanghai (CN); Feng Tang, Shanghai (CN); Le Liu, Nanjing (CN); Chunyan Zhao, Shanghai (CN); Ping Chen, Shanghai (CN); Renhong Tang, Shanghai (CN); Jinsheng Ren, Nanjing (CN)

(73) Assignee: Nanjing Zaiming Pharmaceutical Co., Ltd., Nanjing (CN)

( * ) Notice: Subject to any disclaimer, the term of this patent is extended or adjusted under 35 U.S.C. 154(b) by 510 days.

(21) Appl. No.: 18/260,004

(22) PCT Filed: Dec. 30, 2021

(86) PCT No.: PCT/CN2021/142847
§ 371 (c)(1),
(2) Date: Jun. 29, 2023

(87) PCT Pub. No.: WO2022/143864
PCT Pub. Date: Jul. 7, 2022

(65) Prior Publication Data

US 2024/0124454 A1 Apr. 18, 2024

(30) Foreign Application Priority Data

Dec. 31, 2020 (CN) ......................... 202011637193.3
Feb. 26, 2021 (CN) ......................... 202110213607.8
Apr. 29, 2021 (CN) ......................... 202110477136.1
Jul. 9, 2021 (CN) ......................... 202110780130.1
Aug. 27, 2021 (CN) ......................... 202110998242.4

(51) Int. Cl.
*C07D 471/14* (2006.01)
*C07D 471/04* (2006.01)
*C07D 498/04* (2006.01)
*C07D 498/14* (2006.01)
*C07D 513/14* (2006.01)

(52) U.S. Cl.
CPC ......... *C07D 471/14* (2013.01); *C07D 471/04* (2013.01); *C07D 498/04* (2013.01); *C07D 498/14* (2013.01); *C07D 513/14* (2013.01)

(58) Field of Classification Search
CPC .. C07D 471/14; C07D 471/04; C07D 498/04; C07D 498/14; C07D 513/14
See application file for complete search history.

(56) References Cited

U.S. PATENT DOCUMENTS

2014/0275023 A1 9/2014 Namdev et al.
2022/0013730 A1 1/2022 Parham et al.
2024/0391923 A1 11/2024 Wang et al.

FOREIGN PATENT DOCUMENTS

| | | | | |
|---|---|---|---|---|
| CN | 108658986 | A | 10/2018 | |
| CN | 113372184 | A | 9/2021 | |
| CN | 115244060 | A | 10/2022 | |
| EP | 459505 | A1 * | 12/1991 | ............ C07D 47/14 |
| WO | WO 2008/127274 | A2 | 10/2008 | |
| WO | WO 2014/164729 | A1 | 10/2014 | |
| WO | WO 2018/039972 | A1 | 3/2018 | |
| WO | WO 2018/045071 | A1 | 3/2018 | |
| WO | WO 2019/191470 | A1 | 10/2019 | |
| WO | WO 2020/109434 | A1 | 6/2020 | |
| WO | WO 2020/123395 | A1 | 6/2020 | |
| WO | WO 2020/139992 | A1 | 7/2020 | |
| WO | WO 2020/243376 | A1 | 12/2020 | |
| WO | WO 2021/139775 | A1 | 7/2021 | |
| WO | WO 2023/143356 | A1 | 8/2023 | |

OTHER PUBLICATIONS

Chemical Abstracts Registry No. 2343952-36-1, indexed in the Registry file on STN CAS Online Jun. 23, 2019. (Year: 2019).*
Chemical Abstracts Registry No. 2248030-54-6, indexed in the Registry file on STN CAS Online Nov. 13, 2018. (Year: 2018).*
Rowe, Raymond C, Paul J. Sheskey, and Marian E Quinn. Handbook of Pharmaceutical Excipients. London: Pharmaceutical Press, 6th Edition, 2009, pp. 766-770. (Year: 2009).*
Horlein, U. "4-Hydroxycarbostyril-alkancarbonsauren und Dihydrobenzazepinolon-carbonsaureester. II. Mit *" Arch. Pharmaz. 304/71(2) (Jan. 1, 1971):99-108.
Huang et al. "One-pot synthesis of pyrrolo[1,2-a]quinoxalines" Org. Biomol. Chem. 9(21) (Jan. 1, 2011):7351-7357.
Marjon et al. "MTAP Deletions in Cancer Create Vulnerability to Targeting of the MAT2A/PRMT5/RIOK1 Axis" Cell Reports 15(3) (2016):574-587.

(Continued)

*Primary Examiner* — Laura L Stockton
(74) *Attorney, Agent, or Firm* — Knobbe, Martens, Olson & Bear, LLP

(57) ABSTRACT

The compound as shown in formula (I) or a pharmaceutically acceptable salt or pharmaceutical composition thereof, and a preparation method therefor, and the use thereof as an MAT2A inhibitor. Ring A, ring Q, X, Y, $X_1$, $X_2$, L and $R^1$ in formula (I) are as defined in the description.

(I)

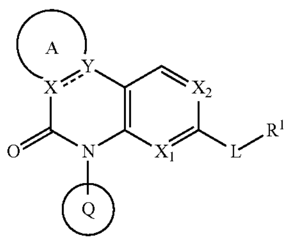

17 Claims, No Drawings

(56) References Cited

OTHER PUBLICATIONS

Padmavathi et al. "Pd(II)-Catalyzed 8-aminoquinoline-aided sp2 δ-C—H intramolecular amidation/annulation: en route to phenanthridin-6(5H)-ones (tricyclic quinolones)" Asian J. Org. Chem 8(6) (Jun. 6, 2019):899-908 (10.1002/ajoc.201900109).
Quinlan et al. "Targeting S-adenosylmethionine biosynthesis with a novel allosteric inhibitor or Mat2A" Nature Chemical Biology, 13(7) (Jul. 1, 2017):785-792.
Zhang et al. "Copper(I) Catalyzed C(sp2)-N bond formation: Synthesis of Pyrrolo[3,2-c]quinolinone Derivatives" Organic Chemistry Frontiers, 3(3) (Jan. 1, 2016):344-348.
Furuta et al. "Efficient Synthesis of Phenanthridinone Derivatives via a Palladium-Catalyzed Coupling Process." *Organic Letters*, vol. 9, No. 2, Dec. 16, 2006, pp. 183-186.
Thorat et al. "Nickel-Catalyzed Denitrogenative Annulation of 1, 2, 3-Benzotriazin-4-(3H)-ones with Benzynes for Construction of Phenanthridinone Scaffolds." *Advanced Synthesis & Catalysis*, vol. 360, No. 2, Dec. 12, 2017, pp. 284-289.
Moon et al. "Visible-Light-Photocatalyzed Synthesis of Phenanthridinones and Quinolinones via Direct Oxidative C—H Amidation." *Advanced Synthesis & Catalysis*, vol. 20, No. 1, Dec. 14, 2017, pp. 240-243.
Kehl et al. "Electrochemical Synthesis of 5-Aryl-phenanthridin-6-one by Dehydrogenative N, C Bond Formation." *Chem. Eur. J.*, vol. 24, No. 65, Oct. 30, 2018, pp. 17230-17233.
Honeycutt et al. Nickel-Catalyzed Oxidative Decarboxylative Annulation for the Synthesis of Heterocycle-Containing Phenanthridinones. *Organic Letters*, vol. 20, No. 22, Nov. 5, 2018, pp. 7216-7219.
Meng et al. "Palladium-catalyzed decarbonylative annulation of phthalimides with arynes: direct construction of phenanthridinones." *Chemical Communications*, vol. 55, No. 64, Jul. 15, 2019, pp. 9507-9510.
International Search Report mailed Apr. 2, 2022 for PCT Application No. PCT/CN2021/142847, filled Dec. 30, 2021.
STN Registry: No. 1344146-25-3, entered Nov. 10, 2011.
STN Registry: No. 1344146-21-9, entered Nov. 10, 2011.
Ding et al., "Synthesis of Phenanthridinones by Palladium-Catalyzed Cyclization of N-Aryl-2-aminopyridines with 2-Iodobenzoic Acids in Water" Synlett (2019) 30:A-E.
STN Registry: No. 2343942-49-6, entered Jun. 23, 2019.
STN Registry: No. 2343952-48-5, entered Jun. 23, 2019.
STN Registry: No. 2343952-47-4, entered Jun. 23, 2019.
STN Registry: No. 2343952-46-3, entered Jun. 23, 2019.
STN Registry: No. 1361044-58-7, entered Mar. 15, 2012.
STN Registry: No. 1071853-28-5, entered Nov. 10, 2008.
STN Registry: No. 1071853-27-4, entered Nov. 10, 2008.
STN Registry: No. 2172385-78-1, entered Jan. 31, 2018.
Usami et al., "Transition-Metal-Free Synthesis of Phenanthridinones through Visible-Light-Driven Oxidative C—H Amidation." Eur. J. Org. Chem. (2020):1496-1504.

* cited by examiner

TRICYCLIC COMPOUND AND USE THEREOF

CROSS-REFERENCE TO RELATED APPLICATIONS

The present application is the U.S. national phase entry of PCT Application No. PCT/CN2021/142847, filed Dec. 30, 2021, which claims the benefit of priority to the following applications: Chinese Patent Application No. 202011637193.3 filed with China National Intellectual Property Administration on Dec. 31, 2020 and entitled "TRICYCLIC COMPOUND AND USE THEREOF", Chinese Patent Application No. 202110213607.8 filed with China National Intellectual Property Administration on Feb. 26, 2021 and entitled "TRICYCLIC COMPOUND AND USE THEREOF", Chinese Patent Application No. 202110477136.1 filed with China National Intellectual Property Administration on Apr. 29, 2021 and entitled "TRICYCLIC COMPOUND AND USE THEREOF", Chinese Patent Application No. 202110780130.1 filed with China National Intellectual Property Administration on Jul. 9, 2021 and entitled "TRICYCLIC COMPOUND AND USE THEREOF", and Chinese Patent Application No. 202110998242.4 filed with China National Intellectual Property Administration on Aug. 27, 2021 and entitled "TRICYCLIC COMPOUND AND USE THEREOF". The patent applications described above are incorporated herein by reference in their entireties.

TECHNICAL FIELD

The present application belongs to the field of pharmaceuticals, and particularly relates to a novel tricyclic compound or a pharmaceutically acceptable salt thereof, a pharmaceutical composition comprising same, and use thereof as an MAT2A inhibitor.

BACKGROUND

Methionine adenosyltransferase (MAT), also known as S-adenosylmethionine synthetase, is a class of enzymes that catalyze the reaction of methionine (Met) with ATP to produce S-adenosyl-L-methionine (SAM). SAM can be used as the main methyl donor of in vivo methyltransferases, and can regulate the expression, transcription, and translation of genes through a transmethylation reaction, thereby having an important influence on the growth, death, and differentiation of cells. Protein arginine N-methyltransferase 5 (PRMT5) is a methyltransferase using SAM as a substrate, and plays an important role in the regulation of tumor cell proliferation or other aspects.

MAT enzymes have three major subtypes, MAT1A, MAT2A, and MAT2B. MAT1A is mainly present in normal hepatocytes, whereas MAT2A is widely distributed in extrahepatic cells. The two subtypes have differences in catalytic efficiency and regulation mode. MAT2B does not have the ability to catalyze the synthesis of SAM, but acts as a regulatory subunit of MAT2A to, after forming a complex with MAT2A, modulate the catalytic activity of MAT2A.

It has been found that cancer cell lines with deletion of methylthioadenosine phosphorylase (MTAP) are sensitive to MAT2A inhibition (Cell Reports 15 (3) (2016) 574-587). MTAP is widely expressed in normal tissue cells. The enzyme can catalyze the conversion of 5' methylthioadenosine (MTA) to 5-methylthioribose-1-phosphate and adenine. This process is also an important pathway for methionine compensation in humans. When MTAP is deleted, the metabolic pathway of MTA is inhibited, resulting in the accumulation of MTA in vivo in a large amount. The accumulation of MTA in a large amount will partially inhibit the activity of PRMT5, leading to an increased sensitivity of PRMT5 to changes in a SAM level in vivo; therefore, in tumors with deletion of MTAP, by inhibiting MAT2A and reducing the SAM level in vivo, the activity of PRMT5 will be further inhibited, and synthetic lethality will occur.

The gene encoding human MTAP is located in the chromosome 9p21 region (chr9p21) and has a homozygous deletion frequency in all tumors of about 15%, and the deletion frequency varies among different tumors. The tumor with a high deletion frequency includes glioma, mesothelioma, melanoma, gastric cancer, esophageal cancer, bladder cancer, pancreatic cancer, non-small cell lung cancer, astrocytoma, osteosarcoma, head and neck cancer, mucinous chondrosarcoma, ovarian cancer, endometrial cancer, breast cancer, soft tissue sarcoma, non-Hodgkin lymphoma, and the like.

The human chromosome 9p21 region comprises not only the gene encoding MTAP, but also the tumor suppressor genes p16INK4A (also known as CDKN2A) and p15INK4B. In 80%-90% of tumors with deletion of CDKN2A, MTAP is also in a deleted state.

Given that the expression level of MAT2A is abnormally increased in various tumors, including gastric cancer, colon cancer, liver cancer, pancreatic cancer, and the like, and selective inhibition of MAT2A can reduce the proliferative activity of cancer cells with deletion of MTAP, selective inhibition of MAT2A could be an effective tumor treatment.

The patent documents WO2018039972, WO2018045071, WO2019191470, WO2020123395, and the like disclose heterocyclic MAT2A inhibitors for treating a tumor.

DETAILED DESCRIPTION OF THE INVENTION

The present application provides a compound of general formula (I) or a pharmaceutically acceptable salt thereof:

(I)

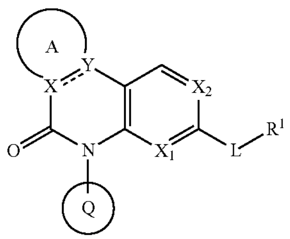

wherein,

L is selected from a chemical bond, NH, and O;

$R^1$ is selected from halogen and the following groups optionally substituted with $R^{1a}$: $C_1$-$C_{10}$ alkyl, $C_3$-$C_{10}$ cycloalkyl, and 3- to 10-membered heterocyclyl;

$X_1$ and $X_2$ are each independently selected from N and CH;

ring A is selected from $C_6$-$C_{10}$ aryl, 5- to 10-membered heteroaryl, and 4- to 7-membered heterocyclyl, and the $C_6$-$C_{10}$ aryl, the 5- to 10-membered heteroaryl, or the 4- to 7-membered heterocyclyl is optionally substituted with $R^2$;

X and Y are ring atoms of ring A, and are each independently selected from a C atom and an N atom; X and Y are connected by a single bond when at least one of X and Y is selected from an N atom; X and Y may be connected by a single bond or a double bond when X and Y are both selected from a C atom;

$R^2$ is selected from halogen, =O, OH, CN, and the following groups optionally substituted with $R^{2a}$: $NH_2$, $C_1$-$C_{10}$ alkyl, $C_3$-$C_{10}$ cycloalkyl, 3- to 10-membered heterocyclyl, $C_1$-$C_{10}$ alkoxy, $C_3$-$C_{10}$ cycloalkyloxy, and 3- to 10-membered heterocyclyloxy;

ring Q is selected from $C_6$-$C_{10}$ aryl and 5- to 10-membered heteroaryl, and the $C_6$-$C_{10}$ aryl or the 5- to 10-membered heteroaryl is optionally substituted with $R^3$;

$R^3$ is selected from halogen, =O, OH, CN, $NO_2$, and the following groups optionally substituted with $R^{3a}$: SH, $NH_2$, $C_2$-$C_{10}$ alkenyl, $C_2$-$C_{10}$ alkynyl, $C_1$-$C_{10}$ alkyl, $C_3$-$C_{10}$ cycloalkyl, 3- to 10-membered heterocyclyl, $C_1$-$C_{10}$ alkoxy, $C_3$-$C_{10}$ cycloalkyloxy, and 3- to 10-membered heterocyclyloxy; $R^{1a}$, $R^{2a}$, and $R^{3a}$ are each independently selected from a deuterium atom, F, Cl, Br, I, OH, CN, =O, and the following groups optionally substituted with $R^b$: $NH_2$, $C_1$-$C_6$ alkyl, $C_3$-$C_6$ cycloalkyl, 4- to 7-membered heterocyclyl, 5- to 6-membered heteroaryl, $C_1$-$C_6$ alkoxy, $C_3$-$C_6$ cycloalkyloxy, and 4- to 7-membered heterocyclyloxy;

$R^b$ is each independently selected from F, Cl, Br, I, OH, CN, =O, $NH_2$, SH, $C_1$-$C_6$ alkyl, $C_3$-$C_6$ cycloalkyl, and 4- to 7-membered heterocyclyl.

In some embodiments, $R^3$ is selected from halogen, =O, OH, CN, and the following groups optionally substituted with $R^{3a}$: $NH_2$, $C_2$-$C_{10}$ alkenyl, $C_2$-$C_{10}$ alkynyl, $C_1$-$C_{10}$ alkyl, $C_3$-$C_{10}$ cycloalkyl, 3-10 membered heterocyclyl, $C_1$-$C_{10}$ alkoxy, $C_3$-$C_{10}$ cycloalkyloxy, and 3-10 membered heterocyclyloxy; $R^{1a}$, $R^{2a}$, and $R^{3a}$ are each independently selected from a deuterium atom, F, Cl, Br, I, OH, CN, =O, and the following groups optionally substituted with $R^b$: $NH_2$, $C_1$-$C_6$ alkyl, $C_3$-$C_6$ cycloalkyl, 4-7 membered heterocyclyl, $C_1$-$C_6$ alkoxy, $C_3$-$C_6$ cycloalkyloxy, and 4-7 membered heterocyclyloxy; each $R^b$ is independently selected from F, Cl, Br, I, OH, CN, =O, $NH_2$, SH, $C_1$-$C_6$ alkyl, $C_3$-$C_6$ cycloalkyl, and 4-7 membered heterocyclyl.

In some embodiments, the compound of formula (I) or the pharmaceutically acceptable salt thereof is a compound of formula (Ia) or a pharmaceutically acceptable salt thereof:

(Ia)

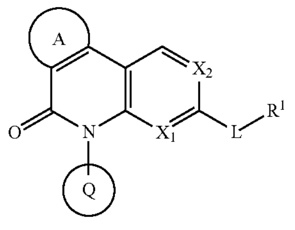

wherein,

L is selected from a chemical bond, NH, and O;

$R^1$ is selected from halogen and the following groups optionally substituted with $R^{1a}$: $C_1$-$C_{10}$ alkyl, $C_3$-$C_{10}$ cycloalkyl, and 3- to 10-membered heterocyclyl;

$X_1$ and $X_2$ are each independently selected from N and CH;

ring A is selected from $C_6$-$C_{10}$ aryl, 5- to 10-membered heteroaryl, and 4- to 7-membered heterocyclyl, and the $C_6$-$C_{10}$ aryl, the 5- to 10-membered heteroaryl, or the 4- to 7-membered heterocyclyl is optionally substituted with $R^2$;

$R^2$ is selected from halogen, =O, OH, CN, and the following groups optionally substituted with $R^{2a}$: $NH_2$, $C_1$-$C_{10}$ alkyl, $C_3$-$C_{10}$ cycloalkyl, 3- to 10-membered heterocyclyl, $C_1$-$C_{10}$ alkoxy, $C_3$-$C_{10}$ cycloalkyloxy, and 3- to 10-membered heterocyclyloxy;

ring Q is selected from $C_6$-$C_{10}$ aryl and 5- to 10-membered heteroaryl, and the $C_6$-$C_{10}$ aryl or the 5- to 10-membered heteroaryl is optionally substituted with $R^3$;

$R^3$ is selected from halogen, =O, OH, CN, and the following groups optionally substituted with $R^{3a}$: $NH_2$, $C_2$-$C_{10}$ alkenyl, $C_2$-$C_{10}$ alkynyl, $C_1$-$C_{10}$ alkyl, $C_3$-$C_{10}$ cycloalkyl, 3-10 membered heterocyclyl, $C_1$-$C_{10}$ alkoxy, $C_3$-$C_{10}$ cycloalkyloxy, and 3-10 membered heterocyclyloxy;

Each $R^{1a}$, $R^{2a}$, and $R^{3a}$ is independently selected from F, Cl, Br, I, OH, CN, =O, and the following groups optionally substituted with $R^b$: $NH_2$, $C_1$-$C_6$ alkyl, $C_3$-$C_6$ cycloalkyl, 4-7 membered heterocyclyl, $C_1$-$C_6$ alkoxy, $C_3$-$C_6$ cycloalkyloxy, and 4-7 membered heterocyclyloxy;

$R^b$ is each independently selected from F, Cl, Br, I, OH, CN, =O, $NH_2$, SH, $C_1$-$C_6$ alkyl, $C_3$-$C_6$ cycloalkyl, and 4- to 7-membered heterocyclyl.

In some embodiments, the 3-10 membered heterocyclyl comprises 1-3 or 1-5 heteroatoms or heteroatom groups, and the heteroatom or the heteroatom group is independently selected from N, O, S, P, B, —S(=O)$_2$—, —S(=O)—, —P(=O)$_2$—, —P(=O)—, —NH—, —S(=O)(=NH)—, —C(=O)NH—, and —NHC(=O)NH—.

In some embodiments, the 3-10 membered heterocyclyl comprises 1-3 heteroatoms or heteroatom groups, and the heteroatom or the heteroatom group is independently selected from N, O, S, —S(=O)$_2$—, and —NH—. In some embodiments, the 4-7 membered heterocyclyl comprises 1-3 heteroatoms or heteroatom groups, and the heteroatom or the heteroatom group is independently selected from N, O, S, —S(=O)$_2$—, and —NH—. In some embodiments, the 4-7 membered heterocyclyl comprises 1, 2, or 3 heteroatoms, and the heteroatom is independently selected from N, O, and S.

In some embodiments, the 5-10 membered heteroaryl comprises 1-3 or 1-5 heteroatoms, and the heteroatom is independently selected from N, O, and S. In some embodiments, the 5-6 membered heteroaryl comprises 1-3 heteroatoms, and the heteroatom is independently selected from N, O, and S.

In some embodiments, X and Y are ring atoms and X and Y are both C, and X and Y are connected by a single bond or a double bond; or one of X and Y is C and the other is N, and X and Y are connected by a single bond.

In some embodiments, X and Y are both C, and X and Y are connected by a single bond or a double bond; $X_1$ is N, and $X_2$ is CH or N; or $X_1$ and $X_2$ are both CH. In some embodiments, X and Y are both C, and X and Y are connected by a double bond; $X_1$ is N, and $X_2$ is CH; or $X_1$ and $X_2$ are both CH; or $X_1$ and $X_2$ are both N.

In some embodiments, L is selected from NH; $R^1$ is selected from $C_1$-$C_6$ alkyl, $C_3$-$C_6$ cycloalkyl, and 4-7 membered heterocyclyl, and the $C_1$-$C_6$ alkyl, the $C_3$-$C_6$ cycloalkyl, or the 4-7 membered heterocyclyl is optionally substituted with F, Cl, Br, I, OH, CN, =O, $NH_2$, NH($C_1$-$C_3$ alkyl), N($C_1$-$C_3$ alkyl)$_2$, $C_1$-$C_3$ alkyl, or $C_1$-$C_3$ alkoxy.

In some embodiments, L is selected from NH and $R^1$ is selected from $C_1$-$C_6$ alkyl.

In some embodiments, L is selected from NH, $X_1$ is selected from N, and $X_2$ is selected from CH.

In some embodiments, L is selected from a chemical bond and O.

In some embodiments, L is selected from a chemical bond.

In some embodiments, L is selected from O.

In some embodiments, $R^1$ is selected from halogen and the following groups optionally substituted with $R^{1a}$: $C_1$-$C_3$ alkyl, $C_3$-$C_6$ cycloalkyl, and 4-7 membered heterocyclyl.

In some embodiments, $R^1$ is selected from halogen and the following groups optionally substituted with $R^{1a}$: $C_1$-$C_3$ alkyl and 4-7 membered heterocyclyl.

In some embodiments, $R^1$ is selected from halogen and $C_1$-$C_3$ alkyl optionally substituted with $R^{1a}$.

In some embodiments, $R^1$ is selected from halogen and the following groups optionally substituted with $R^{1a}$: methyl, ethyl, and oxetanyl.

In some embodiments, $R^1$ is selected from halogen and the following groups optionally substituted with $R^{1a}$: methyl and ethyl.

In some embodiments, $R^1$ is selected from methyl optionally substituted with $R^{1a}$.

In some embodiments, each $R^{1a}$ is independently selected from F, Cl, Br, I, OH, CN, =O, and the following groups optionally substituted with $R^b$: $NH_2$, $C_1$-$C_6$ alkyl, $C_3$-$C_6$ cycloalkyl, 4-7 membered heterocyclyl, and $C_1$-$C_6$ alkoxy.

In some embodiments, each $R^{1a}$ is independently selected from F, Cl, Br, and I.

In some embodiments, each $R^{1a}$ is independently selected from F.

In some embodiments, $R^1$ is selected from Cl, $CH_3$, $CF_3$, ethyl, and oxetanyl.

In some embodiments, $R^1$ is selected from $CF_3$, ethyl, and oxetanyl.

In some embodiments, $R^1$ is selected from Cl, $CH_3$, $CF_3$, and ethyl.

In some embodiments, $R^1$ is selected from Cl, $CF_3$, and ethyl.

In some embodiments, $R^1$ is selected from $CF_3$ and ethyl.

In some embodiments, $R^1$ is selected from $CF_3$.

In some embodiments, L is a chemical bond; $R^1$ is selected from halogen, $C_1$-$C_6$ alkyl, $C_3$-$C_6$ cycloalkyl, and 4-7 membered heterocyclyl, and the $C_1$-$C_6$ alkyl, the $C_3$-$C_6$ cycloalkyl, or the 4-7 membered heterocyclyl is optionally substituted with F, Cl, Br, I, OH, CN, =O, $NH_2$, $NH(C_1$-$C_3$ alkyl), $N(C_1$-$C_3$ alkyl$)_2$, $C_1$-$C_3$ alkyl, or $C_1$-$C_3$ alkoxy.

In some embodiments, L is a chemical bond; $R^1$ is selected from halogen and $C_1$-$C_3$ alkyl optionally substituted with $R^{1a}$; each $R^{1a}$ is independently selected from F, Cl, Br, and I.

In some embodiments, L is O; $R^1$ is selected from $C_1$-$C_6$ alkyl, $C_3$-$C_6$ cycloalkyl, and 4-7 membered heterocyclyl, and the $C_1$-$C_6$ alkyl, the $C_3$-$C_6$ cycloalkyl, or the 4-7 membered heterocyclyl is optionally substituted with F, Cl, Br, I, OH, CN, =O, $NH_2$, $NH(C_1$-$C_3$ alkyl), $N(C_1$-$C_3$ alkyl$)_2$, $C_1$-$C_3$ alkyl, or $C_1$-$C_3$ alkoxy.

In some embodiments, L is O; $R^1$ is selected from $C_1$-$C_6$ alkyl and 4-7 membered heterocyclyl.

In some embodiments, a structural unit

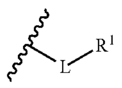

is selected from Cl, $CH_3$, $CF_3$, $OCH_2CH_3$, $NHCH_2CH_3$, and

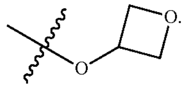 [SMILES: *OC1COC1]

In some embodiments, a structural unit

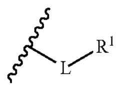

is selected from $CF_3$, $OCH_2CH_3$, $NHCH_2CH_3$, and

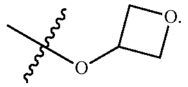 [SMILES: *OC1COC1]

In some embodiments, a structural unit

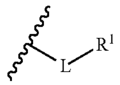

is selected from Cl, $CH_3$, $CF_3$, and $OCH_2CH_3$.

In some embodiments, a structural unit

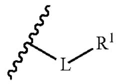

is selected from Cl, $CF_3$, and $OCH_2CH_3$.

In some embodiments, a structural unit

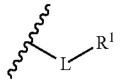

is selected from $CF_3$ and $OCH_2CH_3$.

In some embodiments, a structural unit

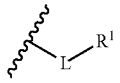

is selected from $CF_3$.

In some embodiments, $X_1$ is selected from N.

In some embodiments, $X_1$ is selected from CH.

In some embodiments, $X_2$ is selected from CH.

In some embodiments, $X_1$ is N and $X_2$ is CH. In some embodiments, $X_1$ and $X_2$ are both CH. In some embodiments, $X_1$ and $X_2$ are both N.

In some embodiments, $X_1$ is selected from N and CH, and $X_2$ is selected from CH.

In some embodiments, ring A is selected from 5-6 membered heteroaryl and 4-7 membered heterocyclyl, and the 5-6 membered heteroaryl or the 4-7 membered heterocyclyl is optionally substituted with $R^2$.

In some embodiments, ring A is selected from 5-6 membered heteroaryl and 5-7 membered heterocyclyl, ring atoms of the 5-6 membered heteroaryl or the 5-7 membered heterocyclyl include at least one heteroatom or heteroatom group selected from N, O, S, and $S(O)_2$, and the 5-6 membered heteroaryl or the 5-7 membered heterocyclyl is optionally substituted with $R^2$.

In some embodiments, ring A is selected from the following groups optionally substituted with $R^2$: pyrrolyl, pyrazolyl, imidazolyl, oxazolyl, isoxazolyl, triazolyl,

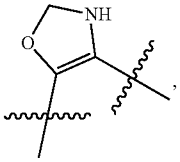
,
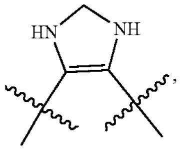
,
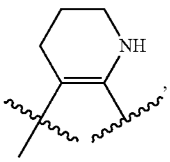
,
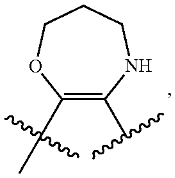
,
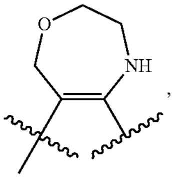
,
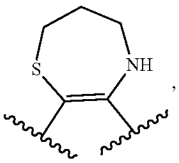
,
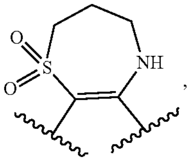
,
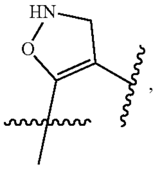
, and
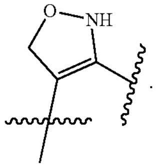
.

In some embodiments, ring A is selected from the following groups optionally substituted with $R^2$: pyrrolyl, pyrazolyl, imidazolyl, oxazolyl, isoxazolyl, triazolyl,

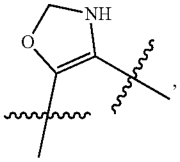
,
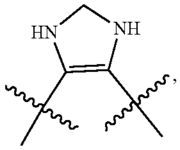
,
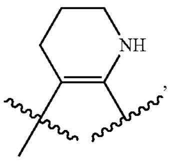
,
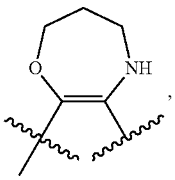
,

-continued

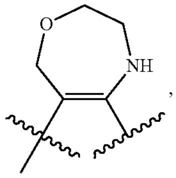
,
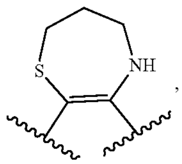
, and
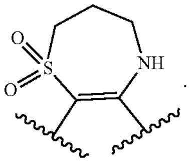
.

In some embodiments, ring A is selected from the following groups optionally substituted with $R^2$:

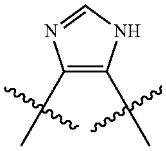
,
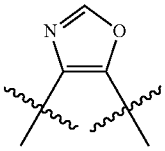
,
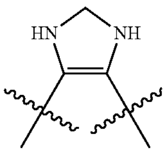
,
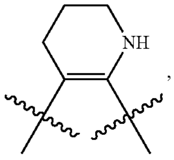
,
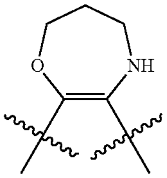
,
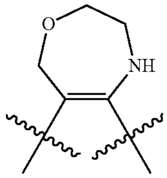
,
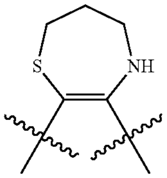
,
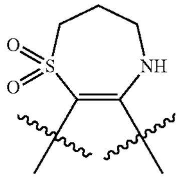
,
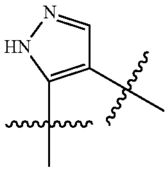
,
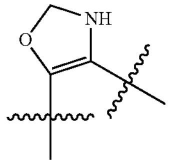
,
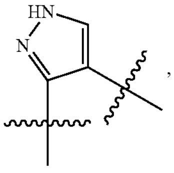
,
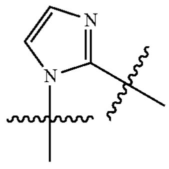
,
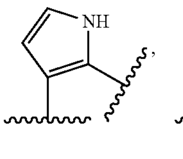
,
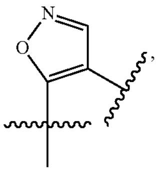
, -continued

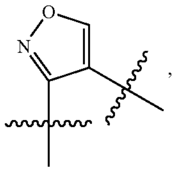

, and

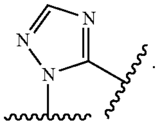

.

In some embodiments, ring A is selected from imidazolyl, oxazolyl

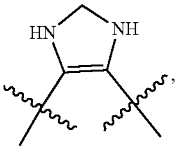

,

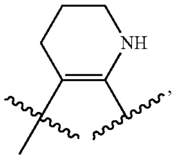

,

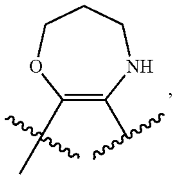

,

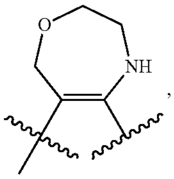

,

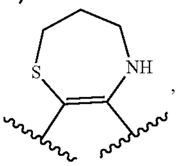

, and

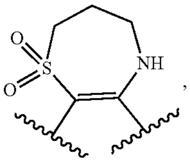

, and the imidazolyl, the oxazolyl, the

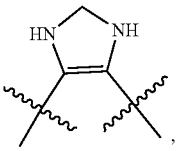

, the

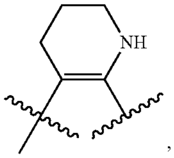

, the

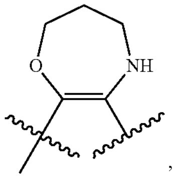

, the

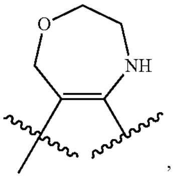

, the

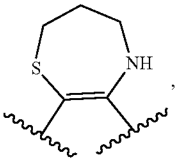

, or the

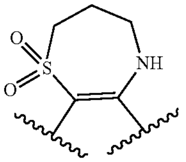 [SMILES: *C1=C(*)S(=O)(=O)CCCN1]

is optionally substituted with R.

In some embodiments, ring A is selected from pyrrolyl, pyrazolyl, imidazolyl, oxazolyl,

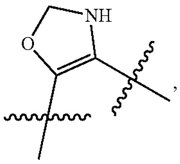

, and

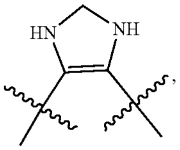

, and the pyrrolyl, the pyrazolyl, the imidazolyl, the oxazolyl, the

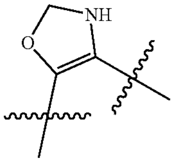

, or the

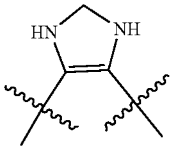 [SMILES: *C1=C(*)NCN1]

is optionally substituted with $R^2$.

In some embodiments, ring A is selected from the following groups optionally-substituted with $R^2$:

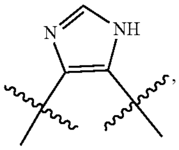

,

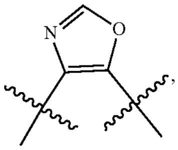

,

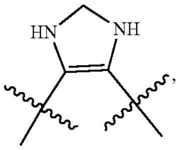

,

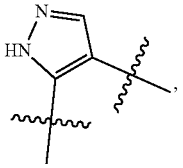

,

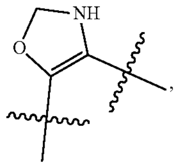

,

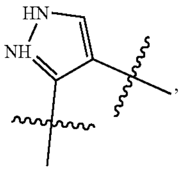

, and

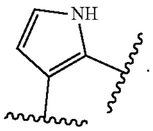

.

In some embodiments, ring A is selected from imidazolyl and pyrazolyl, and the imidazolyl or the pyrazolyl is optionally substituted with $R^2$.

In some embodiments, $R^2$ is selected from =O and the following groups optionally substituted with $R^{2a}$: $NH_2$, $C_1$-$C_6$ alkyl, $C_3$-$C_6$ cycloalkyl, and $C_1$-$C_6$ alkoxy.

In some embodiments, $R^2$ is selected from =O and the following groups optionally substituted with $R^{2a}$: $C_1$-$C_3$ alkyl and $C_1$-$C_6$ alkoxy.

In some embodiments, $R^2$ is selected from =O and $C_1$-$C_3$ alkyl optionally substituted with $R^{2a}$.

In some embodiments, $R^{2a}$ is selected from a deuterium atom, F, Cl, Br, I, OH, $C_1$-$C_3$ alkyl, $NH_2$ optionally substituted with $C_1$-$C_3$ alkyl, and 5-6 membered heteroaryl optionally substituted with $C_1$-$C_3$ alkyl.

In some embodiments, $R^{2a}$ is selected from a deuterium atom, F, Cl, Br, I, OH, $C_1$-$C_3$ alkyl, $NH_2$ optionally substituted with $C_1$-$C_3$ alkyl, and pyrazolyl optionally substituted with $C_1$-$C_3$ alkyl.

In some embodiments, $R^{2a}$ is selected from a deuterium atom, F, Cl, Br, I, $C_1$-$C_3$ alkyl, and $NH_2$ optionally substituted with $C_1$-$C_3$ alkyl.

In some embodiments, $R^{2a}$ is selected from $NH_2$ optionally substituted with $C_1$-$C_3$ alkyl.

In some embodiments, $R^{2a}$ is selected from a deuterium atom, methyl, F, and $N(CH_3)_2$.

In some embodiments, $R^{2a}$ is selected from $N(CH_3)_2$.

In some embodiments, $R^2$ is selected from =O, methyl, ethyl, $CD_3$, $CH_2CH_2N(CH_3)_2$, $CH_2CH_2OH$, $CH_2CH_2NH(CH_3)$, $CH_2CH_2NH_2$, $OCH_3$, $NHCH_3$, $CHF_2$, $CF_3$, cyclopropyl, and

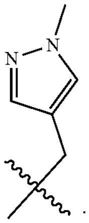 [SMILES: *Cc1cnn(C)c1]
.

In some embodiments, $R^2$ is selected from =O, methyl, $CD_3$, $CH_2CH_2N(CH_3)_2$, $OCH_3$, $NHCH_3$, $CF_3$, and cyclopropyl.

In some embodiments, $R^2$ is selected from =O, methyl, $CD_3$, and $OCH_3$.

In some embodiments, $R^2$ is selected from =O, methyl, and $CH_2CH_2N(CH_3)_2$.

In some embodiments, $R^2$ is selected from =O, methyl, and methoxy.

In some embodiments, ring A is selected from the following groups optionally substituted with $R^2$:

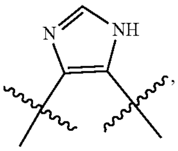
,
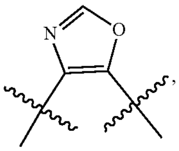
,
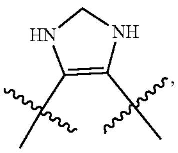
,
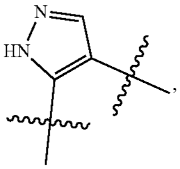
,

-continued

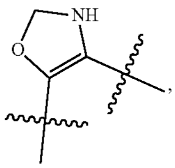
,
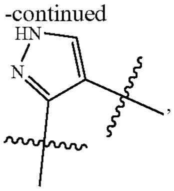
, and
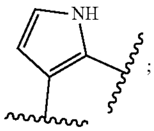
;

$R^2$ is selected from =O, methyl, $CD_3$, $OCH_3$, and $CF_3$.

In some embodiments, ring A is selected from the following groups optionally substituted with $R^2$:

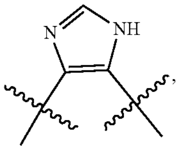
,
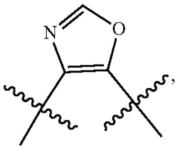
,
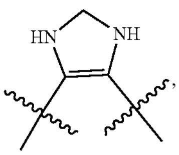
,
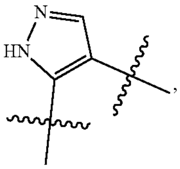
,
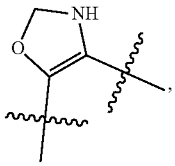
,
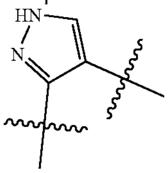
, and
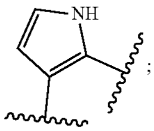
;

$R^2$ is selected from =O, methyl, ethyl, $CD_3$, $CH_2CH_2N(CH_3)_2$, $CH_2CH_2OH$, $CH_2CH_2NH(CH_3)$, $CH_2CH_2NH_2$, $OCH_3$, $NHCH_3$, $CHF_2$, $CF_3$, cyclopropyl, and

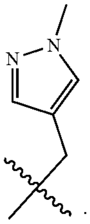
.

In some embodiments, ring A is selected from

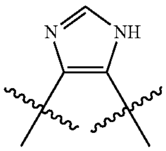
,
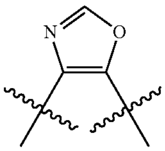
,

-continued
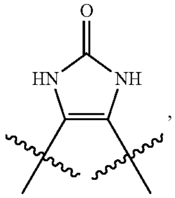, 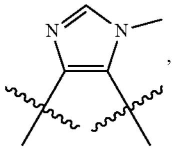,
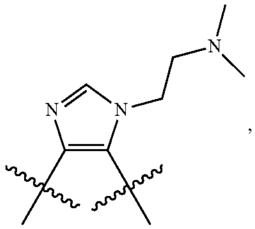, 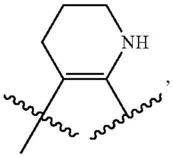,
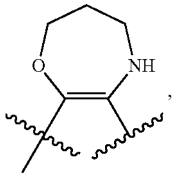, 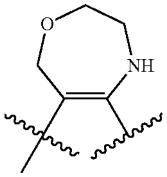,
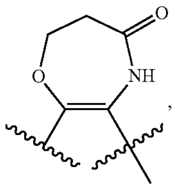, 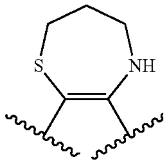,
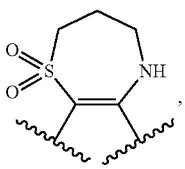, 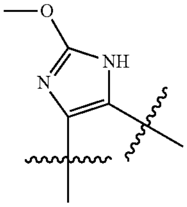,
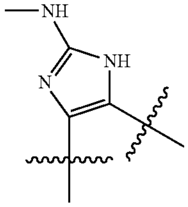, 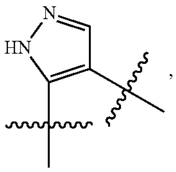,
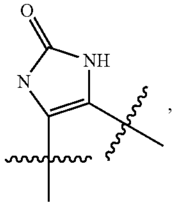, 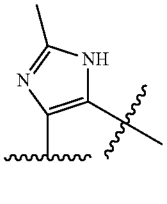,
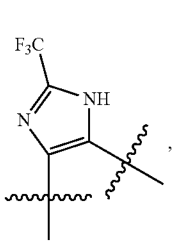, 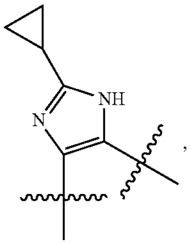,
-continued
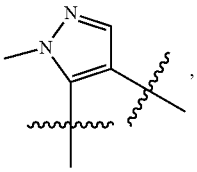, 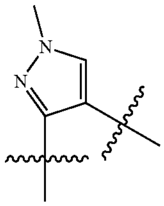,
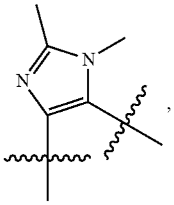, 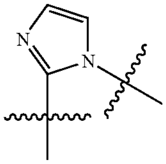,
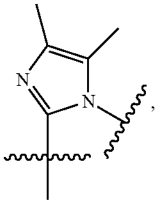, 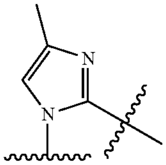, 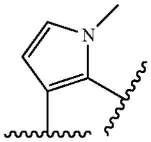,
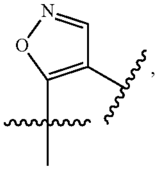, 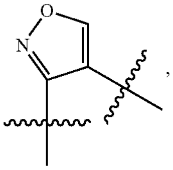, 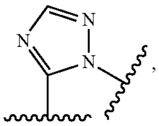,
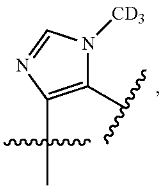, 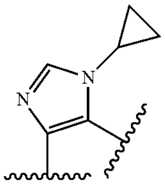, 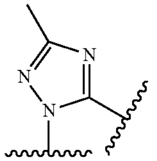,
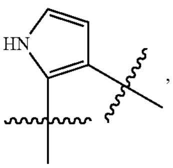, 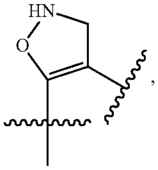, 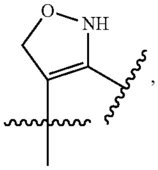,
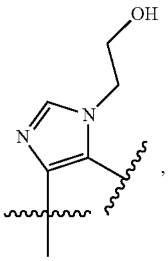, 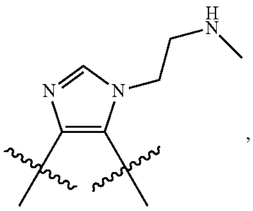,
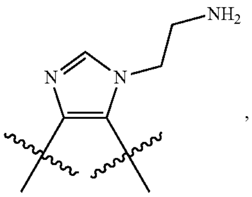, 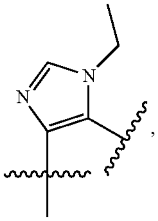, -continued
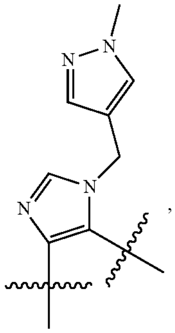, and 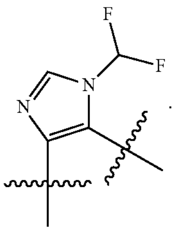.
In some embodiments, ring A is selected from
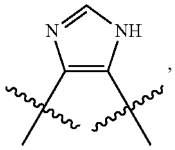, 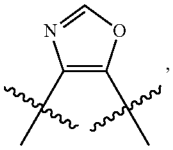, 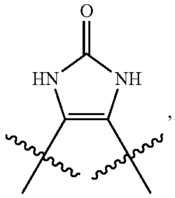, 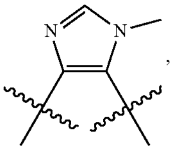, 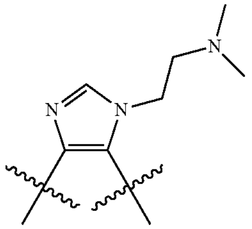, 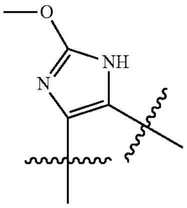, 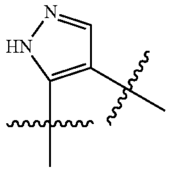, 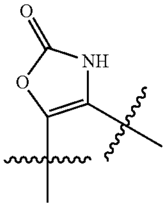, 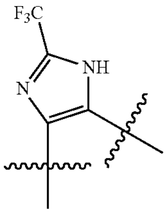, 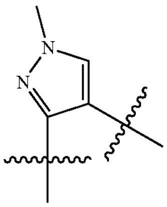, 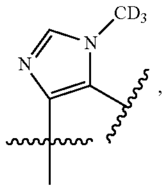, 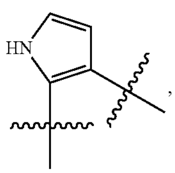, 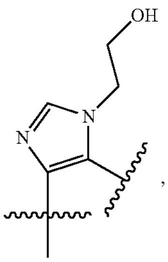,
-continued
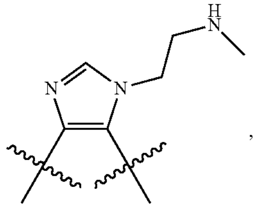, 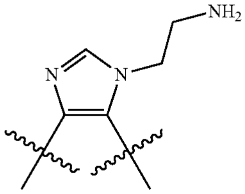, 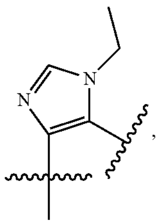, 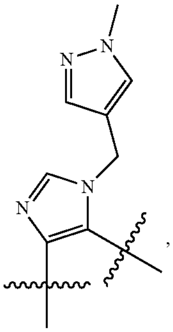, and 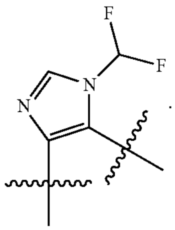.
In some embodiments, ring A is selected from
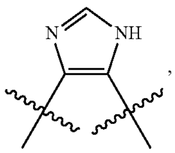, 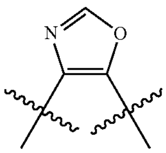, 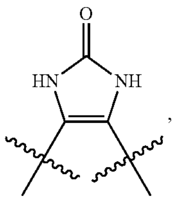, 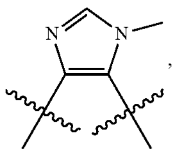, 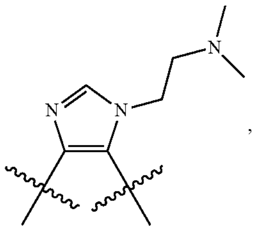, 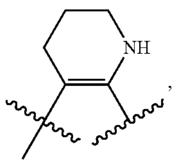, 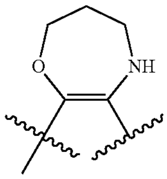, 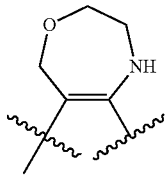, -continued
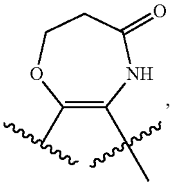,
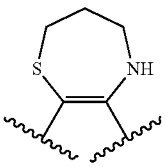,
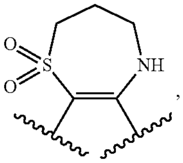,
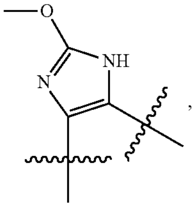,
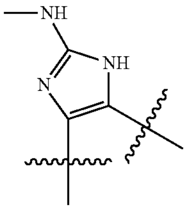,
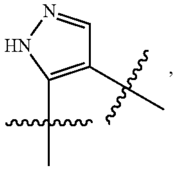,
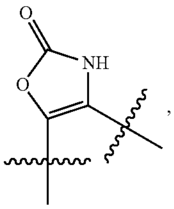,
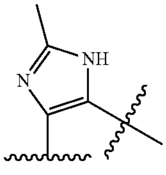,
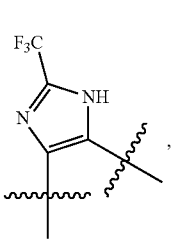,
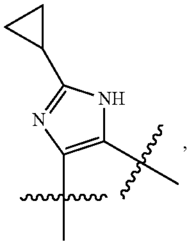,
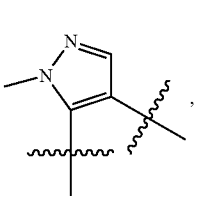,
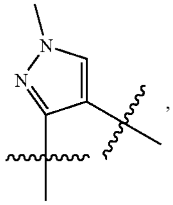,
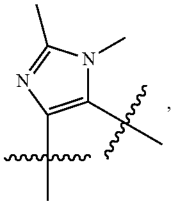,
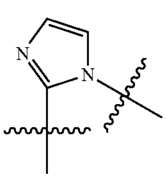,
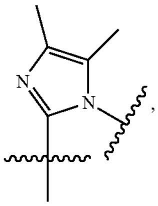,
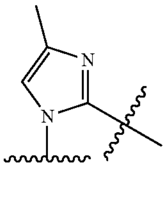,
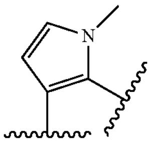,
-continued
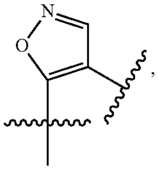,
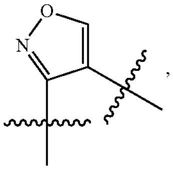,
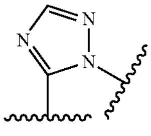,
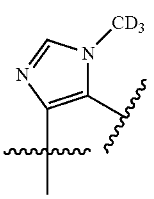,
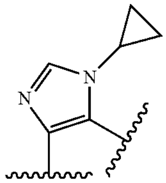,
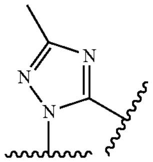,
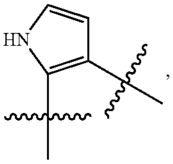,
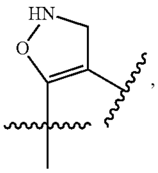, and
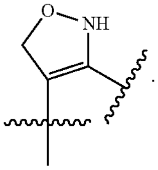.
In some embodiments, ring A is selected from
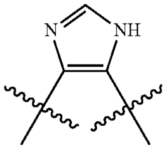,
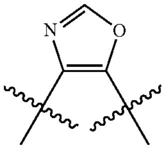,
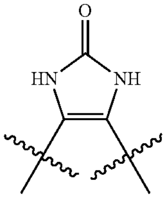,
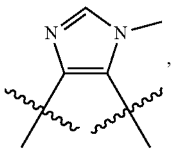,
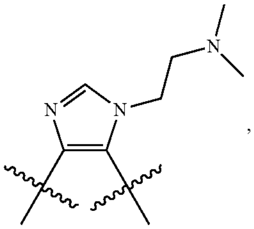,
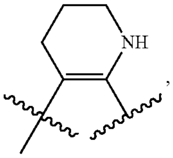,
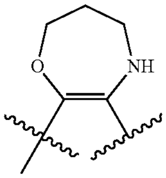,
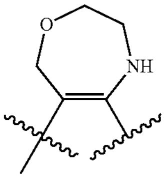, -continued
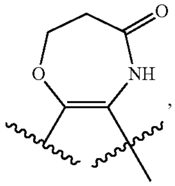, 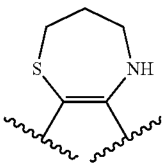,
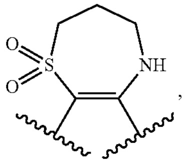, 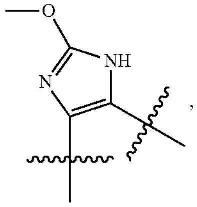,
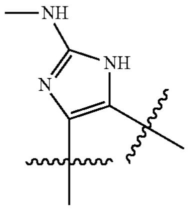, 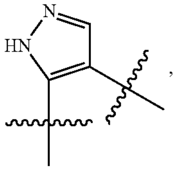,
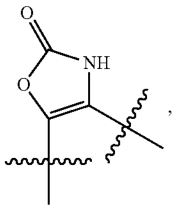, 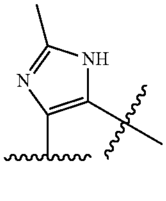,
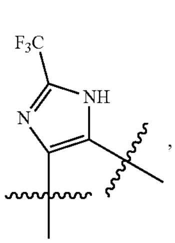, 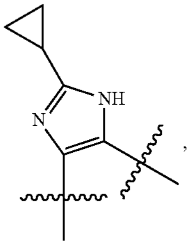,
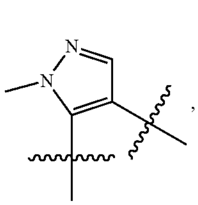, 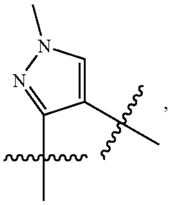,
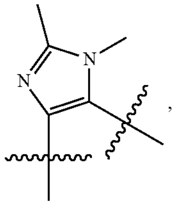, 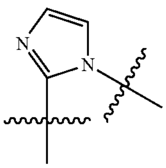,
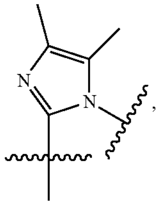, 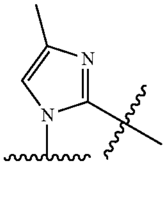, 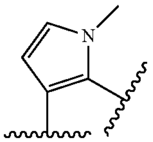,
-continued
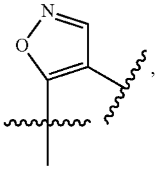, 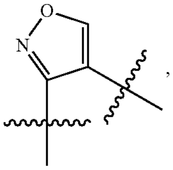, 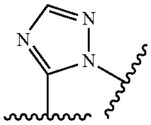,
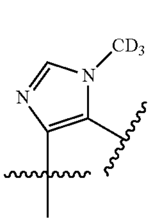, 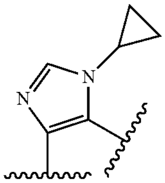,
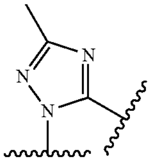, and 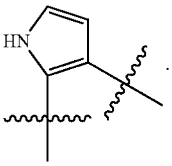.
In some embodiments, ring A is selected from
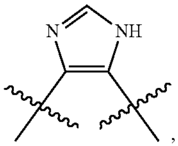, 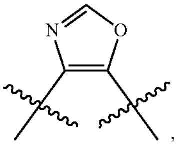,
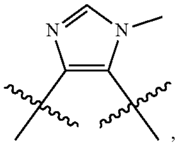, 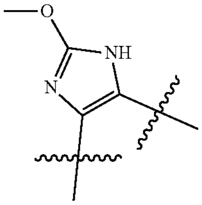,
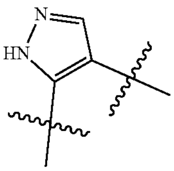, 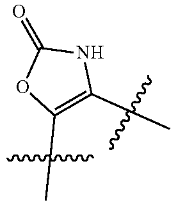,
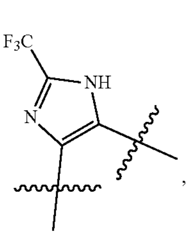, 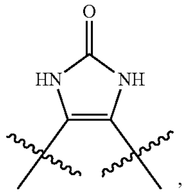,
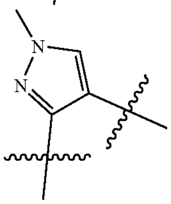, 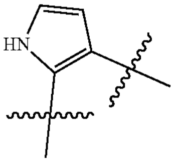, and -continued
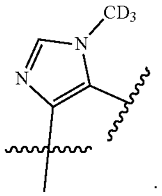
In some embodiments, ring A is selected from
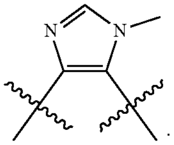 [SMILES: *c1ncn(C)c1*]
In some embodiments, ring A is selected from
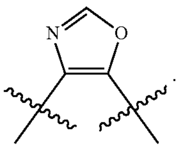 [SMILES: *c1ncoc1*]
In some embodiments, ring A is selected from
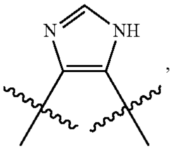
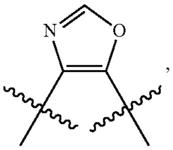
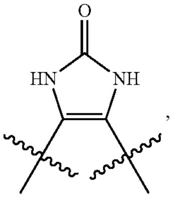
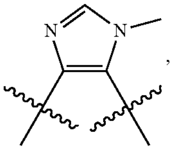
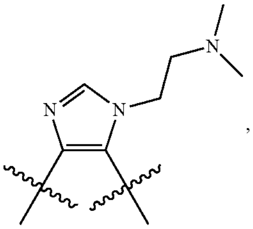
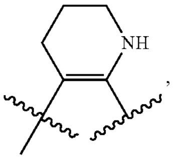
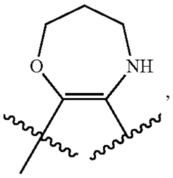
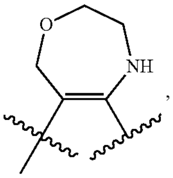
-continued
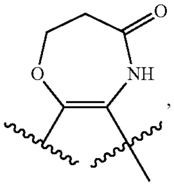
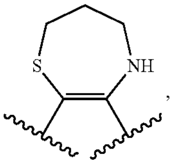
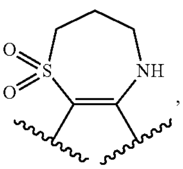
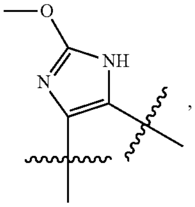
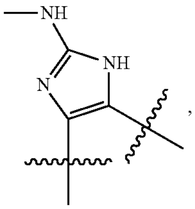
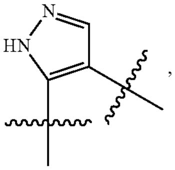
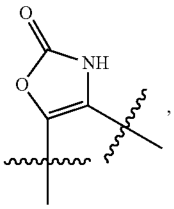
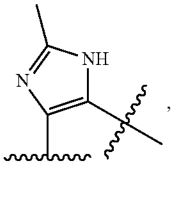
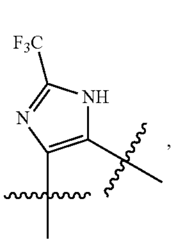
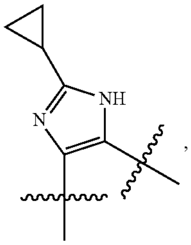
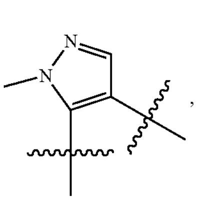
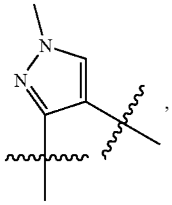
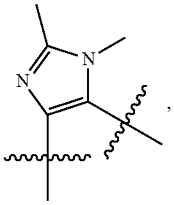
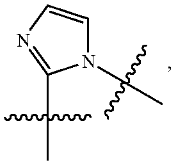
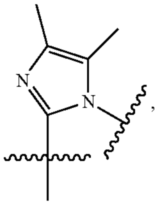
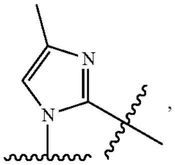
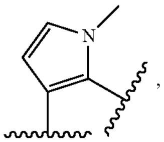

-continued

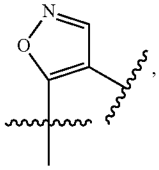,
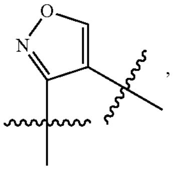,
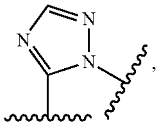,
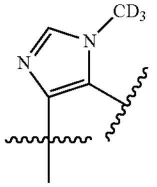,
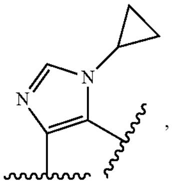, and
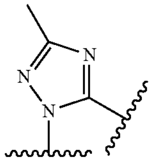.

In some embodiments, ring A is selected from

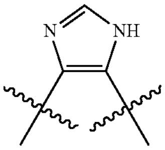,
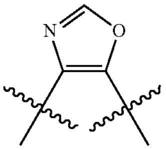,
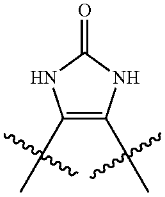,
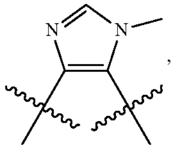,
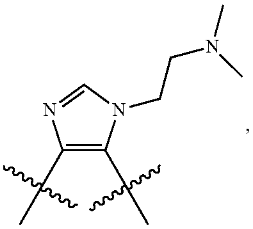,
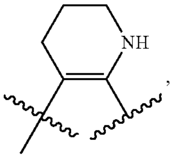,
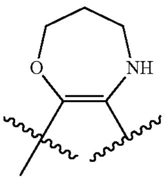,
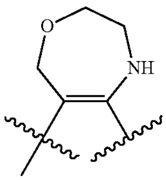,
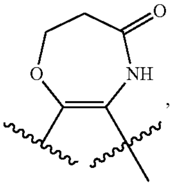,
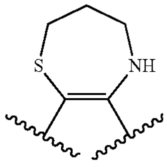, and -continued

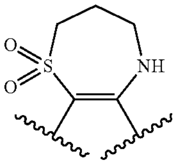.

In some embodiments, ring A is selected from

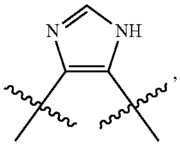,
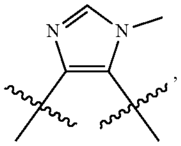,
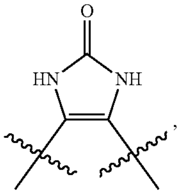,
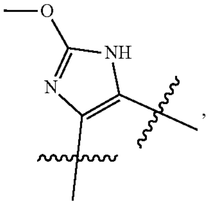, and
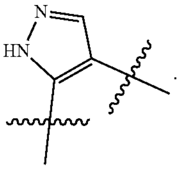.

In some embodiments, ring Q is selected from phenyl and 5-6 membered heteroaryl, and the phenyl or the 5-6 membered heteroaryl is optionally substituted with $R^3$.

In some embodiments, ring Q is selected from phenyl, pyridinyl, pyrazolyl, pyrimidinyl, and pyrazinyl, and the phenyl, the pyridinyl, the pyrazolyl, the pyrimidinyl, or the pyrazinyl is optionally substituted with $R^3$.

In some embodiments, ring Q is selected from phenyl and pyridinyl, and the phenyl or the pyridinyl is optionally substituted with $R^3$.

In some embodiments, ring Q is selected from phenyl, and the phenyl is optionally substituted with $R^3$.

In some embodiments, $R^3$ is selected from halogen, =O, OH, CN, and the following groups optionally substituted with $R^{3a}$: SH, $C_2$-$C_3$ alkynyl, $C_1$-$C_6$ alkyl, $C_3$-$C_6$ cycloalkyl, $C_1$-$C_6$ alkoxy, and $C_3$-$C_6$ cycloalkyloxy.

In some embodiments, $R^3$ is selected from halogen, =O, OH, CN, and the following groups optionally substituted with $R^{3a}$: $C_2$-$C_3$ alkynyl, $C_1$-$C_6$ alkyl, $C_3$-$C_6$ cycloalkyl, and $C_1$-$C_6$ alkoxy.

In some embodiments, $R^3$ is selected from halogen, =O, OH, CN, and the following groups optionally substituted with $R^{3a}$: ethynyl, $C_1$-$C_6$ alkyl, $C_3$-$C_6$ cycloalkyl, $C_1$-$C_6$ alkoxy, and $C_3$-$C_6$ cycloalkyloxy.

In some embodiments, $R^3$ is selected from halogen, =O, OH, CN, and the following groups optionally substituted with $R^{3a}$: $C_1$-$C_6$ alkyl, $C_3$-$C_6$ cycloalkyl, $C_1$-$C_6$ alkoxy, and $C_3$-$C_6$ cycloalkyloxy.

In some embodiments, $R^{3a}$ is selected from halogen, CN, and $C_1$-$C_3$ alkyl.

In some embodiments, $R^{3a}$ is selected from halogen, e.g., F.

In some embodiments, $R^{3a}$ is selected from F.

In some embodiments, $R^3$ is selected from halogen, CN, $C_3$-$C_6$ cycloalkyl, $C_2$-$C_3$ alkynyl, $C_1$-$C_6$ alkyl optionally substituted with halogen, and $C_1$-$C_6$ alkoxy optionally substituted with halogen.

In some embodiments, $R^3$ is selected from halogen, CN, $C_3$-$C_6$ cycloalkyl, $C_1$-$C_6$ alkyl optionally substituted with halogen, and $C_1$-$C_6$ alkoxy optionally substituted with halogen.

In some embodiments, $R^3$ is selected from halogen, CN, $C_1$-$C_6$ alkyl, and $C_1$-$C_6$ alkoxy optionally substituted with halogen.

In some embodiments, $R^3$ is selected from halogen, CN, $C_1$-$C_3$ alkyl, and $C_1$-$C_3$ alkoxy optionally substituted with halogen.

In some embodiments, $R^3$ is selected from halogen and $C_1$-$C_6$ alkoxy optionally substituted with halogen.

In some embodiments, $R^3$ is selected from halogen, CN, isopropyl, cyclopropyl, methyl optionally substituted with halogen, and methoxy optionally substituted with halogen.

In some embodiments, $R^3$ is selected from halogen, CN, methyl, isopropyl, and methoxy optionally substituted with halogen.

In some embodiments, $R^3$ is selected from halogen, CN, methyl, and methoxy optionally substituted with halogen.

In some embodiments, $R^3$ is selected from halogen and methoxy optionally substituted with halogen.

In some embodiments, $R^3$ is selected from halogen, CN, isopropyl, cyclopropyl, methyl optionally substituted with F, and methoxy optionally substituted with F.

In some embodiments, $R^3$ is selected from halogen, CN, methyl, and methoxy optionally substituted with F.

In some embodiments, $R^3$ is selected from halogen and methoxy optionally substituted with F.

In some embodiments, $R^3$ is selected from F, Cl, Br, CN, SH, isopropyl, cyclopropyl, methyl, ethyl, trifluoromethyl, ethynyl, $OCHF_2$, methoxy, and methylthio.

In some embodiments, $R^3$ is selected from F, Cl, Br, CN, isopropyl, cyclopropyl, methyl, ethyl, trifluoromethyl, ethynyl, $OCHF_2$, and methoxy.

In some embodiments, $R^3$ is selected from F, Cl, Br, CN, isopropyl, cyclopropyl, methyl, trifluoromethyl, $OCHF_2$, and methoxy.

In some embodiments, $R^3$ is selected from F, Cl, Br, CN, methyl, isopropyl, $OCHF_2$, and methoxy.

In some embodiments, $R^3$ is selected from F, $C_1$, methyl, isopropyl, $OCHF_2$, and methoxy.

In some embodiments, $R^3$ is selected from Cl, Br, CN, methyl, $OCHF_2$, and methoxy.

In some embodiments, $R^3$ is selected from $C_1$ and $OCHF_2$.

In some embodiments, ring Q is selected from phenyl and pyridinyl, and the phenyl or the pyridinyl is optionally substituted with $R^3$; each $R^3$ is independently selected from halogen, CN, isopropyl, cyclopropyl, methyl optionally substituted with halogen (e.g., F), and methoxy optionally substituted with halogen (e.g., F).

In some embodiments, ring Q is selected from phenyl and pyridinyl, and the phenyl or the pyridinyl is optionally substituted with $R^3$; each $R^3$ is independently selected from F, Cl, Br, CN, isopropyl, cyclopropyl, methyl, trifluoromethyl, $OCHF_2$, and methoxy.

In some embodiments, ring Q is selected from phenyl, pyridinyl, pyrazolyl, pyrimidinyl, and pyrazinyl, and the phenyl, the pyridinyl, the pyrazolyl, the pyrimidinyl, or the pyrazinyl is optionally substituted with $R^3$; each $R^3$ is independently selected from halogen, CN, $C_3$-$C_6$ cycloalkyl, $C_2$-$C_3$ alkynyl, $C_1$-$C_6$ alkyl optionally substituted with halogen (e.g., F), and $C_1$-$C_6$ alkoxy optionally substituted with halogen (e.g., F).

In some embodiments, ring Q is selected from phenyl, pyridinyl, pyrazolyl, pyrimidinyl, and pyrazinyl, and the phenyl, the pyridinyl, the pyrazolyl, the pyrimidinyl, or the pyrazinyl is optionally substituted with $R^3$; each $R^3$ is independently selected from F, Cl, Br, CN, isopropyl, cyclopropyl, methyl, ethyl, trifluoromethyl, ethynyl, $OCHF_2$, and methoxy.

In some embodiments, ring Q is selected from

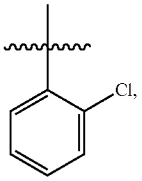 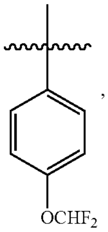 , 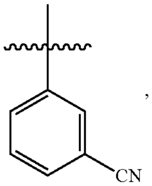 ,

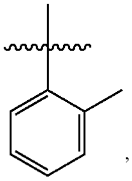 , 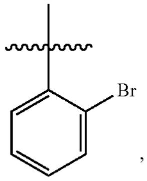 , 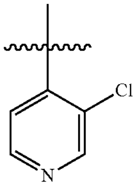 ,

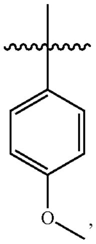 , 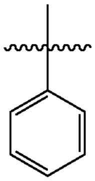 , 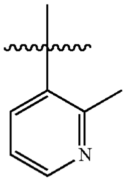 , 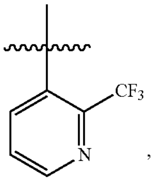 ,

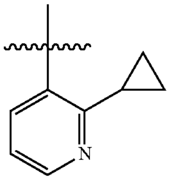 , 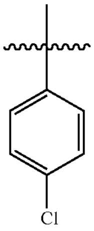 , 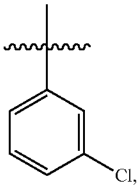

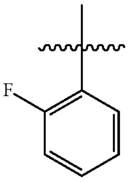 , 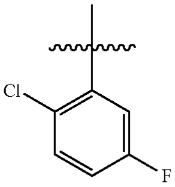 , 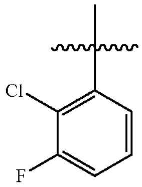 ,

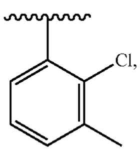 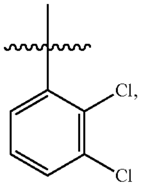 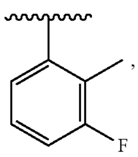 ,

-continued
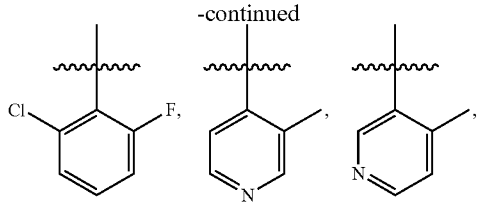
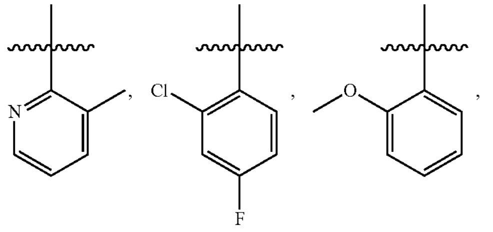
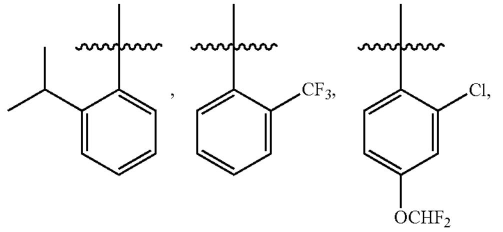
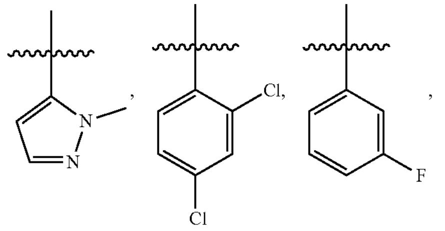
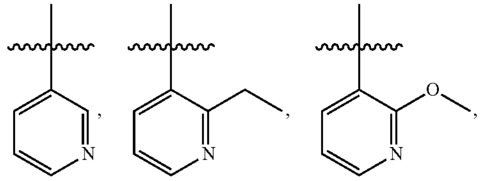
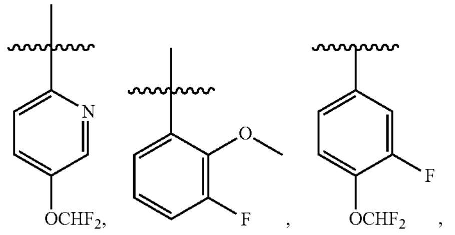
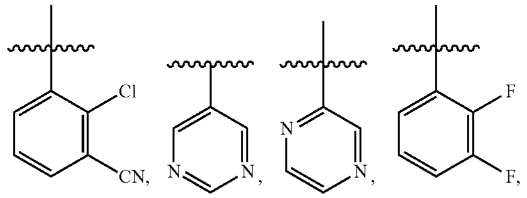
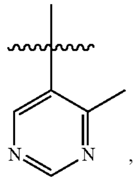
, and
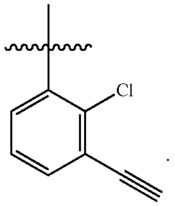
.
In some embodiments, ring Q is selected from
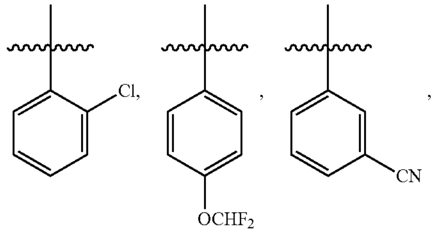
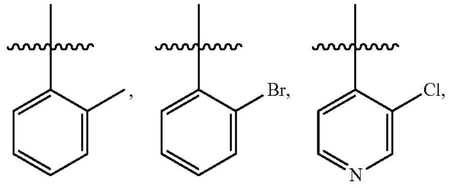
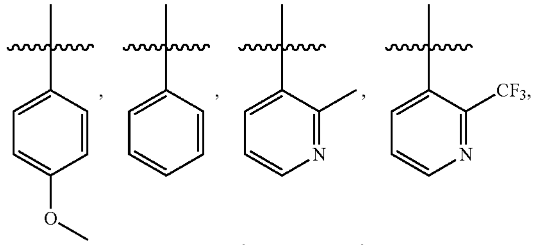
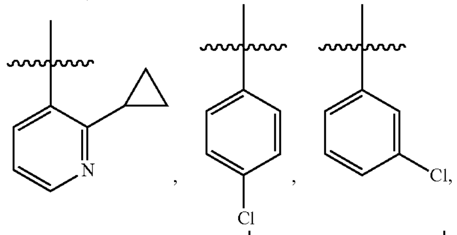
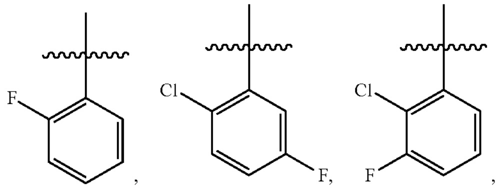
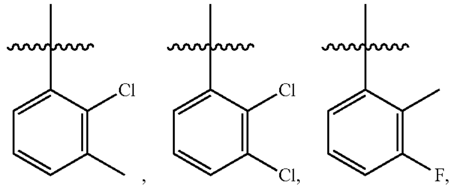
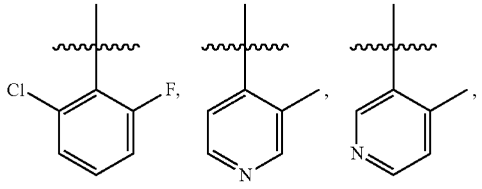
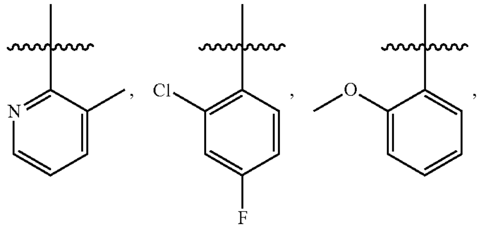
and -continued
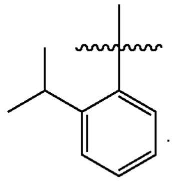 [SMILES: *c1ccccc1C(C)C]
In some embodiments, ring Q is selected from
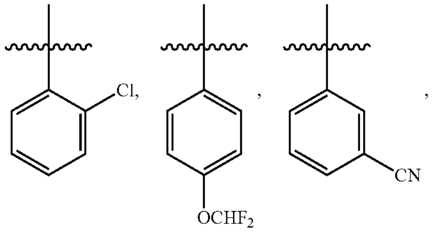
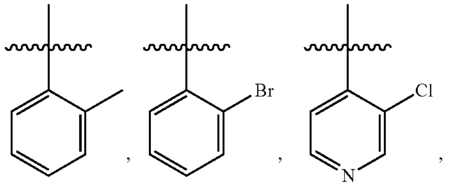
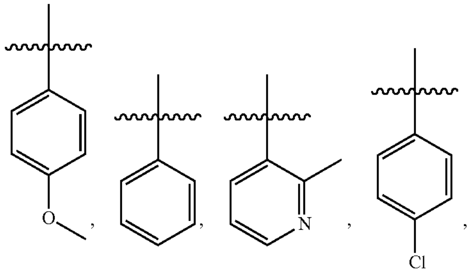
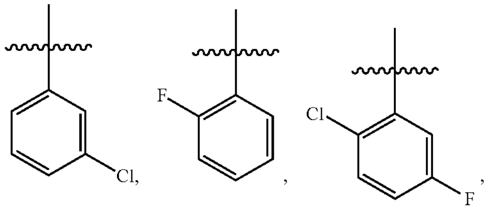
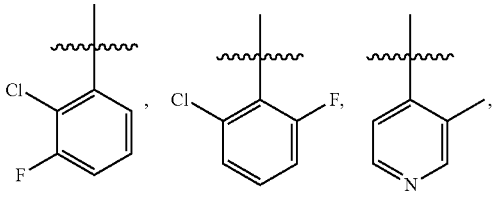
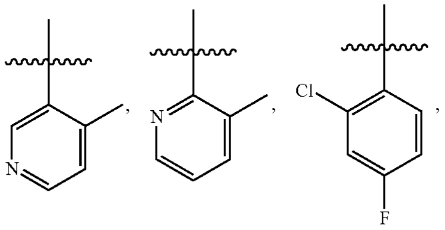
-continued
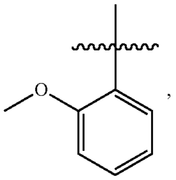
, and
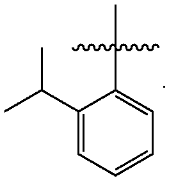
In some embodiments, ring Q is selected from
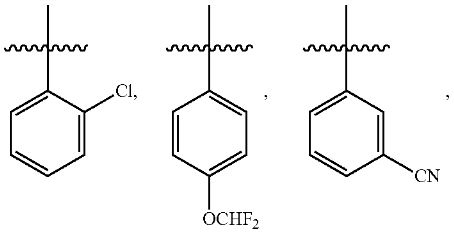
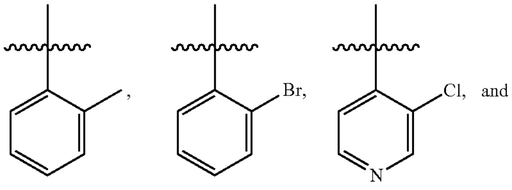
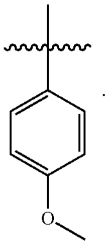
In some embodiments, ring Q is selected from
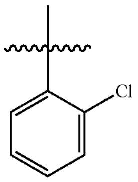
and
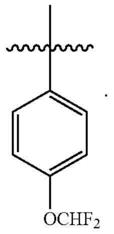
In some embodiments, the compound of general formula (I) or the pharmaceutically acceptable salt thereof is selected from the following compounds or pharmaceutically acceptable salts thereof:

1
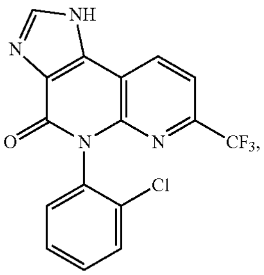
2
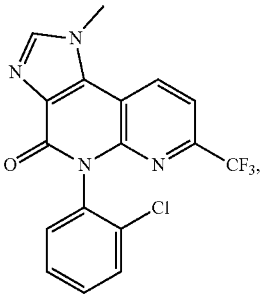
3
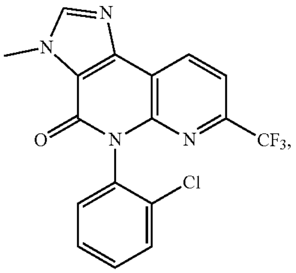
4
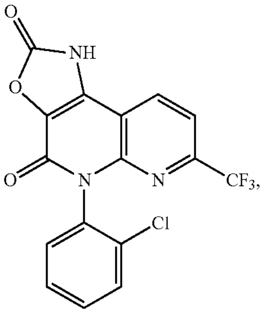
5
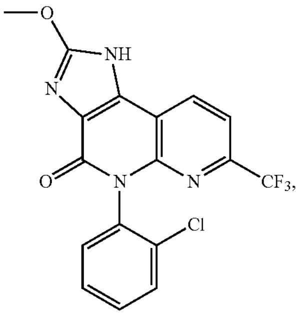
-continued
6
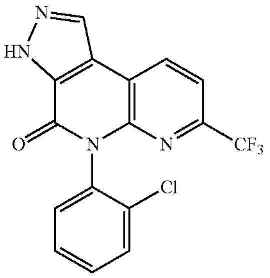
7
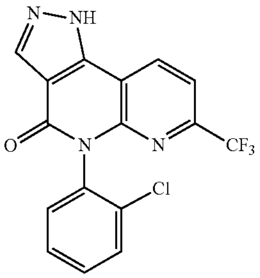
8
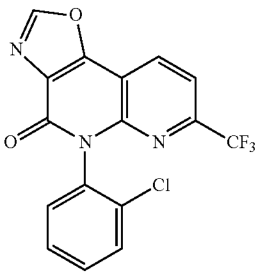
9
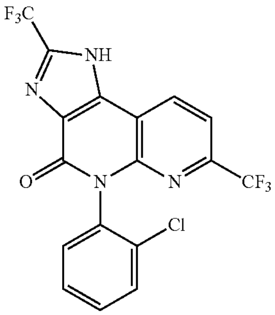
10
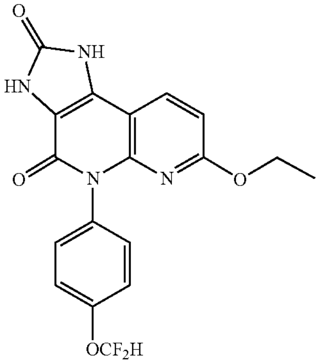

-continued
11
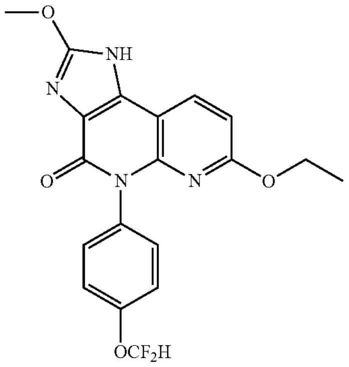
12
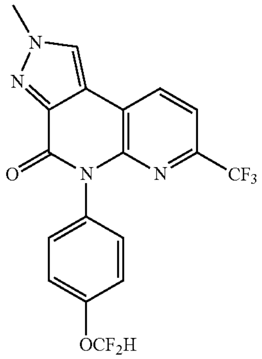
13
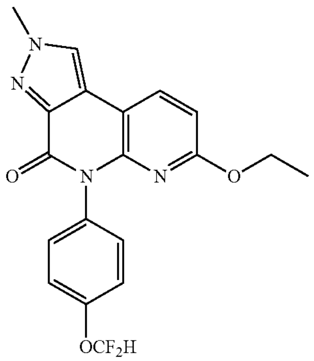
14
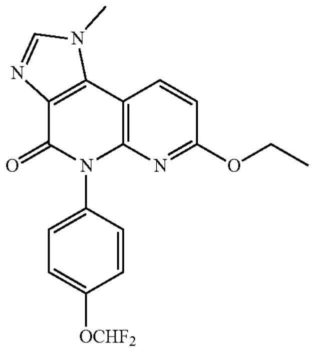
-continued
15
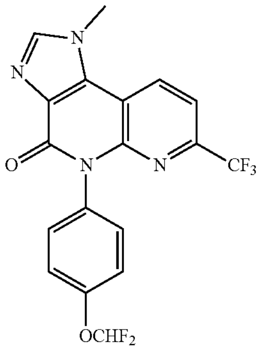
16
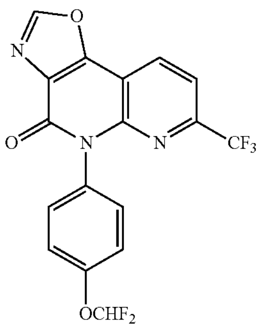
17
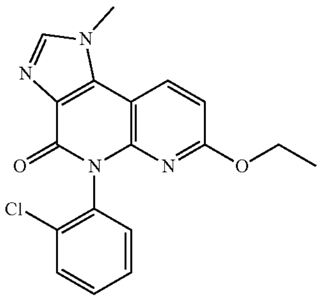
18
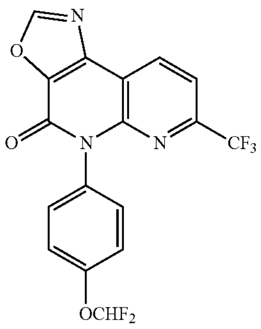

-continued
19
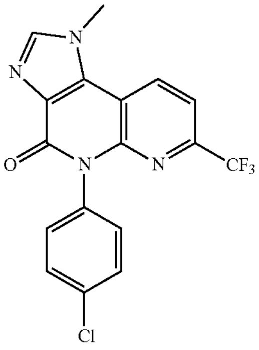
20
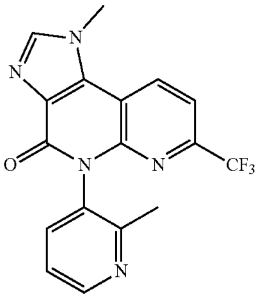
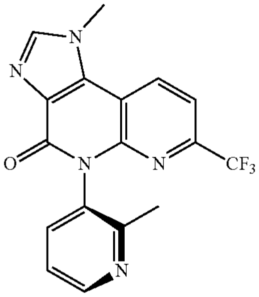
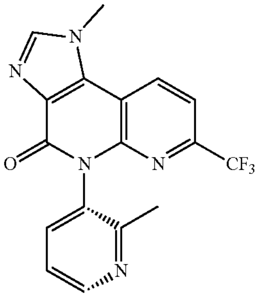
21
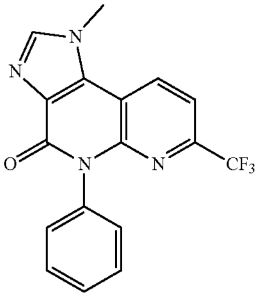
22
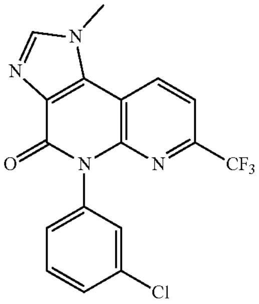
-continued
23
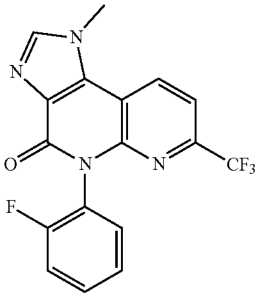
24
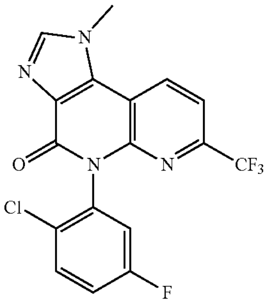
25
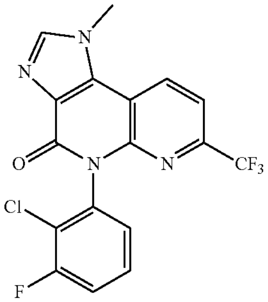
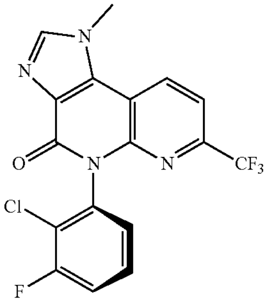
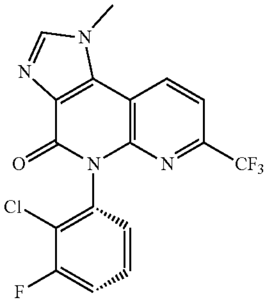

-continued
26
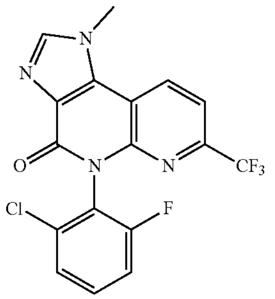
27
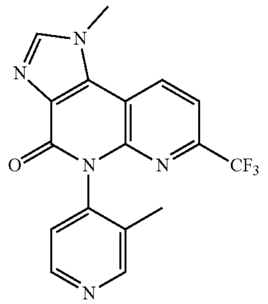
28
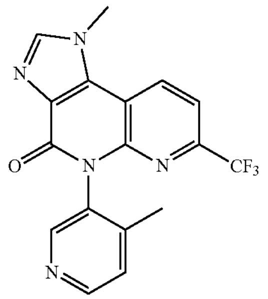
29
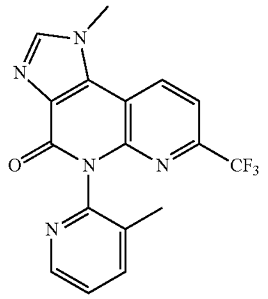
30
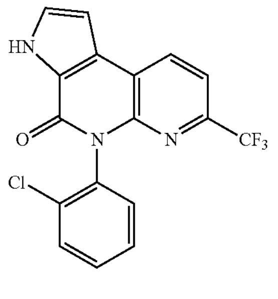
-continued
31
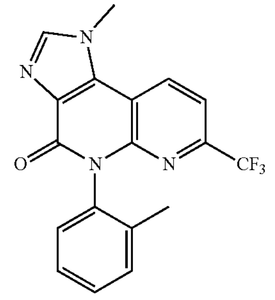
32
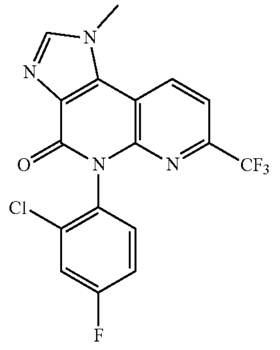
33
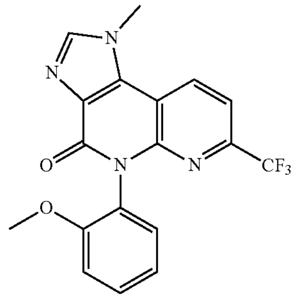
34
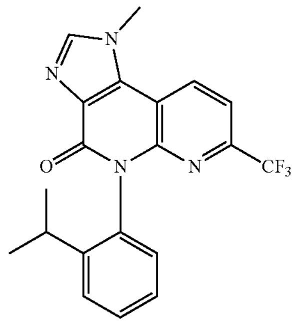
35
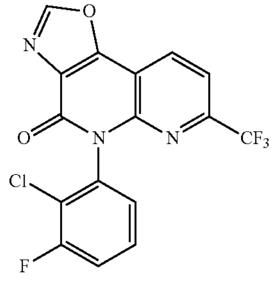

-continued
36
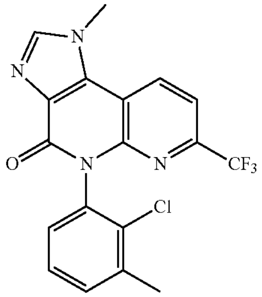
37
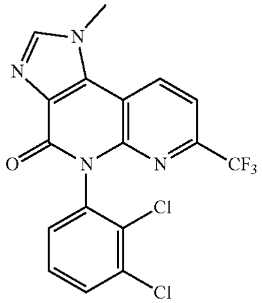
38
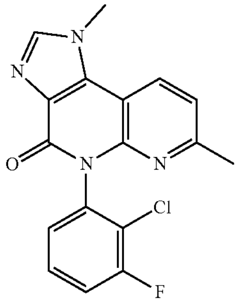
39
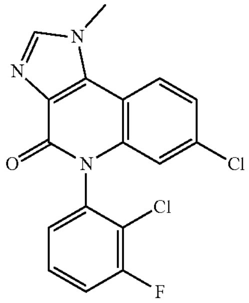
40
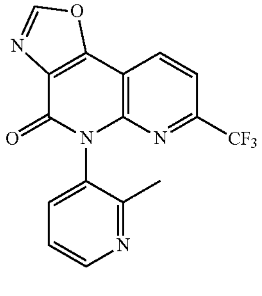
-continued
41
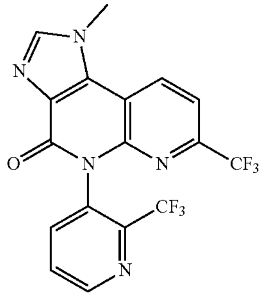
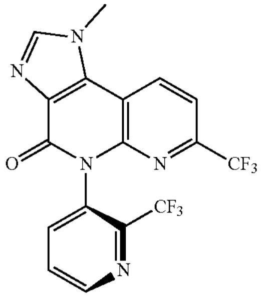
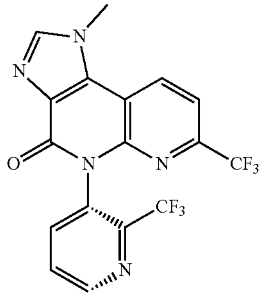
42
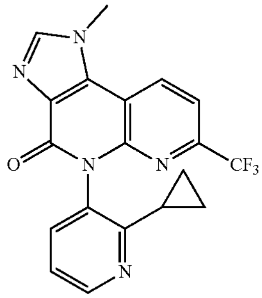
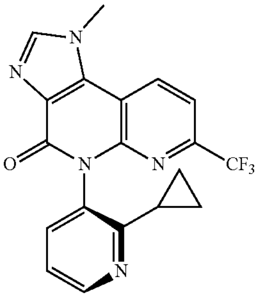
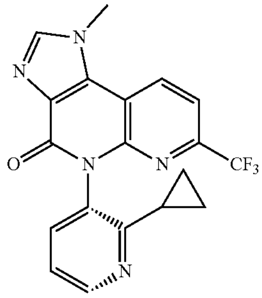
43
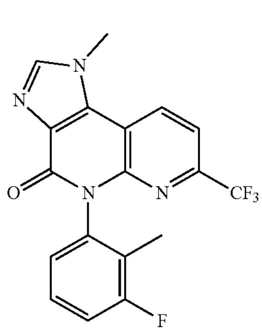
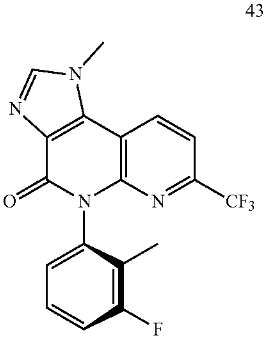

-continued
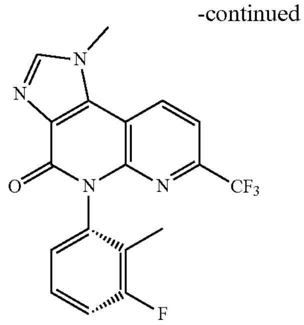
44
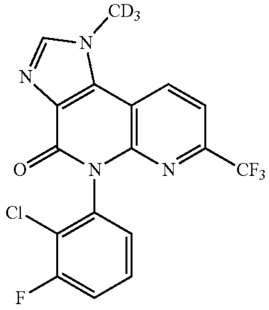
45
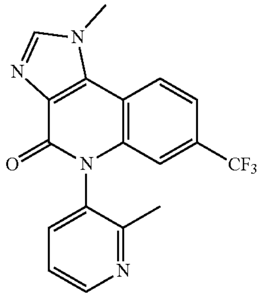
46
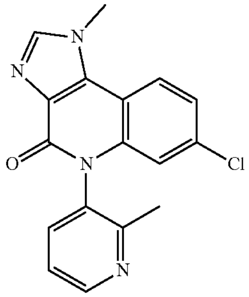
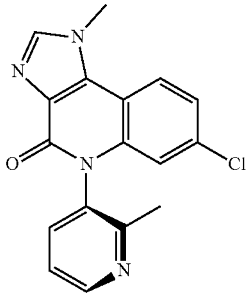
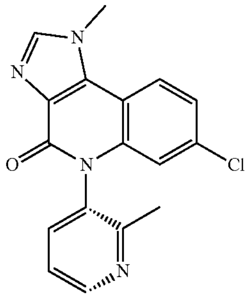
-continued
47
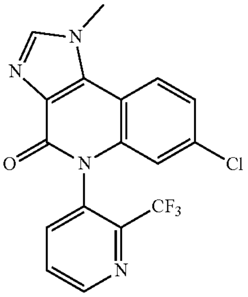
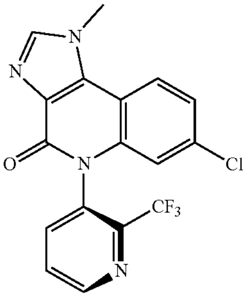
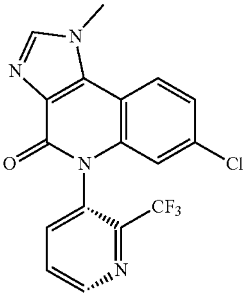
48
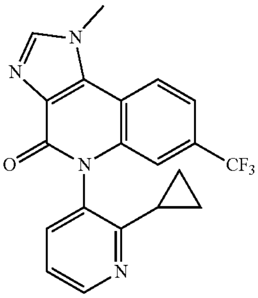
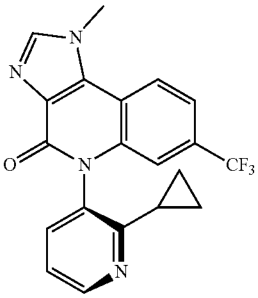
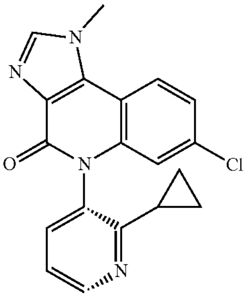
49
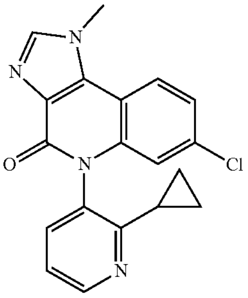
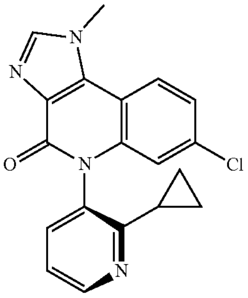

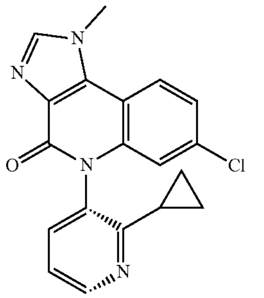
50
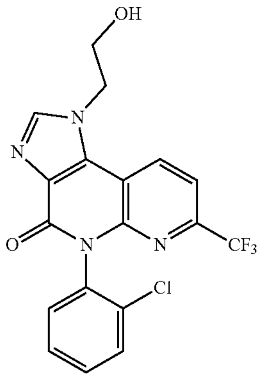
51
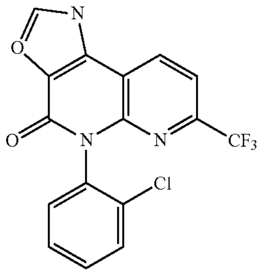
52
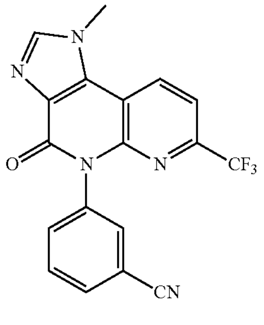
53
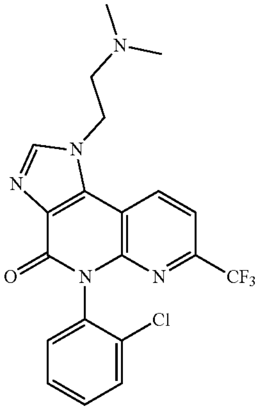
54
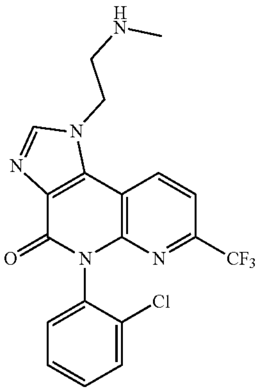
55
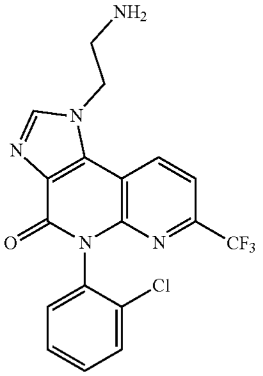
56
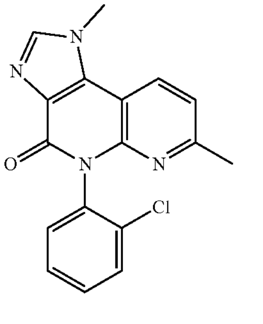

-continued
57
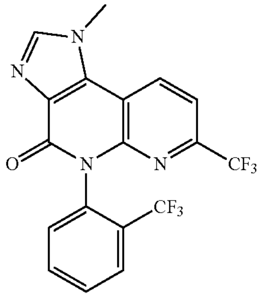
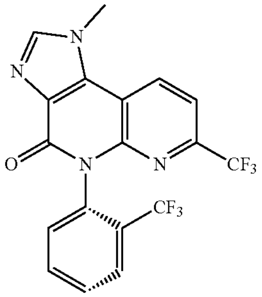
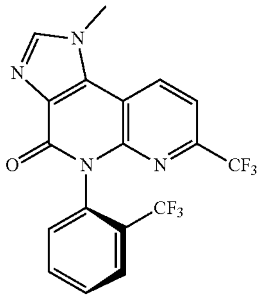
58
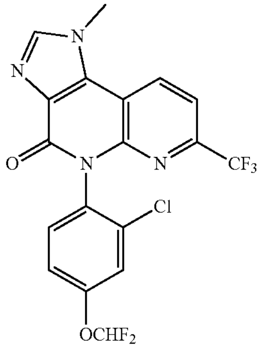
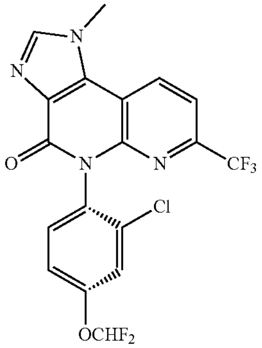
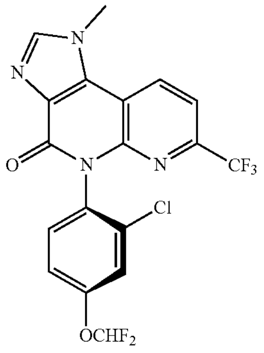
-continued
59
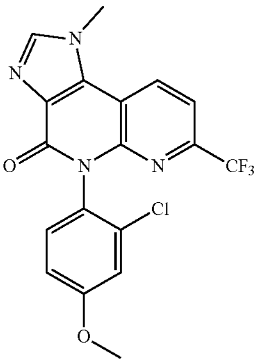
60
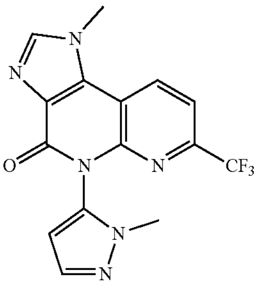
61
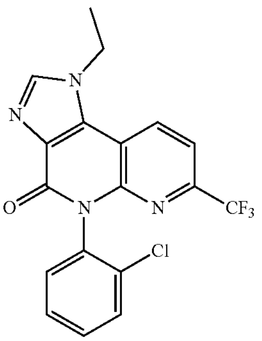
62
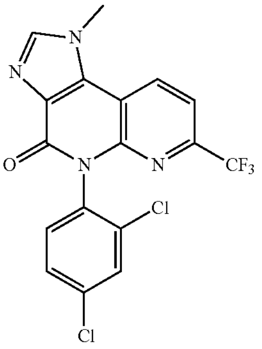

-continued
63
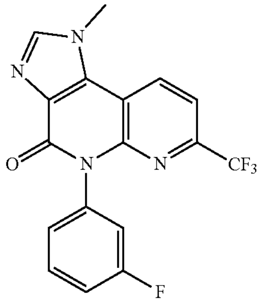
64
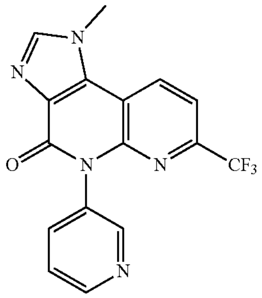
65
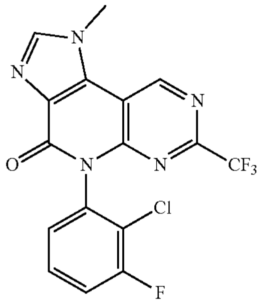
66
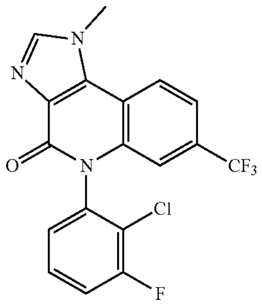
67
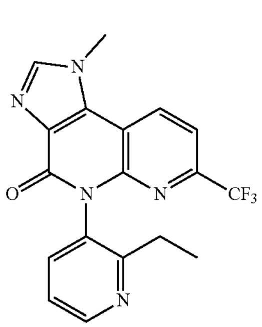
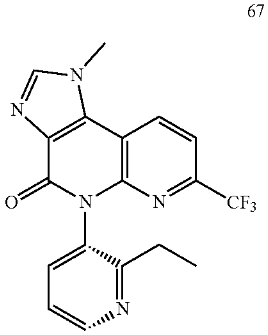
-continued
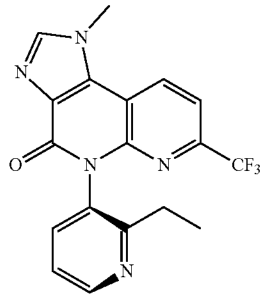
68
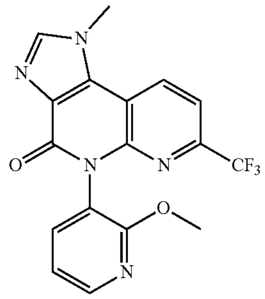
69
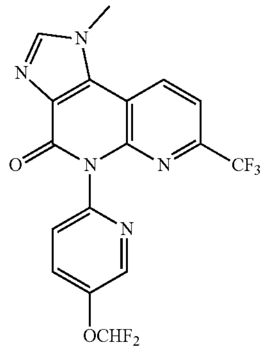
70
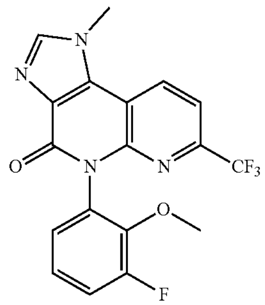
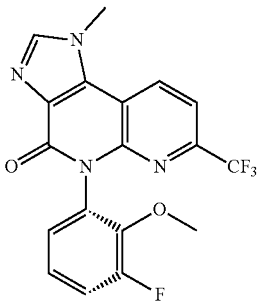
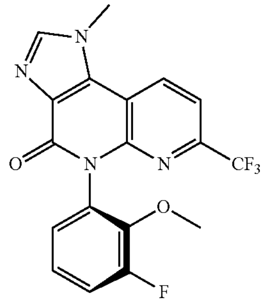

71
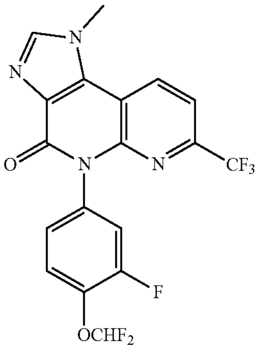
72
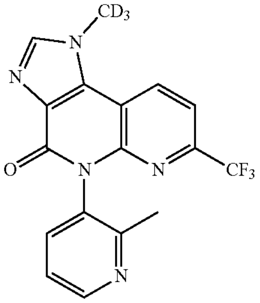
73
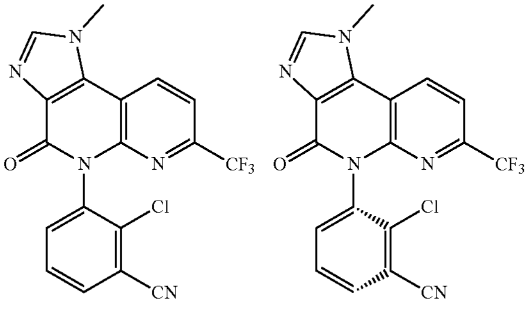
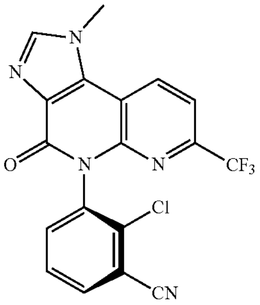
74
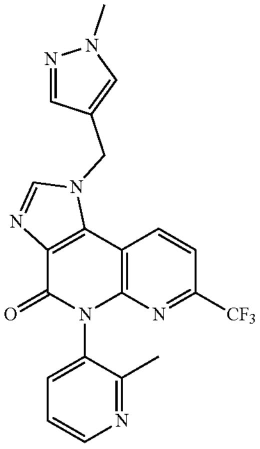
75
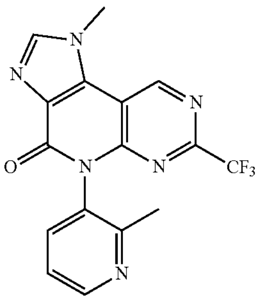
76
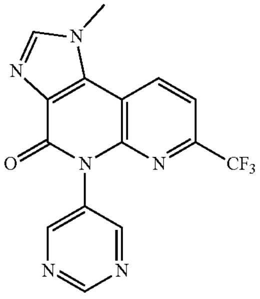
77
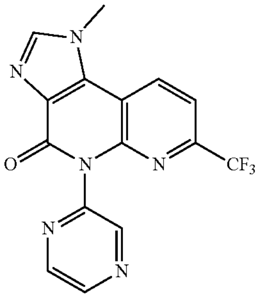

-continued
78
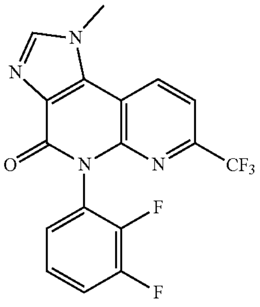
79
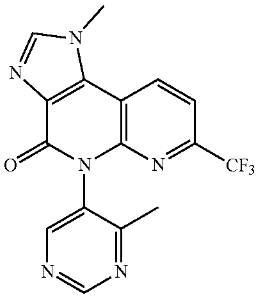
80
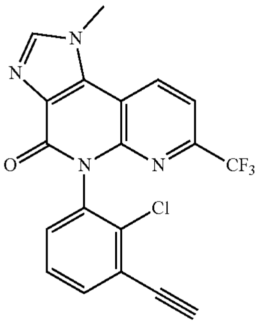
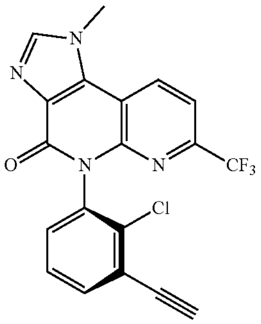
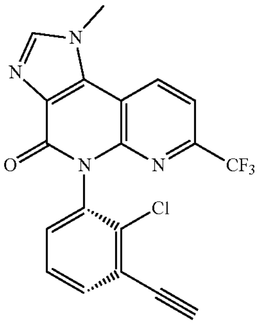
81
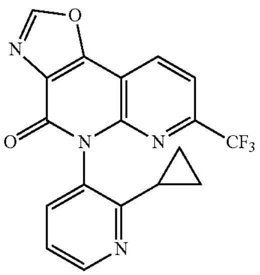
-continued
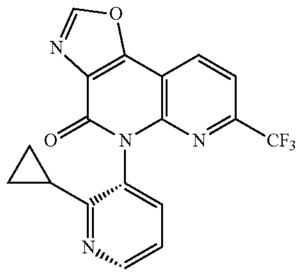
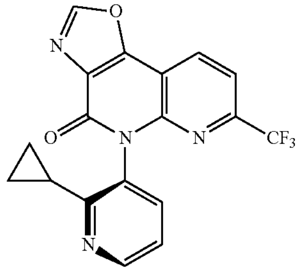
82
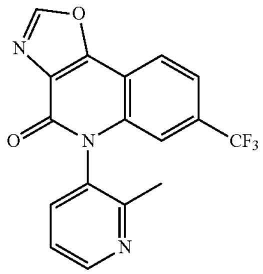
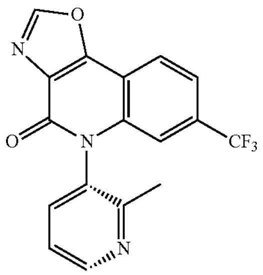
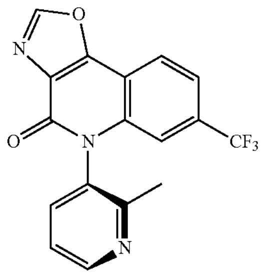
83
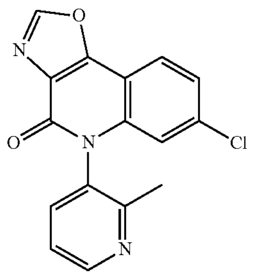
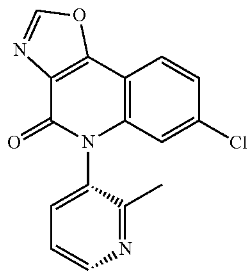
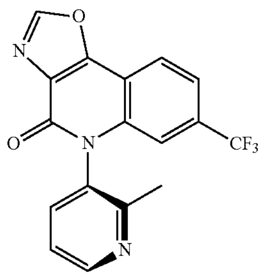

-continued
84
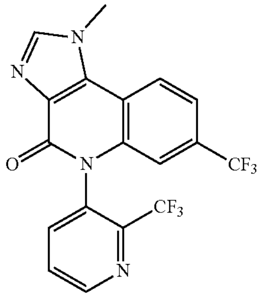
85
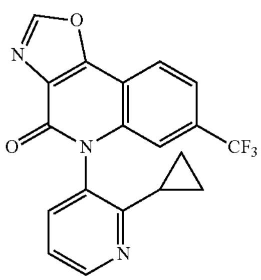
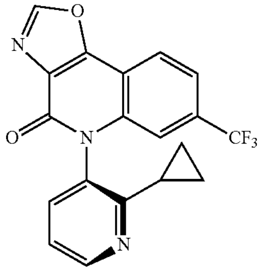
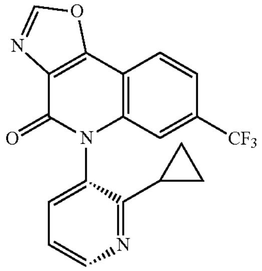
86
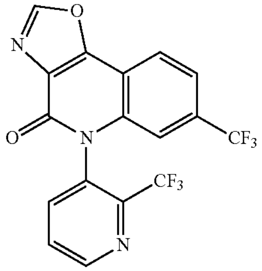
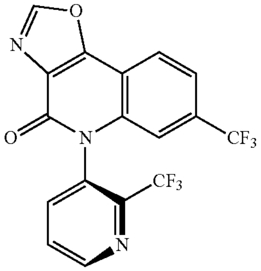
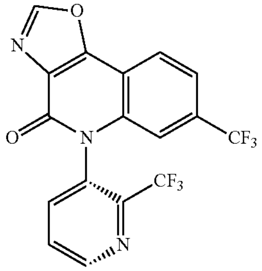
-continued
87
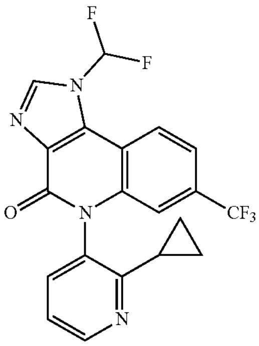
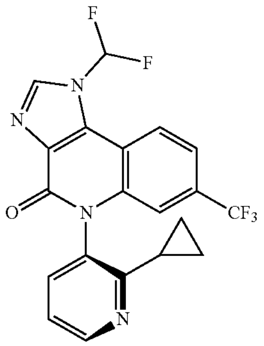
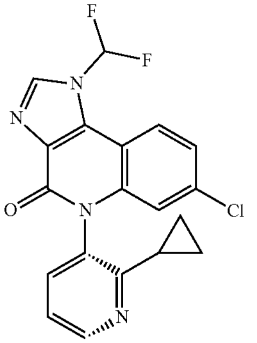
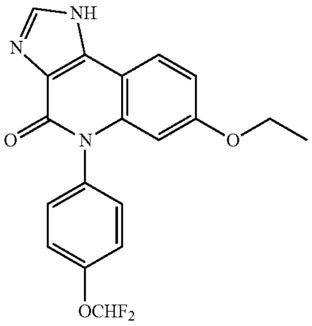
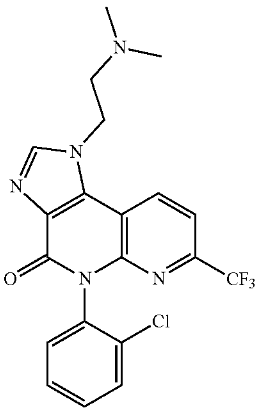

-continued
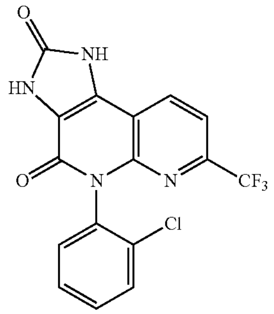
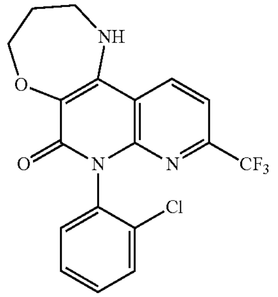
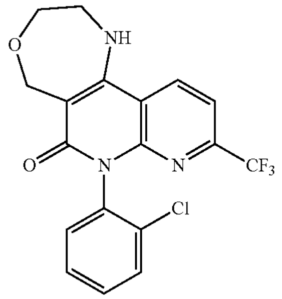
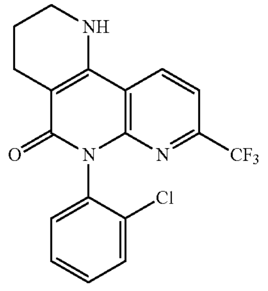
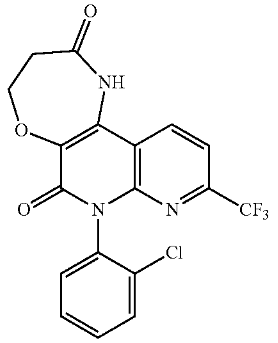
-continued
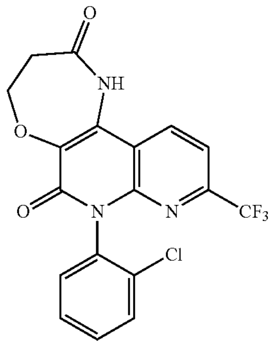
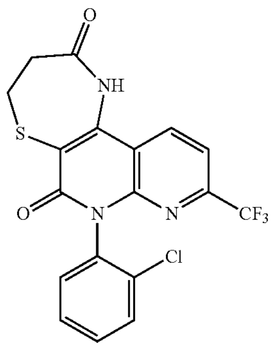
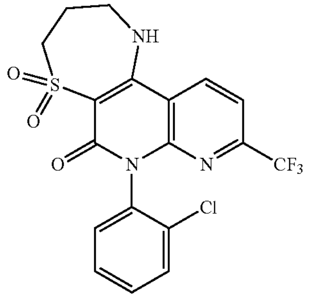
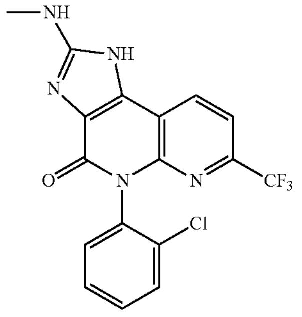
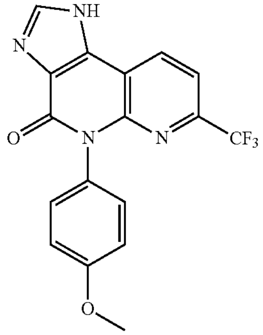
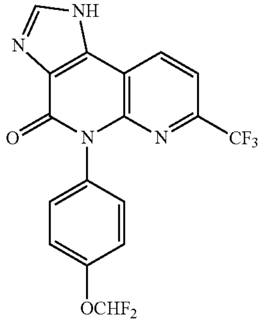

-continued
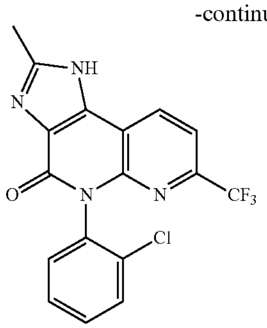
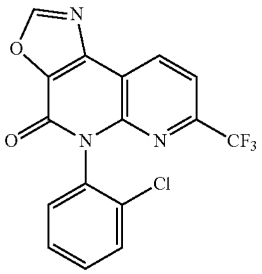
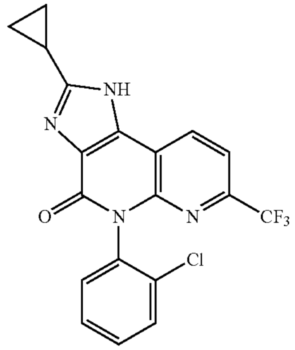
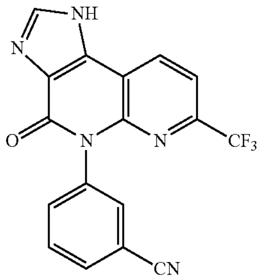
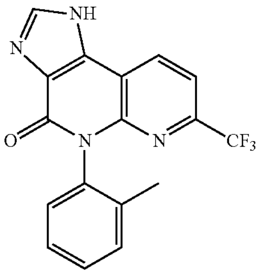
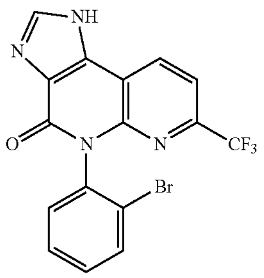
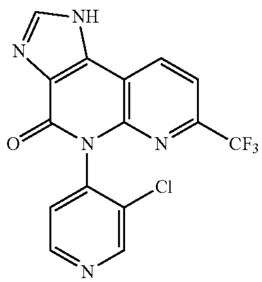
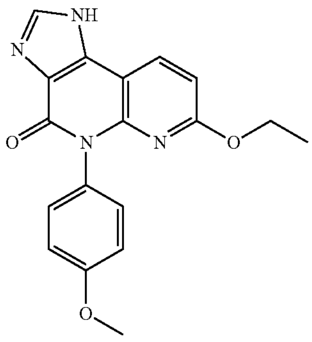
-continued
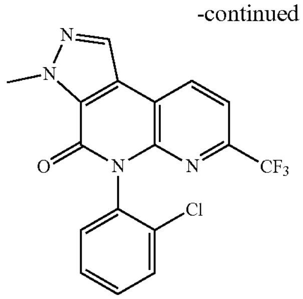
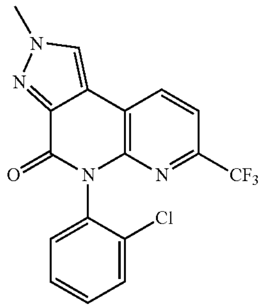
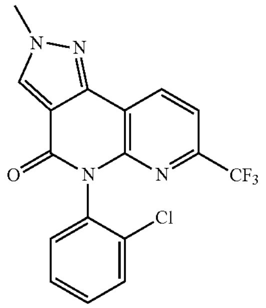
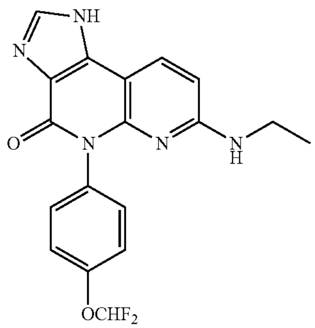
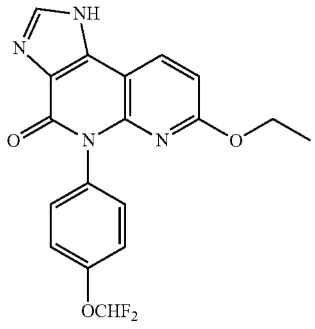

-continued
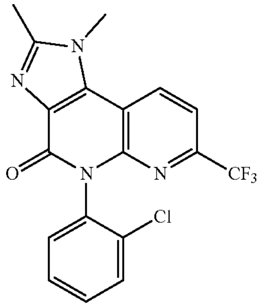
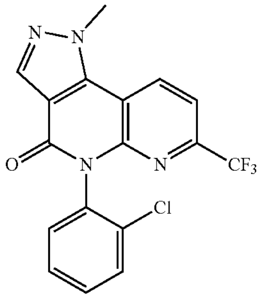
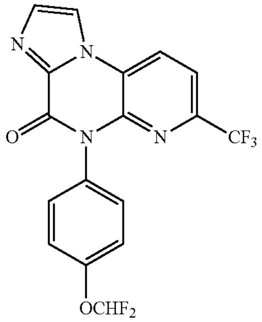
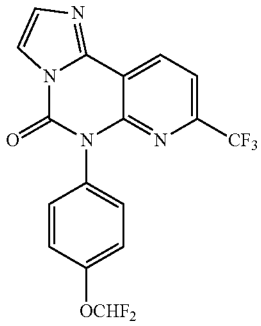
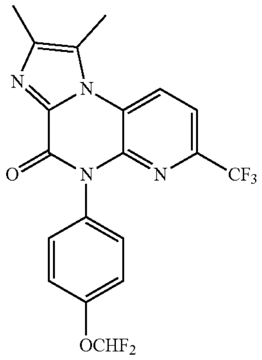
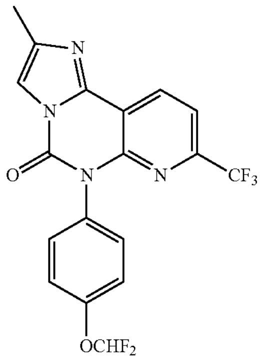
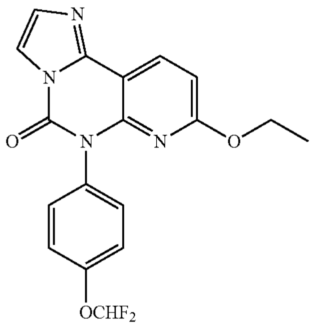
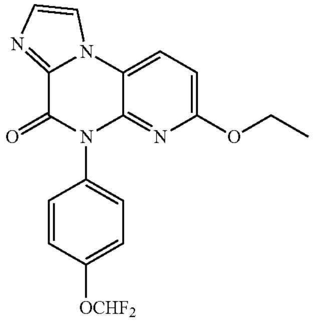
-continued
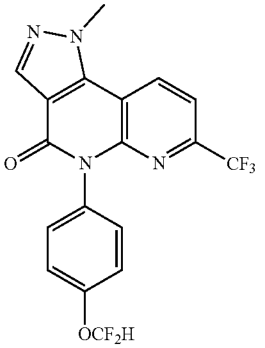
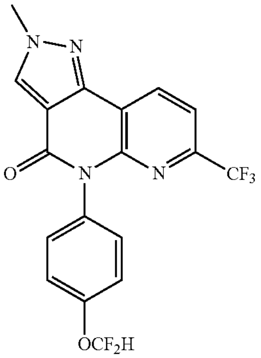
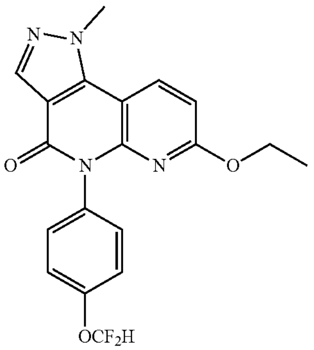
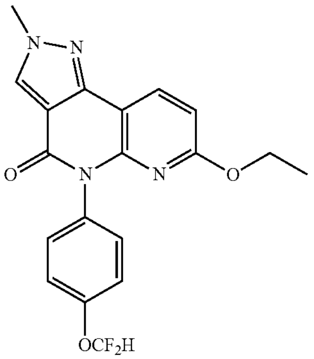
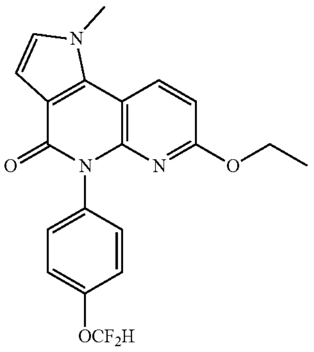

-continued
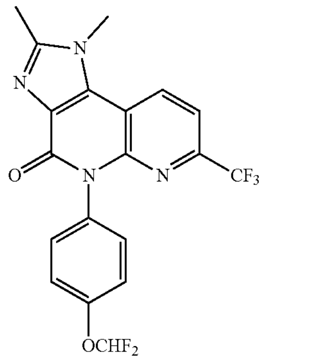 [SMILES: Cc1nc2c(=O)n(-c3ccc(OC(F)F)cc3)c3nc(C(F)(F)F)ccc3c2n1C]
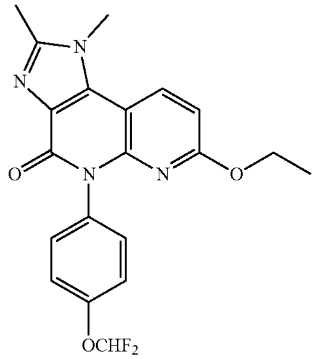
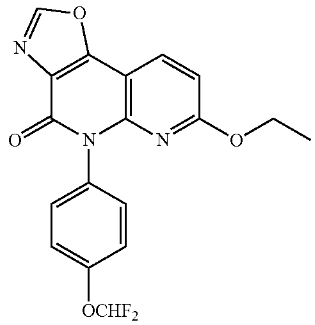
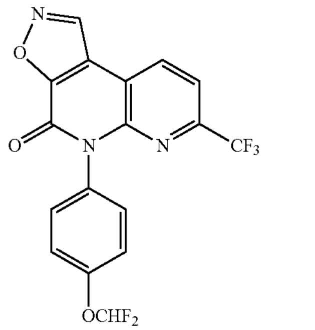
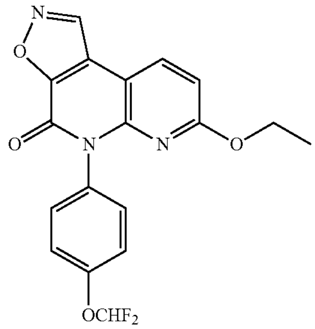
-continued
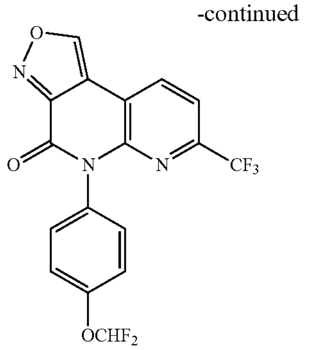
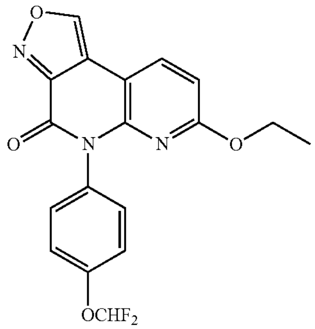
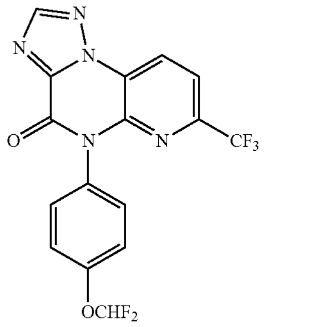
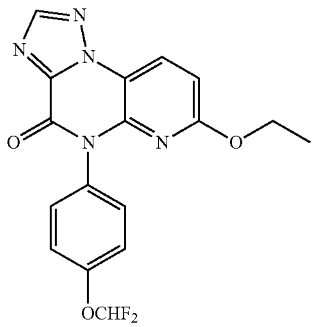

-continued

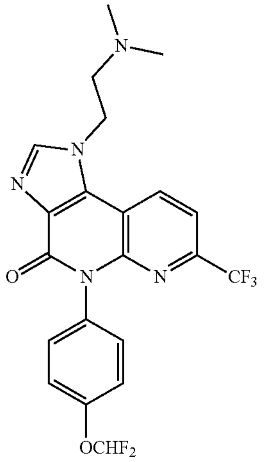

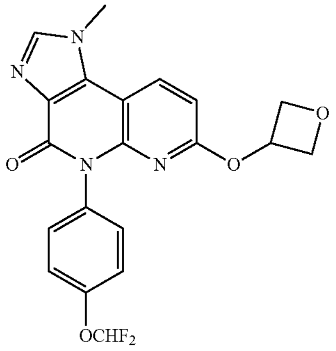

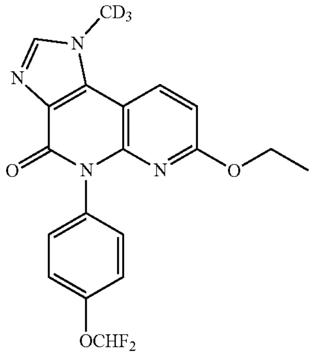

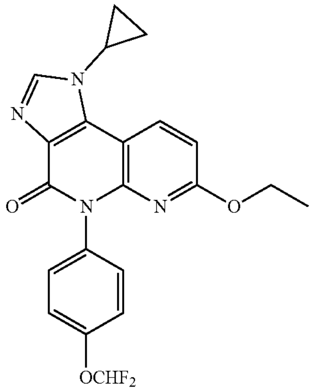

and

-continued

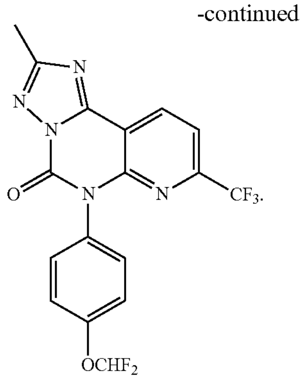

The present application also provides a pharmaceutical composition comprising the compound of formula (I) or the pharmaceutically acceptable salt thereof and a pharmaceutically acceptable excipient.

Furthermore, the present application relates to use of the compound of general formula (I) or the pharmaceutically acceptable salt thereof, or the pharmaceutical composition thereof, in preparing an anti-tumor medicament.

Furthermore, the present application relates to use of the compound of general formula (I) or the pharmaceutically acceptable salt thereof, or the pharmaceutical composition thereof, in preparing a medicament for preventing or treating a tumor with a reduction or deletion of MTAP activity.

Furthermore, the present application relates to use of the compound of general formula (I) or the pharmaceutically acceptable salt thereof, or the pharmaceutical composition thereof, in anti-tumor effects.

Furthermore, the present application relates to use of the compound of general formula (I) or the pharmaceutically acceptable salt thereof, or the pharmaceutical composition thereof, in preventing or treating a tumor with a reduction or deletion of MTAP activity.

Furthermore, the present application relates to the anti-tumor compound of general formula (I) or the pharmaceutically acceptable salt thereof, or the pharmaceutical composition thereof.

Furthermore, the present application relates to the compound of general formula (I) preventing or treating a tumor with a reduction or deletion of MTAP activity or the pharmaceutically acceptable salt thereof, or the pharmaceutical composition thereof.

The present application also relates to a method for treating a tumor comprising administering to a patient a therapeutically effective amount of a pharmaceutical formulation comprising the compound of general formula (I) or the pharmaceutically acceptable salt thereof described herein.

The present application also relates to a method for treating a tumor with a reduction or deletion of MTAP activity, comprising administering to a patient a therapeutically effective amount of a pharmaceutical formulation comprising the compound of general formula (I) or the pharmaceutically acceptable salt thereof described herein.

The present application also relates to a method for treating a tumor comprising administering to a patient a therapeutically effective amount of the compound of general formula (I) or the pharmaceutically acceptable salt thereof, or the pharmaceutical composition thereof described herein.

The present application also relates to a method for treating a tumor with a reduction or deletion of MTAP activity, comprising administering to a patient a therapeutically effective amount of the compound of general formula (I) or the pharmaceutically acceptable salt thereof, or the pharmaceutical composition thereof described herein.

In some embodiments, the tumor is gastric cancer, colon cancer, liver cancer, or pancreatic cancer.

Terminology and Definitions

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification. When referring to a trade name, it is intended to refer to its corresponding commercial product or its active ingredient.

Herein, the bond  depicted by a solid line and a dotted line represents a single bond or a double bond.

Herein, "

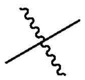

" represents a connection site.

The illustration of the pure compounds of the racemate or the enantiomer herein is from Maehr, *J. Chem. Ed.* 1985, 62: 114-120. Unless otherwise stated, the absolute configuration of a stereogenic center is represented by a wedged bond and a wedged dashed bond ( and ), and the relative configuration of a stereogenic center (e.g., cis- or trans-configuration of alicyclic compounds) is represented by a black solid bond and a dashed bond ( and ).

The term "tautomer" refers to functional isomers resulting from the rapid movement of an atom in a molecule between two positions. The compounds disclosed herein may exhibit the tautomerism. Tautomeric compounds may exist in two or more interconvertible forms. Tautomers generally exist in an equilibrium form. Trying to separate a single tautomer usually leads to a mixture, the physicochemical properties of which are consistent with the mixture of the compound. The position of the equilibrium depends on the chemical properties of the molecule. For example, in many aliphatic aldehydes and ketones such as acetaldehyde, the keto form predominates; whereas in phenol, the enol form predominates. The present application comprises all tautomeric forms of the compound.

The term "stereoisomer" refers to isomers resulting from different spatial arrangements of atoms in a molecule, including cis-trans isomers, enantiomers, and diastereoisomers.

The compound of the present application may have an asymmetric atom such as a carbon atom, a sulfur atom, a nitrogen atom, a phosphorus atom, or an asymmetric double bond, and thus the compound of the present application may exist in the form of a particular geometric isomer or stereoisomer. The form of a particular geometric isomer or stereoisomer may be cis and trans isomers, E and Z geometric isomers, (−)- and (+)-enantiomers, (R)- and (S)-enantiomers, diastereoisomers, (D)-isomers, (L)-isomers, atropisomers, and racemic mixtures or other mixtures thereof, such as an enantiomer or diastereoisomer enriched mixture, and all of the above isomers as well as mixtures thereof are encompassed within the definition scope of the compound of the present application. An additional asymmetric carbon atom, asymmetric sulfur atom, asymmetric nitrogen atom, or asymmetric phosphorus atom may be present in substituents such as alkyl. All of these isomers and mixtures thereof referred to in the substituents are also encompassed within the definition scope of the compound of the present application. The compound with asymmetric atoms disclosed herein can be separated in an optically active pure form or in a racemic form. The optically active pure form can be isolated from a racemic mixture or synthesized by using chiral starting materials or chiral reagents.

The compound of the present application may exist in the form of an atropisomer, which is a stereoisomer that occurs when the rotation of a single bond within the molecule is hindered or greatly slowed. If the rotational barrier around a single bond is sufficiently high and the interconversion between isomers is sufficiently slow, individual isomers may be separated by methods known in the art, for example, crystallization or chiral chromatography. An atropisomer of the compound of the present application may be represented in either the "P" or "M" configuration, or may be labeled in other ways commonly used and well known in the art. For details on atropisomers, see the following reference: Andrew Clark, Introduction to Stereochemistry, 147-148 (2020, first edition).

The term "substituted" means that any one or more hydrogen atoms on a specific atom are substituted with substituents, wherein the substituents may be deuterium and hydrogen variants, as long as the valence of the specific atom is normal and the substituted compound is stable. When the substituent is oxo (namely =O), it means that two hydrogen atoms are substituted, and oxo is not available on an aromatic group.

The term "optional" or "optionally" means that the subsequently described event or circumstance may, but not necessarily, occur. The description includes instances where the event or circumstance occurs and instances where it does not. For example, an ethyl "optionally" substituted with halogen, means that the ethyl may be unsubstituted ($CH_2CH_3$), monosubstituted (e.g., $CH_2CH_2F$, $CH_2CH_2C_1$, or the like), polysubstituted (e.g., $CHFCH_2F$, $CH_2CHF_2$, $CHFCH_2Cl$, $CH_2CHCl_2$, or the like), or fully substituted ($CF_2CF_3$, $CF_2CCl_3$, $CCl_2CCl_3$, or the like). It will be understood by those skilled in the art that for any group comprising one or more substituents, no substitution or substituting pattern that is spatially impossible and/or cannot be synthesized will be introduced.

When any variable (e.g., $R^a$ or $R^b$) occurs more than once in the constitution or structure of a compound, the variable is independently defined in each case. For example, if a group is substituted with 2 $R^b$, the definition of each $R^b$ is independent.

When the number of a linking group is 0, such as $-(CH_2)_0-$, it means that the linking group is a bond.

When one of variables is selected from a chemical bond or is absent, it means that the two groups which it links are linked directly. For example, when L in A-L-Z represents a bond, it means that the structure is actually A-Z.

When the linking direction of the linking group referred to herein is not specified, the linking direction is arbitrary. For example, when $L^1$ in the structural unit

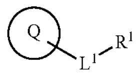

is selected from "$C_1$-$C_3$ alkylene-O", then $L^1$ may link ring Q and $R^1$ in a direction from left to right to constitute "ring Q-$C_1$-$C_3$ alkylene-O—$R^1$", or link ring Q and $R^1$ in a direction from right to left to constitute "ring Q-O—$C_1$-$C_3$ alkylene-$R^1$".

When a bond of a substituent is cross-linked to two atoms on a ring, the substituent can be bonded to any atom on the ring. For example, the structural unit

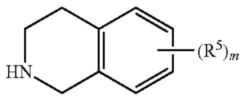

represents that $R^5$ may be substituted at any position on the benzene ring.

$C_m$-$C_n$ used herein means that the portion has an integer number of carbon atoms in the range of m-n. For example, "$C_1$-$C_{10}$" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "alkyl" refers to hydrocarbyl with a general formula of $C_nH_{2n+1}$. The alkyl may be linear or branched. The term "$C_1$-$C_{10}$ alkyl" should be understood to represent a linear or branched saturated hydrocarbyl group having 1, 2, 3, 4, 5, 6, 7, 8, 9, or 10 carbon atoms. Specific examples of the alkyl include, but are not limited to, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl, and the like. The term "$C_1$-$C_6$ alkyl" may be understood to represent an alkyl group having 1-6 carbon atoms. Specific examples include, but are not limited to, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, and the like. The term "$C_1$-$C_3$ alkyl" may be understood to represent a linear or branched saturated alkyl group having 1-3 carbon atoms. The "$C_1$-$C_{10}$ alkyl" may include "$C_1$-$C_6$ alkyl", "$C_1$-$C_3$ alkyl" or the like, and the "$C_1$-$C_6$ alkyl" may further include "$C_1$-$C_3$ alkyl".

The term "alkoxy" refers to a group derived from a linear or branched alcohol by loss of a hydrogen atom from hydroxyl, and may be understood as "alkyloxy" or "alkyl-O—". The term "$C_1$-$C_{10}$ alkoxy" may be understood as "$C_1$-$C_{10}$ alkyloxy" or "$C_1$-$C_{10}$ alkyl-O—"; the term "$C_1$-$C_6$ alkoxy" may be understood as "$C_1$-$C_6$ alkyloxy" or "$C_1$-$C_6$ alkyl-O—". The "$C_1$-$C_{10}$ alkoxy" may include "$C_1$-$C_6$ alkoxy", "$C_1$-$C_3$ alkoxy" or the like, and the "$C_1$-$C_6$ alkoxy" may further include "$C_1$-$C_3$ alkoxy".

The term "alkenyl" refers to a linear or branched unsaturated aliphatic hydrocarbyl group consisting of carbon atoms and hydrogen atoms and having at least one double bond. The term "$C_2$-$C_{10}$ alkenyl" may be understood to represent a linear or branched unsaturated hydrocarbyl group comprising one or more double bonds and having 2, 3, 4, 5, 6, 7, 8, 9, or 10 carbon atoms, and the "$C_2$-$C_{10}$ alkenyl" is preferably "$C_2$-$C_6$ alkenyl", further preferably "$C_2$-$C_4$ alkenyl", and still further preferably "$C_2$-$C_3$ alkenyl". It should be understood that in the case that the alkenyl comprises more than one double bond, the double bonds can be separated from one another or conjugated. The alkenyl includes, but is not limited to, vinyl, allyl, (E)-2-methylvinyl, (Z)-2-methylvinyl, (E)-but-2-enyl, (Z)-but-2-enyl, (E)-but-1-enyl, (Z)-but-1-enyl, isopropenyl, 2-methylprop-2-enyl, 1-methylprop-2-enyl, 2-methylprop-1-enyl, (E)-1-methylprop-1-enyl, and (Z)-1-methylprop-1-enyl.

The term "alkynyl" refers to a linear or branched unsaturated aliphatic hydrocarbyl group consisting of carbon atoms and hydrogen atoms and having at least one triple bond. The term "$C_2$-$C_{10}$alkynyl" may be understood to represent a linear or branched unsaturated hydrocarbyl group comprising one or more triple bonds and having 2, 3, 4, 5, 6, 7, 8, 9, or 10 carbon atoms. Examples of "$C_2$-$C_{10}$ alkynyl" include, but are not limited to, ethynyl (—C≡CH), propynyl (—C≡$CCH_3$ or —$CH_2$C≡CH), but-1-ynyl, but-2-ynyl, and but-3-ynyl. "$C_2$-$C_{10}$ alkynyl" may include "$C_2$-$C_3$ alkynyl", and examples of "$C_2$-$C_3$ alkynyl" include ethynyl (—C≡CH), prop-1-ynyl (—C≡$CCH_3$), and prop-2-ynyl (—$CH_2$C≡CH).

The term "cycloalkyl" refers to a fully saturated carbocyclic group that exists in the form of a monocycle, fused cycle, bridged cycle, spiro cycle, or the like. Unless otherwise specified, the carbon ring is generally a 3-10 membered ring. For example, the term "$C_3$-$C_{10}$ cycloalkyl" refers to a cycloalkyl group having 3, 4, 5, 6, 7, 8, 9, or 10 ring carbon atoms. Specific examples of the cycloalkyl include, but are not limited to, cyclopropyl, cyclobutyl, cyclopentyl, cyclohexyl, cycloheptyl, cyclooctyl, cyclononyl, cyclodecyl, norbornyl (bicyclo[2.2.1]heptyl), bicyclo[2.2.2]octyl, adamantyl, spiro[4.5]decane, and the like. The term "$C_3$-$C_{10}$ cycloalkyl" may include "$C_3$-$C_6$ cycloalkyl", and the term "$C_3$-$C_6$ cycloalkyl" refers to a cycloalkyl group having 3, 4, 5, or 6 ring carbon atoms. Specific examples include, but are not limited to, cyclopropyl, cyclobutyl, cyclopentyl, cyclohexyl, and the like.

The term "cycloalkyloxy" may be understood as "cycloalkyl-O—". Preferably, "$C_3$-$C_{10}$cycloalkyloxy" may include "$C_3$-$C_6$ cycloalkyloxy".

The term "heterocyclyl" refers to a fully saturated or partially saturated monocyclic, fused cyclic, spiro cyclic, or bridged cyclic group, and ring atoms of the group include 1-5 heteroatoms or heteroatom groups (i.e., heteroatom-containing atom groups). The "heteroatom or heteroatom group" includes, but is not limited to, a nitrogen atom (N), an oxygen atom (O), a sulfur atom (S), a phosphorus atom (P), a boron atom (B), —S(═O)$_2$—, —S(═O)—, —P(═O)$_2$—, —P(═O)—, —NH—, —S(═O)(═NH)—, —C(═O)NH—, —NHC(═O)NH—, and the like. The term "3-10 membered heterocyclyl" refers to a heterocyclyl group having a ring atom number of 3, 4, 5, 6, 7, 8, 9, or 10, and ring atoms of the heterocyclyl group include 1-5 heteroatoms or heteroatom groups independently selected from those described above. The "heterocyclyl" is non-aromatic on the whole. The term "3-10 membered heterocyclyl" may comprise 1, 2, or 3 heteroatoms or heteroatom groups. For example, the heteroatom may be selected from a nitrogen atom (N), an oxygen atom (O), a sulfur atom (S), a phosphorus atom (P), and a boron atom (B); the heteroatom group may be selected from —S(═O)$_2$—, —S(═O)—, —P(═O)$_2$—, —P(═O)—, —NH—, —S(═O)(═NH)—, —C(═O)NH—, and —NHC(═O)NH—. The "4-7 membered heterocyclyl" and "5-7 membered heterocyclyl" may each comprise 1, 2, or 3 heteroatoms or heteroatom groups. Preferably, "3-10 membered heterocyclyl" includes the ranges of "4-10 membered heterocyclyl", "4-7 membered heterocyclyl", "5-7 membered heterocyclyl", or the like, wherein examples of 4-membered heterocyclyl include, but are not limited to, azetidinyl and oxetanyl; examples of 5-membered heterocyclyl include, but are not limited to, tetrahydrofuranyl, dioxolyl, pyrrolidinyl, imidazolidinyl, pyrazolidinyl, pyrrolinyl, 4,5-dihydrooxazolyl, and 2,5-dihydro-1H-pyrrolyl; examples of 6-membered heterocyclyl include, but are not limited to, tetrahydropyranyl, piperidyl, morpholinyl, dithianyl, thiomorpholinyl, piperazinyl, trithianyl, tetrahydropyridinyl, and 4H-[1,3,4]thiadiazinyl; and examples of 7-membered heterocyclyl include, but are not limited to, diazepanyl. The heterocyclyl may also be a bicyclic group, wherein specific examples of 5,5-membered bicyclic groups include, but are not limited to, hexahydrocyclopenta[c]pyrrol-2 (1H)-yl; and specific examples of 5,6-membered bicyclic groups include, but are not limited to, hexahydropyrrolo[1,2-a]pyrazin-2 (1H)-yl, 5,6,7,8-tetrahydro-[1,2,4]triazolo[4,3-a]pyrazinyl, and 5,6,7,8-tetrahydroimidazo[1,5-a]pyrazinyl. Optionally, the heterocyclyl may be a benzo-fused ring group of the 4-7 membered heterocyclyl described above. Examples include, but are not limited to, dihydroisoquinolyl and the like. Preferably, "3-10 membered heterocyclyl" may include "4-7 membered heterocyclyl", "5-7 membered heterocyclyl", "5-6 membered heterocyclyl", "4-7 membered heterocycloalkyl", "5-7 membered heterocycloalkyl", "5-6 membered heterocycloalkyl", and the like, and the "4-7 membered heterocyclyl" may further include "5-7 membered heterocyclyl", "5-6 membered heterocyclyl", "5-7 membered heterocycloalkyl", "5-6 membered heterocycloalkyl", and the like. Although some bicyclic heterocyclyl herein comprise, in part, a benzene ring or a heteroaromatic ring, the heterocyclyl is still non-aromatic on the whole.

The term "heterocyclyloxy" may be understood as "heterocyclyl-O—", and the term "3-10 membered heterocyclyloxy" may be understood as "3-10 membered heterocyclyl-O—".

The term "heterocycloalkyl" refers to a fully saturated cyclic group that exists in the form of a monocycle, fused cycle, bridged cycle, spiro cycle, or the like, and ring atoms of the group include 1-5 heteroatoms or heteroatom groups (i.e., heteroatom-containing atom groups). The "heteroatom or heteroatom group" includes, but is not limited to, a nitrogen atom (N), an oxygen atom (O), a sulfur atom (S), a phosphorus atom (P), a boron atom (B), $—S(=O)_2—$, —S(=O)—, —NH—, —S(=O)(=NH)—, —C(=O)NH—, —NHC(=O)NH—, or the like. The term "3-10 membered heterocycloalkyl" may comprise 1, 2, or 3 heteroatoms or heteroatom groups. For example, the heteroatom may be selected from a nitrogen atom (N), an oxygen atom (O), a sulfur atom (S), a phosphorus atom (P), and a boron atom (B); the heteroatom group may be selected from $—S(=O)_2—$, —S(=O)—, $—P(=O)_2—$, —P(=O)—, —NH—, —S(=O)(=NH)—, —C(=O)NH—, and —NHC(=O)NH—. The "4-7 membered heterocycloalkyl" and "5-7 membered heterocycloalkyl" may each comprise 1, 2, or 3 heteroatoms or heteroatom groups. The term "3-10 membered heterocycloalkyl" refers to a heterocycloalkyl group having a ring atom number of 3, 4, 5, 6, 7, 8, 9, or 10, and ring atoms of the heterocycloalkyl group include 1-5 heteroatoms or heteroatom groups independently selected from those described above. Preferably, 3-10 membered heterocycloalkyl includes 4-7 membered heterocycloalkyl, wherein examples of 4-membered heterocycloalkyl include, but are not limited to, azetidinyl, oxetanyl and thietanyl; examples of 5-membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; examples of 6-membered heterocycloalkyl include, but are not limited to, piperidinyl, tetrahydropyranyl, tetrahydrothiapyranyl, morpholinyl, piperazinyl, 1,4-oxathianyl, 1,4-dioxanyl, sulfomorpholinyl, 1,3-dithianyl, and 1,4-dithianyl; and examples of 7-membered heterocycloalkyl include, but are not limited to, azacycloheptanyl, oxacycloheptanyl, and thiocycloheptanyl.

The term "heterocycloalkyloxy" may be understood as "heterocycloalkyl-O—".

The term "heteroaryl" refers to an aromatic cyclic group having an aromatic monocyclic or fused polycyclic system in which at least one ring atom selected from N, O, and S is comprised, while the remaining ring atoms are C. The term "5-10 membered heteroaryl" should be understood as a monovalent aromatic monocyclic or bicyclic ring system which has 5, 6, 7, 8, 9, or 10 ring atoms, in particular 5, 6, 9, or 10 ring atoms, comprises 1-5, preferably 1-3, heteroatoms independently selected from N, O, and S, and may be benzo-fused in each case. In particular, "5-10 membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl and the like and benzo derivatives thereof, such as benzofuranyl, benzothienyl, benzothiazolyl, benzoxazolyl, benzoisoxazolyl, benzimidazolyl, benzotriazolyl, indazolyl, indolyl, isoindolyl, and the like; or pyridinyl, pyridazinyl, pyrimidinyl, pyrazinyl, triazinyl and the like and benzo derivatives thereof, such as quinolyl, quinazolinyl, isoquinolyl, and the like.

The term "5-6 membered heteroaryl" should be understood as a monovalent aromatic ring system which has 5 or 6 ring atoms, and comprises 1-3 heteroatoms independently selected from N, O, and S. In particular, "5-6 membered heteroaryl" is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, and the like.

The term "heteroaryloxy" may be understood as "heteroaryl-O—".

The term "aryl" refers to an aromatic monocyclic or fused polycyclic group of carbon atoms with the conjugated pi-electron system. The term "$C_6$-$C_{10}$ aryl" should be understood to preferably represent an aromatic or partially aromatic monovalent hydrocarbon ring having 6-10 carbon atoms, in particular a ring having 6 carbon atoms ("$C_6$ aryl"), such as phenyl, a ring having 9 carbon atoms ("$C_9$ aryl"), such as indanyl or indenyl, or a ring having 10 carbon atoms ("$C_{10}$ aryl"), such as tetrahydronaphthyl, dihydronaphthyl, or naphthyl.

The term "aryloxy" may be understood as "aryl-O—".

The term "halo-" or "halogen" refers to fluorine, chlorine, bromine and iodine.

The term "preventing" or "prevention" means preventing the occurrence of a disease or a disease state in a mammal, in particular when such mammal is predisposed to the disease state but has not yet been diagnosed as having it.

The term "treating" or "treatment" means administering the compound or formulation described herein to ameliorate or eliminate a disease or one or more symptoms associated with the disease, and includes:

(i) inhibiting a disease or a disease state, i.e., arresting its development; and (i) alleviating a disease or a disease state, i.e., causing its regression.

The term “therapeutically effective amount” refers to an amount of the compound of the present application for (i) treating a specific disease, condition or disorder; (ii) alleviating, ameliorating or eliminating one or more symptoms of a specific disease, condition or disorder, or (iii) delaying onset of one or more symptoms of a specific disease, condition or disorder described herein. The amount of the compound disclosed herein constituting the “therapeutically effective amount” varies dependently on the compound, the disease state and its severity, the administration regimen, and the age of the mammal to be treated, but can be determined routinely by those skilled in the art in accordance with their knowledge and the present disclosure.

The term “pharmaceutically acceptable excipients” refers to those which do not have a significant irritating effect on an organic entity and do not impair the biological activity and properties of the active compound. Suitable excipients are well known to those skilled in the art, such as carbohydrate, wax, water-soluble and/or water-swellable polymers, hydrophilic or hydrophobic materials, gelatin, oil, solvent, water, and the like.

The word “comprise” and variations thereof such as “comprises” or “comprising” should be understood in an open, non-exclusive sense, i.e., “including but not limited to”.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The present application also comprises isotopically-labeled compounds which are identical to those documented herein but have one or more atoms replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine and chlorine, such as $^{2}H$ (i.e., D), $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$, $^{36}Cl$, and the like.

Certain isotopically-labeled compounds disclosed herein (e.g., those labeled with $^{3}H$ and $^{14}C$) can be used to analyze compounds and/or substrate tissue distribution. Tritiated (i.e., $^{3}H$) and carbon-14 (i.e., $^{14}C$) isotopes are particularly preferred for their ease of preparation and detectability. Positron emitting isotopes, such as $^{15}O$, $^{13}N$, $^{11}C$ and $^{18}F$ can be used in positron emission tomography (PET) studies to determine substrate occupancy. Isotopically-labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^{2}H$, D) may provide certain therapeutic advantages (e.g., increased in vivo half-life or reduced dosage) resulting from greater metabolic stability and thus may be preferred in certain circumstances in which deuterium substitution may be partial or complete, wherein partial deuterium substitution refers to substitution of at least one hydrogen with at least one deuterium.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, aerosol, and the like.

Typical routes of administration of the compound or the pharmaceutically acceptable salt thereof or the pharmaceutical composition thereof disclosed herein include, but are not limited to, oral, rectal, local, inhalation, parenteral, sublingual, intravaginal, intranasal, intraocular, intraperitoneal, intramuscular, subcutaneous and intravenous administration.

The pharmaceutical composition disclosed herein can be manufactured by methods well known in the art, such as by conventional mixing, dissolving, granulating, dragee-making, levigating, emulsifying, lyophilizing, and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents, and the like.

The pharmaceutical compositions may also be suitable for parenteral administration, such as sterile solutions, suspensions or lyophilized products in suitable unit dosage forms.

In all of the administration methods of the compound of general formula (I) described herein, the daily dose administered is from 0.01 mg/kg to 100 mg/kg body weight, preferably from 0.05 mg/kg to 50 mg/kg body weight, and more preferably from 0.1 mg/kg to 30 mg/kg body weight, given in individual or separated doses.

The chemical reactions of the specific embodiments disclosed herein are conducted in a suitable solvent that must be suitable for the chemical changes in the present application and the reagents and materials required. In order to obtain the compounds disclosed herein, it is sometimes necessary for those skilled in the art to modify or select a synthesis procedure or a reaction process based on the existing embodiments.

EXAMPLES

The present invention is described in detail below by way of examples, which, however, are not intended to disadvantageously limit the scope of the present application in any way. Although the present application has been described in detail herein and specific embodiments have also been disclosed, it will be apparent to those skilled in the art that various changes and modifications can be made to the specific embodiments without departing from the spirit and scope of the present application. All reagents used are commercially available and can be used without further purification.

Unless otherwise stated, the ratio represented by a mixed solvent is a volume mixing ratio.

Unless otherwise stated, % refers to wt %.

Compounds are named either manually or by ChemDraw® software, and supplier's catalog names are given for commercially available compounds.

The structures of the compounds are determined by nuclear magnetic resonance (NMR) and/or mass spectrometry (MS). NMR shifts are given in $10^{-6}$ (ppm). Solvents for NMR determination are deuterated dimethyl sulfoxide, deuterated chloroform, deuterated methanol or the like, and internal standard is tetramethylsilane (TMS); "$IC_{50}$" refers to the half maximal inhibitory concentration, which is the concentration at which half of the maximal inhibitory effect is achieved.

Description of Terms or Abbreviations

Me: methyl
Et: ethyl
Ph: phenyl
t-Bu: tert-butyl
DMF: N,N-dimethylformamide
LCMS/LC-MS: liquid chromatography-mass spectrometry
DCE: 1,2-dichloroethane
t-BuONO: tert-butyl nitrite
THF: tetrahydrofuran
NBS: N-bromosuccinimide
DPPA: diphenylphosphoryl azide
TEA: triethylamine
toluene: toluene
DCM: dichloromethane
SEMCl: 2-(trimethylsilyl)ethoxymethyl chloride
SEM: 2-(trimethylsilyl)ethoxymethyl
$Pd(dppf)Cl_2$/$PdCl_2(dppf)$: [1,1'-bis(diphenylphosphino)ferrocene]palladium dichloride
dioxane: dioxane
$Pd(dtbpf)Cl_2$: [1,1'-bis(di-tert-butylphosphino)ferrocene] palladium dichloride
DMSO: dimethyl sulfoxide
$Pd_2(dba)_3$: tris(dibenzylideneacetone)dipalladium(0)
XantPhos: 4,5-bis(diphenylphosphino)-9,9-dimethylxanthene
$Pin_2B_2$: bis(pinacolato)diboron
NMP: N-methyl-2-pyrrolidone
TFA: trifluoroacetic acid
LiHMDS: lithium bis(trimethylsilyl)amide
BrettPhos: dicyclohexyl(2,4,6-triisopropyl-3,6-dimethoxy-[1,1-biphenyl]-2-yl)phosphine
BrettPhos Pd G3: methanesulfonato(2-dicyclohexylphosphino-3,6-dimethoxy-2',4',6'-tri-i-propyl-1,1'-biphenyl)-2-(2'-amino-1,1'-biphenyl)palladium(II)
t-AmylOH: tert-amyl alcohol
HATU: 0-(7-azabenzotriazol-1-yl)-N,N,N',N'-tetramethyluronium hexafluorophosphate
DIEA: diisopropylethylamine
xylene: xylene
DBU: 1,8-diazabicyclo[5.4.0]undec-7-ene
ACN: acetonitrile
$CD_3I$: deuterated iodomethane
Methanol: methanol
—OTBS: (tert-butyldimethylsilyl)oxy
MsCl: methanesulfonyl chloride
NCS: N-chlorosuccinimide
EtI: iodoethane
$O(Tf)_2$: trifluoromethanesulfonic anhydride
Lutidine: 2,6-dimethylpyridine
Chloroform: chloroform
$Pd(PPh_3)_4$: tetrakis(triphenylphosphine)palladium
$SOCl_2$: thionyl chloride
LDA: lithium diisopropylamide
Ruphos: 2-dicyclohexylphosphonium-2,6-diisopropoxy-1,1-biphenyl
Ruphos Pd G3: (2-dicyclohexylphosphino-2,6-diisopropoxy-1,1-biphenyl)(2-amino-1,1-biphenyl-2-yl)palladium(II) methanesulfonate
LiHMDS: lithium bis(trimethylsilyl)amide
TMAF: tetramethylammonium fluoride
BTMPO: N,N-bis(2,4,6-trimethoxyphenyl)ethanediamide
acetone: acetone Example 1. 5-(2-chlorophenyl)-7-(trifluoromethyl)-1,5-dihydro-4H-imidazo[4,5-c][1,8]naphthyridin-4-one (Compound 1)

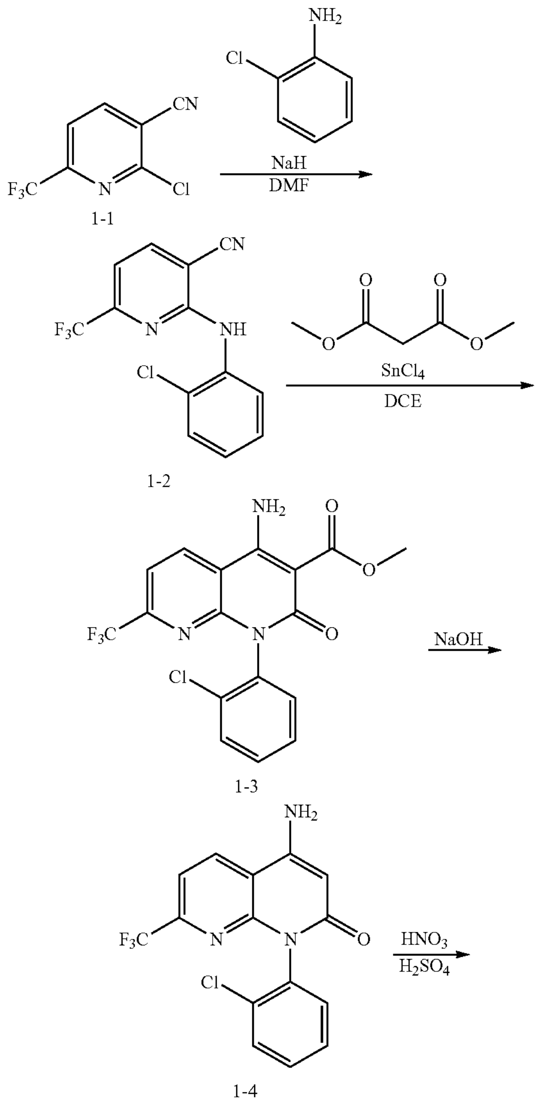

1-1

1-2

1-3

1-4

-continued

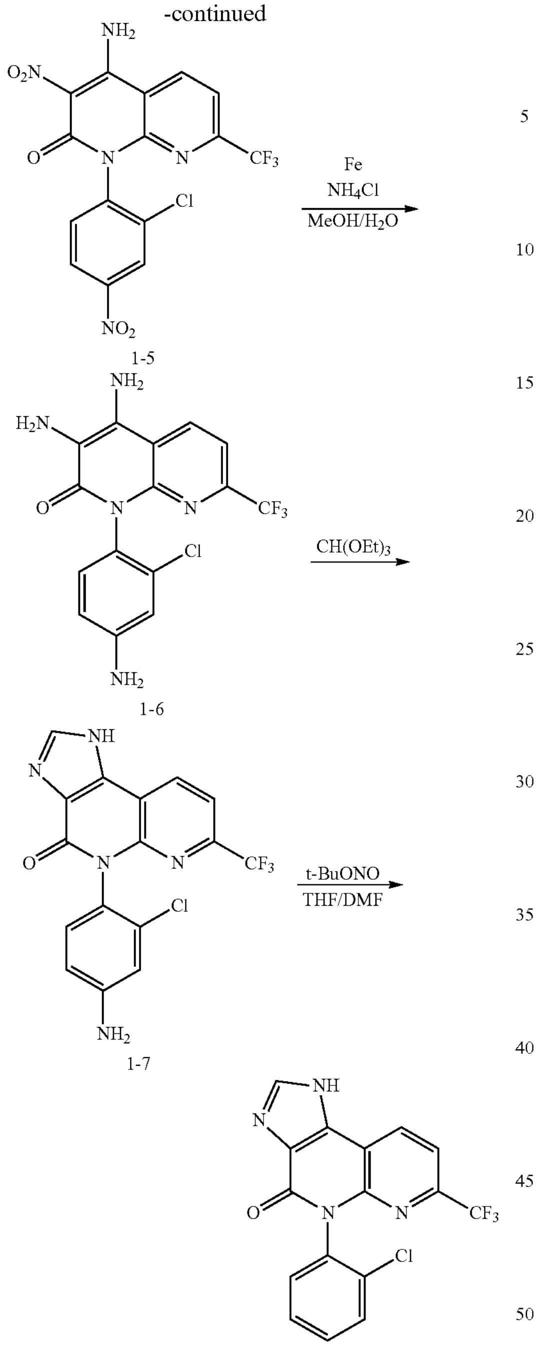

1-5

1-6

1-7

Compound 1

Step 1: synthesis of 2-((2-chlorophenyl)amino)-6-(trifluoromethyl)-3-cyanopyridine (Intermediate 1-2)

o-chloroaniline (7.20 g, 56.46 mmol) was dissolved in DMF (100 mL), and sodium hydride (9.68 g, 242.07 mmol, 60% effective content) was added at 0° C. under nitrogen atmosphere. The mixture was kept at 0° C. for 1 h. A solution of reactant 1-1 (10 g, 48.41 mmol) in DMF (20 mL) was added dropwise to the reaction system at 0° C. and the reaction mixture was stirred for reaction at 25° C. for 16 h. After the reaction was completed as detected by LCMS, the reaction mixture was quenched with 200 mL water at 0° C., then diluted with 200 mL ethyl acetate, and extracted thrice with ethyl acetate (200 mL×3). The organic phase was washed thrice with brine (400 mL×3), dried over anhydrous sodium sulfate, filtered, and concentrated under reduced pressure. The concentrated liquid was separated by column chromatography (ISCO®; 120 g of SepaFlash© flash silica gel column; eluent: 0-2% ethyl acetate/petroleum ether, gradient @ 100 mL/min) to give the title compound (5.16 g).

MS m/z (ESI): 297.9 $[M+H]^+$.

Step 2: synthesis of methyl 4-amino-1-(2-chlorophenyl)-2-oxo-7-(trifluoromethyl)-1,2-dihydro-1,8-naphthyridine-3-carboxylate (intermediate 1-3)

Intermediate 1-2 (5.16 g, 17.34 mmol) and tin tetrachloride (18.06 g, 69.34 mmol) were dissolved in 1,2-dichloroethane (100 mL), dimethyl malonate (6.87 g, 52.01 mmol) was added at 25° C. under nitrogen atmosphere, and the reaction mixture was warmed to 70° C. and stirred for reaction at 70° C. for 16 h. Then additional tin tetrachloride (2.23 g, 8.56 mmol) and dimethyl malonate (1.15 g, 8.70 mmol) were added at 25° C. under nitrogen atmosphere, and the reaction mixture was warmed to 70° C. and stirred for reaction at 70° C. for 4 h. After the reaction was completed as detected by LC-MS, the reaction mixture was quenched with water (150 mL), diluted with ethyl acetate (150 mL), and extracted thrice with ethyl acetate (150 mL×3). The organic phase was dried over anhydrous sodium sulfate, filtered, and concentrated to dryness under reduced pressure. The concentrated liquid was separated by column chromatography (ISCO®; 120 g of SepaFlash® flash silica gel column; eluent: 0-100% ethyl acetate/petroleum ether, gradient @100 mL/min; eluent: 0-20% methanol/ethyl acetate, gradient @ 100 mL/min) to give the title compound (crude product, 11.64 g).

MS m/z (ESI): 389.0 $[M+H]^+$.

Step 3: synthesis of 4-amino-1-(2-chlorophenyl)-7-(trifluoromethyl)-1,8-naphthyridin-2 (1H)-one (intermediate 1-4)

Intermediate 1-3 (11.64 g, 29.27 mmol) was dissolved in methanol (115 mL), and aqueous sodium hydroxide (10 M, 87.80 mL) was added dropwise at 0° C. The temperature of the reaction system was raised to 25° C. and the reaction mixture was stirred for reaction at 25° C. for 16 h. Then the temperature of the reaction system was raised to 50° C. and the reaction mixture was stirred for reaction at 50° C. for 70 h. After the reaction was completed as detected by LC-MS, the reaction mixture was concentrated under reduced pressure to remove methanol. The concentrated liquid was diluted with water (150 mL) and extracted four times with ethyl acetate (200 mL×4). The organic phase was dried over sodium sulfate, filtered, and concentrated to dryness under reduced pressure. The residue was separated by column chromatography (ISCO®; 80 g of SepaFlash® flash silica gel column; eluent: 0-4% methanol/dichloromethane, gradient @ 100 mL/min) to give the title compound (4.5 g).

MS m/z (ESI): 340.1 $[M+H]^+$.

Step 4: synthesis of 4-amino-1-(2-chloro-4-nitrophenyl)-3-nitro-7-(trifluoromethyl)-1,8-naphthyridin-2 (1H)-one (intermediate 1-5)

Intermediate 1-4 (100 mg, 294.38 μmol) was dissolved in sulfuric acid (552.00 mg, 5.63 mmol), fuming nitric acid (92.75 mg, 1.47 mmol) was added at 0° C., and the reaction mixture was stirred for reaction at 25° C. for 0.5 h. The starting material had been consumed completely and a target product was generated as detected by LC-MS. The reaction mixture was slowly poured into water (20 mL) at 0° C., then adjusted to pH=8 with a saturated aqueous sodium bicarbonate solution, and extracted thrice with ethyl acetate. The organic layer was concentrated to dryness under reduced pressure. The title compound (crude product, 135 mg) was given.

MS m/z (ESI): 430.1 $[M+H]^+$.

Step 5: synthesis of 3,4-diamino-1-(4-amino-2-chlorophenyl)-7-(trifluoromethyl)-1,8-naphthyridin-2(1H)-one (intermediate 1-6)

Intermediate 1-5 (110 mg, 256.00 μmol) was dissolved in methanol (4 mL), and iron powder (220.00 mg), ammonium chloride (109.55 mg, 2.05 mmol), and water (1 mL) were added. The reaction mixture was stirred for reaction at 90° C. for 16 h. The starting material had been consumed completely and a target product was generated as detected by LC-MS. The reaction mixture was concentrated under reduced pressure and extracted thrice with ethyl acetate. The organic layer was concentrated to dryness under reduced pressure. The title compound (crude product, 94 mg) was given.

MS m/z (ESI): 370.1 $[M+H]^+$.

Step 6: synthesis of 5-(4-amino-2-chlorophenyl)-7-(trifluoromethyl)-1,5-dihydro-4H-imidazo[4,5-c][1,8]naphthyridin-4-one (intermediate 1-7)

Intermediate 1-6 (90 mg, 243.42 μmol) was dissolved in triethyl orthoformate (2.45 g, 16.56 mmol). The reaction mixture was stirred for reaction at 120° C. for 4 h under nitrogen atmosphere. The starting material had been consumed completely and a target product was generated as detected by LC-MS. The reaction mixture was concentrated under reduced pressure to remove triethyl orthoformate to give the title compound (crude product, 92 mg).

MS m/z (ESI): 379.9 $[M+H]^+$.

Step 7: synthesis of 5-(2-chlorophenyl)-7-(trifluoromethyl)-1,5-dihydro-4H-imidazo[4,5-c][1,8]naphthyridin-4-one (Compound 1)

Intermediate 1-7 (90 mg, 237.01 μmol) was dissolved in tetrahydrofuran (5 mL) and DMF (0.5 mL), and tert-butyl nitrite (36.66 mg, 355.52 μmol) was added at 25° C. The reaction mixture was stirred for reaction at 70° C. for 1 h. The starting material had been consumed completely and a target product was generated as detected by LC-MS. The reaction mixture was concentrated under reduced pressure to remove tetrahydrofuran, and the residue was purified by high performance liquid chromatography ((column: YMC Triart C18 150×30 mm×5 μm; mobile phase: [A: 0.05% ammonia water (v/v), B: acetonitrile]; B %: 30%-50%, 11 min)) to give the title compound (7.2 mg).

$^1H$ NMR (400 MHz, DMSO-$d_6$) δ=14.17 (s, 1H), 8.79 (d, J=7.8 Hz, 1H), 8.51 (s, 1H), 7.87 (d, J=7.8 Hz, 1H), 7.75-7.67 (m, 1H), 7.59-7.50 (m, 3H);

MS m/z (ESI): 365.0 $[M+H]^+$.

Example 2. 5-(2-chlorophenyl)-1-methyl-7-(trifluoromethyl)-1,5-dihydro-4H-imidazo[4,5-c][1,8]naphthyridin-4-one (Compound 2)

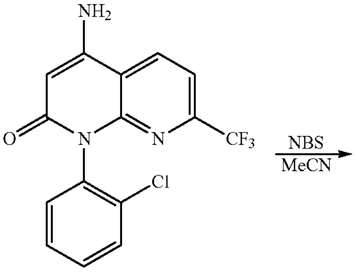

1-4

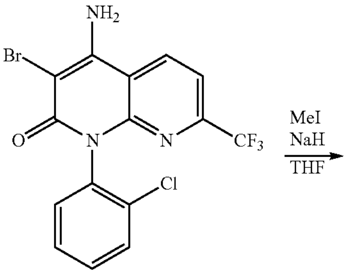

2-1

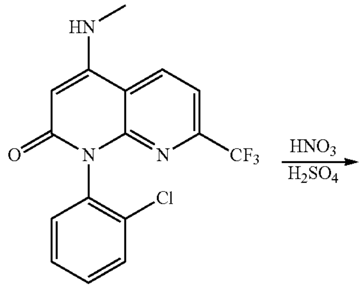

2-2

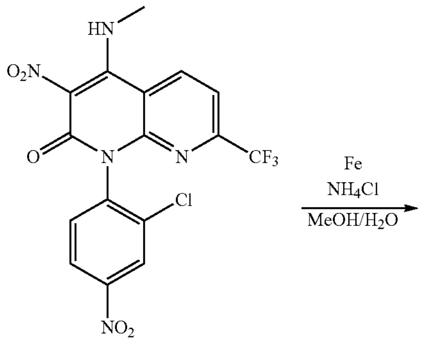

2-3

-continued

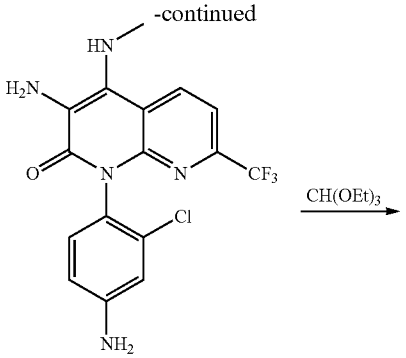

2-4

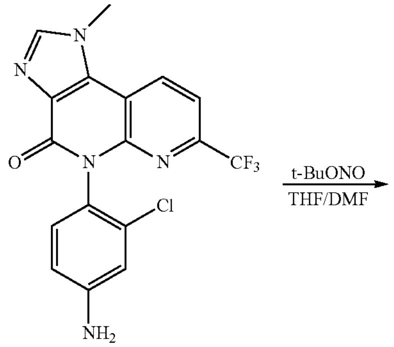

2-5

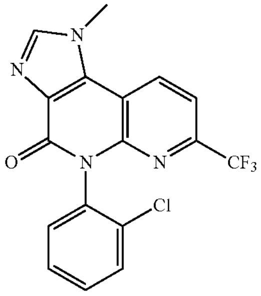

Compound 2

Step 1: synthesis of 4-amino-3-bromo-1-(2-chloro-phenyl)-7-(trifluoromethyl)-1,8-naphthyridin-2 (1H)-one (intermediate 2-1)

Intermediate 1-4 (400 mg, 1.18 mmol) was dissolved in acetonitrile (8 mL), N-bromosuccinimide (209.58 mg, 1.18 mmol) was added at 25° C., and the reaction mixture was stirred for reaction at 25° C. for 0.1 h. The starting material had been consumed completely and a target product was generated as detected by LC-MS. The reaction mixture was concentrated to dryness under reduced pressure, and the residue was purified by column chromatography (silica, petroleum ether/ethyl acetate=48%-100%) to give the title compound (488.0 mg).

MS m/z (ESI): 420.1 $[M+H]^+$.

Step 2: synthesis of 1-(2-chlorophenyl)-4-(methyl-amino)-7-(trifluoromethyl)-1,8-naphthyridin-2 (1H)-one (intermediate 2-2)

Intermediate 2-1 (488.0 mg, 1.17 mmol) was dissolved in THF (10 mL), and sodium hydride (93.59 mg, 2.34 mmol, 60% effective content) was added at 0° C. under nitrogen atmosphere. The mixture was reacted at 0° C. for 0.5 h. Iodomethane (166.07 mg, 1.17 mmol) was added at 0° C., and the reaction mixture was stirred for reaction at 20° C. for 16 h. The starting material had been consumed completely and a target product was generated as detected by LC-MS. The reaction mixture was quenched with water (10 mL) at 0° C. and extracted thrice with ethyl acetate. The organic phase was dried over anhydrous sodium sulfate, filtered, and concentrated to dryness under reduced pressure, and the residue was purified by column chromatography (column: ISCO®; 12 g of SepaFlash©; mobile phase: ethyl acetate/petroleum ether; ethyl acetate %: 0-74%) to give the title compound (109 mg).

MS m/z (ESI): 353.9 $[M+H]^+$.

Step 3: synthesis of 1-(2-chloro-4-nitrophenyl)-4-(methylamino)-3-nitro-7-(trifluoromethyl)-1,8-naphthyridin-2 (1H)-one (intermediate 2-3)

Intermediate 2-2 (109 mg, 308.15 μmol) was dissolved in sulfuric acid (0.3 mL), nitric acid (38.83 mg, 616.30 μmol) was added dropwise at 0° C., and the mixture was reacted at 0° C. for 1 h. The starting material had been consumed completely and a target product was generated as detected by LC-MS. The reaction mixture was diluted with water (50 mL) at 0° C., adjusted to pH=8 with a saturated aqueous sodium carbonate solution, and extracted thrice with ethyl acetate. The organic phase was dried over anhydrous sodium sulfate, filtered, and concentrated to dryness under reduced pressure to give the title compound (129 mg).

MS m/z (ESI): 444.0 $[M+H]^+$.

Step 4: synthesis of 3-amino-1-(4-amino-2-chloro-phenyl)-4-(methylamino)-7-(trifluoromethyl)-1,8-naphthyridin-2 (1H)-one (intermediate 2-4)

Intermediate 2-3 (129 mg, 290.72 μmol) was dissolved in methanol (2 mL), iron powder (243.53 mg, 4.36 mmol), ammonium chloride (124.41 mg, 2.33 mmol), and water (0.5 mL) were added at 25° C., and the reaction mixture was reacted at 90° C. for 16 h. The starting material had been consumed completely and a target product was generated as detected by LC-MS. The reaction mixture was filtered and concentrated under reduced pressure to remove methanol. The mixture was extracted thrice with ethyl acetate. The organic phase was dried over anhydrous sodium sulfate, filtered, and concentrated to dryness under reduced pressure to give the title compound (97 mg).

MS m/z (ESI): 384.0 $[M+H]^+$.

Step 5: synthesis of 5-(4-amino-2-chlorophenyl)-1-methyl-7-(trifluoromethyl)-1,5-dihydro-4H-imidazo [4,5-c][1,8]naphthyridin-4-one (intermediate 2-5)

Intermediate 2-4 (97 mg, 252.77 μmol) was dissolved in triethyl orthoformate (864.27 mg, 5.83 mmol, 970.00 μL), and the reaction mixture was reacted at 120° C. for 4 h. The starting material had been consumed completely and a target product was generated as detected by LC-MS. The reaction mixture was concentrated to dryness under reduced pressure to give the title compound (110 mg).

MS m/z (ESI): 393.9 $[M+H]^+$.

Step 6: synthesis of 5-(2-chlorophenyl)-1-methyl-7-(trifluoromethyl)-1,5-dihydro-4H-imidazo[4,5-c][1,8]naphthyridin-4-one (Compound 2)

Intermediate 2-5 (110 mg, 279.37 μmol) was dissolved in tetrahydrofuran (2 mL), tert-butyl nitrite (129.64 mg, 1.26 mmol) and N,N-Dimethylformamide (DMF) (2.04 mg, 27.94 μmol) were added at 25° C., and the reaction mixture was reacted at 70° C. for 1 h. The starting material had been consumed completely and a target product was generated as detected by LC-MS. The reaction mixture was concentrated to dryness under reduced pressure, and the residue was purified by high performance liquid chromatography (column: YMC-Actus Triart C18 150x30 mmx5 μm; mobile phase: [A: water (containing 0.05% ammonia water v/v), B: acetonitrile]; B %: 38%-58%, 11 min) to give the title compound (3.1 mg).

$^1$H NMR (400 MHz, METHANOL-$d_4$) δ 8.90 (d, J=8.1 Hz, 1H), 8.35-8.19 (m, 1H), 7.79 (d, J=8.2 Hz, 1H), 7.71-7.63 (m, 1H), 7.60-7.50 (m, 2H), 7.48-7.41 (m, 1H), 4.35 (s, 3H);

MS m/z (ESI): 379.0 [M+H]$^+$.

Example 3. 5-(2-chlorophenyl)-3-methyl-7-(trifluoromethyl)-3,5-dihydro-4H-imidazo[4,5-c][1,8]naphthyridin-4-one (Compound 3)

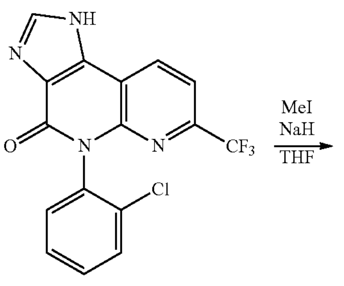

Compound 1

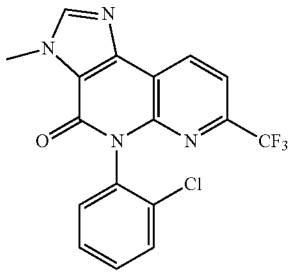

Compound 3

Compound 1 (117 mg, 320.80 μmol) was dissolved in N,N-dimethylformamide (1.5 mL), sodium hydride (25.66 mg, 641.61 μmol, 60% effective content) was added at 0° C., and the reaction mixture was reacted at 0° C. for 0.1 h. Iodomethane (45.53 mg, 320.80 μmol) was added dropwise to the reaction system at 0° C., and the reaction mixture was reacted at 0° C. for 0.9 h. A target product was generated as detected by LC-MS. The reaction mixture was quenched with water, diluted with methanol (1.5 mL), and purified by high performance liquid chromatography ((column: YMC-Actus Triart C18 150x30 mmx5 μm; mobile phase: [A: water (0.05% ammonia water v/v), B: acetonitrile]; B %: 40%-60%, 11 min)) to give the title compound (5.2 mg).

$^1$H NMR (400 MHz, Methanol-$d_4$) δ 8.81 (d, J=8.0 Hz, 1H), 8.36 (s, 1H), 7.78 (d, J=8.0 Hz, 1H), 7.71-7.65 (m, 1H), 7.60-7.51 (m, 2H), 7.50-7.44 (m, 1H), 4.20 (s, 3H);

MS m/z (ESI): 379.0 [M+H]$^+$.

Example 4. 5-(2-chlorophenyl)-7-(trifluoromethyl)-3,5-dihydro-1H-imidazo[4,5-c][1,8]naphthyridine-2,4-dione (Compound 4)

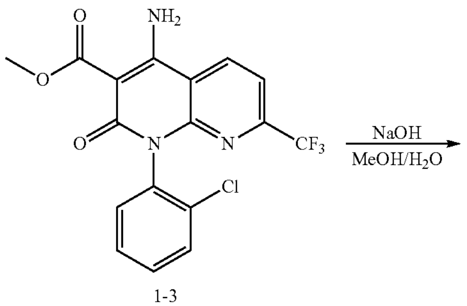

1-3

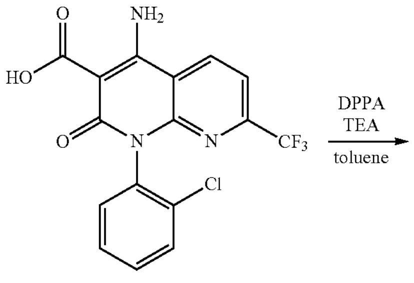

4-1

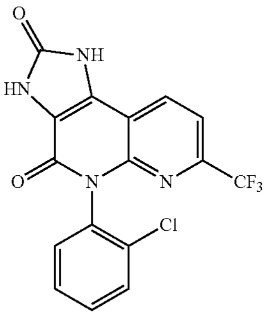

Compound 4

Step 1: Synthesis of Intermediate 4-1

Intermediate 1-3 (1 g, 2.51 mmol) was dissolved in methanol, aqueous sodium hydroxide (10 M) was added, and the reaction mixture was stirred for reaction at 25° C. for 16 h. The starting material had been consumed completely and a target product was generated as detected by LC-MS. Hydrochloric acid (6 M) was added to the reaction mixture to adjust the pH to 7, and the reaction mixture was extracted thrice with ethyl acetate. The organic layer was concentrated to dryness under reduced pressure to give the title compound (crude product, 590 mg).

MS m/z (ESI): 384.0[M+H]$^+$.

Step 2: synthesis of 5-(2-chlorophenyl)-7-(trifluoromethyl)-3,5-dihydro-1H-imidazo[4,5-c][1,8]naphthyridine-2,4-dione (Compound 4)

Intermediate 4-1 (50 mg, 130.31 μmol) was dissolved in toluene, triethylamine (19.78 mg, 195.46 μmol) and diphenylphosphoryl azide (39.45 mg, 143.34 μmol) were added, and the reaction mixture was stirred for reaction at 100° C.

for 16 h. The starting material had been consumed completely and a target product was generated as detected by LC-MS. The organic layer was concentrated to dryness under reduced pressure, and the residue was purified by column chromatography (silica, petroleum ether:(ethyl acetate/ethanol=3/1)=1:1), and then purified by high performance liquid chromatography (column: YMC-Actus Triart C18 150×30 mm×5 μm; mobile phase: [A: water (0.05% ammonia water v/v), B: acetonitrile]; B %: 20%-40%, 11 min) to give the title compound (3.4 mg).

MS m/z (ESI): 381.1[M+H]$^+$.

$^1$H NMR (400 MHz, Methanol-d$_4$) δ 8.48 (d, J=8.5 Hz, 1H), 7.76 (d, J=8.0 Hz, 1H), 7.67 (d, J=9.3 Hz, 1H), 7.58-7.51 (m, 2H), 7.47-7.41 (m, 1H).

Example 5. 5-(2-chlorophenyl)-2-methoxy-7-(trifluoromethyl)-1,5-dihydro-4H-imidazo[4,5-c][1,8]naphthyridin-4-one (Compound 5)

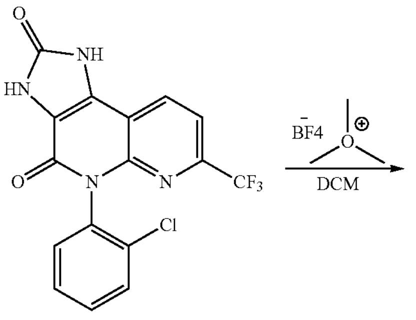

Compound 4

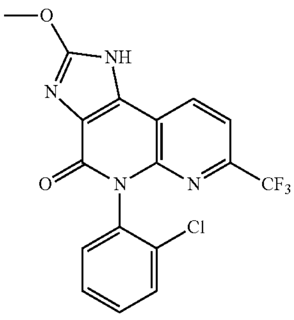

Compound 5

Compound 4 (60 mg, 157.60 μmol) was dissolved in dichloromethane, trimethyloxonium tetrafluoroborate (46.62 mg, 315.20 μmol) was added, and the reaction mixture was stirred for reaction at 40° C. for 16 h. The starting material had been consumed completely and a target product was generated as detected by LC-MS. The organic layer was concentrated to dryness under reduced pressure and purified by high performance liquid chromatography (column: Waters Xbridge BEH C18 100×25 mm×5 μm; mobile phase: [A: water (0.225% formic acid v/v), B: acetonitrile]; B %: 25%-55%, 12 min) to give the title compound (3.7 mg).

MS m/z (ESI): 395.0 [M+H]$^+$.

$^1$H NMR (400 MHz, DMSO-d$_6$) δ13.48 (s, 1H), 8.67 (d, J=8.6 Hz, 1H), 7.81 (d, J=9.1 Hz, 1H), 7.70 (d, J=5.1 Hz, 1H), 7.56-7.52 (m, 3H), 4.18 (s, 3H).

Example 6. 5-(2-chlorophenyl)-7-(trifluoromethyl)-3,5-dihydro-4H-pyrazolo[3,4-c][1,8]naphthyridin-4-one (Compound 6)

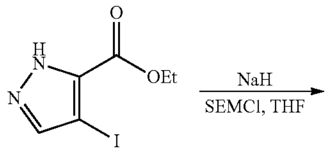

6-1

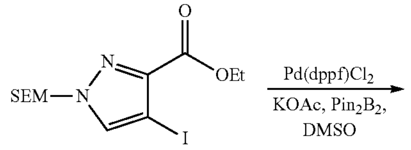

6-2

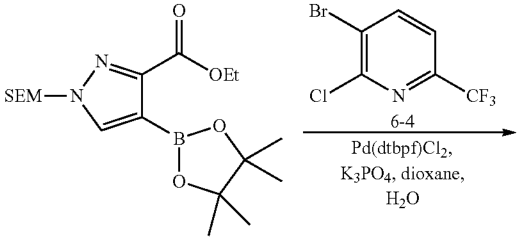

6-3

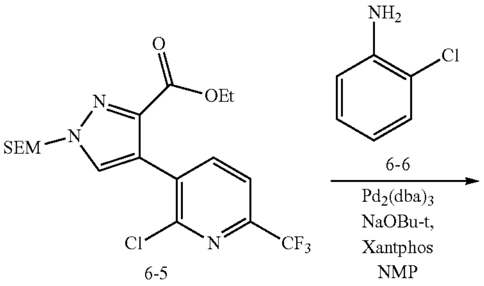

6-5

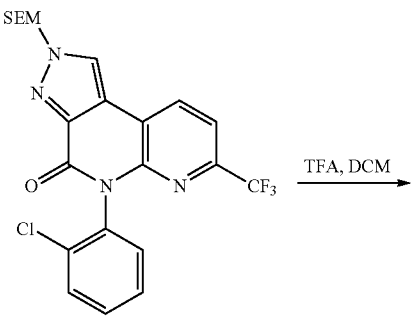

6-7

-continued

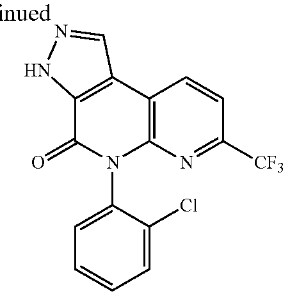

Compound 6

Step 1: synthesis of ethyl 4-iodo-1-((2-(trimethylsilyl)ethoxy)methyl)-1H-pyrazole-3-carboxylate (intermediate 6-2)

Intermediate 6-1 (1 g, 3.75 mmol) was dissolved in THF (15 mL), and sodium hydride (300 mg, 7.51 mmol, 60% effective content) was added after the reaction mixture was cooled to 0° C. The reaction mixture was stirred at 25° C. for 0.5 h, and 2-(trimethylsilyl)ethoxymethyl chloride (936 mg, 5.63 mmol) was added to the reaction mixture under an ice-water bath. The reaction mixture was stirred at 25° C. for 15 h under nitrogen atmosphere. The reaction was completed as detected by LC-MS. After the reaction was cooled to room temperature, the mixture was slowly quenched with ice water (10 mL) and then extracted with ethyl acetate (30 mL×3). The combined organic phases were washed with brine (50 mL×3), dried over anhydrous $Na_2SO_4$, filtered, concentrated under reduced pressure, and purified by preparative thin-layer chromatography (silica, petroleum ether: ethyl acetate=10:3) to give the title compound (700 mg).

MS m/z (ESI): 397 $[M+H]^+$.

Step 2: synthesis of ethyl 4-(4,4,5,5-tetramethyl-1,3,2-dioxaborane-2-yl)-1-((2-(trimethylsilyl)ethoxy)methyl)-1H-pyrazole-3-carboxylate (intermediate 6-3)

Intermediate 6-2 (700 mg, 1.76 mmol) and bis(pinacolato) diboron (897 mg, 3.53 mmol) were dissolved in anhydrous dimethyl sulfoxide (10 mL), potassium acetate (345 mg, 3.53 mmol) and [1,1'-bis(diphenylphosphino)ferrocene]palladium dichloride ($Pd(dppf)Cl_2$) (128 mg, 0.17 mmol) were added thereto, and the reaction mixture was stirred at 100° C. for 15 h under nitrogen atmosphere.

The reaction was completed as detected by LC-MS. After the reaction was cooled to room temperature, water (20 mL) and ethyl acetate (40 mL) were added sequentially. The organic phase was washed with water (30 mL×2), and the washed organic phase was dried over an appropriate amount of anhydrous sodium sulfate. The organic phase was purified by preparative thin-layer chromatography (silica, dichloromethane:methanol=10:1) to give the title compound (500 mg).

MS m/z (ESI): 397 $[M+H]^+$.

Step 3: synthesis of ethyl 4-(2-chloro-6-(trifluoromethyl)pyridin-3-yl)-1-((2-(trimethylsilyl)ethoxy)methyl)-1H-pyrazole-3-carboxylate (intermediate 6-5)

Intermediate 6-3 (500 mg, 1.25 mmol) and intermediate 6-4 (489 mg, 1.88 mmol) were dissolved in dioxane (6 mL) and water (2 mL), potassium phosphate (534 mg, 2.51 mmol) and $Pd(dtbpf)Cl_2$ (81.98 mg, 0.12 mmol) were added thereto, and the reaction mixture was stirred at 100° C. for 16 h under nitrogen atmosphere. The reaction was completed as detected by LC-MS. After the reaction was cooled to room temperature, water (30 mL) and ethyl acetate (40 mL) were added sequentially. The organic phase was washed with water (30 mL×2), and the washed organic phase was dried over an appropriate amount of anhydrous sodium sulfate. The organic phase was purified by preparative thin-layer chromatography (silica, dichloromethane: methanol=5:1) to give the title compound (300 mg).

MS m/z (ESI): 450 $[M+H]^+$.

Step 4: synthesis of 5-(2-chlorophenyl)-7-(trifluoromethyl)-2-((2-(trimethylsilyl)ethoxy)methyl)-2,5-dihydro-4H-pyrazolo[3,4-c][1,8]naphthyridin-4-one (Intermediate 6-7)

Intermediate 6-5 (150 mg, 0.33 mmol) and intermediate 6-6 (85 mg, 0.66 mmol) were dissolved in N-methyl-2-pyrrolidone (4 mL), sodium tert-butoxide (63.56 mg, 0.64 mmol), 4,5-bis(diphenylphosphino)-9,9-dimethylxanthene (XantPhos) (20 mg, 0.03 mmol), and tris(dibenzylideneacetone)dipalladium(0) ($Pd_2(dba)_3$) (30.51 mg, 33.33 μmol) were added thereto, and the reaction mixture was stirred at 100° C. for 15 h under nitrogen atmosphere. The reaction was completed as detected by LC-MS. After the reaction was cooled to room temperature, water (15 mL) and ethyl acetate (20 mL) were added sequentially. The organic phase was washed with water (30 mL×2), and the washed organic phase was dried over an appropriate amount of anhydrous sodium sulfate. The organic phase was concentrated under reduced pressure to give the title compound (crude product, 160 mg).

MS m/z (ESI): 495 $[M+H]^+$.

Step 5: synthesis of 5-(2-chlorophenyl)-7-(trifluoromethyl)-3,5-dihydro-4H-pyrazolo[3,4-c][1,8]naphthyridin-4-one (Compound 6)

Intermediate 6-7 (160 mg) was dissolved in dichloromethane (3 mL). Trifluoroacetic acid (1.5 mL) was added thereto, and the reaction mixture was stirred at 25° C. for 0.5 h. After the reaction was completed as detected by TLC, saturated aqueous sodium bicarbonate (20 mL) was added to adjust the pH to 8. The mixture was extracted with dichloromethane (20 mL×3). The organic phase was washed with water (30 mL×2), and the washed organic phase was dried over an appropriate amount of anhydrous sodium sulfate, concentrated to dryness under reduced pressure, and purified by preparative high performance liquid chromatography (column: Gemini NX C18 5 μm×10×150 mm; mobile phase: A: 0.05% TFA v/v, B: acetonitrile; B %:40%-45%, 12 min) to give the title compound (2.3 mg).

MS m/z (ESI): 365 $[M+H]^+$.

$^1H$ NMR (400 MHz, DMSO-$d_6$) δ 14.70 (s, 1H), 8.86 (s, 1H), 8.80 (d, J=7.9 Hz, 1H), 7.85 (d, J=8.0 Hz, 1H), 7.79-7.67 (m, 1H), 7.59-7.51 (m, 3H).

Example 7. 5-(2-chlorophenyl)-7-(trifluoromethyl)-1,5-dihydro-4H-pyrazolo[4,3-c][1,8]naphthyridin-4-one (Compound 7)

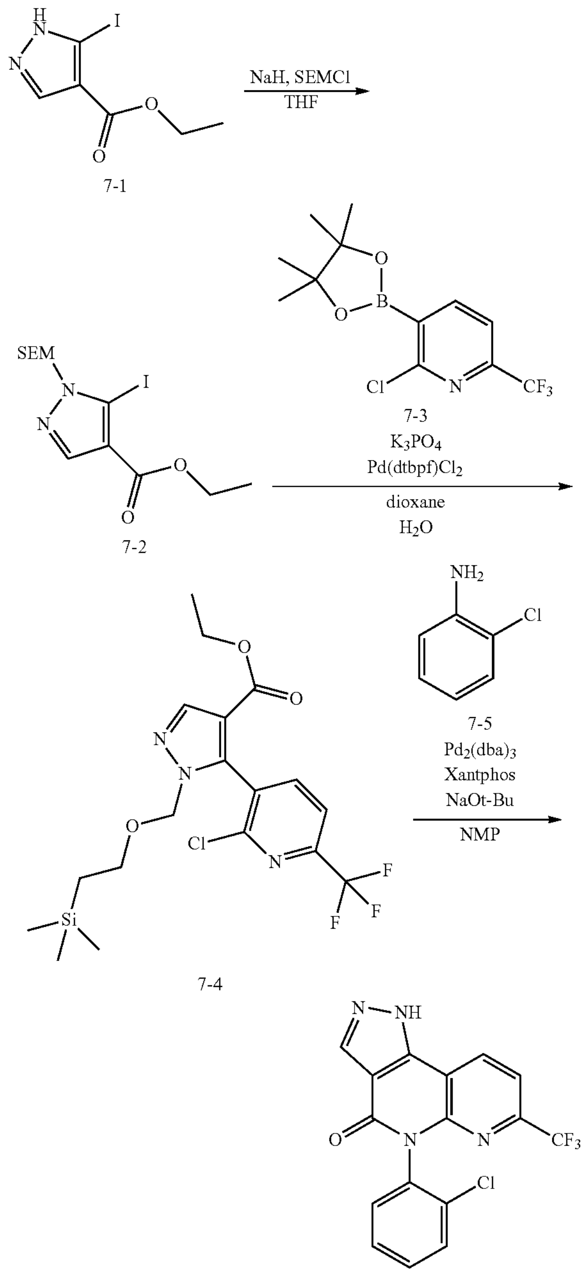

7-1

7-3

7-2

7-5

7-4

Compound 7

Step 1: synthesis of ethyl 5-iodo-1-((2-(trimethylsilyl)ethoxy)methyl)-1H-pyrazole-4-carboxylate (intermediate 7-2)

Intermediate 7-1 (4.0 g, 15.04 mmol) was dissolved in a tetrahydrofuran solution (40 mL), sodium hydride (60% effective content) (820 mg, 20.5 mmol) was added at 0-5° C., and the reaction mixture was stirred at 5° C. for 0.5 h. 2-(trimethylsilyl)ethoxymethyl chloride (SEMCl) (4.56 g, 26.34 mmol) was added to the reaction mixture, and the reaction mixture was stirred at room temperature for 12 h after the addition. After the reaction was completed as detected by LC-MS, the reaction mixture was slowly poured into a saturated aqueous ammonium chloride solution (50 mL). The mixture was extracted with ethyl acetate (60 mL×2). The organic phases were combined and washed with saturated brine (100 mL), and the washed organic phase was dried over an appropriate amount of anhydrous sodium sulfate. After the organic phase was filtered, the organic phase was concentrated to dryness under reduced pressure, and the residue was purified by preparative thin-layer chromatography (silica, petroleum ether:ethyl acetate=10:1) to give the title compound (2.7 g).

MS m/z (ESI): 397.0 $[M+H]^+$.

Step 2: synthesis of ethyl 5-(2-chloro-6-(trifluoromethyl)pyridin-3-yl)-1-((2-(trimethylsilyl)ethoxy)methyl)-1H-pyrazole-4-carboxylate (intermediate 7-4)

Intermediate 7-2 (1.4 g, 4.55 mmol) and intermediate 7-3 (2.17 g, 5.46 mmol) were dissolved in anhydrous dioxane (15 mL), water (4 mL), potassium phosphate (1.93 g, 9.11 mmol) and $Pd(dtbpf)Cl_2$ (297 mg, 0.46 mmol) were added thereto, and the reaction mixture was stirred at 80° C. for 2 h under nitrogen atmosphere. The reaction was completed as detected by LC-MS. After the reaction was cooled to room temperature, water (15 mL) and ethyl acetate (15 mL) were added sequentially. The organic phase was washed with water (15 mL×2), and the washed organic phase was dried over an appropriate amount of anhydrous sodium sulfate. After the organic phase was filtered, the organic phase was concentrated to dryness under reduced pressure, and the residue was purified by preparative thin-layer chromatography (silica, petroleum ether:ethyl acetate=10:1) to give the title compound (800 mg).

MS m/z (ESI): 450.0 $[M+H]^+$.

Step 3: synthesis of 5-(2-chlorophenyl)-7-(trifluoromethyl)-1,5-dihydro-4H-pyrazolo[4,3-c][1,8]naphthyridin-4-one (Compound 7)

Intermediate 7-4 (250.0 mg, 0.56 mmol) was dissolved in an N-methyl-2-pyrrolidone solution (3 mL), intermediate 7-5 (141.8 mg, 1.11 mmol), sodium tert-butoxide (106.8 mg, 1.11 mmol), 4,5-bis(diphenylphosphino)-9,9-dimethylxanthene (XantPhos) (64.3 mg, 0.11 mmol), and $Pd_2(dba)_3$ (50.9 mg, 0.06 mmol) were added, and the reaction mixture was stirred at 100° C. for 12 h under nitrogen atmosphere. After the reaction was completed as detected by LC-MS, the reaction mixture was filtered, concentrated to dryness under reduced pressure, and purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 55%-80%, 13 min] to give the title compound (2 mg).

MS m/z (ESI): 365.0 $[M+H]^+$.

$^1H$ NMR (400 MHz, Methanol-$d_4$) δ 8.79 (d, J=7.7 Hz, 1H), 8.59 (s, 1H), 7.74 (d, J=8.0 Hz, 1H), 7.65-7.63 (m, 1H), 7.54-7. 49 (m, 2H), 7.44-7.41 (m, 1H).

Example 8. 5-(2-chlorophenyl)-7-(trifluoromethyl) oxazolo[4,5-c][1,8]naphthyridin-4 (5H)-one (Compound 8)

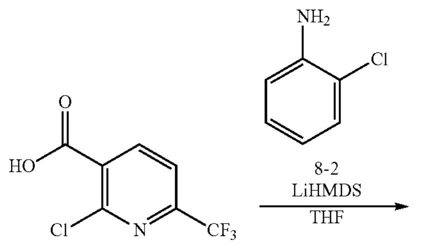

8-1

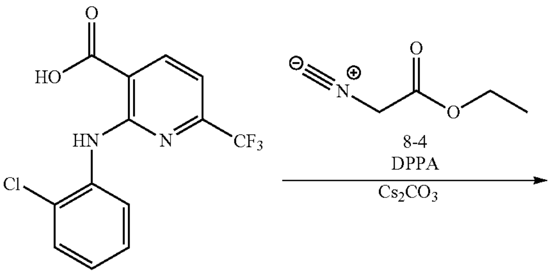

8-3

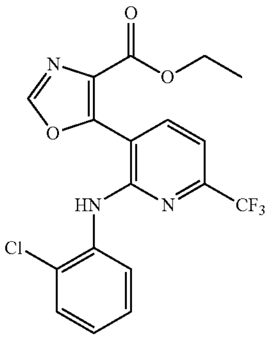

8-5

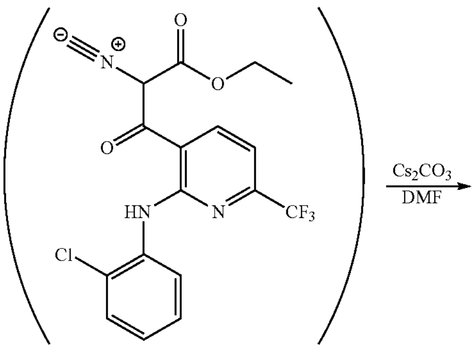

-continued

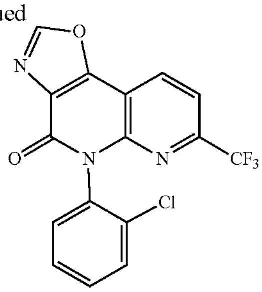

Compound 8

Step 1: synthesis of 2-((2-chlorophenyl)amino)-6-(trifluoromethyl)pyridine-3-formic acid (Intermediate 8-3)

Intermediate 8-1 (1.0 g, 4.5 mmol) was dissolved in anhydrous tetrahydrofuran (10 mL), and a solution of lithium bis(trimethylsilyl)amide (LiHMDS) in THF (1 M, 9.76 mL, 9.76 mmol) was added dropwise thereto at −78° C. The mixture was reacted at −78° C. for 1 h, and intermediate 8-2 (840.66 mg, 5.3 mmol) was added to the reaction mixture. The reaction system was warmed to room temperature and reacted for 3 h. Saturated ammonium chloride (10 mL) and ethyl acetate (10 mL×3) were added sequentially to the reaction mixture. The organic phase was washed with water (10 mL×2), and the washed organic phase was dried over an appropriate amount of anhydrous sodium sulfate and concentrated. The organic phase was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (400 mg).

MS m/z (ESI): 317.1 $[M+H]^+$.

Step 2: synthesis of ethyl 5-(2-((2-chlorophenyl) amino)-6-(trifluoromethyl)pyridin-3-yl)oxazole-4-carboxylate (intermediate 8-5)

Intermediate 8-3 (200 mg, 631.59 μmol) and cesium carbonate (412 mg, 1.26 mmol) were dissolved in N,N-dimethylformamide (4 mL), diphenylphosphoryl azide (DPPA) (347.63 mg, 1.26 mmol) was added thereto at 0° C., and the mixture was reacted at room temperature for 1 h after the addition. Intermediate 8-4 (71.4 mg, 631.59 μmol) was added at 0° C., and the reaction mixture was stirred at 25° C. for 2 h after the addition. Water (5 mL) and ethyl acetate (5 mL×3) were added sequentially to the reaction mixture. After liquid separation, the organic phase was washed with saturated brine (5 mL×2), and the washed organic phase was dried over an appropriate amount of anhydrous sodium sulfate and purified by preparative thin-layer chromatography (silica, petroleum ether:ethyl acetate=100:0-50:50) to give the title compound (90 mg).

MS m/z (ESI): 411.9 $[M+H]^+$.

Step 3: synthesis of 5-(2-chlorophenyl)-7-(trifluoromethyl)oxazolo[4,5-c][1,8]naphthyridin-4 (5H)-one (Compound 8)

Intermediate 8-5 (80 mg, 194.29 μmol) and cesium carbonate (190 mg, 582.86 μmol) were dissolved in N,N-dimethylformamide (1 mL), and the mixture was reacted at 60° C. for 3 h. The reaction mixture was filtered and purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (30 mg).

MS m/z (ESI): 366.1 $[M+H]^+$.

$^1H$ NMR (400 MHz, DMSO-$d_6$) δ 9.15 (s, 1H), 8.84 (d, J=8.0 Hz, 1H), 7.96 (d, J=8.1 Hz, 1H), 7.78-7.70 (m, 1H), 7.62-7.55 (m, 3H).

Example 9. 5-(2-chlorophenyl)-2,7-bis(trifluoromethyl)-1,5-dihydro-4H-imidazo[4,5-c][1,8]naphthyridin-4-one (Compound 9)

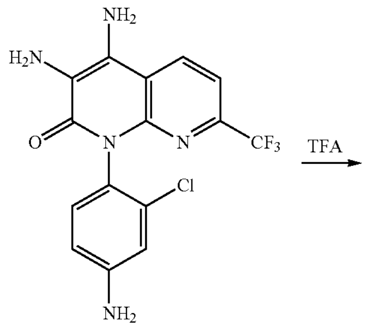

1-6

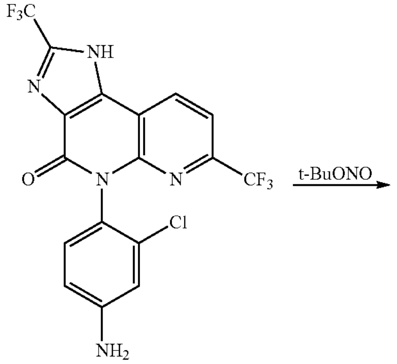

9-1

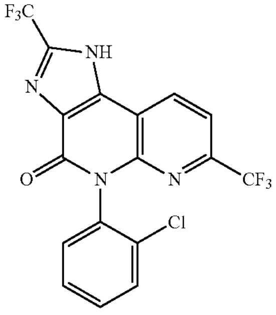

Compound 9

Step 1: synthesis of 5-(4-amino-2-chlorophenyl)-2,7-bis(trifluoromethyl)-1,5-dihydro-4H-imidazo[4,5-c][1,8]naphthyridin-4-one (intermediate 9-1)

Intermediate 1-6 (58 mg, 156.87 μmol) was added to trifluoroacetic acid, and the reaction mixture was stirred for reaction at 70° C. for 16 h. A target product was generated as detected by LCMS. The reaction mixture was concentrated to dryness under reduced pressure to give the title compound (60 mg).

MS m/z (ESI): 448.0 $[M+H]^+$.

Step 2: synthesis of 5-(2-chlorophenyl)-2,7-bis(trifluoromethyl)-1,5-dihydro-4H-imidazo[4,5-c][1,8]naphthyridin-4-one (Compound 9)

Intermediate 9-1 (60 mg, 134.01 μmol) was dissolved in N,N-dimethylformamide and tetrahydrofuran, tert-butyl nitrite (62.19 mg, 603.05 μmol) was added, and the reaction mixture was stirred for reaction at 70° C. for 1 h. A target product was generated as detected by LCMS. The reaction mixture was concentrated to dryness under reduced pressure and purified by preparative liquid chromatography (column: Waters Xbridge BEH C18 100×25 mm×5 μm; mobile phase: [A: water (0.225% formic acid), B: acetonitrile]; B %: 39%-59%, 12 min) to give the title compound (13.9 mg).

MS m/z (ESI): 433.0 $[M+H]^+$.

$^1H$ NMR (400 MHz, Methanol-$d_4$) δ=8.85 (d, J=7.9 Hz, 1H), 7.82 (d, J=7.9 Hz, 1H), 7.71-7.66 (m, 1H), 7.59-7.55 (m, 2H), 7.51-7.46 (m, 1H)

Example 10. 5-(4-(difluoromethoxy)phenyl)-7-ethoxy-3,5-dihydro-1H-imidazo[4,5-c][1,8]naphthyridine-2,4-dione (Compound 10)

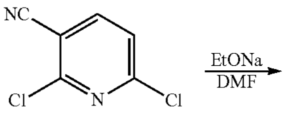

10-1

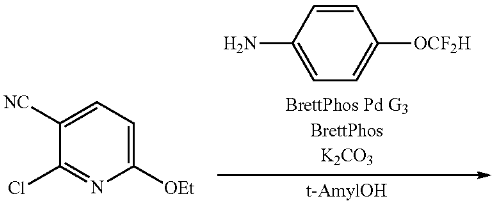

10-2

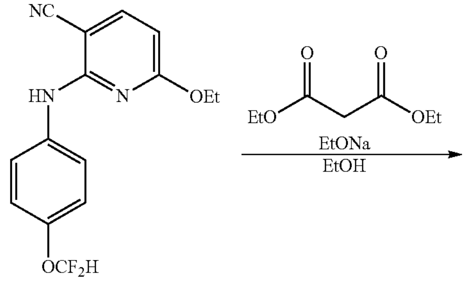

10-3

-continued

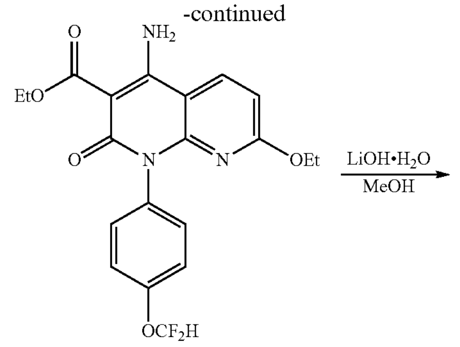

10-4

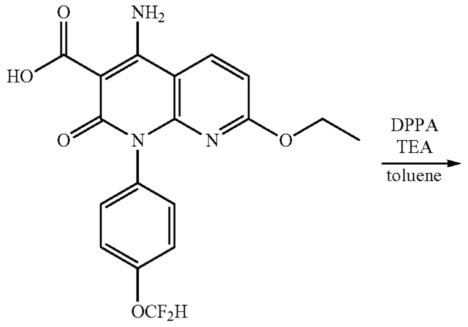

10-5

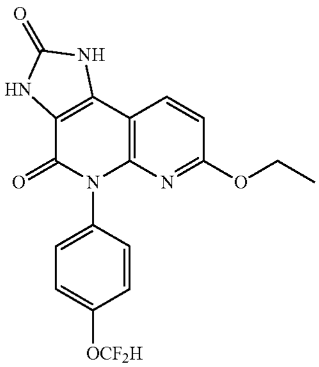

Compound 10

Step 1: synthesis of 2-chloro-6-ethoxy-3-cyanopyridine (intermediate 10-2)

Intermediate 10-1 (10 g, 57.80 mmol) was dissolved in N,N-dimethylformamide (200 mL) at 25° C., sodium ethoxide (3.93 g, 57.80 mmol) was then added, and the reaction mixture was stirred for reaction at 25° C. for 16 h under nitrogen atmosphere. A target product had been generated as detected by LCMS. After the reaction was completed, ethyl acetate (200 mL) and water (400 mL) were added to the reaction mixture, and the mixture was extracted 2 times with an aqueous lithium chloride solution (500 mL). The organic phases were combined and dried over anhydrous sodium sulfate. The organic phase was filtered and concentrated under reduced pressure to remove the solvent. The title compound (9.7 g) was given.

MS m/z (ESI): 183.1 $[M+H]^+$.

Step 2: synthesis of 2-((4-(difluoromethoxy)phenyl) amino)-6-ethoxy-3-cyanopyridine (Intermediate 10-3)

Intermediate 10-2 (7.7 g, 42.17 mmol) was dissolved in tert-amyl alcohol (120 mL) at 20° C., and potassium carbonate (17.48 g, 126.50 mmol), dicyclohexyl(2,4,6-triisopropyl-3,6-dimethoxy-[1,1-biphenyl]-2-yl)phosphine (BrettPhos) (1.13 g, 2.11 mmol), methanesulfonato(2-dicyclohexylphosphino-3,6-dimethoxy-2',4',6'-tri-i-propyl-1,1'-biphenyl)-2-(2'-amino-1,1'-biphenyl)palladium(II) (BrettPhos Pd G3) (1.91 g, 2.11 mmol), and p-difluoromethoxyaniline (8.05 g, 50.60 mmol) were added to the reaction mixture. The reaction mixture was stirred for reaction at 100° C. for 16 h under nitrogen atmosphere. A target product was generated as detected by LCMS. After the reaction was completed, the organic phase was concentrated under reduced pressure to remove the solvent. Ethyl acetate (50 mL) and water (100 mL) were added thereto, and the mixture was extracted 2 times with water (100 mL). The organic phases were combined and dried over anhydrous sodium sulfate. The organic phase was filtered and concentrated under reduced pressure to remove the solvent. The residue was purified by silica gel column chromatography (petroleum ether/ethyl acetate=1/0 to 9/1) to give the title compound (6 g).

MS m/z (ESI): 305.9 $[M+H]^+$.

Step 3: synthesis of ethyl 4-amino-1-(4-(difluoromethoxy)phenyl)-7-ethoxy-2-oxo-1,2-dihydro-1,8-naphthyridine-3-formate (intermediate 10-4)

Intermediate 10-3 (5.2 g, 17.03 mmol) was dissolved in ethanol (60 mL) at 20° C., and sodium ethoxide (4.64 g, 68.13 mmol) and diethyl malonate (8.18 g, 51.10 mmol) were added to the reaction mixture. The reaction mixture was stirred for reaction at 90° C. for 16 h under nitrogen atmosphere. A target product was generated as detected by LCMS. After the reaction was completed, the organic phase was concentrated under reduced pressure to remove the solvent. Ethyl acetate (100 mL) and water (200 mL) were added thereto, and the mixture was extracted and washed 2 times with water (200 mL). The organic phases were combined and dried over anhydrous sodium sulfate. The organic phase was filtered and concentrated under reduced pressure to remove the solvent. The residue was purified by silica gel column chromatography (petroleum ether/ethyl acetate=1/0 to 0/1) to give the title compound (4.5 g).

MS m/z (ESI): 420.1 $[M+H]^+$.

Step 4: synthesis of 4-amino-1-(4-(difluoromethoxy)phenyl)-7-ethoxy-2-oxo-1,2-dihydro-1,8-naphthyridine-3-carboxylic acid (intermediate 10-5)

Intermediate 10-4 (2 g, 4.77 mmol) was dissolved in methanol (32 mL) at 20° C., and lithium hydroxide monohydrate (4.00 g, 95.38 mmol) was added to the reaction mixture. The reaction mixture was stirred for reaction at 50° C. for 16 h under nitrogen atmosphere. A target product was generated as detected by LCMS. After the reaction was completed, the organic phase was concentrated under reduced pressure to remove the solvent. Ethyl acetate (30 mL) and water (60 mL) were added thereto, and the mixture was extracted 2 times with water (60 mL). The organic phases were combined and dried over anhydrous sodium sulfate sulfate. The organic phase was filtered and concentrated under reduced pressure to remove the solvent. The title compound (1.8 g) was given.

MS m/z (ESI): 392.0 $[M+H]^+$.

Step 5: synthesis of 5-(4-(difluoromethoxy)phenyl)-7-ethoxy-3,5-dihydro-1H-imidazo[4,5-c][1,8]naphthyridine-2,4-dione (Compound 10)

Intermediate 10-5 (900 mg, 2.30 mmol) was dissolved in a toluene (8 mL) solution at 20° C., and diphenylphosphoryl azide (1.27 g, 4.60 mmol) and triethylamine (349.08 mg, 3.45 mmol) were added to the reaction mixture. The reaction mixture was stirred for reaction at 100° C. for 16 h. A target product was generated as detected by LCMS. After the reaction was completed, ethyl acetate (20 mL) and water (40 mL) were added to the reaction mixture, and the mixture was extracted 2 times with water (40 mL). The organic phases were combined and dried over anhydrous sodium sulfate.

The organic phase was filtered and concentrated under reduced pressure (0.01 MPa) to remove the solvent. The residue was purified by silica gel column chromatography (petroleum ether/tetrahydrofuran=1/0 to 0/1) to give the title compound (700 mg). The title compound (50 mg) was taken and purified by high performance liquid chromatography (column: YMC-Actus Triart C18 150×30 mm×5 μm; mobile phase: A: water (0.05% ammonia water), B: acetonitrile; B %: 25%-45%, 11 min) to give the title compound (6.5 mg).

MS m/z (ESI): 389.1 $[M+H]^+$.

$^1$H NMR (400 MHz, Methanol-$d_4$) δ=8.80 (d, J=8.5 Hz, 1H), 8.43 (s, 1H), 7.38-7.29 (m, 4H), 6.93 (t, J=74.4 Hz, 1H), 6.75 (d, J=3.1 Hz, 1H), 4.02 (d, J=7.0 Hz, 2H), 1.18-1.13 (m, 3H).

Example 11. 5-(4-(difluoromethoxy)phenyl)-7-ethoxy-2-methoxy-1,5-dihydro-4H-imidazo[4,5-c][1,8]naphthyridin-4-one (Compound 11)

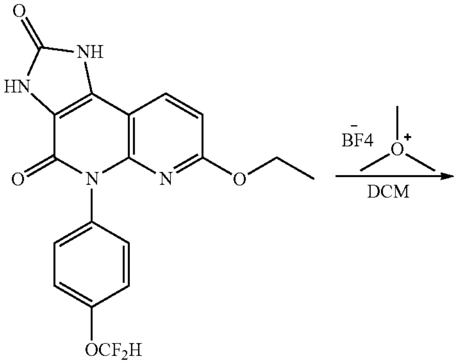

Compound 10

-continued

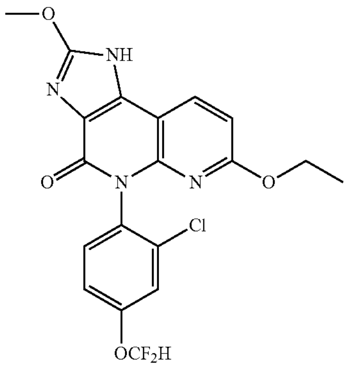

Compound 11

Compound 10 (100 mg, 257.52 μmol) was dissolved in a dichloromethane solution (1 mL) at 20° C., and trimethyloxonium tetrafluoroborate (76.18 mg, 515.03 μmol) was added to the reaction mixture. The reaction mixture was stirred for reaction at 40° C. for 16 h. A target product was generated as detected by LCMS. After the reaction was completed, dichloromethane (5 mL) and water (10 mL) were added to the reaction mixture, and the mixture was extracted 2 times with water (10 mL). The organic phases were combined and dried over anhydrous sodium sulfate. The organic phase was filtered and concentrated under reduced pressure to remove the solvent. The residue was purified by high performance liquid chromatography (column: Waters Xbridge BEH C18 100×25 mm×5 μm; mobile phase: A: water (0.225% formic acid), B: acetonitrile; B %: 25%-55%, 12 min) to give the title compound (7.9 mg).

$^1$H NMR (400 MHz, Methanol-$d_4$) δ=8.43 (s, 1H), 7.35 (s, 4H), 6.95 (t, J=73.8 Hz, 1H), 6.73 (d, J=8.5 Hz, 1H), 4.23 (s, 3H), 3.97 (q, J=7.1 Hz, 2H), 1.13 (t, J=7.0 Hz, 3H).

MS m/z (ESI): 403.1 $[M+H]^+$.

Example 12. 5-(4-(difluoromethoxy)phenyl)-2-methyl-7-(trifluoromethyl)-2,5-dihydro-4H-pyrazolo[3,4-c][1,8]naphthyridin-4-one (Compound 12)

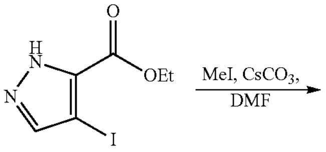

12-1

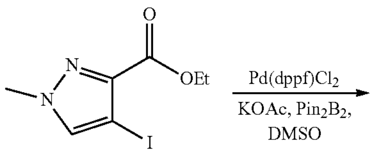

12-2

-continued

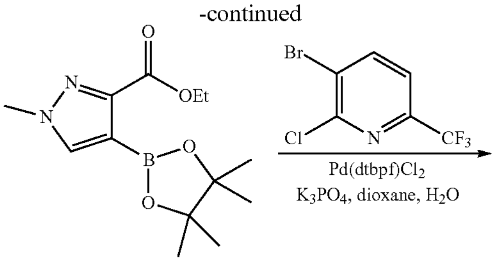

12-3

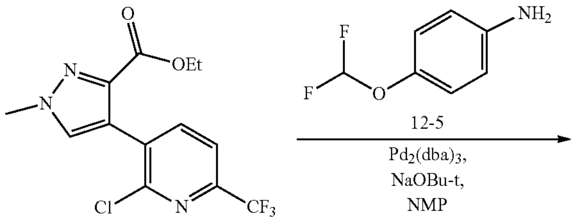

12-4

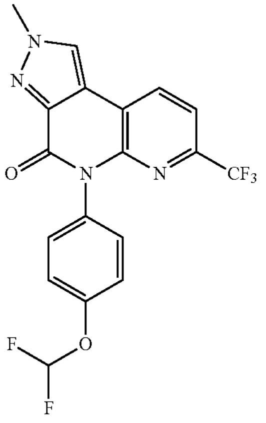

Compound 12

Step 1: synthesis of ethyl 4-iodo-1-methyl-1H-pyrazole-3-carboxylate (intermediate 12-2)

Intermediate 12-1 (5 g, 18.79 mmol) was dissolved in DMF (50 mL), and cesium carbonate (12 g, 37.59 mmol) and iodomethane (5.3 g, 37.59 mmol) were added to the reaction mixture. The reaction mixture was stirred at 25° C. for 18 h under nitrogen atmosphere. Water (50 mL) and ethyl acetate (100 mL) were added sequentially. The organic phase was washed with water (30 mL×2), and the washed organic phase was dried over anhydrous $Na_2SO_4$, filtered, concentrated under reduced pressure, and purified by preparative thin-layer chromatography (silica, petroleum ether: ethyl acetate=10:3) to give the title compound (2 g).

MS m/z (ESI): 281.0 $[M+H]^+$.

Step 2: synthesis of ethyl 1-methyl-4-(4,4,5,5-tetramethyl-1,3,2-dioxaborolan-2-yl)-1H-pyrazole-3-carboxylate (intermediate 12-3)

Intermediate 12-2 (1.5 g, 5.33 mmol) and bis(pinacolato) diboron (2.7 g, 10.67 mmol) were dissolved in anhydrous dimethyl sulfoxide (10 mL), potassium acetate (1.04 g, 10.67 mmol) and Pd(dppf)$Cl_2$ (387 mg, 0.53 mmol) were added thereto, and the reaction mixture was stirred at 100° C. for 15 h under nitrogen atmosphere. After the reaction was cooled to room temperature, water (60 mL) and ethyl acetate (80 mL) were added sequentially. The organic phase was washed with water (30 mL×2), and the washed organic phase was dried over an appropriate amount of anhydrous sodium sulfate. The organic phase was purified by preparative thin-layer chromatography (silica, dichloromethane: methanol=10:1) to give the title compound (750 mg).

MS m/z (ESI): 281.0 $[M+H]^+$.

Step 3: synthesis of ethyl 4-(2-chloro-6-(trifluoromethyl)pyridin-3-yl)-1-methyl-1H-pyrazole-3-carboxylate (intermediate 12-4)

Intermediate 12-3 (350 mg, 1.24 mmol) and 3-bromo-2-chloro-6-(trifluoromethyl)pyridine (483 mg, 1.86 mmol) were dissolved in dioxane (6 mL) and water (2 mL), potassium phosphate (534 mg, 2.51 mmol) and Pd(dtbpf)$Cl_2$ (81.98 mg, 0.12 mmol) were added thereto, and the reaction mixture was stirred at 100° C. for 16 h under nitrogen atmosphere. After the reaction was cooled to room temperature, water (30 mL) and ethyl acetate (40 mL) were added sequentially. The organic phase was washed with water (30 mL×2), and the washed organic phase was dried over an appropriate amount of anhydrous sodium sulfate. The organic phase was purified by preparative thin-layer chromatography (silica, dichloromethane:methanol=5:1) to give the title compound (300 mg).

MS m/z (ESI): 334.1$[M+H]^+$.

Step 4: synthesis of 5-(4-(difluoromethoxy)phenyl)-2-methyl-7-(trifluoromethyl)-2,5-dihydro-4H-pyrazolo[3,4-c][1,8]naphthyridin-4-one (Compound 12)

Intermediate 12-4 (70 mg, 0.21 mmol) and intermediate 12-5 (50 mg, 0.31 mmol) were dissolved in N-methyl-2-pyrrolidone (2 mL), sodium tert-butoxide (40 mg, 0.42 mmol) and $Pd_2(dba)_3$ (1.9 mg, 0.02 mmol) were added thereto, and the reaction mixture was stirred at 100° C. for 15 h under nitrogen atmosphere. After the reaction was cooled to room temperature, water (15 mL) and ethyl acetate (30 mL) were added sequentially. The organic phase was washed with water (30 mL×2), and the washed organic phase was dried over an appropriate amount of anhydrous sodium sulfate and concentrated under reduced pressure. The residue was purified by TLC (dichloromethane:methanol=10:1) and then purified by preparative high performance liquid chromatography (column: Gemini NX C18 5 μm×10×150 mm; mobile phase: A: 0.05% trifluoroacetic acid v/v, B: acetonitrile; B %: 40%-45%, 12 min) to give the title compound (2.5 mg).

MS m/z (ESI): 411.0 $[M+H]^+$.

$^1H$ NMR (400 MHz, Methanol-$d_4$) δ 8.69 (s, 1H), 8.54 (d, J=8.0 Hz, 1H), 7.65 (d, J=8.0 Hz, 1H), 7.38-7.27 (m, 4H), 7.16-6.73 (m, 1H), 4.24 (s, 3H).

Example 13. 5-(4-(difluoromethoxy)phenyl)-7-ethoxy-2-methyl-2,5-dihydro-4H-pyrazolo[3,4-c][1,8]naphthyridin-4-one (Compound 13)

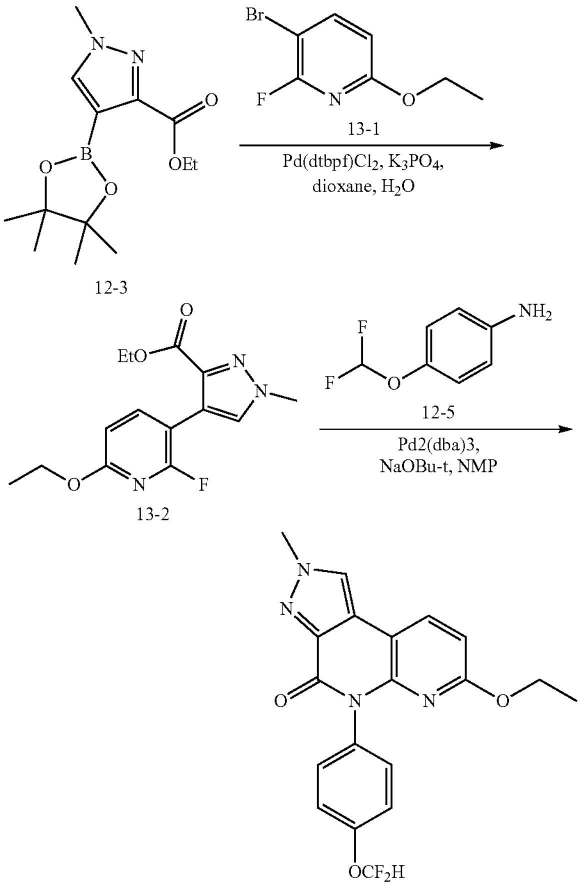

12-3 13-1 13-2 12-5 Compound 13

Step 1: synthesis of ethyl 4-(6-ethoxy-2-fluoropyridin-3-yl)-1-methyl-1H-pyrazole-3-carboxylate (intermediate 13-2)

Intermediate 12-3 (350 mg, 1.24 mmol) and intermediate 13-1 (409 mg, 1.86 mmol) were dissolved in dioxane (6 mL) and water (2 mL), potassium phosphate (534 mg, 2.51 mmol) and Pd(dtbpf)$Cl_2$ (81.98 mg, 0.12 mmol) were added thereto, and the reaction mixture was stirred at 100° C. for 16 h under nitrogen atmosphere. After the reaction was cooled to room temperature, water (30 mL) and ethyl acetate (40 mL) were added sequentially. The organic phase was washed with water (30 mL×2), and the washed organic phase was dried over an appropriate amount of anhydrous sodium sulfate. The organic phase was purified by preparative thin-layer chromatography (silica, dichloromethane: methanol=5:1) to give the title compound (250 mg).

MS m/z (ESI): 294.0 $[M+H]^+$.

Step 2: synthesis of 5-(4-(difluoromethoxy)phenyl)-7-ethoxy-2-methyl-2,5-dihydro-4H-pyrazolo[3,4-c][1,8]naphthyridin-4-one (Compound 13)

Intermediate 13-2 (70 mg, 0.23 mmol) and intermediate 12-5 (50 mg, 0.31 mmol) were dissolved in N-methyl-2-pyrrolidone (2 mL), sodium tert-butoxide (40 mg, 0.46 mmol) and $Pd_2(dba)_3$ (1.9 mg, 0.02 mmol) were added thereto, and the reaction mixture was stirred at 100° C. for 15 h under nitrogen atmosphere. After the reaction was cooled to room temperature, water (15 mL) and ethyl acetate (30 mL) were added sequentially. The organic phase was washed with water (30 mL×2), and the washed organic phase was dried over an appropriate amount of anhydrous sodium sulfate and concentrated under reduced pressure. The residue was purified by TLC (dichloromethane:methanol=10:1) and then purified by preparative high performance liquid chromatography (column: Gemini NX C18 5 μm×10×150 mm; mobile phase: A: 0.05% trifluoroacetic acid v/v, B: acetonitrile; B %: 40%-48%, 12 min) to give the title compound (5.2 mg).

MS m/z (ESI): 387.0 $[M+H]^+$.

$^1H$ NMR (400 MHz, DMSO-$d_6$) δ 8.64 (s, 1H), 8.30 (d, J=8.4 Hz, 1H), 7.64-7.00 (m, 5H), 6.70 (d, J=8.4 Hz, 1H), 4.16 (s, 3H), 3.87 (q, J=7.0 Hz, 2H), 1.04 (t, J=7.0 Hz, 3H).

Example 14. 5-(4-(difluoromethoxy)phenyl)-7-ethoxy-1-methyl-1,5-dihydro-4H-imidazo[4,5-c][1,8]naphthyridin-4-one (Compound 14)

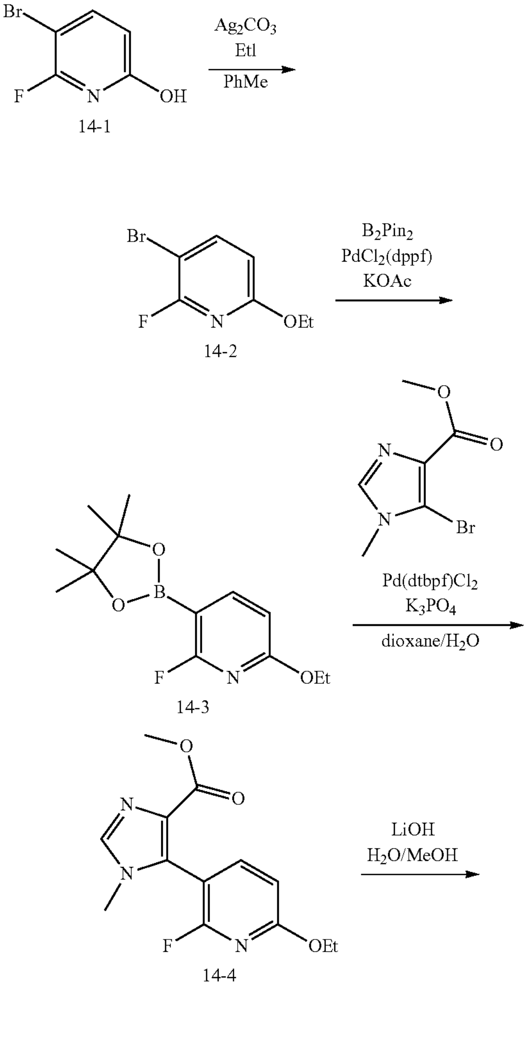

14-1 14-2 14-3 14-4

-continued

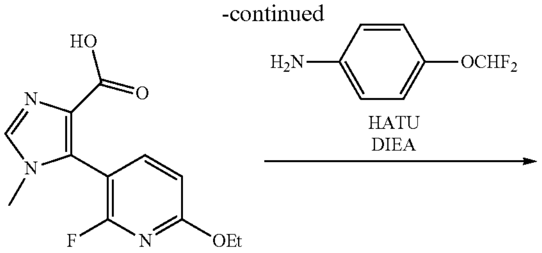

14-5

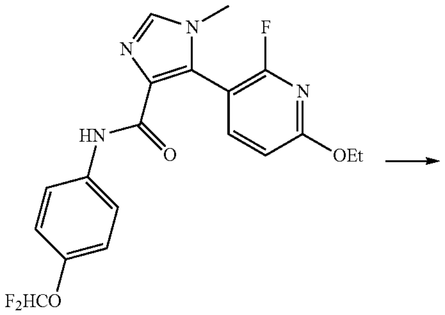

14-6

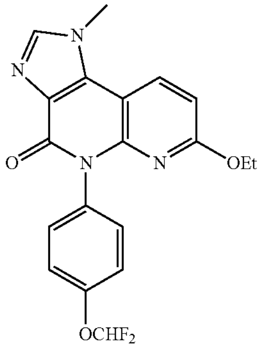

Compound 14

Step 1: synthesis of 3-bromo-6-ethoxy-2-fluoropyridine (intermediate 14-2)

Intermediate 14-1 (0.9 g, 4.69 mmol) was dissolved in toluene (5 mL), silver carbonate (1.55 g, 5.63 mmol) and iodoethane (1.46 g, 9.38 mmol) were added sequentially, and the mixture was warmed to 100° C. and stirred for 16 h. After the reaction was completed, the mixture was cooled to room temperature, and water (10 mL) was added. The mixture was extracted 3 times with ethyl acetate (10 mL). The organic phases were combined and concentrated to dryness under reduced pressure. The residue was purified by a flash silica gel column (ISCO®; 12 g of SepaFlash© silica gel column; eluent: 0-12% ethyl acetate/petroleum ether, gradient 30 mL/min) to give the title compound (600 mg).

MS m/z (ESI): 219.0 $[M+H]^+$.

Step 2: synthesis of 6-ethoxy-2-fluoro-3-(4,4,5,5-tetramethyl-1,3,2-dioxaborolan-2-yl)pyridine (intermediate 14-3)

Intermediate 14-2 (300 mg, 1.36 mmol) and bis(pinacolato)diboron (380.84 mg, 1.50 mmol) were dissolved in dioxane (8 mL), and potassium acetate (401.41 mg, 4.09 mmol) was added. $PdCl_2$(dppf) (49.88 mg, 68.17 μmol) was added under nitrogen atmosphere, and the reaction mixture was stirred for reaction at 90° C. for 2 h. After the reaction was completed, the reaction mixture was filtered, and the filtrate was concentrated to give the title compound (364 mg).

Step 3: synthesis of methyl 5-(6-ethoxy-2-fluoropyridin-3-yl)-1-methyl-1H-imidazole-4-formate (intermediate 14-4)

Intermediate 14-3 (360 mg, 1.35 mmol) and methyl 5-bromo-1-methyl-1H-imidazole-4-carboxylate (206.65 mg, 943.45 μmol, which can be synthesized according to the method reported in Patent Document WO 2017218960) were dissolved in dioxane (3 mL) and water (0.5 mL). Pd(dtbpf)$Cl_2$ (87.84 mg, 134.78 μmol) and potassium phosphate (286.10 mg, 1.35 mmol) were added under nitrogen atmosphere, and the mixture was stirred for reaction at 50° C. for 16 h. After the reaction was completed, the mixture was cooled to 20° C. and extracted twice with ethyl acetate (10 mL). The organic phase was concentrated to dryness under reduced pressure, and the residue was purified by preparative thin-layer chromatography (silica, petroleum ether:ethyl acetate=3:1). The title compound (0.5 g) was given.

MS m/z (ESI): 280.0 $[M+H]^+$.

Step 4: synthesis of 5-(6-ethoxy-2-fluoropyridin-3-yl)-1-methyl-1H-imidazole-4-formic acid (intermediate 14-5)

Intermediate 14-4 (170 mg, 608.74 μmol) was dissolved in water (2 mL) and methanol (2 mL), lithium hydroxide monohydrate (80 mg, 1.91 mmol) was added, and the reaction mixture was stirred at 60° C. for 2 h. After the reaction was completed, the mixture was concentrated to dryness under reduced pressure. The title compound (161 mg) was given.

MS m/z (ESI): 265.9 $[M+H]^+$.

Step 5: synthesis of 5-(4-(difluoromethoxy)phenyl)-7-ethoxy-1-methyl-1,5-dihydro-4H-imidazo[4,5-c][1,8]naphthyridin-4-one (Compound 14)

Intermediate 14-5 (161 mg, 607.00 μmol) and 4-(difluoromethoxy)aniline (193.19 mg, 1.21 mmol) were dissolved in N,N-dimethylformamide (2 mL), O-(7-azabenzotriazol-1-yl)-N,N,N',N'-tetramethyluronium hexafluorophosphate (HATU) (346.20 mg, 910.50 μmol) and diisopropylethylamine (156.90 mg, 1.21 mmol) were added sequentially, and the mixture was stirred for reaction at 20° C. for 16 h. After the conversion into an intermediate was completed, lithium hydroxide monohydrate (76.42 mg, 1.82 mmol) was added, and the reaction mixture was stirred for reaction at 100° C. for 5 h. After the reaction was completed, the mixture was filtered, and the filtrate was purified by preparative high performance liquid chromatography (column: Boston Prime C18 150×30 mm×5 μm; mobile phase: [A: water (0.05% ammonia water+10 mM ammonium bicarbonate), B: acetonitrile]; B %: 36%-66%, 10 min). The residue was purified by high performance liquid chromatography (formic acid condition; column: Waters Xbridge BEH C18 100×25 mm×5 μm; mobile phase: [A: water (0.225% formic acid), B: acetonitrile]; B %: 20%-50%, 12 min) to give the title compound (14.8 mg).

MS m/z (ESI): 387.0 $[M+H]^+$.

$^1$H NMR (400 MHz, Methanol-$d_4$) δ=8.53 (d, J=8.8 Hz, 1H), 8.05 (s, 1H), 7.39-7.28 (m, 4H), 6.94 (t, J=74.4 Hz, 1H), 6.76 (d, J=8.5 Hz, 1H), 4.23 (s, 3H), 3.95 (q, J=7.0 Hz, 2H), 1.10 (t, J=7.2 Hz, 3H).

Example 15. 5-(4-(difluoromethoxy)phenyl)-1-methyl-7-(trifluoromethyl)-1H-imidazo[4,5-c][1,8]naphthyridin-4 (5H)-one (Compound 15)

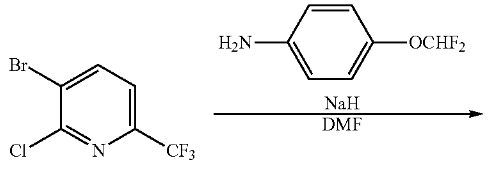

15-1

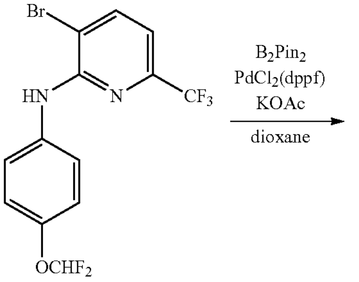

15-2

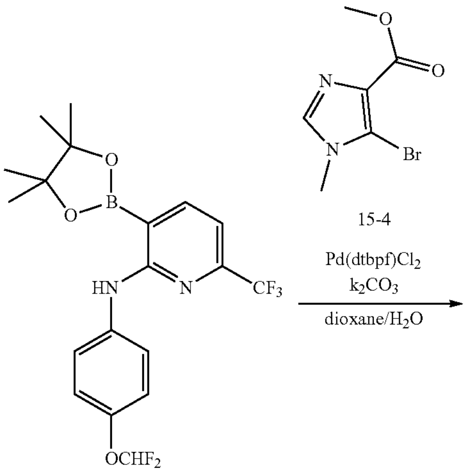

15-4

15-3

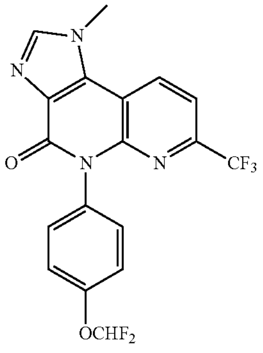

Compound 15

Step 1: synthesis of 3-bromo-N-(4-(difluoromethoxy)phenyl)-6-(trifluoromethyl)pyridin-2-amine (intermediate 15-2)

p-difluoromethoxyaniline (611.02 mg, 3.84 mmol) was dissolved in N,N-dimethylformamide (15 mL), and sodium hydride (60% effective content, 230.38 mg, 5.76 mmol) was added at 0° C. After the reaction mixture was stirred for reaction at 0° C. for 2 h, intermediate 15-1 (1 g, 3.84 mmol) was dissolved in N,N-dimethylformamide (3 mL) and added dropwise to the reaction mixture. The reaction mixture was stirred for reaction at 0° C. for 12 h. The reaction mixture was quenched with water (5 mL), and the mixture was extracted thrice with ethyl acetate (10 mL×3). The organic layer was washed with saturated brine and concentrated to dryness under reduced pressure, and the residue was purified by silica gel column chromatography (petroleum ether:ethyl acetate=10:1) to give the title compound (300 mg).

MS m/z (ESI): 384.9 $[M+H]^+$.

Step 2: synthesis of N-(4-(difluoromethoxy)phenyl)-3-(4,4,5,5-tetramethyl-1,3,2-dioxaborolan-2-yl)-6-(trifluoromethyl)pyridin-2-amine (intermediate 15-3)

Intermediate 15-2 (100 mg, 261.02 μmol) was dissolved in dioxane (4 mL), and bis(pinacolato)diboron (79.54 mg, 313.23 μmol), potassium acetate (76.85 mg, 783.06 μmol), and Pd(dppf)$Cl_2$ (9.55 mg, 13.05 μmol) were added. The reaction mixture was warmed to 80° C. and stirred for reaction for 2 h under nitrogen atmosphere. The title compound was given and used directly in the next step.

MS m/z (ESI): 431.1$[M+H]^+$.

Step 3: synthesis of 5-(4-(difluoromethoxy)phenyl)-1-methyl-7-(trifluoromethyl)-1,5-dihydro-4H-imidazo[4,5-c][1,8]naphthyridin-4-one (Compound 15)

A dioxane solution containing intermediate 15-3 (100 mg, 232.46 μmol) was added to water (1 mL), and intermediate 15-4 (152.75 mg, which can be synthesized according to the method reported in Patent Document WO 2017218960), potassium carbonate (48.21 mg, 697.39 μmol), and Pd(dtbpf)$Cl_2$ (15.15 mg, 23.25 μmol) were added. The reaction mixture was stirred for reaction at 100° C. for 1 h under nitrogen atmosphere. The reaction mixture was concentrated to dryness under reduced pressure and purified by preparative high performance liquid chromatography (column: Boston Prime C18 150×30 mm×5 μm; mobile phase: A: water (0.05% ammonia water+10 mM ammonium bicarbonate), B: acetonitrile; B %: 37%-67%,10 min) to give the title compound (13.1 mg).

MS m/z (ESI): 411.0$[M+H]^+$.

$^1$H NMR (400 MHz, Methanol-$d_4$) δ=8.88 (d, J=8.0 Hz, 1H), 8.24 (s, 1H), 7.78 (d, J=8.0 Hz, 1H), 7.35 (s, 4H), 6.98 (t, J=74 Hz, 1H), 4.34 (s, 3H)

Example 16. 5-(4-(difluoromethoxy)phenyl)-7-(trifluoromethyl)oxazolo[4,5-c][1,8]naphthyridin-4(5H)-one (Compound 16)

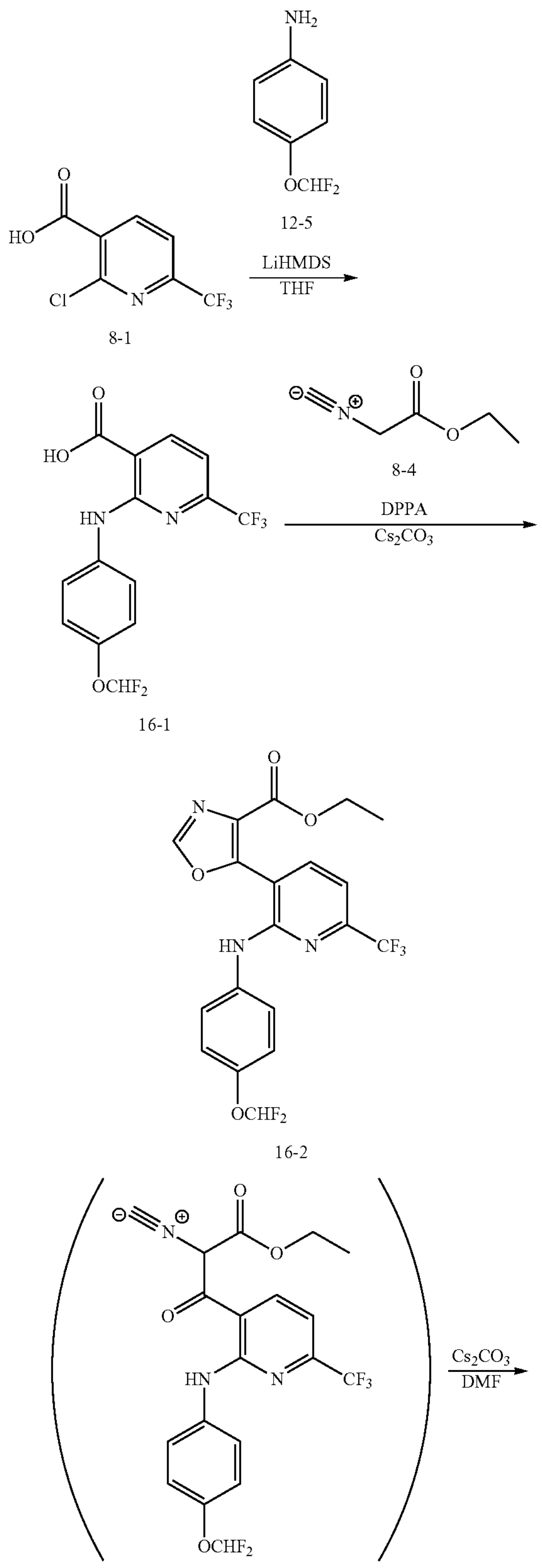

12-5
8-1
8-4
16-1
16-2

-continued

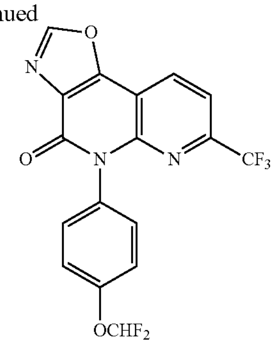

Compound 16

Step 1: synthesis of 2-((4-(difluoromethoxy)phenyl)amino)-6-(trifluoromethyl)pyridine-3-formic acid (intermediate 16-1)

Intermediate 8-1 (1.0 g, 4.5 mmol) was dissolved in anhydrous tetrahydrofuran (10 mL), and a solution of lithium bis(trimethylsilyl)amide in THF (1 M, 9.76 mL, 9.76 mmol) was added dropwise thereto at −78° C. The mixture was reacted at −78° C. for 1 h, and intermediate 12-5 (842.7 mg, 5.3 mmol) was added to the reaction mixture. The mixture was warmed to room temperature and reacted for 3 h. Saturated aqueous ammonium chloride (10 mL) and ethyl acetate (10 mL×3) were added sequentially to the reaction mixture. The organic phase was washed with water (10 mL×2), and the washed organic phase was dried over an appropriate amount of anhydrous sodium sulfate and concentrated. The residue was purified by preparative high performance liquid chromatography (column: Gemini NX C18 5 μm×10×150 mm; mobile phase: A: water (0.225% formic acid v/v), B: acetonitrile; B %: 30%-50%) to give the title compound (900.0 mg).

MS m/z (ESI): 349.1 $[M+H]^+$.

Step 2: synthesis of ethyl 5-(2-((4-(difluoromethoxy)phenyl)amino)-6-(trifluoromethyl)pyridin-3-yl)oxazole-4-carboxylate (intermediate 16-2)

Intermediate 16-1 (150 mg, 430.76 μmol) and cesium carbonate (281 mg, 861.51 μmol) were dissolved in N,N-dimethylformamide (4 mL), diphenylphosphoryl azide (DPPA) (209.52 mg, 861.51 mmol) was added thereto at 0° C., and the mixture was reacted at room temperature for 1 h after the addition. Intermediate 8-4 (48.72 mg, 430.76 μmol) was added at 0° C., and the reaction mixture was stirred at 25° C. for 2 h after the addition. Water (5 mL) and ethyl acetate (5 mL×3) were added sequentially to the reaction mixture. After liquid separation, the organic phase was washed with saturated brine (5 mL×2), and the washed organic phase was dried over an appropriate amount of anhydrous sodium sulfate and purified by preparative thin-layer chromatography (silica, petroleum ether:ethyl acetate=100:0-50:50) to give the title compound (90 mg).

MS m/z (ESI): 433.1 $[M+H]^+$.

Step 3: synthesis of 5-(4-(difluoromethoxy)phenyl)-7-(trifluoromethyl)oxazolo[4,5-c][1,8]naphthyridin-4(5H)-one (Compound 16)

Intermediate 16-2 (100 mg, 225.57 μmol) and cesium carbonate (220.47 mg, 676.71 μmol) were dissolved in N,N-dimethylformamide (4 mL). The mixture was reacted at 60° C. for 3 h. The reaction mixture was filtered and purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (24.0 mg).

MS m/z (ESI): 398.1 $[M+H]^+$.

$^1H$ NMR (400 MHz, DMSO-$d_6$) δ 9.11 (s, 1H), 8.79 (d, J=8.0 Hz, 1H), 7.91 (d, J=8.0 Hz, 1H), 7.62-7.20 (m, 5H).

Example 17. 5-(2-chlorophenyl)-7-ethoxy-1-methyl-1,5-dihydro-4H-imidazo[4,5-c][1,8]naphthyridin-4-one (Compound 17)

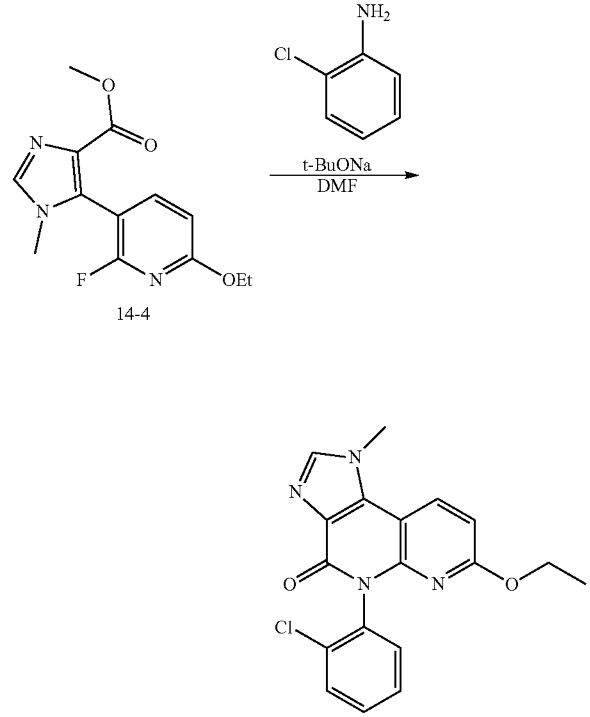

14-4

Compound 17

Intermediate 14-4 (130 mg, 465.51 μmol) and 2-chloroaniline (59.39 mg, 465.51 μmol) were dissolved in N,N-dimethylformamide (3 mL), sodium tert-butoxide (134.21 mg, 1.40 mmol) was added, and the reaction mixture was stirred at 80° C. for 1 h. After the reaction was completed, the mixture was filtered to give a filtrate. The filtrate was purified by preparative high performance liquid chromatography (column: Waters Xbridge BEH C18 100×25 mm×5 μm; mobile phase: [A: water (0.225% formic acid), B: acetonitrile]; B %: 19%-49%, 12 min) to give the title compound (6.4 mg).

MS m/z (ESI): 355.2$[M+H]^+$.

$^1H$ NMR (400 MHz, Methanol-$d_4$) δ=8.57 (d, J=8.8 Hz, 1H), 8.09 (s, 1H), 7.73-7.63 (m, 1H), 7.59-7.50 (m, 2H), 7.48-7.37 (m, 1H), 6.80 (d, J=8.8 Hz, 1H), 4.26 (s, 3H), 3.99-3.85 (m, 2H), 1.09 (t, J=7.0 Hz, 3H)

Example 18. 5-(4-(difluoromethoxy)phenyl)-7-(trifluoromethyl)oxazolo[5,4-c][1,8]naphthyridin-4(5H)-one (Compound 18)

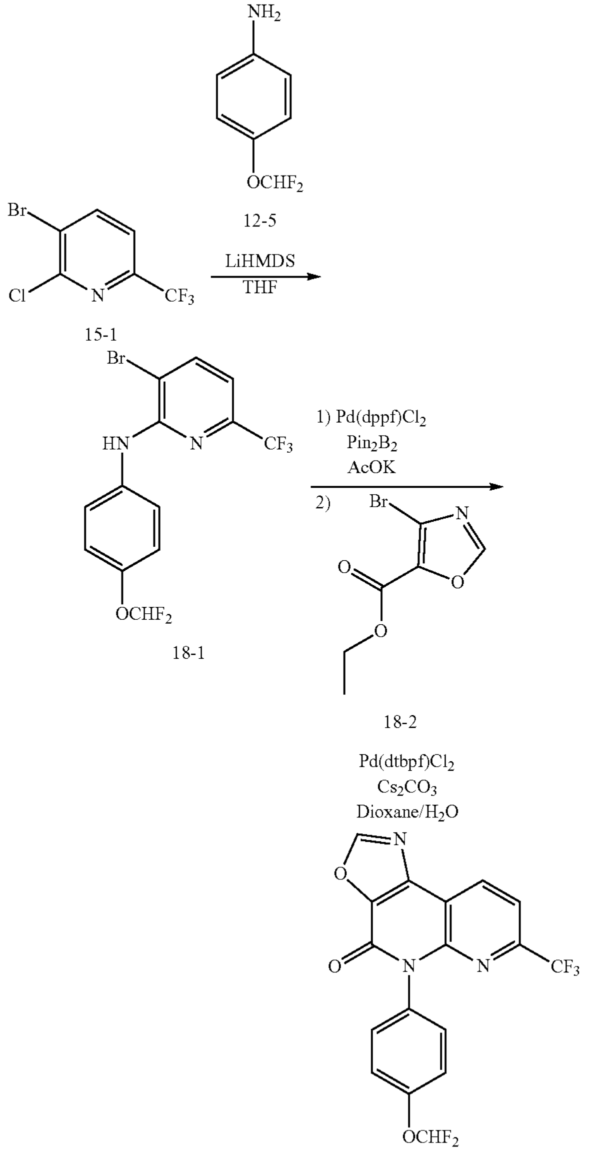

12-5

15-1

18-1

18-2

Compound 18

Step 1: synthesis of 3-bromo-N-(4-(difluoromethoxy)phenyl)-6-(trifluoromethyl)pyridin-2-amine (intermediate 18-1)

Intermediate 15-1 (2.0 g, 7.72 mmol) was dissolved in anhydrous tetrahydrofuran (20 mL), and lithium bis(trimethylsilyl)amide (LiHMDS) (1 M, 9.26 mL, 9.26 mmol) was added dropwise thereto at −78° C. The mixture was reacted at −78° C. for 1 h, and intermediate 12-5 (1.23 g, 7.72 mmol) was added to the reaction mixture. The mixture was warmed to room temperature and reacted for 3 h. Saturated aqueous ammonium chloride (20 mL) and ethyl acetate (20 mL×3) were added sequentially to the reaction mixture. The organic phase was washed with water (20 mL), and the washed organic phase was dried over an appropriate amount of anhydrous sodium sulfate and concentrated. The residue was purified by preparative thin-layer chromatography (silica, petroleum ether:ethyl acetate=100:0 to 50:50) to give the title compound (900 mg).

MS m/z (ESI): 383.1 $[M+H]^+$.

Step 2: synthesis of 5-(4-(difluoromethoxy)phenyl)-7-(trifluoromethyl)oxazolo[5,4-c][1,8]naphthyridin-4(5H)-one (Compound 18)

Intermediate 18-1 (350 mg, 916.23 μmol) and bis(pinacolato)diboron (348 mg, 1.37 mmol) were dissolved in dioxane (5 mL), potassium acetate (179 mg, 1.83 mmol) and $Pd(dppf)Cl_2$ (66.85 mg, 91.36 μmol) were added thereto, and the reaction mixture was stirred at 90° C. for 1 h under nitrogen atmosphere. The reaction mixture was cooled to room temperature. Intermediate 18-2 (239.37 mg, 1.09 mmol), cesium carbonate (591 mg, 1.81 mmol), water (1 mL), and $Pd(dtbpf)Cl_2$ (59.0 mg, 90.66 μmol) were added thereto, and the reaction mixture was stirred at 90° C. for 5 h under nitrogen atmosphere. The reaction mixture was filtered, concentrated to dryness under reduced pressure, and purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (50.0 mg).

MS m/z (ESI): 398.1 $[M+H]^+$.

$^1H$ NMR (400 MHz, DMSO-$d_6$) δ 9.23 (s, 1H), 8.82 (d, J=7.9 Hz, 1H), 7.92 (d, J=8.0 Hz, 1H), 7.61-7.21 (m, 5H).

Example 19. 5-(4-chlorophenyl)-1-methyl-7-(trifluoromethyl)-1,5-dihydro-4H-imidazo[4,5-c][1,8]naphthyridin-4-one (Compound 19)

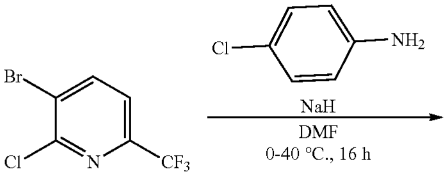

15-1

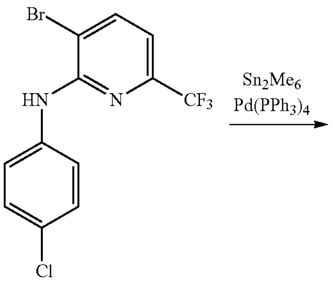

19-1

-continued

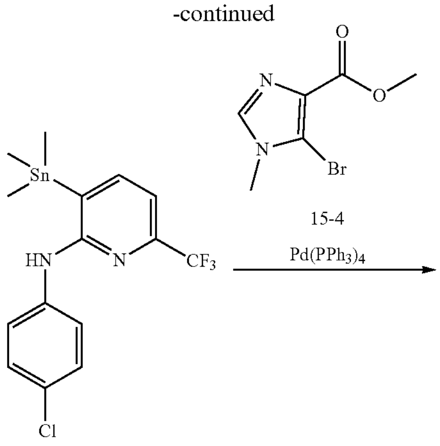

15-4

19-2

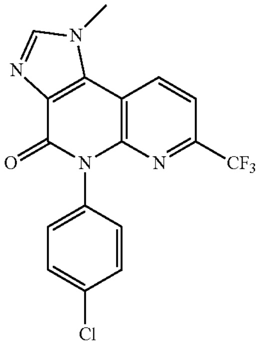

Compound 19

Step 1: synthesis of 3-bromo-N-(4-chlorophenyl)-6-(trifluoromethyl)pyridin-2-amine (Intermediate 19-1)

4-chloroaniline (244.92 mg, 1.92 mmol) was dissolved in N,N-dimethylformamide (5 mL), sodium hydride (60% effective content, 115.18 mg, 2.88 mmol) was added at 0° C., and the mixture was stirred at 0° C. for 30 min. A solution of intermediate 15-1 (500 mg, 1.92 mmol) in N,N-dimethylformamide was added, and the reaction mixture was stirred for reaction at 20° C. for 16 h. Sodium hydride (60% effective content, 76.79 mg, 1.92 mmol) was added again, and the mixture was stirred at 40° C. for 30 min. The mixture was cooled to 0° C., quenched with water (5 mL), extracted with ethyl acetate (30 mL), and washed with brine. The organic phase was concentrated to dryness under reduced pressure. The residue was purified by a flash silica gel column (ISCO®; 4 g of SepaFlash© silica gel column; eluent: 0-15% ethyl acetate/petroleum ether, gradient @ 20 mL/min) to give the title compound (250 mg).

MS m/z (ESI): 352.7 $[M+H]^+$.

Step 2: synthesis of N-(4-chlorophenyl)-6-(trifluoromethyl)-3-(trimethylstannyl)pyridin-2-amine (intermediate 19-2)

Intermediate 19-1 (250 mg, 711.14 μmol), hexamethyldistannane (465.97 mg, 1.42 mmol), and tetrakis(triphenylphosphine)palladium(0) (82.18 mg, 71.11 μmol) were sequentially dissolved in xylene (5 mL), and the mixture was stirred for reaction at 140° C. for 5 h under nitrogen atmosphere. After the reaction was completed, the mixture was cooled to 20° C. and filtered. The filtrate was concentrated to dryness under reduced pressure. The residue was purified by a silica gel column (ISCO®; 12 g of SepaFlash® silica gel column; eluent: 0-10% ethyl acetate/petroleum ether, gradient @ 30 mL/min) to give the title compound (240 mg).

MS m/z (ESI): 436.9 $[M+H]^+$.

Step 3: synthesis of 5-(4-chlorophenyl)-1-methyl-7-(trifluoromethyl)-1,5-dihydro-4H-imidazo[4,5-c][1,8]naphthyridin-4-one (Compound 19)

Intermediate 19-2 (240 mg, 551.14 μmol), intermediate 15-4 (120.72 mg), and tetrakis(triphenylphosphine)palladium(0) (63.69 mg, 55.11 μmol) were dissolved in xylene (4 mL), and the mixture was stirred for reaction at 140° C. for 16 h under nitrogen atmosphere. After the reaction was completed, the reaction mixture was filtered, and the filtrate was concentrated to dryness under reduced pressure. The residue was purified by preparative high performance liquid chromatography (column: Waters Xbridge BEH C18 100×25 mm×5 μm; mobile phase: [A: water (0.225% formic acid), B: acetonitrile]; B %: 26%-46%, 12 min) to give the title compound (47.1 mg).

MS m/z (ESI): 379.0 $[M+H]^+$;

$^1H$ NMR (400 MHz, Methanol-$d_4$) δ=8.86 (d, J=8.3 Hz, 1H), 8.22 (s, 1H), 7.76 (d, J=8.3 Hz, 1H), 7.57 (d, J=8.5 Hz, 2H), 7.29 (d, J=8.5 Hz, 2H), 4.32 (s, 3H).

Example 20. 1-methyl-5-(2-methylpyridin-3-yl)-7-(trifluoromethyl)-1,5-dihydro-4H-imidazo[4,5-c][1,8]naphthyridin-4-one (Compound 20)

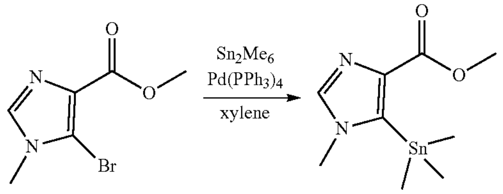

15-4

20-1

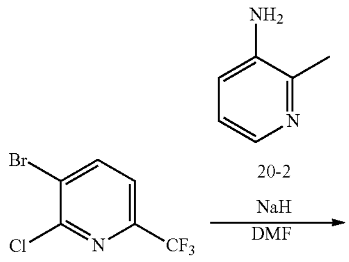

20-2

15-1

-continued

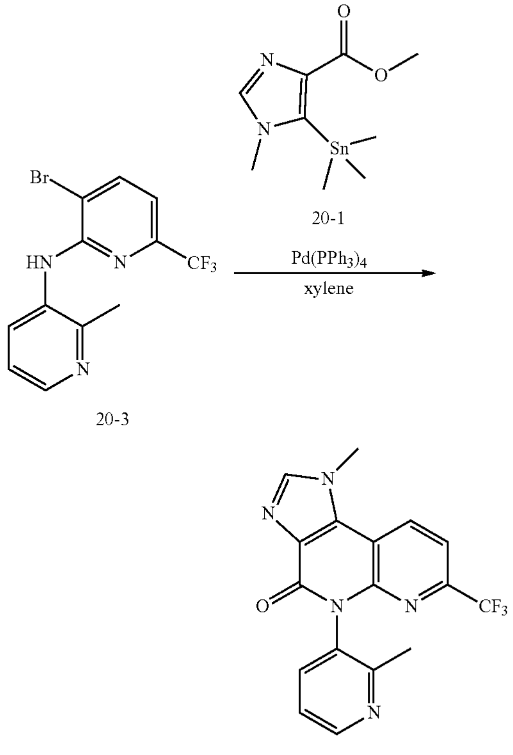

20-1

20-3

Compound 20

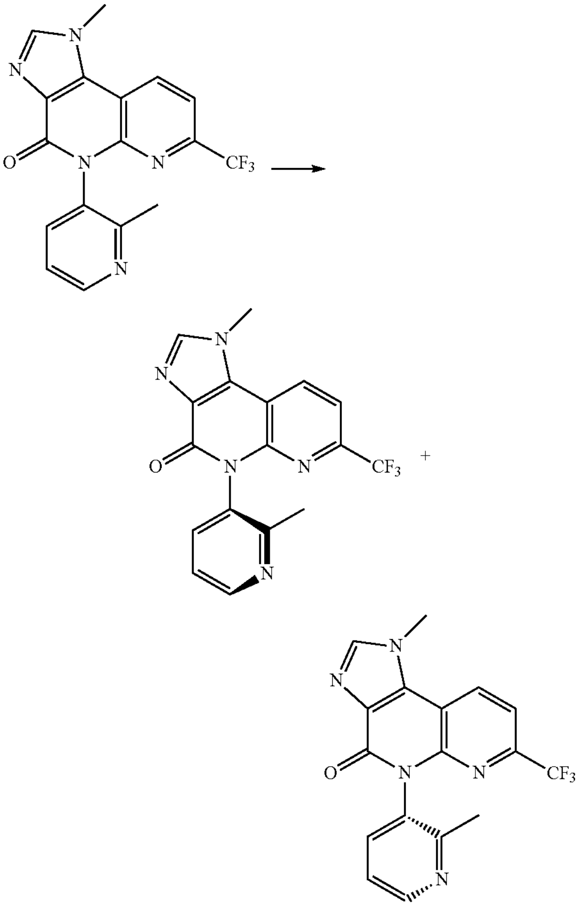

Step 1: synthesis of methyl 1-methyl-5-(trimethylstannyl)-1H-imidazole-4-formate (Intermediate 20-1)

Intermediate 15-4 (1 g) was dissolved in xylene (6 mL), and tetrakis(triphenylphosphine)palladium(0) (11.44 mg, 9.90 μmol) and hexamethyldistannane (2.99 g, 9.13 mmol) were added. The reaction mixture was warmed to 140° C. and stirred for reaction for 4 h under nitrogen atmosphere. After the reaction was completed, the reaction mixture was added dropwise to a saturated potassium fluoride solution (10 mL), and the mixture was stirred for 2 h. Then water (200 mL) was then added. The mixture was extracted with ethyl acetate (100 mL×3 times). The organic phases were combined and dried over anhydrous sodium sulfate. After the organic phase was filtered, the organic layer was concentrated to dryness under reduced pressure, and the residue was purified by silica gel column chromatography (petroleum ether:ethyl acetate=2:1 to 0:1) to give the title compound (470 mg).

MS m/z (ESI): 304.9[M+H]$^+$.

Step 2: synthesis of 3-bromo-N-(2-methylpyridin-3-yl)-6-(trifluoromethyl)pyridin-2-amine (intermediate 20-3)

Intermediate 20-2 (207.61 mg, 1.92 mmol) was dissolved in anhydrous N,N-dimethylformamide (8 mL) under nitrogen atmosphere, sodium hydride (60% effective content, 153.57 mg, 3.84 mmol) was added to the reaction mixture after the reaction mixture was cooled to 0° C., and the reaction mixture was stirred at 0° C. for 30 min. Intermediate 15-1 (500 mg, 1.92 mmol) was then added, and the reaction mixture was stirred at 20° C. for 16 h under nitrogen atmosphere. After the reaction was completed, water (200 mL) was added to the reaction mixture. The mixture was extracted with ethyl acetate (100 mL×3 times). The organic phases were combined and dried over anhydrous sodium sulfate. After the organic phase was filtered, the organic phase was concentrated under reduced pressure to remove the solvent, and the residue was purified by silica gel column chromatography (petroleum ether:ethyl acetate=1:0 to 50:1) to give the title compound (320 mg).

MS m/z (ESI): 331.7 [M+H]$^+$.

$^1$H NMR (400 MHz, Methanol-$d_4$) δ 8.27 (d, J=4.9 Hz, 1H), 8.14-8.03 (m, 2H), 7.35-7.33 (m, 1H), 7.09 (d, J=7.8 Hz, 1H), 2.49 (s, 3H).

Step 3: synthesis of 1-methyl-5-(2-methylpyridin-3-yl)-7-(trifluoromethyl)-1,5-dihydro-4H-imidazo[4,5-c][1,8]naphthyridin-4-one (Compound 20)

Intermediate 20-3 (38.37 mg, 115.53 μmol) was added to anhydrous xylene (1 mL) under nitrogen atmosphere, and $Pd(PPh_3)_4$ (13.35 mg, 11.55 μmol) and intermediate 20-1 (35 mg, 115.53 μmol) were added to the reaction mixture. Subsequently, the reaction mixture was stirred at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 0%-30%, 12 min) to give the title compound (10 mg, racemate).

$^1$H NMR (400 MHz, Methanol-$d_4$) δ 8.93 (d, J=8.3 Hz, 1H), 8.60 (dd, J=1.4, 4.9 Hz, 1H), 8.28 (s, 1H), 7.82 (d, J=8.3 Hz, 1H), 7.75 (dd, J=1.4, 7.9 Hz, 1H), 7.55-7.52 (m, 1H), 4.36 (s, 3H), 2.21 (s, 3H).

MS m/z (ESI): 360.1 [M+H]$^+$.

Compound 20 (80 mg) was prepared and separated by supercritical fluid chromatography (column: DAICEL CHIRALPAK AD (250 mm×30 mm, 10 μm); mobile phase: A: carbon dioxide; B: 35% ethanol (0.1% ammonia water); flow rate: 80 mL/min) to give Compound 20-P1 (10.9 mg, RT: 1.349 min) and Compound 20-P2 (10.7 mg, RT: 1.586 min).

Compound 20-P1:

$^1$H NMR (400 MHz, Methanol-$d_4$) δ 8.93 (d, J=8.0 Hz, 1H), 8.60 (dd, J=1.4, 4.9 Hz, 1H), 8.27 (s, 1H), 7.82 (d, J=8.3 Hz, 1H), 7.75 (dd, J=1.4, 7.9 Hz, 1H), 7.52 (dd, J=4.9, 7.9 Hz, 1H), 4.36 (s, 3H), 2.21 (s, 3H).

MS m/z (ESI): 360.1 [M+H]$^+$.

Compound 20-P2:

$^1$H NMR (400 MHz, Methanol-$d_4$) δ 8.93 (d, J=8.0 Hz, 1H), 8.60 (dd, J=1.4, 4.9 Hz, 1H), 8.27 (s, 1H), 7.82 (d, J=8.3 Hz, 1H), 7.76 (dd, J=1.4, 7.9 Hz, 1H), 7.53 (dd, J=5.0, 8.0 Hz, 1H), 4.36 (s, 3H), 2.21 (s, 3H).

MS m/z (ESI): 360.1 [M+H]$^+$.

Example 21. 1-methyl-5-phenyl-7-(trifluoromethyl)-1,5-dihydro-4H-imidazo[4,5-c][1,8]naphthyridin-4-one (Compound 21)

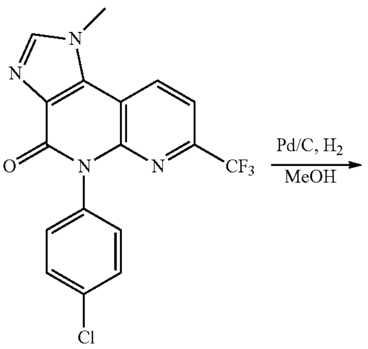

Compound 19

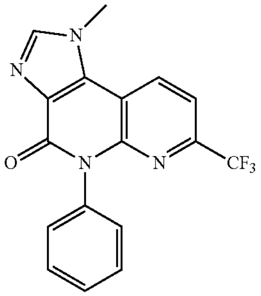

Compound 21

Compound 19 (50 mg, 132.02 μmol) was dissolved in methanol (10 mL), and wet palladium on carbon (7.02 mg, 6.60 μmol, 10% purity) was added. The reaction system was purged with hydrogen and the reaction mixture was stirred at 50° C. for 24 h. After the reaction was completed, the mixture was filtered through celite, and the filtrate was concentrated to dryness under reduced pressure. The residue was purified by high performance liquid chromatography (column: Waters Xbridge BEH C18 100×25 mm×5 μm;

mobile phase: [A: water (0.225% formic acid), B: acetonitrile]; B %: 22%-42%, 12 min) to give the title compound (10.2 mg).

MS m/z (ESI): 345.0 [M+H]$^+$.

$^1$H NMR (400 MHz, Methanol-$d_4$) δ=8.86 (d, J=8.1 Hz, 1H), 8.22 (s, 1H), 7.74 (d, J=8.1 Hz, 1H), 7.61-7.53 (m, 2H), 7.53-7.48 (m, 1H), 7.28 (d, J=7.3 Hz, 2H), 4.33 (s, 3H).

Example 22. 5-(3-chlorophenyl)-1-methyl-7-(trifluoromethyl)-1,5-dihydro-1H-imidazo[4,5-c][1,8]naphthyridin-4-one (Compound 22)

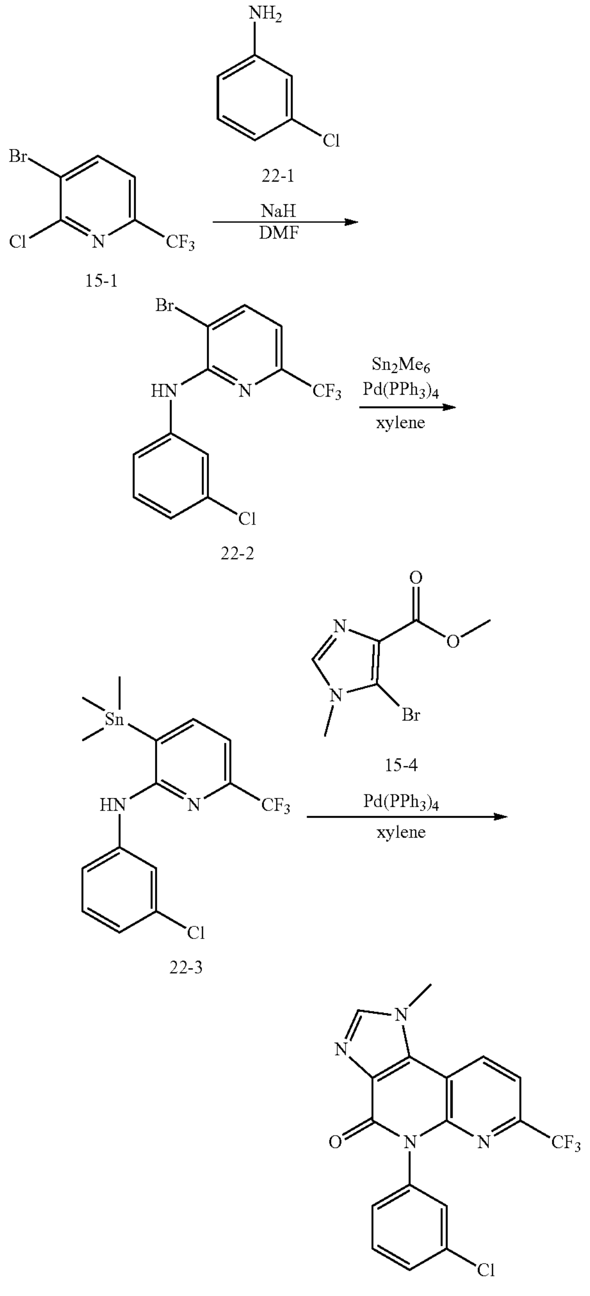

Step 1: synthesis of 3-bromo-N-(3-chlorophenyl)-6-(trifluoromethyl)pyridin-2-amine (Intermediate 22-2)

Intermediate 22-1 (244.92 mg, 1.92 mmol) was dissolved in N,N-dimethylformamide (5 mL), sodium hydride (60% effective content, 153.57 mg, 3.84 mmol) was added at 0° C., and the mixture was stirred at 0° C. for 30 min. A solution of intermediate 15-1 (500 mg, 1.92 mmol) in N,N-dimethylformamide was added, and the reaction mixture was stirred for reaction at 20° C. for 16 h. After the reaction was completed, the reaction mixture was cooled to 0° C. and quenched with water (5 mL), and the mixture was extracted with ethyl acetate (30 mL). The organic phase was concentrated to dryness under reduced pressure. The residue was purified by a flash silica gel column (ISCO®; 4 g of SepaFlash© silica gel column; eluent: 0-5% ethyl acetate/petroleum ether, gradient @ 20 mL/min) to give the title compound (420 mg).

MS m/z (ESI): 352.8 [M+H]$^+$.

Step 2: synthesis of N-(3-chlorophenyl)-6-(trifluoromethyl)-3-(trimethylstannyl)pyridin-2-amine (intermediate 22-3)

Intermediate 22-2 (290 mg, 824.92 μmol), hexamethyldistannane (540.54 mg, 1.65 mmol), and tetrakis(triphenylphosphine)palladium(0) (82.18 mg, 71.11 μmol) were sequentially dissolved in xylene (5 mL), the reaction system was purged with nitrogen 3 times, and the reaction mixture was stirred for reaction at 140° C. for 5 h. After the reaction was completed, the reaction mixture was cooled to 20° C. and filtered. The filtrate was concentrated to dryness under reduced pressure. The residue was purified by a silica gel column (ISCO®; 12 g of SepaFlash© silica gel column; eluent: 0-10% ethyl acetate/petroleum ether, gradient @ 30 mL/min) to give the title compound (270 mg).

MS m/z (ESI): 436.7 [M+H]$^+$.

Step 3: synthesis of 5-(3-chlorophenyl)-1-methyl-7-(trifluoromethyl)-1,5-dihydro-1H-imidazo[4,5-c][1,8]naphthyridin-4-one (Compound 22)

Intermediate 22-3 (270 mg, 620.04 μmol), intermediate 15-4 (135.81 mg), and tetrakis(triphenylphosphine)palladium(0) (71.65 mg, 62.00 μmol) were dissolved in xylene (4 mL), and the mixture was stirred for reaction at 140° C. for 16 h under nitrogen atmosphere. After the reaction was completed, the reaction mixture was filtered, and the filtrate was concentrated to dryness under reduced pressure. The residue was purified by preparative high performance liquid chromatography (column: Waters Xbridge BEH C18 100×25 mm×5 μm; mobile phase: [A: water (0.225% formic acid), B: acetonitrile]; B %: 26%-46%, 12 min) to give the title compound (78.2 mg).

MS m/z (ESI): 379.0 [M+H]$^+$.

$^1$H NMR (400 MHz, Methanol-$d_4$) δ=8.86 (d, J=8.0 Hz, 1H), 8.22 (s, 1H), 7.76 (d, J=8.3 Hz, 1H), 7.60-7.49 (m, 2H), 7.41-7.34 (m, 1H), 7.28-7.22 (m, 1H), 4.32 (s, 3H).

Example 23. 5-(2-fluorophenyl)-1-methyl-7-(trifluoromethyl)-1,5-dihydro-4H-imidazo[4,5-c][1,8]naphthyridin-4-one (Compound 23)

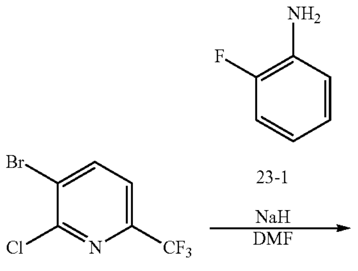

23-1

15-1

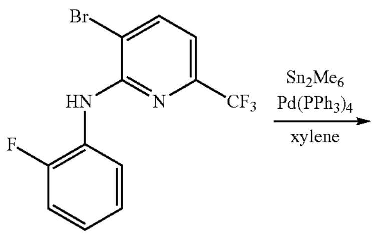

23-2

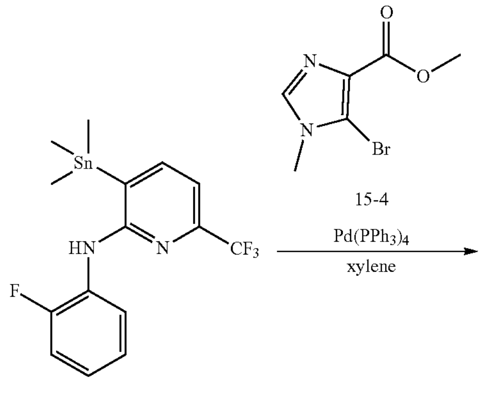

15-4

23-3

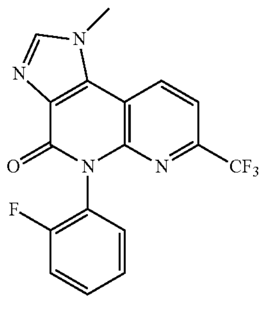

Compound 23

Step 1: synthesis of 3-bromo-N-(2-fluorophenyl)-6-(trifluoromethyl)pyridin-2-amine (Intermediate 23-2)

Reactant 23-1 (213.33 mg, 1.92 mmol, 185.50 μL) was dissolved in N,N-dimethylformamide (5 mL). Sodium hydride (60% effective content, 153.57 mg, 3.84 mmol) was added to the reaction mixture at 0° C. under nitrogen atmosphere, and the mixture was stirred for 30 min. A solution of intermediate 15-1 (500 mg, 1.92 mmol) in N,N-dimethylformamide (2 mL) was added to the reaction mixture at 0° C., and the reaction mixture was stirred for reaction at 20° C. for 16 h. The reaction mixture was quenched with water (20 mL), and the mixture was extracted thrice with ethyl acetate (20 mL). The organic phase was concentrated under reduced pressure, and the residue was purified by column chromatography (ISCO®; 12 g of Sepa-Flash© Silica Flash chromatographic column; eluent: 0-100% ethyl acetate/petroleum ether, gradient @ 40 mL/min) to give the title compound (440 mg).

MS m/z (ESI): 334.9 $[M+H]^+$.

Step 2: synthesis of N-(2-fluorophenyl)-6-(trifluoromethyl)-3-(trimethylstannyl)pyridin-2-amine (intermediate 23-3)

Intermediate 23-2 (150 mg, 447.63 μmol) was dissolved in xylene (2 mL), and $Pd(PPh_3)_4$ (51.73 mg, 44.76 μmol) and hexamethyldistannane (586.63 mg, 1.79 mmol, 371.28 μL) were added at 20° C. The reaction mixture was stirred for reaction at 140° C. for 1 h under nitrogen atmosphere. The reaction mixture was quenched with an aqueous cesium fluoride solution (20 mL), and the mixture was extracted thrice with ethyl acetate (20 mL). The organic phase was concentrated under reduced pressure, and the residue was purified by preparative thin-layer chromatography (silica, petroleum ether:ethyl acetate=15:1) to give the title compound (170 mg).

MS m/z (ESI): 419.0 $[M+H]^+$.

Step 3: synthesis of 5-(2-fluorophenyl)-1-methyl-7-(trifluoromethyl)-1,5-dihydro-4H-imidazo[4,5-c][1,8]naphthyridin-4-one (Compound 23)

Intermediate 23-3 (170 mg, 405.72 μmol) and intermediate 15-4 (133.30 mg) were dissolved in xylene (2 mL), $Pd(PPh_3)_4$ (70.33 mg, 60.86 μmol) was added at 20° C., and the reaction mixture was stirred for reaction at 140° C. for 16 h under nitrogen atmosphere. The reaction mixture was diluted with water, and the mixture was extracted thrice with ethyl acetate (20 mL). The organic phase was concentrated under reduced pressure, and the residue was purified by preparative thin-layer chromatography (silica, petroleum ether:ethyl acetate=15:1). Subsequently, the residue was further purified by high performance liquid chromatography (column: YMC-Actus Triart C18 150×30 mm×5 μm; mobile phase: [A: water (0.05% ammonia water v/v), B: acetonitrile]; B %: 42%-62%, 11 min) to give the title compound (25.5 mg).

MS m/z (ESI): 363.1 $[M+H]^+$.

$^1H$ NMR (400 MHz, DMSO-$d_6$) δ=8.86 (d, J=8.3 Hz, 1H), 8.35 (s, 1H), 7.85 (d, J=8.0 Hz, 1H), 7.61-7.53 (m, 1H), 7.51-7.43 (m, 2H), 7.43-7.36 (m, 1H), 4.27 (s, 3H)

Example 24. 5-(2-chloro-5-fluorophenyl)-1-methyl-7-(trifluoromethyl)-1,5-dihydro-4H-imidazo[4 5-c][1,8]naphthyridin-4-one (Compound 24)

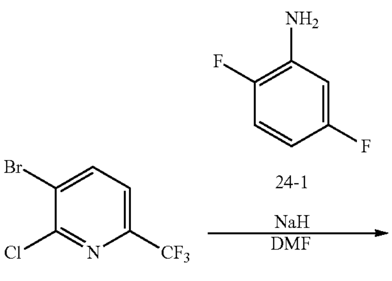

24-1

15-1

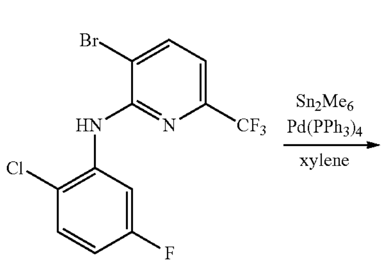

24-2

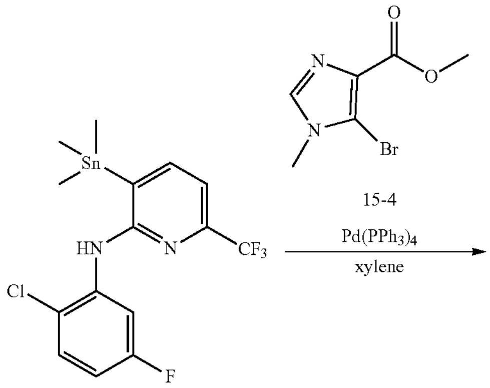

15-4

24-3

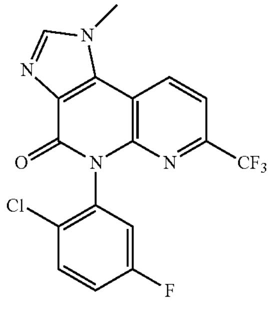

Compound 24

Step 1: synthesis of 3-bromo-N-(2-chloro-5-fluorophenyl)-6-(trifluoromethyl)pyridin-2-amine (intermediate 24-2)

Intermediate 24-1 (558.96 mg, 3.84 mmol) was dissolved in anhydrous N,N-dimethylformamide (10 mL) at 25° C., sodium hydride (60% effective content, 230.38 mg, 5.76 mmol) was added to the reaction mixture after the reaction mixture was cooled to 0° C., and the reaction mixture was stirred at 0° C. for 30 min under nitrogen atmosphere. Intermediate 15-1 (1 g, 3.84 mmol) was added to the reaction mixture. The reaction mixture was stirred at 20° C. for 16 h under nitrogen atmosphere. After the reaction was completed as detected by LCMS, After the reaction mixture was cooled to 0° C., water (10 mL) was added, and the mixture was extracted 2 times with ethyl acetate (10 mL). The organic phases were combined and dried over anhydrous sodium sulfate. After the organic phase was filtered, the organic phase was concentrated under reduced pressure to remove the solvent, and the residue was purified by silica gel column chromatography (mobile phase: petroleum ether: ethyl acetate=0-5%; flow rate: 40 mL/min) to give the title compound (1 g).

MS m/z (ESI): 368.8 $[M+H]^+$.

Step 2: synthesis of N-(2-chloro-5-fluorophenyl)-6-(trifluoromethyl)-3-(trimethylstannyl)pyridin-2-amine (intermediate 24-3)

Intermediate 24-2 (50 mg, 135.30 μmol) was dissolved in an anhydrous xylene (1 mL) solution at 25° C., and $Pd(PPh_3)_4$ (15.64 mg, 13.53 μmol) and hexamethyldistannane (44.33 mg, 135.30 μmol) were added to the reaction mixture. The reaction mixture was stirred at 140° C. for 16 h under nitrogen atmosphere. A target product was generated as detected by LCMS. After the reaction was completed, cesium fluoride (10 mL) was added to the reaction mixture. The mixture was extracted 2 times with ethyl acetate (10 mL). The organic phases were combined and dried over anhydrous sodium sulfate. After the organic phase was filtered, the organic phase was concentrated under reduced pressure to remove the solvent, and the residue was purified by preparative thin-layer chromatography (mobile phase: petroleum ether:ethyl acetate=1:1; flow rate: 40 mL/min) to give the title compound (35 mg).

MS m/z (ESI): 455.0 $[M+H]^+$.

Step 3: synthesis of 5-(2-chloro-5-fluorophenyl)-1-methyl-7-(trifluoromethyl)-1,5-dihydro-4H-imidazo[4,5-c][1,8]naphthyridin-4-one (Compound 24)

Intermediate 24-3 (35.00 mg, 77.19 μmol) was added to anhydrous xylene (1 mL) at 25° C., $Pd(PPh_3)_4$ (8.92 mg, 7.72 μmol) and intermediate 15-4 (25.36 mg) were added to the reaction mixture, and the reaction mixture was reacted at 140° C. for 16 h under nitrogen atmosphere. After the reaction was completed, the reaction mixture was filtered and concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 30%-40%, 12 min) to give the title compound (2.2 mg).

MS m/z (ESI): 397.0 $[M+H]^+$.

$^1H$ NMR (400 MHz, Methanol-$d_4$) δ=8.91 (d, J=8.0 Hz, 1H), 8.26 (s, 1H), 7.81 (d, J=8.3 Hz, 1H), 7.69 (dd, J=5.4, 8.7 Hz, 1H), 7.39-7.30 (m, 2H), 4.35 (s, 3H).

Example 25. 5-(2-chloro-3-fluorophenyl)-1-methyl-7-(trifluoromethyl)-1,5-dihydro-4H-imidazo[4,5-c][1,8]naphthyridin-4-one (Compound 25)

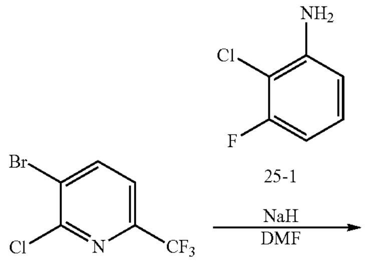

25-1

15-1

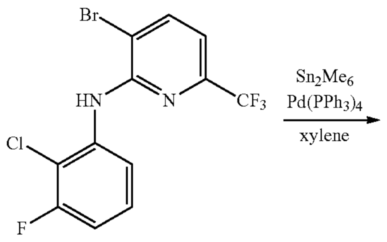

25-2

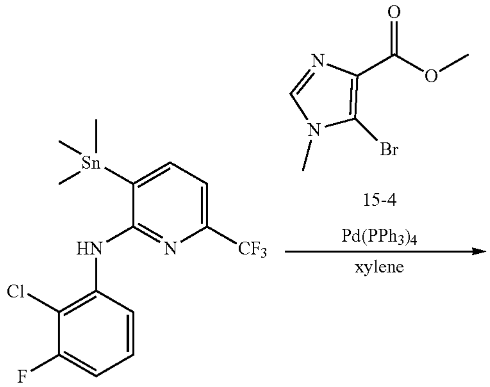

15-4

25-3

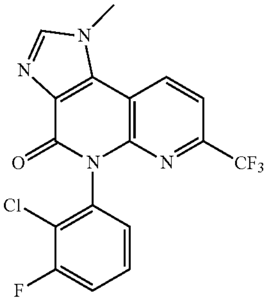

Compound 25

-continued

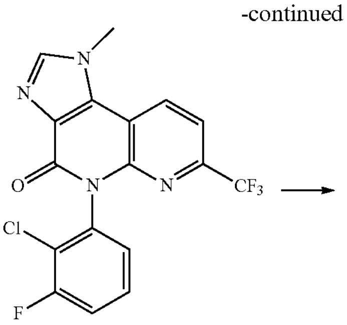

Compound 25

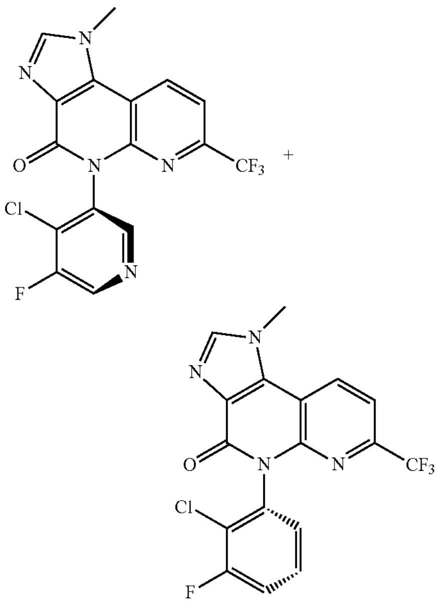

Step 1: synthesis of 3-bromo-N-(2-chloro-3-fluorophenyl)-6-(trifluoromethyl)pyridin-2-amine (intermediate 25-2)

Reactant 25-1 (279.45 mg, 1.92 mmol) was dissolved in N,N-dimethylformamide (5 mL). Sodium hydride (60% effective content, 153.57 mg, 3.84 mmol) was added to the reaction mixture at 0° C. under nitrogen atmosphere, and the mixture was stirred for 30 min. Subsequently, reactant 15- 1 (500 mg, 1.92 mmol) was dissolved in N,N-dimethylformamide (2 mL) and added dropwise to the reaction mixture. The mixture was stirred for reaction at 20° C. for 16 h. The reaction mixture was quenched with water (20 mL), and the mixture was extracted with ethyl acetate (20 mL×3 times). The organic phases were combined, dried, and concentrated under reduced pressure, and the residue was purified by column chromatography (ISCO®; 12 g of SepaFlash© Silica Flash chromatographic column; eluent: 0-100% ethyl acetate/petroleum ether, gradient @ 40 mL/min) to give the title compound (580 mg).

MS m/z (ESI): 368.9 $[M+H]^+$.

$^1H$ NMR (400 MHz, Methanol-$d_4$) δ 8.38 (d, J=8.5 Hz, 1H), 8.17 (d, J=8.0 Hz, 1H), 7.38-7.34 (m, 1H), 7.21 (d, J=8.0 Hz, 1H), 7.03-7.00 (m, 1H).

Step 2: synthesis of N-(2-chloro-3-fluorophenyl)-6-(trifluoromethyl)-3-(trimethylstannyl)pyridin-2-amine (intermediate 25-3)

Intermediate 25-2 (150 mg, 405.91 μmol) was dissolved in xylene (2 mL), $Pd(PPh_3)_4$ (46.91 mg, 40.59 μmol) and hexamethyldistannane (531.95 mg, 1.62 mmol) were added at 20° C., and the mixture was stirred for reaction at 140° C. for 1 h under nitrogen atmosphere. The reaction mixture was quenched with a saturated aqueous cesium fluoride solution. The mixture was extracted with ethyl acetate (20 mL×3 times). The organic phases were combined and dried over anhydrous sodium sulfate. After the organic phase was filtered, the organic phase was concentrated under reduced pressure, and the residue was purified by preparative thin-layer chromatography (petroleum ether:ethyl acetate=15:1) to give the title compound (165 mg).

MS m/z (ESI): 454.9$[M+H]^+$.

Step 3: synthesis of 5-(2-chloro-3-fluorophenyl)-1-methyl-7-(trifluoromethyl)-1,5-dihydro-4H-imidazo [4,5-c][1,8]naphthyridin-4-one (Compound 25)

Intermediate 25-3 (160 mg, 352.85 μmol) and intermediate 15-4 (115.93 mg) were dissolved in xylene (2 mL), $Pd(PPh_3)_4$ (61.16 mg, 52.93 μmol) was added at 20° C., and the reaction mixture was stirred for reaction at 140° C. for 16 h under nitrogen atmosphere. After the reaction was completed, the reaction mixture was diluted with water (20 mL). The mixture was extracted with ethyl acetate (20 mL×3 times). The organic phases were combined and dried over anhydrous sodium sulfate. After the organic phase was filtered, the organic phase was concentrated under reduced pressure, and the residue was purified by preparative thin-layer chromatography (petroleum ether:ethyl acetate=15:1). The residue was further purified by high performance liquid chromatography (column: YMC-Actus Triart C18 150×30 mm×5 μm; mobile phase: [A: water (0.05% ammonia water v/v), B: acetonitrile]; B %: 40%-60%, 11 min) to give the title compound (24.7 mg, racemate).

MS m/z (ESI): 397.0 $[M+H]^+$.

$^1H$ NMR (400 MHz, DMSO-$d_6$) δ 8.89 (d, J=8.0 Hz, 1H), 8.36 (s, 1H), 7.86 (d, J=8.3 Hz, 1H), 7.65-7.57 (m, 2H), 7.43-7.40 (m, 1H), 4.28 (s, 3H).

Compound 25 (26 mg) was prepared and separated by supercritical fluid chromatography (column: DAICEL CHIRALCEL OJ (250 mm×30 mm, 10 μm); mobile phase: A: carbon dioxide; B: isopropanol (0.1% ammonia water); B %: 50%; flow rate: 80 mL/min) to give Compound 25-P1 (7.7 mg, RT: 1.688 min) and Compound 25-P2 (3.9 mg, RT: 2.349 min).

Compound 25-P1:

$^1H$ NMR (400 MHz, DMSO-$d_6$) δ 8.88 (d, J=8.0 Hz, 1H), 8.36 (s, 1H), 7.87 (d, J=8.3 Hz, 1H), 7.65-7.58 (m, 2H), 7.43-7.39 (m, 1H), 4.28 (s, 3H).

MS m/z (ESI): 397.1 $[M+H]^+$.

Compound 25-P2:

$^1H$ NMR (400 MHz, DMSO-$d_6$) δ 8.88 (d, J=8.3 Hz, 1H), 8.36 (s, 1H), 7.87 (d, J=8.3 Hz, 1H), 7.66-7.57 (m, 2H), 7.45-7.38 (m, 1H), 4.28 (s, 3H).

MS m/z (ESI): 397.1 $[M+H]^+$.

Example 26. 5-(2-chloro-6-fluorophenyl)-1-methyl-7-(trifluoromethyl)-1,5-dihydro-4H-imidazo[4,5-c][1,8]naphthyridin-4-one (Compound 26)

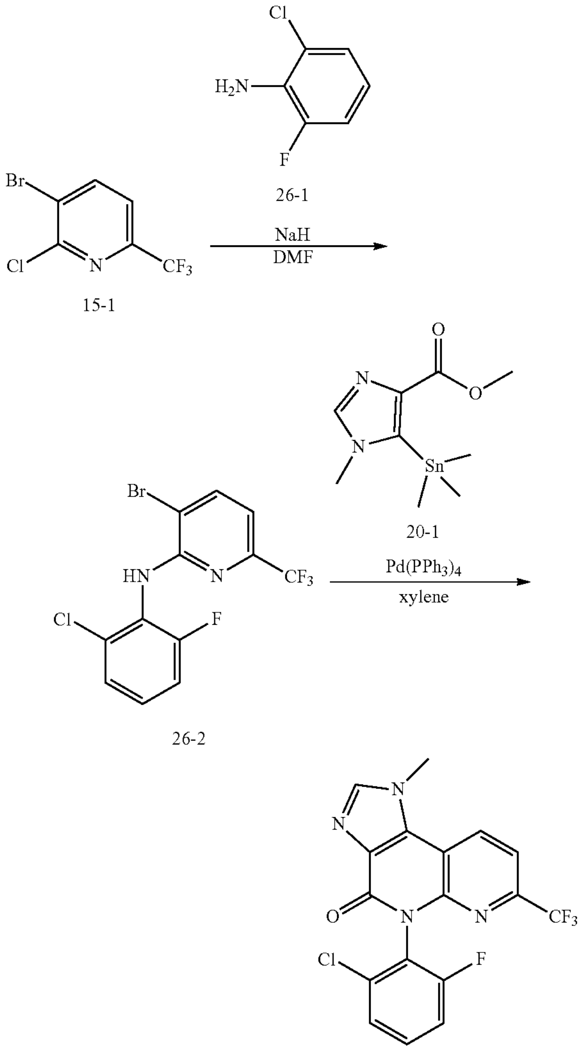

26-1

15-1

20-1

26-2

Compound 26

Step 1: synthesis of 3-bromo-N-(2-chloro-6-fluorophenyl)-6-(trifluoromethyl)pyridin-2-amine (intermediate 26-2)

Reactant 26-1 (279.48 mg, 1.92 mmol) was dissolved in N,N-dimethylformamide (10 mL), and sodium hydride (60% effective content, 115.20 mg, 2.88 mmol) was added at 0° C. After the reaction mixture was stirred for reaction at 0° C. for 2 h, intermediate 15-1 (500 mg, 1.92 mmol) was dissolved in N,N-dimethylformamide (5 mL) and added dropwise to the reaction mixture. The reaction mixture was stirred for reaction at 0° C. for 12 h. The reaction mixture was quenched with water (5 mL), and the mixture was extracted thrice with ethyl acetate (10 mL×3). The organic layer was washed with saturated brine and concentrated to dryness under reduced pressure, and the residue was purified by silica gel column chromatography (petroleum ether:ethyl acetate=10:1) to give the title compound (473 mg).

MS m/z (ESI): 368.7 $[M+H]^+$.

Step 2: synthesis of 5-(2-chloro-6-fluorophenyl)-1-methyl-7-(trifluoromethyl)-1,5-dihydro-4H-imidazo[4,5-c][1,8]naphthyridin-4-one (Compound 26)

Intermediate 26-2 (36.59 mg, 99.03 μmol) was dissolved in xylene (2 mL), and intermediate 20-1 (30 mg, 99.03 μmol) and tetrakis(triphenylphosphine)palladium(0) (11.44 mg, 9.90 μmol) were added. The reaction mixture was warmed to 140° C. and stirred for reaction for 12 h under nitrogen atmosphere. The reaction mixture was concentrated to dryness under reduced pressure, and the residue was purified by preparative high performance liquid chromatography (column: Waters Xbridge BEH C18 100×25 mm×5 μm; mobile phase: [A: water (0.225% formic acid), B: acetonitrile]; B %: 25%-45%, 12 min) to give the title compound (2.5 mg).

MS m/z (ESI): 397.0$[M+H]^+$.

$^1$H NMR (400 MHz, Methanol-$d_4$) δ=8.93 (d, J=8.3 Hz, 1H), 8.27 (s, 1H), 7.83 (d, J=8.2 Hz, 1H), 7.63-7.56 (m, 1H), 7.54-7.50 (m, 1H), 7.41-7.33 (m, 1H), 4.36 (s, 3H)

Example 27. 1-methyl-5-(3-methylpyridin-4-yl)-7-(trifluoromethyl)-1,5-dihydro-4H-imidazo[4,5-c][1,8]naphthyridin-4-one (Compound 27)

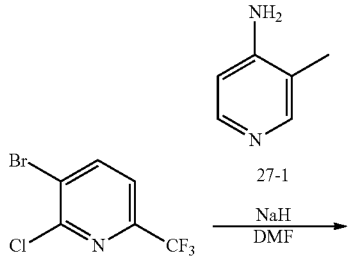

15-1

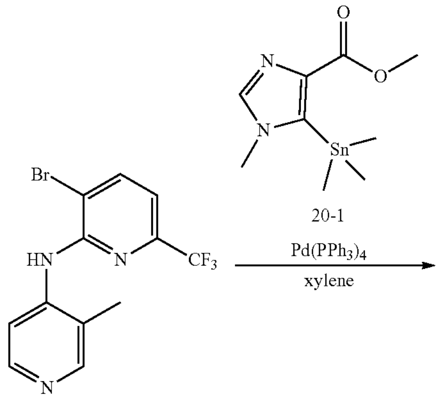

27-2

-continued

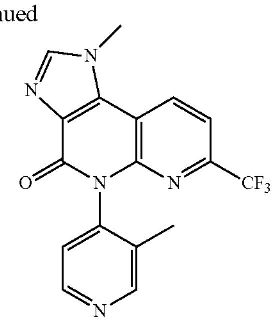

Compound 27

Step 1: synthesis of 3-bromo-N-(3-methylpyridin-4-yl)-6-(trifluoromethyl)pyridin-2-amine (intermediate 27-2)

Intermediate 27-1 (207.61 mg, 1.92 mmol) was dissolved in an anhydrous N,N-dimethylformamide solution (5 mL) at 25° C., and sodium hydride (60% effective content, 153.57 mg, 3.84 mmol) was slowly added thereto after the reaction mixture was cooled to 0° C. After the mixture was stirred for 30 min, intermediate 15-1 (500 mg, 1.92 mmol) was dissolved in an anhydrous N,N-dimethylformamide solution (2 mL) and added to the reaction system. The reaction mixture was stirred for reaction at 25° C. for 16 h under nitrogen atmosphere. A target product had been generated as detected by LCMS. After the reaction was completed, the reaction mixture was cooled to 0° C. and quenched with an aqueous solution (5 mL), and ethyl acetate (50 mL) and water (100 mL) were added to the reaction mixture. The mixture was washed 2 times with a saturated aqueous sodium chloride solution (100 mL). The organic phases were combined and dried over anhydrous sodium sulfate. The organic phase was filtered and concentrated under reduced pressure to remove the solvent. The residue was purified by silica gel column chromatography (ethyl acetate/petroleum ether: 0-70%, 40 mL/min) to give the title compound (300 mg).

MS m/z (ESI): 331.8 $[M+H]^+$.

Step 2: synthesis of 1-methyl-5-(3-methylpyridin-4-yl)-7-(trifluoromethyl)-1,5-dihydro-4H-imidazo[4,5-c][1,8]naphthyridin-4-one (Compound 27)

Intermediate 27-2 (43.85 mg, 132.04 μmol) was dissolved in an anhydrous xylene solution (1 mL) at 20° C., and $Pd(PPh_3)_4$ (15.26 mg, 13.20 μmol) and intermediate 20-1 (40 mg, 132.04 μmol) were added to the reaction mixture. The reaction mixture was stirred for reaction at 140° C. for 16 h under nitrogen atmosphere. A target product was generated as detected by LCMS. After the reaction was completed, ethyl acetate (10 mL) and water (20 mL) were added to the reaction mixture, and the mixture was extracted 2 times with water (20 mL). The organic phases were combined and dried over anhydrous sodium sulfate. The organic phase was filtered and concentrated under reduced pressure to remove the solvent. The residue was purified by high performance liquid chromatography (column: Boston Prime C18 150×30 mm×5 μm; mobile phase: A: water (0.05% ammonia water+10 mM ammonium bicarbonate), B: acetonitrile; B %: 25%-55%, 10 min) to give the title compound (9.2 mg).

MS m/z (ESI): 360.1 $[M+H]^+$.

$^1H$ NMR (400 MHz, Methanol-$d_4$) δ=8.93 (d, J=8.0 Hz, 1H), 8.69 (s, 1H), 8.60 (d, J=5.3 Hz, 1H), 8.28 (s, 1H), 7.82 (d, J=8.3 Hz, 1H), 7.38 (d, J=5.3 Hz, 1H), 4.36 (s, 3H), 2.05 (s, 3H).

Example 28. 1-methyl-5-(4-methylpyridin-3-yl)-7-(trifluromethyl)-1,5-dihydro-4H-imidazo[4,5-c][1,8]naphthyridin-4-one (Compound 28)

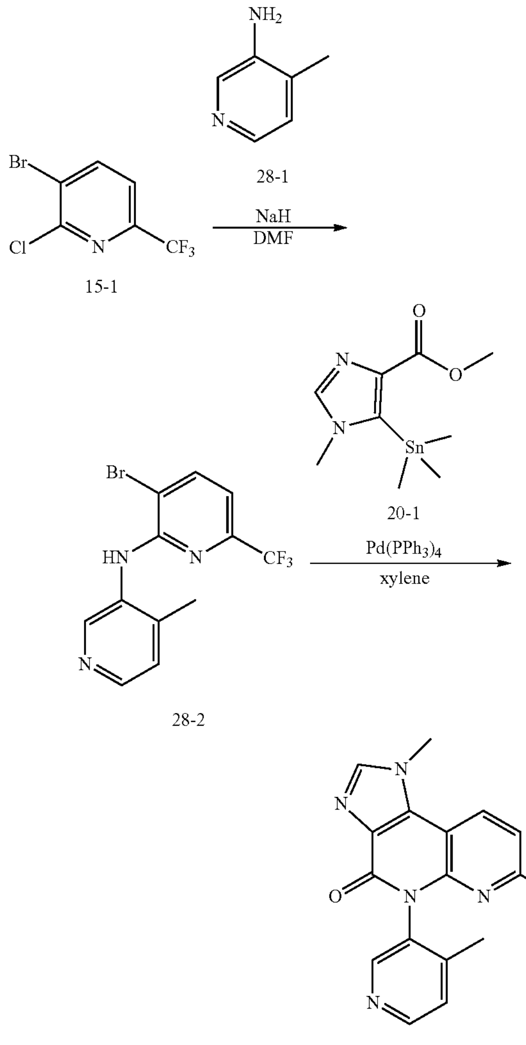

28-1

15-1

20-1

28-2

Compound 28

Step 1: synthesis of 3-bromo-N-(4-methylpyridin-3-yl)-6-(trifluoromethyl)pyridin-2-amine (intermediate 28-2)

Intermediate 28-1 (207.61 mg, 1.92 mmol) was dissolved in an anhydrous N,N-dimethylformamide solution (5 mL) at 25° C., and sodium hydride (60% effective content, 153.57 mg, 3.84 mmol) was slowly added thereto after the reaction mixture was cooled to 0° C. After the mixture was stirred for 30 min, intermediate 15-1 (500 mg, 1.92 mmol) was dissolved in an anhydrous N,N-dimethylformamide solution (2 mL) and added to the reaction system. The reaction mixture was stirred for reaction at 25° C. for 16 h under nitrogen atmosphere. A target product had been generated as detected by LCMS. After the reaction was completed, the reaction mixture was cooled to 0° C. The sodium hydride was quenched with an aqueous solution (5 mL), and ethyl acetate (50 mL) and water (100 mL) were added to the reaction mixture. The mixture was washed 2 times with a saturated aqueous sodium chloride solution (100 mL). The organic phases were combined and dried over anhydrous sodium sulfate. The organic phase was filtered and concentrated under reduced pressure to remove the solvent. The residue was purified by silica gel column chromatography (ethyl acetate/petroleum ether: 0-50%, 40 mL/min) to give the title compound (350 mg).

MS m/z (ESI): 331.8 $[M+H]^+$.

Step 2: synthesis of 1-methyl-5-(4-methylpyridin-3-yl)-7-(trifluoromethyl)-1,5-dihydro-4H-imidazo[4,5-c][1,8]naphthyridin-4-one (Compound 28)

Intermediate 28-2 (43.85 mg, 132.04 μmol) was dissolved in an anhydrous xylene solution (1 mL) at 20° C., and $Pd(PPh_3)_4$ (15.26 mg, 13.20 μmol) and intermediate 20-1 (40 mg, 132.04 μmol) were added to the reaction mixture. The reaction mixture was stirred for reaction at 140° C. for 16 h under nitrogen atmosphere. A target product was generated as detected by LCMS. After the reaction was completed, ethyl acetate (10 mL) and water (20 mL) were added to the reaction mixture, and the mixture was washed 2 times with a saturated sodium chloride solution (20 mL). The organic phases were combined and dried over anhydrous sodium sulfate. The organic phase was filtered and concentrated under reduced pressure to remove the solvent. The residue was purified by high performance liquid chromatography (column: Boston Prime C18 150×30 mm×5 μm; mobile phase: A: water (0.05% ammonia water+10 mM ammonium bicarbonate), B: acetonitrile; B %: 25%-55%, 10 min) to give the title compound (7.5 mg).

$^1H$ NMR (400 MHz, Methanol-$d_4$) δ=8.93 (d, J=8.3 Hz, 1H), 8.56 (d, J=5.3 Hz, 1H), 8.37 (s, 1H), 8.28 (s, 1H), 7.82 (d, J=8.3 Hz, 1H), 7.58 (d, J=5.0 Hz, 1H), 4.36 (s, 3H), 2.08 (s, 3H).

MS m/z (ESI): 360.1 $[M+H]^+$.

Example 29. 1-methyl-5-(3-methylpyridin-2-yl)-7~trifluoromethyl)-1,5-dihydro-4H-imidazo[4,5-c][1,8]naphthyridin-4-one (Compound 29)

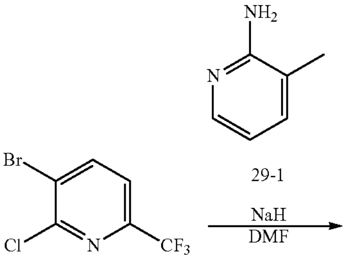

29-1

15-1

-continued

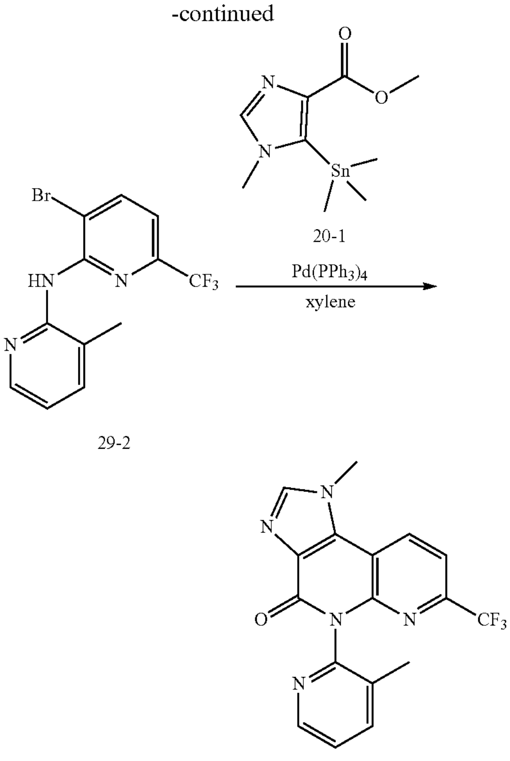

20-1

29-2

Compound 29

Step 1: synthesis of 3-bromo-N-(3-methylpyridin-2-yl)-6-(trifluoromethyl)pyridin-2-amine (intermediate 29-2)

Intermediate 29-1 (207.61 mg, 1.92 mmol) was dissolved in an anhydrous N,N-dimethylformamide solution (5 mL) at 25° C., and sodium hydride (60% effective content, 153.57 mg, 3.84 mmol) was slowly added thereto after the reaction mixture was cooled to 0° C. After the mixture was stirred for 30 min, intermediate 15-1 (500 mg, 1.92 mmol) was dissolved in an anhydrous N,N-dimethylformamide solution (2 mL) and added to the reaction system. The reaction mixture was stirred for reaction at 25° C. for 16 h under nitrogen atmosphere. A target product had been generated as detected by LCMS. After the reaction was completed, the reaction mixture was cooled to 0° C. The sodium hydride was quenched with an aqueous solution (5 mL), and ethyl acetate (50 mL) and water (100 mL) were added to the reaction mixture. The mixture was washed 2 times with a saturated aqueous sodium chloride solution (100 mL). The organic phases were combined and dried over anhydrous sodium sulfate. The organic phase was filtered and concentrated under reduced pressure to remove the solvent. The residue was purified by silica gel column chromatography (ethyl acetate/petroleum ether: 0-5%, 40 mL/min) to give the title compound (200 mg).

MS m/z (ESI): 331.9 $[M+H]^+$.

Step 2: synthesis of 1-methyl-5-(3-methylpyridin-2-yl)-7-(trifluoromethyl)-1,5-dihydro-4H-imidazo[4,5-c][1,8]naphthyridin-4-one (Compound 29)

Intermediate 29-2 (43.85 mg, 132.04 μmol) was dissolved in an anhydrous xylene solution (1 mL) at 20° C., and $Pd(PPh_3)_4$ (15.26 mg, 13.20 μmol) and intermediate 20-2 (40 mg, 132.04 μmol) were added to the reaction mixture. The reaction mixture was stirred for reaction at 140° C. for 16 h under nitrogen atmosphere. A target product was generated as detected by LCMS. After the reaction was completed, ethyl acetate (10 mL) and water (20 mL) were added to the reaction mixture, and the mixture was extracted 2 times with an aqueous solution (20 mL). The organic phases were combined and dried over anhydrous sodium sulfate. The organic phase was filtered and concentrated under reduced pressure to remove the solvent. The residue was purified by high performance liquid chromatography (column: Waters Xbridge BEH C18 100×25 mm×5 μm; mobile phase: A: water (0.225% formic acid), B: acetonitrile; B %: 37%-47%, 12 min) to give the title compound (1.7 mg). 1H NMR (400 MHz, Methanol-$d_4$) δ=8.93 (d, J=8.0 Hz, 1H), 8.50 (d, J=3.5 Hz, 1H), 8.28 (s, 1H), 8.00 (d, J=6.8 Hz, 1H), 7.81 (d, J=8.3 Hz, 1H), 7.57 (m, J=5.0, 7.8 Hz, 1H), 4.36 (s, 3H), 2.10 (s, 3H).

MS m/z (ESI): 360.1 $[M+H]^+$.

Example 30. 5-(2-chlorophenyl)-7-(trifluoromethyl)-3,5-dihydro-4H-pyrrolo[2,3-c][1,8]naphthyridin-4-one (Compound 30)

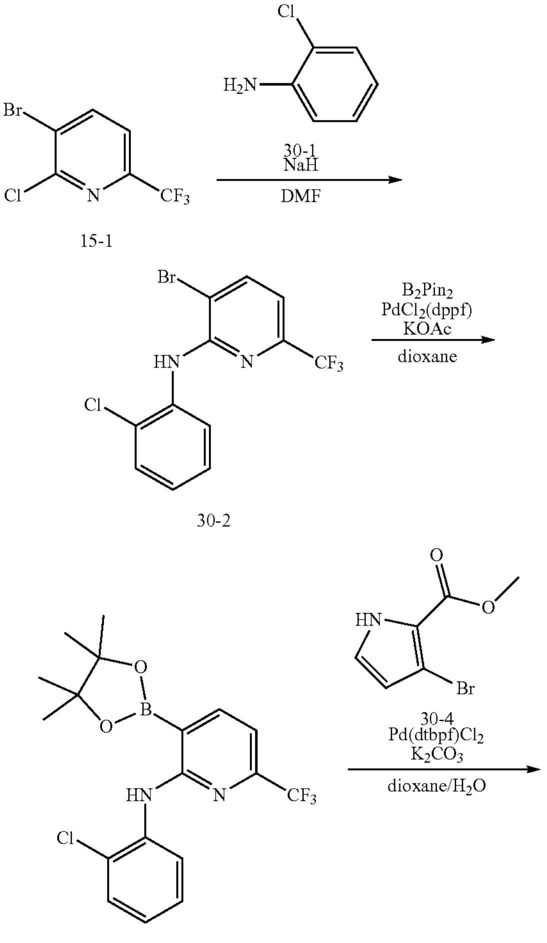

30-1

15-1

30-2

30-4

30-3

-continued

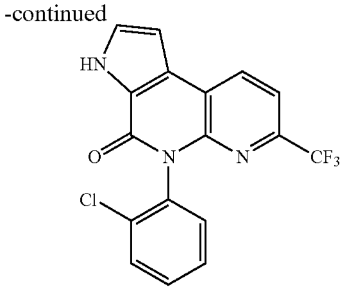

Compound 30

Step 1: synthesis of 3-bromo-N-(2-chlorophenyl)-6-(trifluoromethyl)pyridin-2-amine (Intermediate 30-2)

Reactant 30-1 (489.83 mg, 3.84 mmol) was dissolved in N,N-dimethylformamide (10 mL), and sodium hydride (60% effective content, 230.38 mg, 5.76 mmol) was added at 0° C. After the reaction mixture was stirred for reaction at 0° C. for 2 h, intermediate 15-1 (1 g, 3.84 mmol) was dissolved in N,N-dimethylformamide (5 mL) and added dropwise to the reaction mixture. The reaction mixture was stirred for reaction at 0° C. for 12 h. The reaction mixture was quenched with water (5 mL), and the mixture was extracted thrice with ethyl acetate (10 mL×3). The organic layer was concentrated to dryness under reduced pressure, and the residue was purified by silica gel column chromatography (petroleum ether:ethyl acetate=10:1) to give the title compound (500 mg).

MS m/z (ESI): 350.8 $[M+H]^+$.

Step 2: synthesis of N-(2-chlorophenyl)-3-(4,4,5,5-tetramethyl-1,3,2-dioxaborolan-2-yl)-6-(trifluoromethyl)pyridin-2-amine (intermediate 30-3)

Intermediate 30-2 (450 mg, 1.28 mmol) was dissolved in dioxane (6 mL), and bis(pinacolato)diboron (390.06 mg, 1.54 mmol), potassium acetate (376.87 mg, 3.84 mmol), and $Pd(dppf)Cl_2$ (46.83 mg, 64.00 μmol) were added. The reaction mixture was warmed to 90° C. and stirred for reaction for 1 h under nitrogen atmosphere. Water (5 mL) was added to the reaction mixture, and the mixture was extracted thrice with ethyl acetate (5 mL×3). The organic player was concentrated to dryness under reduced pressure, and the residue was purified by preparative thin-layer chromatography (silica, petroleum ether:ethyl acetate=10:1) to give the title compound (100 mg).

MS m/z (ESI): $399.0[M+H]^+$.

Step 3: synthesis of 5-(2-chlorophenyl)-7-(trifluoromethyl)-3,5-dihydro-4H-pyrrolo[2,3-c][1,8]naphthyridin-4-one (Compound 30)

Intermediate 30-3 (95 mg, 238.33 μmol) was dissolved in dioxane (4 mL) and water (1 mL), and intermediate 30-4 (145.87 mg, 714.98 μmol), potassium carbonate (98.82 mg, 714.98 μmol), and $Pd(dtbpf)Cl_2$ (15.53 mg, 23.83 μmol) were added. The reaction mixture was stirred for reaction at 100° C. for 2 h under nitrogen atmosphere. The reaction mixture was concentrated to dryness under reduced pressure, and the residue was purified by preparative high performance liquid chromatography (column: Waters Xbridge BEH C18 100×25 mm×5 μm; mobile phase: [A: water (0.225% formic acid), B: acetonitrile]; B %: 35%-55%, 12 min) to give the title compound (13.9 mg).

MS m/z (ESI): $364.0[M+H]^+$.

$^1H$ NMR (400 MHz, Methanol-$d_4$) δ=8.64 (d, J=8.0 Hz, 1H), 7.76-7.62 (m, 2H), 7.58-7.49 (m, 3H), 7.47-7.41 (m, 1H), 7.11 (t, J=2.7 Hz, 1H).

Example 31. 1-methyl-5-(2-methylphenyl)-7-(trifluoromethyl)-1,5-dihydro-4H-imidazo[4,5-c][1,8]naphthyridin-4-one (Compound 31)

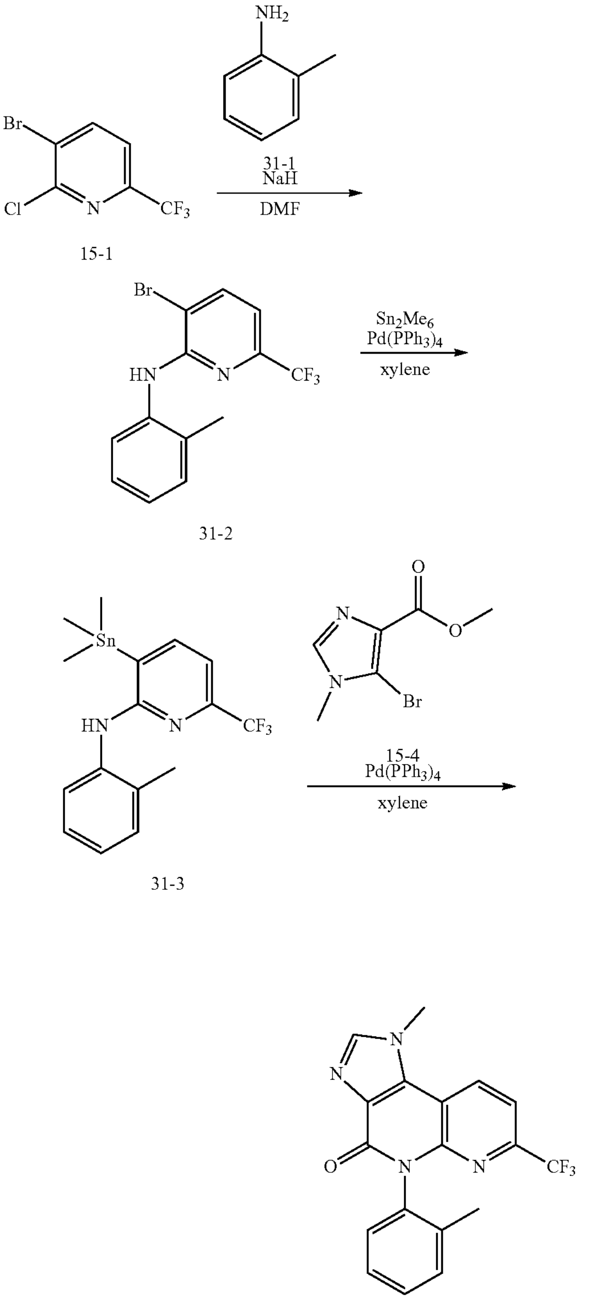

Compound 31

Step 1: synthesis of 3-bromo-N-(2-methylphenyl)-6-(trifluoromethyl)pyridin-2-amine (Intermediate 31-2)

Intermediate 31-1 (205.72 mg, 1.92 mmol) was dissolved in N,N-dimethylformamide (5 mL), sodium hydride (60% effective content, 191.97 mg, 4.80 mmol) was added at 0° C., and the mixture was stirred at 0° C. for 30 min. A solution of intermediate 15-1 (500 mg, 1.92 mmol) in N,N-dimethylformamide was added, and the reaction mixture was stirred for reaction at 20° C. for 16 h. Sodium hydride (76.79 mg, 1.92 mmol, 60% effective content) was added again, and the mixture was stirred at 40° C. for 30 min. The reaction mixture was cooled to 0° C. and quenched with water (5 mL), and the mixture was extracted with ethyl acetate (30 mL). The organic phase was concentrated to dryness under reduced pressure, and the residue was purified by a flash silica gel column (ISCO®; 4 g of SepaFlash® silica gel column; eluent: 0-10% ethyl acetate/petroleum ether, gradient @ 20 mL/min) to give the title compound (140 mg).

MS m/z (ESI): 330.9 $[M+H]^+$.

Step 2: synthesis of N-(2-methylphenyl)-6-(trifluoromethyl)-3-(trimethylstannyl)pyridin-2-amine (intermediate 31-3)

Intermediate 31-2 (110 mg, 332.20 μmol), hexamethyldistannane (217.67 mg, 664.39 μmol), and tetrakis(triphenylphosphine)palladium(0) (38.39 mg, 33.22 μmol) were sequentially dissolved in xylene (5 mL), and the mixture was stirred for reaction at 140° C. for 5 h under nitrogen atmosphere. After the reaction was completed, the reaction mixture was cooled to 20° C. and filtered. The filtrate was concentrated to dryness under reduced pressure. The residue was purified by a silica gel column (ISCO®; 12 g of SepaFlash® silica gel column; eluent: 0-10% ethyl acetate/petroleum ether, gradient @ 30 mL/min) to give the title compound (137 mg).

MS m/z (ESI): 414.9 $[M+H]^+$.

Step 3: synthesis of 1-methyl-5-(2-methylphenyl)-7-(trifluoromethyl)-1,5-dihydro-4H-imidazo[4,5-c][1,8]naphthyridin-4-one (Compound 31)

Intermediate 31-3 (137 mg, 330.09 μmol), intermediate 15-4 (72.30 mg), and tetrakis(triphenylphosphine)palladium (0) (38.14 mg, 33.01 μmol) were dissolved in xylene (4 mL), and the mixture was stirred for reaction at 140° C. for 16 h under nitrogen atmosphere. After the reaction was completed, the reaction mixture was filtered, and the filtrate was concentrated to dryness under reduced pressure. The residue was purified by preparative high performance liquid chromatography (column: Waters Xbridge BEH C18 100×25 mm×5 μm; mobile phase: [A: water (0.225% formic acid), B: acetonitrile]; B %: 30%-60%, 12 min) to give the title compound (5.1 mg).

MS m/z (ESI): 359.1 $[M+H]^+$ $^1H$ NMR (400 MHz, Methanol-$d_4$) δ=8.88 (d, J=8.0 Hz, 1H), 8.24 (s, 1H), 7.76 (d, J=8.0 Hz, 1H), 7.46-7.40 (m, 2H), 7.40-7.34 (m, 1H), 7.15 (d, J=7.5 Hz, 1H), 4.34 (s, 3H), 1.94 (s, 3H).

Example 32. 5-(2-chloro-4-fluorophenyl)-1-methyl-7-(trifluoromethyl)-1,5-dihydro-4H-imidazo[4,5-c][1,8]naphthyridin-4-one (Compound 32)

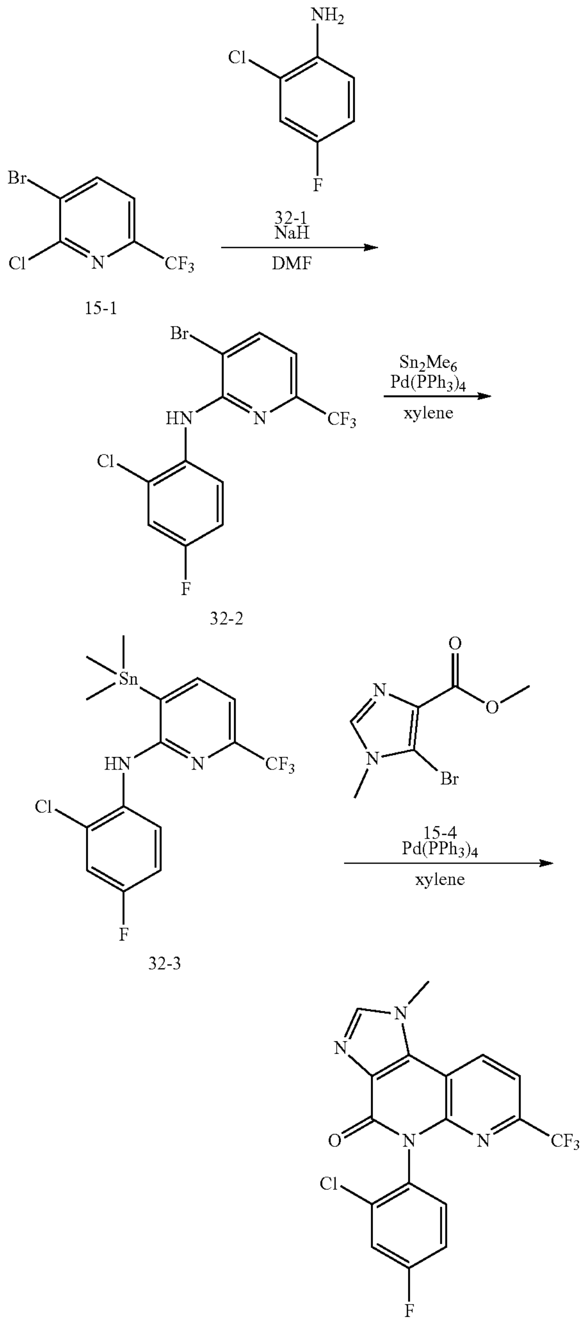

Compound 32

Step 1: synthesis of 3-bromo-N-(2-chloro-4-fluorophenyl)-6-(trifluoromethyl)pyridin-2-amine (intermediate 32-2)

Reactant 32-1 (279.45 mg, 1.92 mmol) was dissolved in N,N-dimethylformamide (10 mL), and sodium hydride (60% effective content, 115.19 mg, 2.88 mmol) was added at 0° C. After the reaction mixture was stirred for reaction at 0° C. for 2 h, intermediate 15-1 (500 mg, 1.92 mmol) was dissolved in N,N-dimethylformamide (5 mL) and added dropwise to the reaction mixture. The reaction mixture was stirred for reaction at 0° C. for 12 h. The reaction mixture was quenched with water (5 mL), and the mixture was extracted thrice with ethyl acetate (10 mL×3). The organic layer was concentrated to dryness under reduced pressure, and the residue was purified by silica gel column chromatography (petroleum ether:ethyl acetate=10:1) to give the title compound (470 mg).

MS m/z (ESI): 368.8 $[M+H]^+$.

Step 2: synthesis of N-(2-chloro-4-fluorophenyl)-6-(trifluoromethyl)-3-(trimethylstannyl)pyridin-2-amine (intermediate 32-3)

Intermediate 32-2 (200 mg, 541.21 μmol) was dissolved in xylene (3 mL), and hexamethyldistannane (709.27 mg, 2.16 mmol) and tetrakis(triphenylphosphine)palladium(0) (62.54 mg, 54.12 μmol) were added. The reaction mixture was warmed to 140° C. and stirred for reaction for 2 h under nitrogen atmosphere. A saturated potassium fluoride solution (5 mL) was added to the reaction mixture, and the mixture was extracted thrice with ethyl acetate (5 mL×3). The organic player was concentrated to dryness under reduced pressure, and the residue was purified by preparative thin-layer chromatography (silica, dichloromethane:methanol=10:1) to give the title compound (190 mg).

MS m/z (ESI): 453.0$[M+H]^+$.

Step 3: synthesis of 5-(2-chloro-4-fluorophenyl)-1-methyl-7-(trifluoromethyl)-1,5-dihydro-4H-imidazo[4,5-c][1,8]naphthyridin-4-one (Compound 32)

Intermediate 32-3 (190 mg, 419.01 μmol) was dissolved in xylene (2 mL), and intermediate 15-4 (91.78 mg) and tetrakis(triphenylphosphine)palladium(0) (48.42 mg, 41.90 μmol) were added. The reaction mixture was stirred for reaction at 140° C. for 12 h under nitrogen atmosphere. The reaction mixture was concentrated to dryness under reduced pressure, and the residue was purified by preparative high performance liquid chromatography (column: Waters Xbridge BEH C18 100×25 mm×5 μm; mobile phase: [A: water (0.225% formic acid), B: acetonitrile]; B %: 30%-50%, 12 min) to give the title compound (4.1 mg).

MS m/z (ESI): 397.0 $[M+H]^+$.

$^1H$ NMR (400 MHz, Methanol-$d_4$) δ=8.91 (d, J=8.5 Hz, 1H), 8.26 (s, 1H), 7.80 (d, J=8.3 Hz, 1H), 7.55-7.51 (m, 2H), 7.36-7.31 (m, 1H), 4.35 (s, 3H) Example 33. 5-(2-methoxyphenyl)-1-methyl-7-(trifluoromethyl)-1,5-dihydro-4H-imidazo[4,5-c][1,8]naphthyridin-4-one (Compound 33)

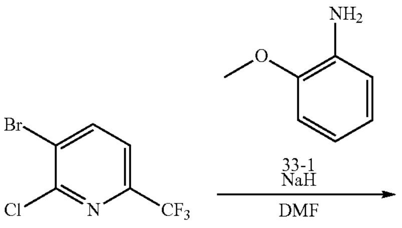

15-1

-continued

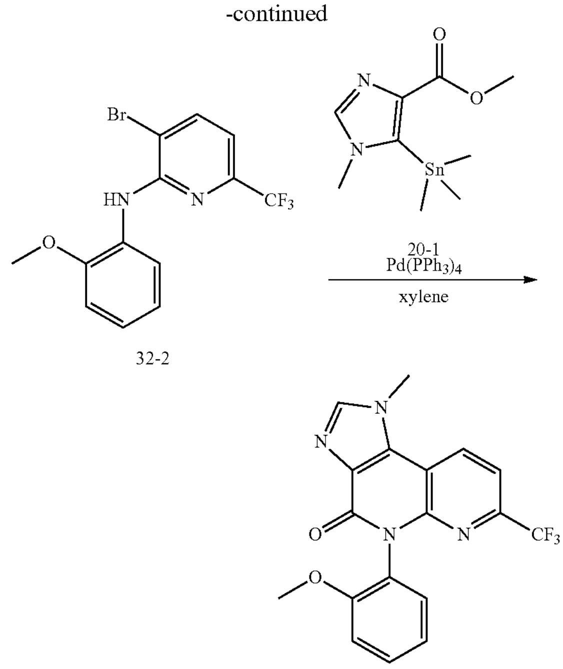

32-2

Compound 33

Step 1: synthesis of 3-bromo-N-(2-methoxyphenyl)-6-(trifluoromethyl)pyridin-2-amine (Intermediate 33-2)

Intermediate 33-1 (236.43 mg, 1.92 mmol) was dissolved in an anhydrous N,N-dimethylformamide solution (8 mL) at 25° C. under nitrogen atmosphere, sodium hydride (60% effective content, 153.57 mg, 3.84 mmol) was added to the reaction mixture after the reaction mixture was cooled to 0° C., and the reaction mixture was stirred at 0° C. for 30 min. Intermediate 15-1 (500 mg, 1.92 mmol) was added thereto. The reaction mixture was stirred at 20° C. for 16 h under nitrogen atmosphere. A target product was generated as detected by LCMS. After the reaction was completed, water (200 mL) was added to the reaction mixture. The mixture was extracted 3 times with ethyl acetate (100 mL). The organic phases were combined and dried over anhydrous sodium sulfate. After the organic phase was filtered, the organic phase was concentrated under reduced pressure to remove the solvent, and the residue was purified by silica gel column chromatography (petroleum ether:ethyl acetate=1:0 to 50:1) to give the title compound (185 mg).

MS m/z (ESI): 346.8 $[M+H]^+$.

Step 2: synthesis of 5-(2-methoxyphenyl)-1-methyl-7-(trifluoromethyl)-1,5-dihydro-4H-imidazo[4,5-c][1,8]naphthyridin-4-one (Compound 33)

Intermediate 33-2 (40.10 mg, 115.53 μmol) was added to anhydrous xylene (1 mL) at 25° C. under nitrogen atmosphere, $Pd(PPh_3)_4$ (13.35 mg, 11.55 μmol) and intermediate 20-1 (35 mg, 115.53 μmol) were added to the reaction mixture, and the reaction mixture was reacted at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [water (0.225% formic acid)-acetonitrile]; B %: 24%-44%, 12 min) to give the title compound (1.7 mg).

$^1$H NMR (400 MHz, Methanol-$d_4$) δ=8.92 (d, J=8.3 Hz, 1H), 8.33 (s, 1H), 7.83 (d, J=8.0 Hz, 1H), 7.62-7.55 (m, 1H), 7.37-7.28 (m, 2H), 7.25-7.19 (m, 1H), 4.38 (s, 3H), 3.73 (s, 3H).

MS m/z (ESI): 375.0 $[M+H]^+$.

Example 34. 5-(2-isopropylphenyl)-1-methyl-7-(trifluoromethyl)-1,5-dihydro-4H-imidazo[4,5-c][1,8]naphthyridin-4-one (Compound 34)

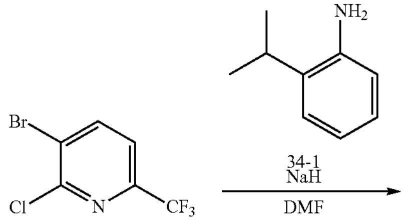

15-1

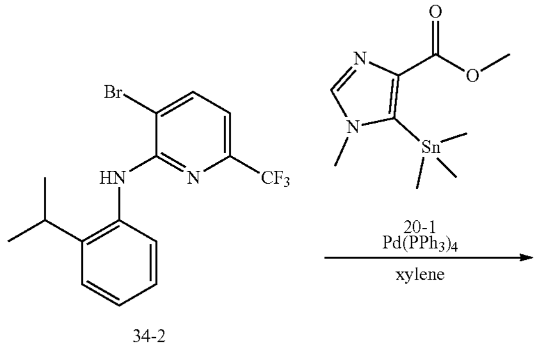

34-2

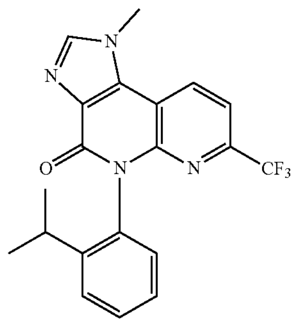

Compound 34

Step 1: synthesis of 3-bromo-N-(2-isopropylphenyl)-6-(trifluoromethyl)pyridin-2-amine (intermediate 34-2)

Intermediate 34-1 (259.57 mg, 1.92 mmol) was dissolved in N,N-dimethylformamide (7 mL), sodium hydride (60% effective content, 230.36 mg, 5.76 mmol) was added at 0° C., and the mixture was stirred at 0° C. for 30 min. A solution of intermediate 15-1 (500 mg, 1.92 mmol) in N,N-dimethylformamide (7 mL) was added, and the reaction mixture was stirred for reaction at 20° C. for 16 h. The reaction mixture was cooled to 0° C. and quenched with water (5 mL), and the mixture was extracted with ethyl acetate (30 mL). The organic phase was concentrated to dryness under reduced pressure, and the residue was purified by a flash silica gel column (ISCO®; 4 g of SepaFlash© silica gel column; eluent: 0-10% ethyl acetate/petroleum ether, gradient @ 40 mL/min) to give the title compound (160 mg).

MS m/z (ESI): 358.8 $[M+H]^+$

Step 2: synthesis of 5-(2-isopropylphenyl)-1-methyl-7-(trifluoromethyl)-1,5-dihydro-4H-imidazo[4,5-c][1,8]naphthyridin-4-one (Compound 34)

Intermediate 34-2 (160 mg, 356.36 μmol), intermediate 20-1 (107.96 mg, 356.36 μmol), and tetrakis(triphenylphosphine)palladium(0) (41.18 mg, 35.64 μmol) were sequentially dissolved in xylene (5 mL), and the mixture was stirred for reaction at 140° C. for 5 h under nitrogen atmosphere. After the reaction was completed, the reaction mixture was cooled to 20° C. and filtered. The filtrate was concentrated to dryness under reduced pressure, and the residue was purified by preparative high performance liquid chromatography (column: Waters Xbridge BEH C18 100×25 mm×5 μm; mobile phase: [water (0.225% formic acid)-acetonitrile; B was acetonitrile; B %: 35%-45%, 12 min). The residue was further purified by preparative high performance liquid chromatography (column: Boston Prime C18 150×30 mm×5 μm; mobile phase: [A: water (0.05% ammonia water+10 mM ammonium hydrogen carbonate), B: acetonitrile]; B %: 40%-70%, 10 min) to give the title compound (5.3 mg).

MS m/z (ESI): 387.1 $[M+H]^+$;

$^1$H NMR (400 MHz, Methanol-$d_4$) δ=8.88 (d, J=8.3 Hz, 1H), 8.23 (s, 1H), 7.75 (d, J=8.0 Hz, 1H), 7.58-7.46 (m, 2H), 7.36-7.34 (m, 1H), 7.13-7.05 (m, 1H), 4.34 (s, 3H), 2.48-2.36 (m, 1H), 1.13 (d, J=6.8 Hz, 3H), 0.99 (d, J=6.8 Hz, 3H).

Example 35. 5-(2-chloro-3-fluorophenyl)-7-(trifluoromethyl)oxazolo[4,5-c][1,8]naphthyridin-4 (5H)-one (Compound 35)

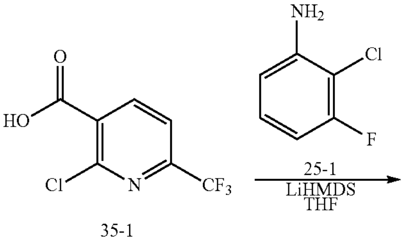

35-1

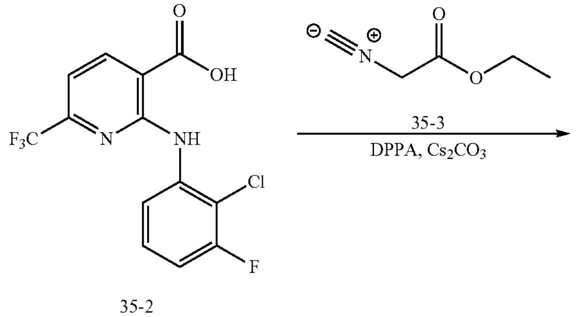

35-2

-continued

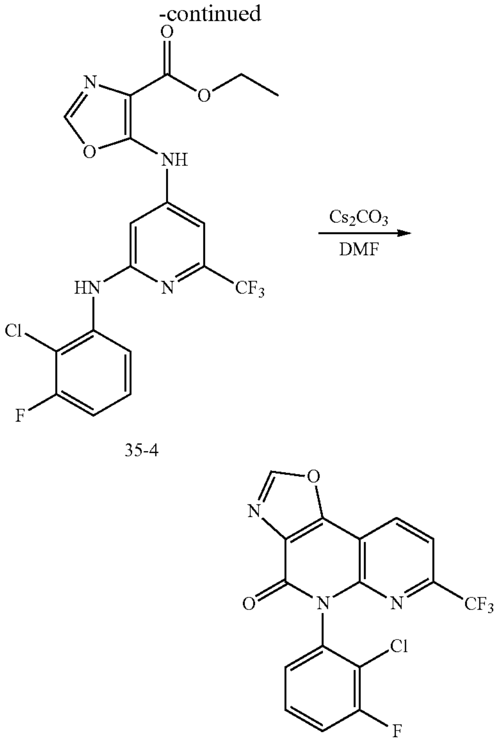

35-4

Compound 35

Step 1: synthesis of 2-((2-chloro-3-fluorophenyl) amino)-6-(trifluoromethyl)pyridine-3-formic acid (intermediate 35-2)

Intermediate 35-1 (1.0 g, 4.5 mmol) was dissolved in anhydrous tetrahydrofuran (10 mL), and LiHMDS (1 M, 9.76 mL, 9.76 mmol) was added dropwise thereto at −78° C. After the dropwise addition, the mixture was stirred at −78° C. for 1 h, and intermediate 25-1 (768 mg, 5.3 mmol) was added to the reaction mixture. The reaction mixture was slowly warmed to room temperature and stirred for 3 h. A saturated aqueous ammonium chloride solution (10 mL) and ethyl acetate (10 mL×3) were added sequentially to the reaction mixture. The organic phase was washed with water (10 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Gemini NX C18 5 μm×10×150 mm; mobile phase: A: water (0.225% formic acid v/v), B: acetonitrile; B %: 30%-50%) to give the title compound (460 mg).

MS m/z (ESI): 335.1 $[M+H]^+$.

Step 2: synthesis of ethyl 5-(2-((2-chloro-3-fluorophenyl)amino)-6-(trifluoromethyl)pyridin-3-yl)oxazole-4-carboxylate (intermediate 35-4)

Intermediate 35-2 (250 mg, 0.75 mmol) and cesium carbonate (489 mg, 1.50 mmol) were dissolved in N,N-dimethylformamide (4 mL), diphenylphosphoryl azide (DPPA) (412 mg, 1.50 mmol) was added thereto at 0° C., and the mixture was stirred at room temperature for 1 h. Intermediate 35-3 (85 mg, 0.75 mmol) was added at 0° C., and the reaction mixture was stirred at 25° C. for 2 h. Water (10 mL) and ethyl acetate (10 mL×3) were added sequentially to the reaction mixture. The organic phase was washed with saturated brine (10 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=100:0-50:50) to give the title compound (169 mg).

MS m/z (ESI): 429.9 $[M+H]^+$.

Step 3: synthesis of 5-(2-chloro-3-fluorophenyl)-7-(trifluoromethyl)oxazolo[4,5-c][1,8]naphthyridin-4(5H)-one (Compound 35)

Intermediate 35-4 (80 mg, 0.19 mmol) and cesium carbonate (182 mg, 0.56 mmol) were dissolved in N,N-dimethylformamide (1 mL), and the mixture was stirred at 60° C. for 3 h. The reaction mixture was filtered, and the residue was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (29 mg).

MS m/z (ESI): 383.9 $[M+H]^+$.

$^1H$ NMR (400 MHz, DMSO-$d_6$) δ 9.15 (s, 1H), 8.85 (d, J=8.0 Hz, 1H), 7.98 (d, J=8.1 Hz, 1H), 7.74-7.59 (m, 2H), 7.49-7.47 (m, 1H).

Example 36. 5-(2-chloro-3-methylphenyl)-1-methyl-7-(trifluoromethyl)-1,5-dihydro-4H-imidazo[4,5-c][1,8]naphthyridin-4-one (Compound 36)

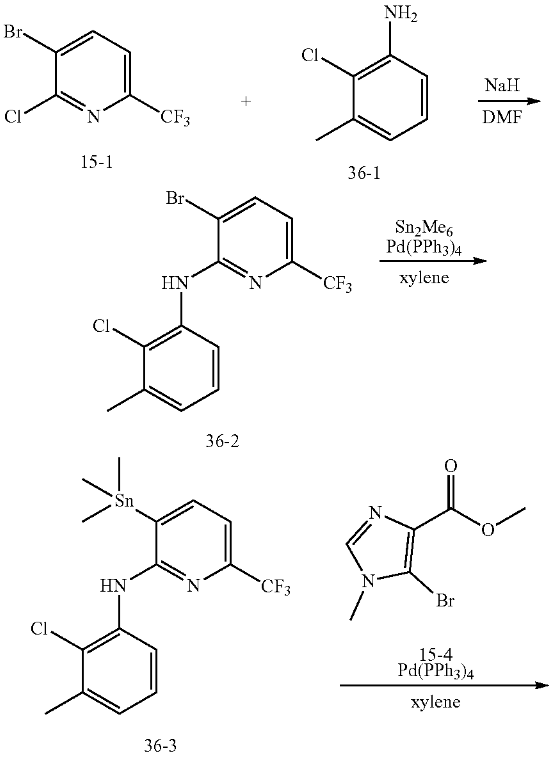

15-1

36-1

36-2

36-3

15-4

-continued

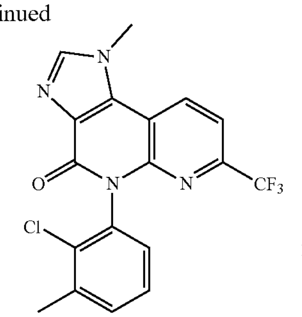

Compound 36

Step 1: synthesis of 3-bromo-N-(2-chloro-3-methylphenyl)-6-(trifluoromethyl)pyridin-2-amine (intermediate 36-2)

Intermediate 36-1 (271.87 mg, 1.92 mmol) was dissolved in N,N-dimethylformamide (5 mL), and NaH (115.19 mg, 2.88 mmol, 60% effective content) was added at 0° C. After the reaction mixture was stirred at 0° C. for 2 h, intermediate 15-1 (500 mg, 1.92 mmol) was dissolved in N,N-dimethylformamide (5 mL) and added dropwise to the reaction mixture. The mixture was stirred at 0° C. for 12 h. After the reaction was completed, water (5 mL) was added to the reaction mixture. The mixture was extracted with ethyl acetate (10 mL×3 times). The organic layer was washed with saturated brine (30 mL) and dried over anhydrous sodium sulfate. After the organic phase was filtered, the organic phase was concentrated under reduced pressure to remove the solvent, and the residue was purified by silica gel column chromatography (petroleum ether:ethyl acetate=10:1) to give the title compound (400 mg).

MS m/z (ESI): 364.9 $[M+H]^+$.

Step 2: synthesis of N-(2-chloro-3-methylphenyl)-6-(trifluoromethyl)-3-(trimethylstannyl)pyridin-2-amine (intermediate 36-3)

Intermediate 36-2 (400 mg, 1.09 mmol) was dissolved in xylene (4 mL), and hexamethyldistannane (716.96 mg, 2.19 mmol) and tetrakis(triphenylphosphine)palladium(0) (126.44 mg, 109.42 μmol) were added. The reaction mixture was warmed to 140° C. and stirred for reaction for 2 h under nitrogen atmosphere. After the reaction was completed, a saturated potassium fluoride solution (5 mL) was added to the reaction mixture. The mixture was extracted with ethyl acetate (5 mL×3 times). The organic phases were combined and dried over anhydrous sodium sulfate. After the organic phase was filtered, the organic phase was concentrated under reduced pressure to remove the solvent, and the residue was purified by preparative thin-layer chromatography (dichloromethane:methanol=10:1) to give the title compound (320 mg).

MS m/z (ESI): 451.0$[M+H]^+$.

Step 3: synthesis of 5-(2-chloro-3-methylphenyl)-1-methyl-7-(trifluoromethyl)-1,5-dihydro-4H-imidazo[4,5-c][1,8]naphthyridin-4-one (Compound 36)

Intermediate 36-3 (320 mg, 711.93 μmol) was dissolved in xylene (3 mL), and intermediate 15-4 (155.94 mg, 711.93 μmol) and tetrakis(triphenylphosphine)palladium(0) (82.27 mg, 71.19 μmol) were added. The reaction mixture was stirred for reaction at 140° C. for 12 h under nitrogen atmosphere. The reaction mixture was concentrated to dryness under reduced pressure, and the residue was purified by preparative high performance liquid chromatography (column: Waters Xbridge BEH C18 100×25 mm×5 μm; mobile phase: [water (0.225% formic acid)-acetonitrile], B: acetonitrile; B %: 35%-55%, 12 min) to give the title compound (29.9 mg).

MS m/z (ESI): 393.0$[M+H]^+$.

1H NMR (400 MHz, Methanol-$d_4$) δ=8.90 (d, J=8.3 Hz, 1H), 8.25 (s, 1H), 7.79 (d, J=8.1 Hz, 1H), 7.52-7.48 (m, 1H), 7.43 (t, J=7.8 Hz, 1H), 7.26 (d, J=6.9 Hz, 1H), 4.36 (s, 3H), 2.50 (s, 3H)

Example 37. 5-(2,3-dichlorophenyl)-1-methyl-7-(trifluoromethyl)-1,5-dihydro-4H-imidazo[4,5-c][1,8]naphthyridin-4-one (Compound 37)

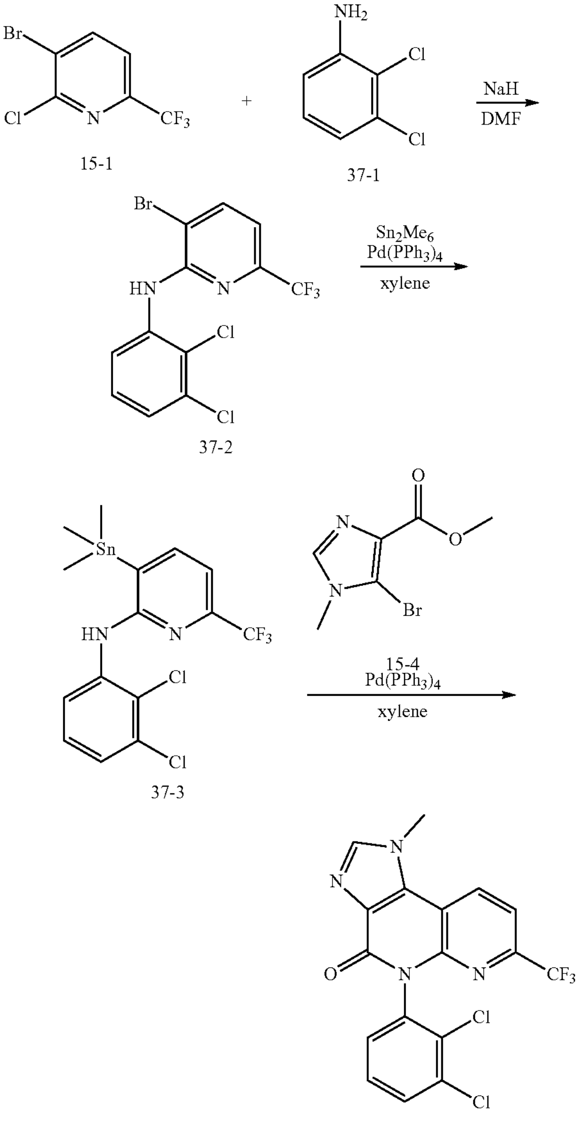

15-1 37-1 37-2 37-3 Compound 37

Step 1: synthesis of 3-bromo-N-(2,3-dichlorophenyl)-6-(trifluoromethyl)pyridin-2-amine (intermediate 37-2)

Intermediate 37-1 (273.72 mg, 1.69 mmol) was dissolved in N,N-dimethylformamide (6 mL). NaH (122.86 mg, 3.07 mmol, 60% effective content) was added to the reaction mixture at 0° C. under nitrogen atmosphere, and the mixture was stirred for 30 min. Intermediate 15-1 (400 mg, 1.54 mmol) dissolved in N,N-dimethylformamide (2 mL) was added to the reaction mixture at 0° C., and the reaction mixture was stirred at 20° C. for 16 h. After the reaction was completed, the reaction mixture was quenched with water (20 mL). The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by silica gel column chromatography (column: ISCO®; 12 g of SepaFlash©; mobile phase: 100% petroleum ether @ 40 mL/min) to give the title compound (500 mg).

MS m/z (ESI): =384.8 [M+H]+.

Step 2: synthesis of N-(2,3-dichlorophenyl)-6-(trifluoromethyl)-3-(trimethylstannyl)pyridin-2-amine (intermediate 37-3)

Intermediate 37-2 (300 mg, 777.21 μmol) was dissolved in xylene (3 mL), and $Pd(PPh_3)_4$ (89.81 mg, 77.72 μmol) and hexamethyldistannane (1.02 g, 3.11 mmol, 644.65 μL) were added at 20° C. The reaction mixture was stirred for reaction at 140° C. for 1 h under nitrogen atmosphere. After the reaction was completed, the reaction mixture was quenched with an aqueous cesium fluoride solution (20 mL). The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by silica gel column chromatography (columns: ISCO®; 20 g of SepaFlash© 100% petroleum ether @ 40 mL/min) to give the title compound (283 mg).

MS m/z (ESI): 470.9 [M+H]+.

Step 3: synthesis of 5-(2,3-dichlorophenyl)-1-methyl-7-(trifluoromethyl)-1,5-dihydro-4H-imidazo[4,5-c][1,8]naphthyridin-4-one (Compound 37)

Intermediate 37-3 (150 mg, 319.21 μmol) and intermediate 15-4 (104.88 mg, 478.82 μmol) were dissolved in xylene (2 mL), $Pd(PPh_3)_4$ (55.33 mg, 47.88 μmol) was added at 20° C., and the reaction mixture was stirred for reaction at 140° C. for 16 h under nitrogen atmosphere. After the reaction was completed, the reaction mixture was diluted with water (20 mL). The mixture was extracted with ethyl acetate (10 mL×3 times). The organic phases were combined and dried over anhydrous sodium sulfate. After the organic phase was filtered, the organic phase was concentrated under reduced pressure to remove the solvent. The residue was purified by silica gel column chromatography (petroleum ether/tetrahydrofuran=10:1), and was then further purified by high performance liquid chromatography (column: YMC-Actus Triart C18 250×50 mm×7 μm; mobile phase: [A: water (0.05% ammonia water v/v), B: acetonitrile]; B %: 42%-62%, 11 min) to give the title compound (33.2 mg).

$^1H$ NMR (400 MHz, DMSO-$d_6$) δ=8.88 (d, J=8.0 Hz, 1H), 8.36 (s, 1H), 7.86 (d, J=8.3 Hz, 1H), 7.83 (dd, J=1.6, 7.9 Hz, 1H), 7.62-7.52 (m, 2H), 4.28 (s, 3H).

MS m/z (ESI): 412.9 [M+H]+.

Example 38. 5-(2-chloro-3-fluorophenyl)-1,7-dimethyl-1,5-dihydro-4H-imidazo[4,5-c][1,8]naphthyridin-4-one (Compound 38)

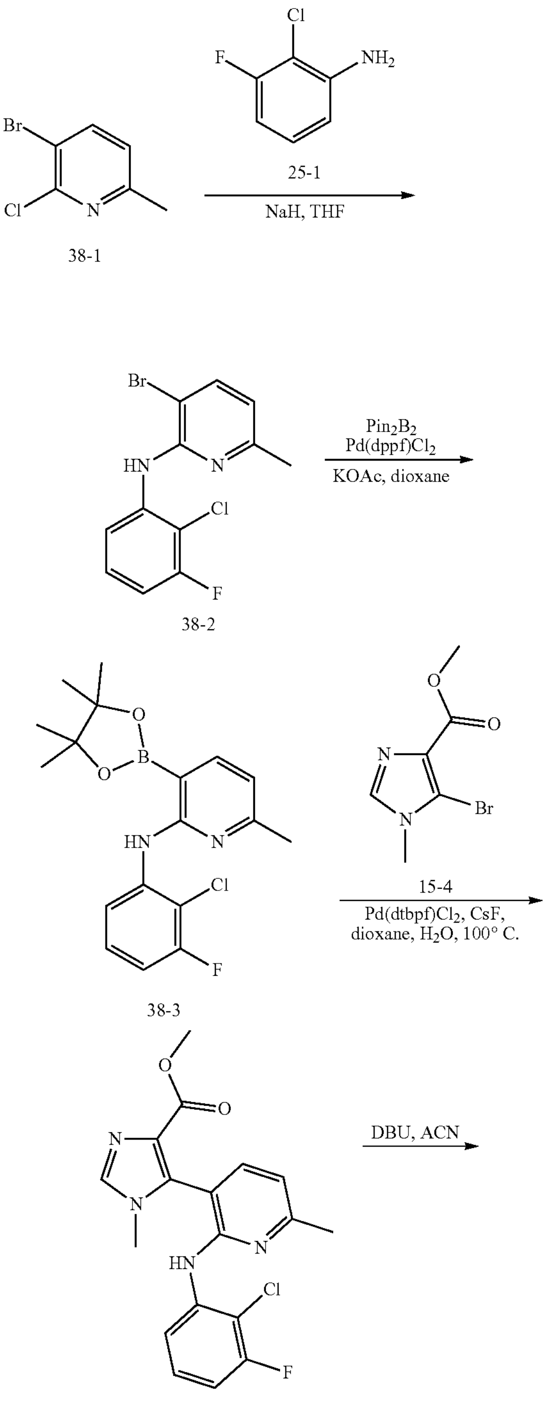

25-1
38-1
38-2
15-4
38-3
38-4

-continued

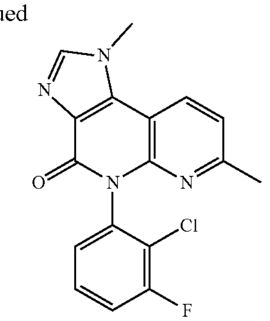

Compound 38

Step 1: synthesis of 3-bromo-N-(2-chloro-3-fluoro-phenyl)-6-methylpyridin-2-amine (Intermediate 38-2)

Intermediate 25-1 (2 g, 13.79 mmol) was dissolved in tetrahydrofuran (20 mL), NaH (1.1 g, 27.5 mmol, 60% effective amount) was added after the reaction mixture was cooled to 0° C., and the reaction mixture was stirred at 25° C. for 0.5 h. After the reaction mixture was cooled to 0° C., intermediate 38-1 (2.8 g, 13.79 mmol) was added to the reaction mixture. The reaction mixture was stirred at room temperature for 4 h. Subsequently, the reaction mixture was cooled to 0° C. and slowly quenched with ice water (10 mL). The mixture was then extracted with ethyl acetate (20 mL×3). The combined organic phases were washed with brine (20 mL×3), dried over anhydrous $Na_2SO_4$, filtered, and concentrated under reduced pressure to remove the solvent. The residue was purified by preparative thin-layer chromatography (petroleum ether:ethyl acetate=10:3) to give the title compound (900 mg).

MS m/z (ESI): 315.1 $[M+H]^+$.

Step 2: synthesis of N-(2-chloro-3-fluorophenyl)-6-methyl-3-(4,4,5,5-tetramethyl-1,3,2-dioxaborolan-2-yl)pyridin-2-amine (intermediate 38-3)

Intermediate 38-2 (900 mg, 2.87 mmol) and bis(pinacolato)diboron (1.4 g, 5.7 mmol) were dissolved in 1,4-dioxane (10 mL), potassium acetate (560 mg, 5.7 mmol) and $Pd(dppf)Cl_2$ (209 mg, 0.28 mmol) were added thereto, and the reaction mixture was stirred at 100° C. for 15 h under nitrogen atmosphere. After the reaction mixture was cooled to room temperature, water (60 mL) and ethyl acetate (80 mL) were added sequentially. The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (dichloromethane: methanol=10:1) to give the title compound (200 mg).

MS m/z (ESI): 363.2 $[M+H]^+$.

Step 3: synthesis of methyl 5-(2-((2-chloro-3-fluorophenyl)amino)-6-methylpyridin-3-yl)-1-methyl-1H-imidazole-4-carboxylate (intermediate 38-4)

Intermediate 38-3 (200 mg, 0.55 mmol) and intermediate 15-4 (180 mg, 0.82 mmol) were dissolved in dioxane (6 mL) and water (2 mL), cesium fluoride (249 mg, 1.65 mmol) and $Pd(dtbpf)Cl_2$ (35 mg, 0.05 mmol) were added thereto, and the reaction mixture was stirred at 100° C. for 16 h under nitrogen atmosphere. After the reaction was cooled to room temperature, water (30 mL) and ethyl acetate (40 mL) were added sequentially. The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (dichloromethane:methanol=5:1) to give the title compound (55 mg).

MS m/z (ESI): 375.3 $[M+H]^+$.

Step 4: synthesis of 5-(2-chloro-3-fluorophenyl)-1,7-dimethyl-1,5-dihydro-4H-imidazo[4,5-c][1,8]naphthyridin-4-one (Compound 38)

Intermediate 38-4 (55 mg, 0.15 mmol) was dissolved in acetonitrile (2 mL), and 1,8-diazabicyclo[5.4.0]undec-7-ene (DBU) (112 mg, 0.73 mmol) was added thereto. The reaction mixture was stirred at 25° C. for 15 h. The reaction mixture was concentrated under reduced pressure, and the residue was purified by preparative high performance liquid chromatography (column: Gemini NX C18 5 μm×10×150 mm; mobile phase: A: 0.05% TFA v/v, B: acetonitrile; B %: 40%-45%, 12 min) to give the title compound (15 mg).

MS m/z (ESI): 343.2 $[M+H]^+$.

$^1H$ NMR (400 MHz, DMSO-$d_6$) δ 8.53 (d, J=8.1 Hz, 1H), 8.20 (s, 1H), 7.62-7.52 (m, 2H), 7.40-7.30 (m, 1H), 7.28 (d, J=8.1 Hz, 1H), 4.21 (s, 3H), 2.34 (s, 3H).

Example 39. 7-chloro-5-(2-chloro-3-fluorophenyl)-1-methyl-1,5-dihydro-4H-imidazo[4,5-c]quinolin-4-one (Compound 39)

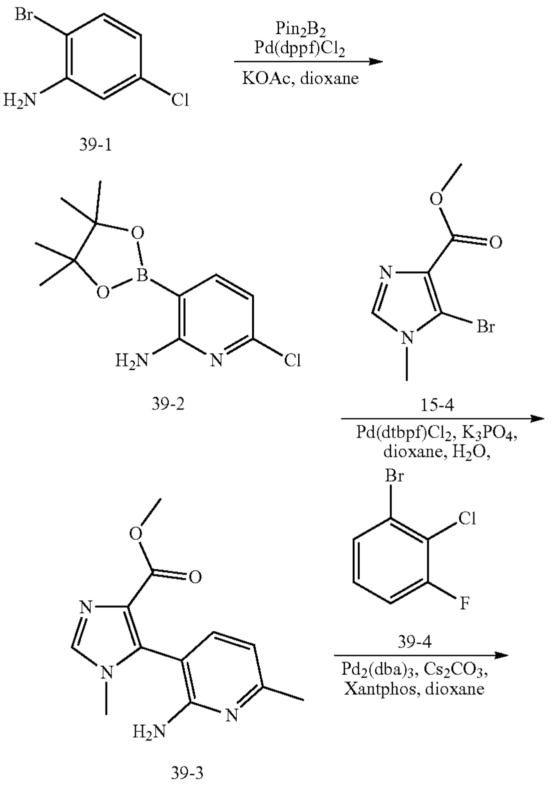

-continued

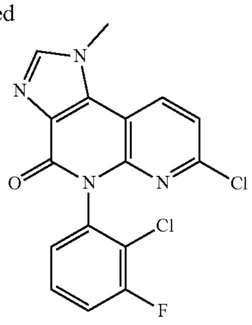

Compound 39

Step 1: synthesis of 5-chloro-2-(4,4,5,5-tetramethyl-1,3,2-dioxaborolan-2-yl)aniline (Intermediate 39-2)

Intermediate 39-1 (5 g, 24.2 mmol) was dissolved in anhydrous 1,4-dioxane (50 mL), bis(pinacolato)diboron (7.4 g, 29.0 mmol), Pd(dppf)$Cl_2$ (1.8 g, 2.4 mmol), and potassium acetate (4.8 g, 48.4 mmol) were added thereto, and the reaction mixture was stirred at 100° C. for 12 h under nitrogen atmosphere. After the reaction mixture was cooled to room temperature, water (100 mL) and ethyl acetate (100 mL) were added sequentially. The organic phase was washed with water (50 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=100:1) to give the title compound (5 g).

MS m/z (ESI): 254.0 $[M+H]^+$.

Step 2: synthesis of methyl 5-(2-amino-4-chlorophenyl)-1-methyl-1H-imidazole-4-carboxylate (intermediate 39-3)

Intermediate 39-2 (25 mg, 98.6 μmol) and intermediate 15-4 (21.6 mg, 98.6 μmol) were dissolved in 1,4-dioxane (2.5 mL) and water (0.5 mL), Pd(dtpf)$Cl_2$ (6.4 mg, 9.8 μmol) and $K_3PO_4$ (62.7 mg, 295.8 μmol) were added thereto, and the reaction mixture was stirred at 100° C. for 12 h under nitrogen atmosphere. After the reaction was cooled to room temperature, water (5 mL) and ethyl acetate (5 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=1:1) to give the title compound (15 mg).

MS m/z (ESI): 266.0 $[M+H]^+$.

Step 3: synthesis of 7-chloro-5-(2-chloro-3-fluorophenyl)-1-methyl-1,5-dihydro-4H-imidazo[4,5-c]quinolin-4-one (Compound 39)

Intermediate 39-3 (10 mg, 37.6 μmol) and intermediate 39-4 (11 mg, 56.4 μmol) were dissolved in an anhydrous 1,4-dioxane solution (5 mL), $Pd_2(dba)_3$ (3.45 mg, 3.7 μmol), $Cs_2CO_3$ (24 mg, 75 μmol), and 4,5-bis(diphenylphosphino)-9,9-dimethylxanthene (Xantphos) (2.18 mg, 3.76 μmol) were added thereto, and the reaction mixture was stirred at 100° C. for 12 h under nitrogen atmosphere. After the reaction was cooled to room temperature, the reaction mixture was filtered and concentrated to dryness under reduced pressure, and the residue was purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 40%-70%, 15 min] to give the title compound (5.0 mg).

MS m/z (ESI): 362.0 $[M+H]^+$.

$^1$H NMR (400 MHz, $CDCl_3$) δ 8.01 (d, J=8.6 Hz, 1H), 7.82 (s, 1H), 7.56-7.44 (m, 1H), 7.42-7.36 (m, 1H), 7.32-7.28 (m, 1H), 7.22-7.17 (m, 1H), 6.63 (d, J=2.0 Hz, 1H), 4.22 (s, 3H).

Example 40. 5-(2-methylpyridin-3-yl)-7-(trifluoromethyl)oxazolo[4,5 -c][1,8]naphthyridin-4 (5H)-one (Compound 40)

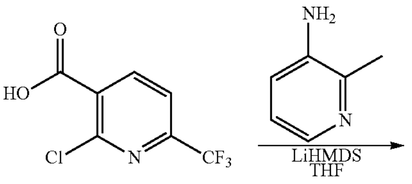

35-1

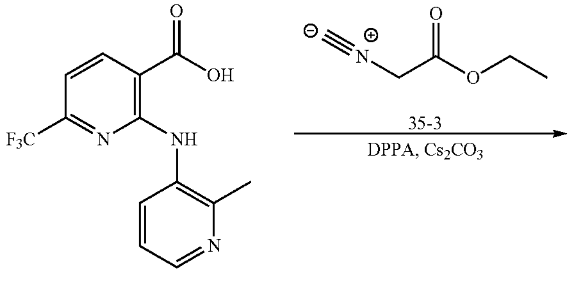

40-1

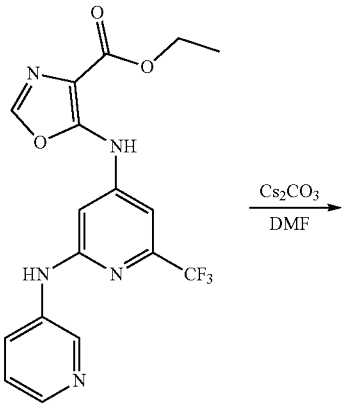

40-2

-continued

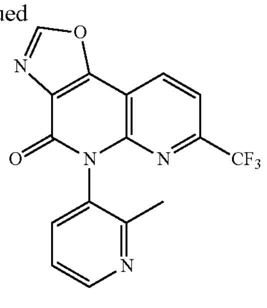

Compound 40

Step 1: synthesis of 2-((2-methylpyridine)amino)-6-(trifluoromethyl)pyridine-3-formic acid (intermediate 40-1)

Intermediate 35-1 (200 mg, 0.89 mmol) was dissolved in anhydrous tetrahydrofuran (2 mL), and a solution of LiHMDS in THF (1 M, 1.8 mL, 1.8 mmol) was added dropwise thereto at −78° C. After the addition, the mixture was stirred at −78° C. for 1 h, and 3-amino-2-methylpyridine (115 mg, 1.1 mmol) was added to the reaction mixture. The reaction system was warmed to room temperature and reacted for 3 h. A saturated aqueous ammonium chloride solution (8 mL) and ethyl acetate (8 mL×3) were added sequentially to the reaction mixture. The organic phase was washed with water (8 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Gemini NX C18 5 μm×10×150 mm; mobile phase: A: water (0.225% formic acid v/v), B: acetonitrile; B %: 30%-50%) to give the title compound (105 mg).

MS m/z (ESI): 298.0 $[M+H]^+$.

Step 2: synthesis of ethyl 5-(2-((2-methylpyridin-3-yl)amino)-6-(trifluoromethyl)pyridin-3-yl)oxazole-4-carboxylate (intermediate 40-2)

Intermediate 40-1 (105 mg, 0.35 mmol) and cesium carbonate (228 mg, 0.70 mmol) were dissolved in N,N-dimethylformamide (1 mL), diphenylphosphoryl azide (DPPA) (192 mg, 0.70 mmol) was added thereto at 0° C., and the mixture was reacted at room temperature for 1 h after the addition. Intermediate 35-3 (40 mg, 0.35 μmol) was added at 0° C., and the reaction mixture was stirred at 25° C. for 2 h after the addition. Water (5 mL) and ethyl acetate (5 mL×3) were added sequentially to the reaction mixture. The organic phase was washed with saturated brine (5 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=100:0-50:50) to give the title compound (75 mg).

MS m/z (ESI): 393.1 $[M+H]^+$.

Step 3: synthesis of 5-(2-methylpyridin-3-yl)-7-(trifluoromethyl)oxazolo[4,5-c][1,8]naphthyridin-4(5H)-one (Compound 40)

Intermediate 40-2 (58 mg, 0.15 mmol) and cesium carbonate (147 mg, 0.45 mmol) were dissolved in N,N-dimethylformamide (1 mL), and the mixture was stirred at 60° C. for 3 h. The reaction mixture was filtered, and the residue was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (14 mg).

MS m/z (ESI): 347.1 $[M+H]^+$.

$^1H$ NMR (400 MHz, DMSO-$d_6$) δ 9.05 (s, 1H), 8.75 (d, J=8.0 Hz, 1H), 8.53 (dd, J=4.8, 1.5 Hz, 1H), 7.87 (d, J=8.1 Hz, 1H), 7.67 (dd, J=7.9, 1.5 Hz, 1H), 7.39 (dd, J=7.9, 4.8 Hz, 1H), 2.06 (s, 3H).

Example 41. 1-methyl-7-(trifluoromethyl)-5-(2-(trifluoromethyl)pyridin-3-yl)-1,5-dihydro-4H-imidazo[4,5-c][1,8]naphthyridin-4-one (Compound 41)

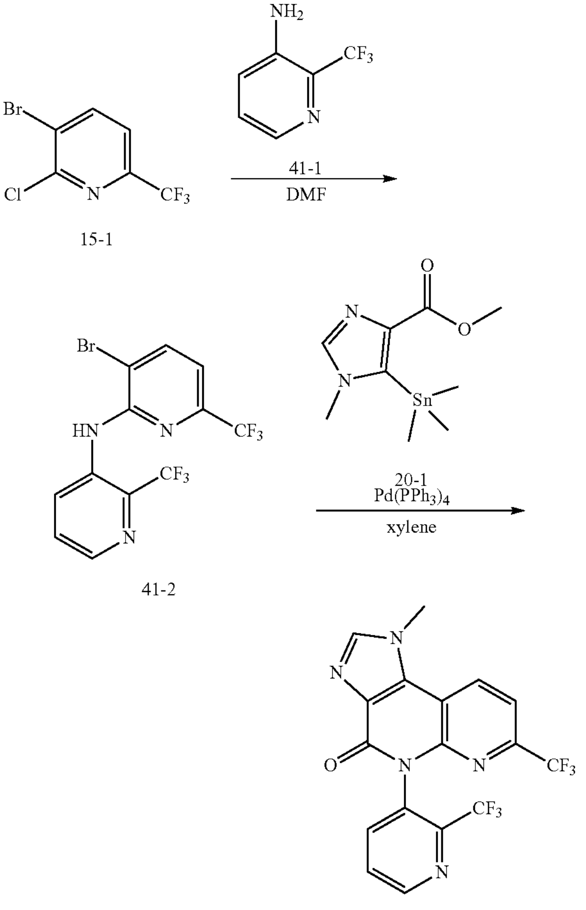

Compound 41

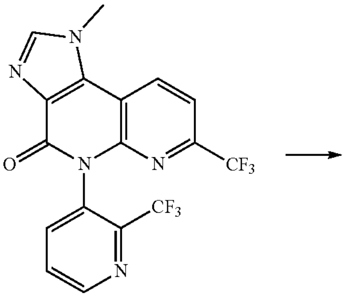

Compound 41

-continued

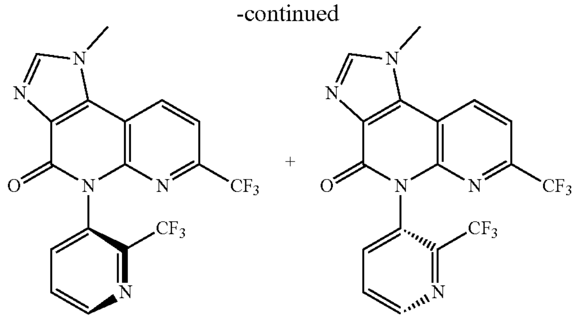

Step 1: synthesis of 3-bromo-6-(trifluoromethyl)-N-(2-(trifluoromethyl)pyridin-3-yl)pyridin-2-amine (intermediate 41-2)

Intermediate 15-1 (300 mg, 1.15 mmol) and intermediate 41-1 (186.74 mg, 1.15 mmol) were dissolved in anhydrous N,N-dimethylformamide (5 mL) under nitrogen atmosphere, potassium tert-butoxide (323.14 mg, 2.88 mmol) was added to the reaction mixture, and the reaction mixture was stirred at 20° C. for 16 h. After the reaction was completed, water (20 mL) was added to the reaction mixture. The mixture was extracted with ethyl acetate (20 mL×3 times). The organic phases were combined and dried over anhydrous sodium sulfate. After the organic phase was filtered, the organic phase was concentrated under reduced pressure to remove the solvent, and the residue was purified by thin-layer chromatography (petroleum ether:ethyl acetate=10:1) to give the title compound (247.9 mg).

MS m/z (ESI): 387.8 $[M+H]^+$.

Step 2: synthesis of 1-methyl-7-(trifluoromethyl)-5-(2-(trifluoromethyl)pyridin-3-yl)-1,5-dihydro-4H-imidazo[4,5-c][1,8]naphthyridin-4-one (Compound 41)

Intermediate 41-2 (127.45 mg, 330.09 μmol) was added to anhydrous xylene (6 mL) under nitrogen atmosphere, and tetrakis(triphenylphosphine)palladium(0) (38.14 mg, 33.01 μmol) and intermediate 20-1 (100 mg, 330.09 μmol) were added to the reaction mixture. Subsequently, the reaction mixture was stirred at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 27%-47%, 14 min) to give the title compound (15.3 mg).

MS m/z (ESI): 414.1 $[M+H]^+$.

$^1$H NMR (400 MHz, Methanol-$d_4$) δ 8.93 (d, J=8.1 Hz, 1H), 8.89 (d, J=4.3 Hz, 1H), 8.28 (s, 1H), 8.05-8.00 (m, 1H), 7.93 (dd, J=4.7, 8.1 Hz, 1H), 7.82 (d, J=8.3 Hz, 1H), 4.36 (s, 3H).

Compound 41 (13.6 mg) was prepared and separated by supercritical fluid chromatography (column: DAICEL CHIRALPAK AD (250 mm×30 mm, 10 μm); mobile phase: A: carbon dioxide; B: ethanol (0.1% ammonia water); B %: 25%; flow rate: 70 mL/min) to give Compound 41-P1 (2.3 mg, RT: 3.547 min) and Compound 41-P2 (2.3 mg, RT: 3.954 min).

Compound 41-P1:

$^1$H NMR (400 MHz, Methanol-$d_4$) δ=8.93 (d, J=8.3 Hz, 1H), 8.89 (d, J=4.5 Hz, 1H), 8.27 (s, 1H), 8.03 (d, J=8.0 Hz, 1H), 7.92 (dd, J=4.6, 8.2 Hz, 1H), 7.81 (d, J=8.3 Hz, 1H), 4.36 (s, 3H).

MS m/z (ESI): 414.0 $[M+H]^+$.

Compound 41-P2:

$^1$H NMR (400 MHz, Methanol-$d_4$) δ=8.93 (d, J=8.3 Hz, 1H), 8.89 (d, J=3.8 Hz, 1H), 8.27 (s, 1H), 8.03 (d, J=7.5 Hz, 1H), 7.92 (dd, J=4.8, 8.0 Hz, 1H), 7.81 (d, J=8.3 Hz, 1H), 4.36 (s, 3H).

MS m/z (ESI): 414.0 $[M+H]^+$.

Example 42. 5-(2-cyclopropylpyridin-3-yl)-1-methyl-7-(trifluoromethyl)-1,5-dihydro-4H-imidazo[4,5-c][1,8]naphthyridin-4-one (Compound 42)

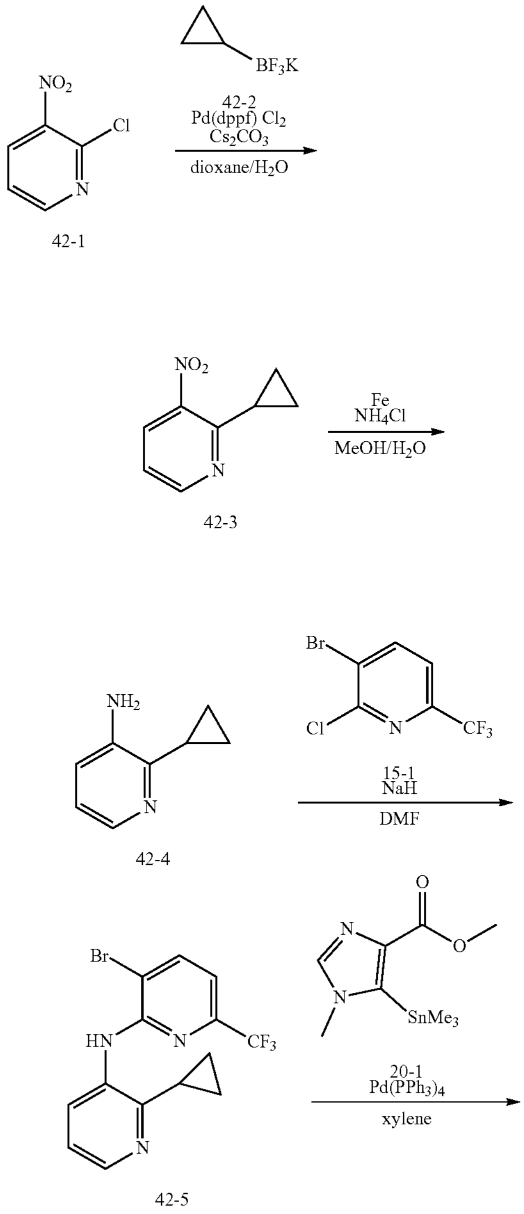

-continued

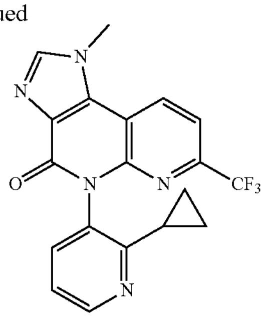

Compound 42

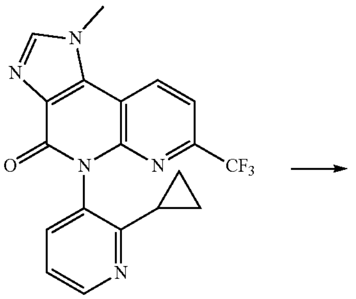

Compound 42

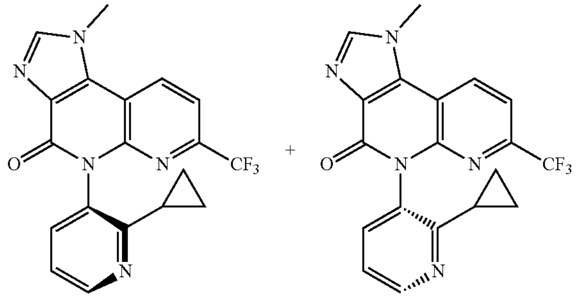

Step 1: synthesis of 2-cyclopropyl-3-nitropyridine (intermediate 42-3)

Intermediate 42-1 (2.5 g, 15.77 mmol) and intermediate 42-2 (4.67 g, 31.54 mmol) were dissolved in dioxane (50 mL) and water (17 mL) under nitrogen atmosphere, and cesium carbonate (10.28 g, 31.54 mmol) and Pd(dppf)$Cl_2$ (576.90 mg, 788.43 μmol) were added to the reaction mixture. The reaction mixture was stirred at 90° C. for 16 h under nitrogen atmosphere. After the reaction was completed, water (40 mL) was added to the reaction mixture. The mixture was extracted with ethyl acetate (40 mL×3 times). The organic phases were combined and dried over anhydrous sodium sulfate. After the organic phase was filtered, the organic phase was concentrated under reduced pressure to remove the solvent, and the residue was purified by flash column chromatography (ISCO®; 20 g of SepaFlash© Silica Flash chromatographic column; eluent: 0-12% ethyl acetate/petroleum ether, gradient @ 80 mL/min) to give the title compound (2.0 g).

MS m/z (ESI): 164.8 $[M+H]^+$.

Step 2: synthesis of 2-cyclopropylpyridin-3-amine (intermediate 42-4)

Intermediate 42-3 (2.00 g, 12.15 mmol) was dissolved in methanol (30 mL) and water (15 mL) under nitrogen atmosphere, and iron powder (3.39 g, 60.76 mmol) and ammonium chloride (6.50 g, 121.53 mmol) were added to the reaction mixture. The reaction mixture was stirred at 25° C. for 16 h under nitrogen atmosphere. After the reaction was completed, water (40 mL) was added to the reaction mixture. The mixture was extracted with ethyl acetate (40 mL×3 times). The organic phases were combined and dried over anhydrous sodium sulfate. After the organic phase was filtered, the organic phase was concentrated under reduced pressure to remove the solvent, and the residue was purified by column chromatography (ISCO®; 12 g of SepaFlash© Silica Flash chromatographic column; eluent: 0-15% ethyl acetate/petroleum ether, gradient @ 40 mL/min) to give the title compound (254.7 mg).

MS m/z (ESI): 134.9 $[M+H]^+$.

Step 3: synthesis of 3-bromo-N-(2-cyclopropylpyridin-3-yl)-6-(trifluoromethyl)pyridin-2-amine (intermediate 42-5)

Intermediate 42-4 (154.56 mg, 1.15 mmol) was dissolved in anhydrous N,N-dimethylformamide (3 mL) under nitrogen atmosphere, NaH (69.11 mg, 1.73 mmol, 60% effective content) was added to the reaction mixture after the reaction mixture was cooled to 0° C., and the reaction mixture was stirred at 0° C. for 30 min. Intermediate 15-1 (300 mg, 1.15 mmol) was then added, and the reaction mixture was stirred at 20° C. for 16 h under nitrogen atmosphere. After the reaction was completed, water (10 mL) was added to the reaction mixture. The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by column chromatography (ISCO®; 12 g of SepaFlash© Silica Flash chromatographic column; eluent: 0-13% ethyl acetate/petroleum ether, gradient @ 40 mL/min) to give the title compound (60.9 mg).

MS m/z (ESI): 357.9 $[M+H]^+$.

Step 4: synthesis of 5-(2-cyclopropylpyridin-3-yl)-1-methyl-7-(trifluoromethyl)-1,5-dihydro-4H-imidazo[4,5-c][1,8]naphthyridin-4-one (Compound 42)

Intermediate 42-5 (58.14 mg, 162.33 μmol) was added to anhydrous xylene (2 mL) under nitrogen atmosphere, and tetrakis(triphenylphosphine)palladium(0) (41.96 mg, 36.31 μmol) and intermediate 20-1 (110.00 mg, 363.10 μmol) were added to the reaction mixture. The reaction mixture was stirred at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 16%-36%, 12 min) to give the title compound (19.1 mg).

MS m/z (ESI): 386.1 $[M+H]^+$.

$^1H$ NMR (400 MHz, Methanol-$d_4$) δ 8.92 (d, J=8.1 Hz, 1H), 8.53 (dd, J=1.3, 4.8 Hz, 1H), 8.26 (s, 1H), 7.80 (d, J=8.3 Hz, 1H), 7.66 (dd, J=1.4, 7.9 Hz, 1H), 7.38 (dd, J=4.9, 7.9 Hz, 1H), 4.35 (s, 3H), 1.60-1.51 (m, 1H), 1.15-1.07 (m, 1H), 0.90-0.82 (m, 1H), 0.79-0.70 (m, 1H), 0.65-0.55 (m, 1H).

Compound 42 (17.0 mg) was prepared and separated by supercritical fluid chromatography (column: DAICEL CHIRALPAK AD (250 mm×30 mm, 10 μm); mobile phase: A:

carbon dioxide; B: ethanol (0.1% ammonia water); B %: 30%; flow rate: 70 mL/min) to give Compound 42-P1 (3.3 mg, RT: 4.350 min) and Compound 42-P2 (3.4 mg, RT: 4.073 min).

Compound 42-P1:

$^1$H NMR (400 MHz, Methanol-$d_4$) δ=8.92 (d, J=8.3 Hz, 1H), 8.54 (dd, J=1.6, 4.9 Hz, 1H), 8.27 (s, 1H), 7.81 (d, J=8.3 Hz, 1H), 7.67 (dd, J=1.5, 8.0 Hz, 1H), 7.39 (dd, J=4.8, 7.8 Hz, 1H), 4.36 (s, 3H), 1.60-1.52 (m, 1H), 1.16-1.09 (m, 1H), 0.91-0.83 (m, 1H), 0.80-0.72 (m, 1H), 0.64-0.56 (m, 1H).

MS m/z (ESI): 386.1 $[M+H]^+$.

Compound 42-P2:

$^1$H NMR (400 MHz, Methanol-$d_4$) δ=8.92 (d, J=8.0 Hz, 1H), 8.54 (dd, J=1.5, 4.8 Hz, 1H), 8.27 (s, 1H), 7.81 (d, J=8.3 Hz, 1H), 7.67 (dd, J=1.6, 7.9 Hz, 1H), 7.39 (dd, J=4.8, 8.0 Hz, 1H), 4.36 (s, 3H), 1.60-1.52 (m, 1H), 1.16-1.09 (m, 1H), 0.91-0.84 (m, 1H), 0.80-0.71 (m, 1H), 0.64-0.56 (m, 1H).

MS m/z (ESI): 386.1 $[M+H]^+$.

Example 43. 5-(3-fluoro-2-methylphenyl)-1-methyl-7-(trifluoromethyl)-1,5-dihydro-4H-imidazo[4,5-c][1,8]naphthyridin-4-one (Compound 43)

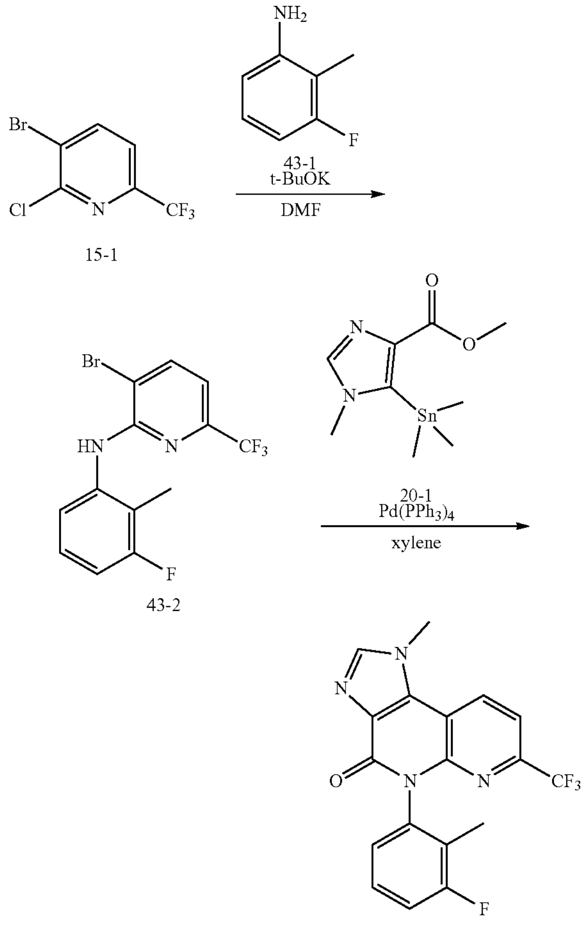

-continued

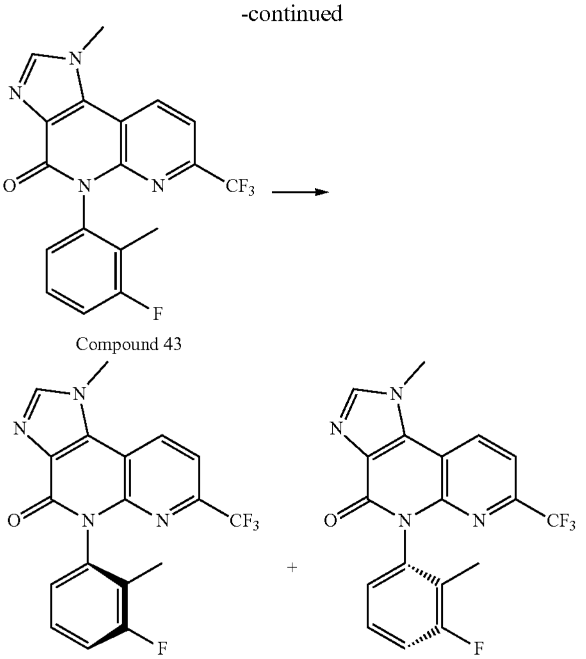

Step 1: synthesis of 3-bromo-N-(3-fluoro-2-methylphenyl)-6-(trifluoromethyl)pyridin-2-amine (intermediate 43-2)

Intermediate 15-1 (300 mg, 1.15 mmol) and intermediate 43-1 (143.91 mg, 1.15 mmol) were dissolved in anhydrous N,N-dimethylformamide (5 mL) under nitrogen atmosphere, and potassium tert-butoxide (322.60 mg, 2.88 mmol) was added to the reaction mixture. The reaction mixture was stirred at 20° C. for 16 h. After the reaction was completed, water (20 mL) was added to the reaction mixture. The mixture was extracted with ethyl acetate (20 mL×3 times). The organic phases were combined and dried over anhydrous sodium sulfate. After the organic phase was filtered, the organic phase was concentrated under reduced pressure to remove the solvent, and the residue was purified by thin-layer chromatography (petroleum ether:ethyl acetate=10:1) to give the title compound (126.3 mg).

MS m/z (ESI): 348.8 $[M+H]^+$.

Step 2: synthesis of 5-(3-fluoro-2-methylphenyl)-1-methyl-7-(trifluoromethyl)-1,5-dihydro-4H-imidazo[4,5-c][1,8]naphthyridin-4-one (Compound 43)

Intermediate 43-2 (115.24 mg, 330.09 μmol) was added to anhydrous xylene (6 mL) under nitrogen atmosphere, and tetrakis(triphenylphosphine)palladium(0) (38.14 mg, 33.01 μmol) and intermediate 20-1 (100 mg, 330.09 μmol) were added to the reaction mixture. Subsequently, the reaction mixture was stirred at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 25%-45%, 14 min), and was then purified by preparative supercritical fluid chromatography (column: DAICEL CHIRALCEL OJ (250 mm×30 mm, 10 μm);

mobile phase: [A: carbon dioxide, B: ethanol]; B %: 20%) to give Compound 43-P1 (1.0 mg, RT: 3.432 min) and Compound 43-P2 (1.5 mg, RT: 3.643 min).

Compound 43-P1:

MS m/z (ESI): 377.1 $[M+H]^+$.

$^1H$ NMR (400 MHz, Methanol-$d_4$) δ 8.91 (d, J=7.9 Hz, 1H), 8.26 (s, 1H), 7.79 (d, J=7.9 Hz, 1H), 7.41-7.38 (m, 1H), 7.25 (t, J=8.6 Hz, 1H), 7.04 (d, J=7.4 Hz, 1H), 4.35 (s, 3H), 1.88 (s, 3H).

Compound 43-P2:

MS m/z (ESI): 377.1 $[M+H]^+$.

$^1H$ NMR (400 MHz, Methanol-$d_4$) δ 8.79 (d, J=8.1 Hz, 1H), 8.14 (s, 1H), 7.67 (d, J=8.1 Hz, 1H), 7.32-7.23 (m, 1H), 7.13 (t, J=8.8 Hz, 1H), 6.92 (d, J=7.8 Hz, 1H), 4.23 (s, 3H), 1.76 (s, 3H).

Example 44. 5-(2-chloro-3-fluorophenyl)-1-(methyl-$d_3$)-7-(trifluoromethyl)-1,5-dihydro-4H-imidazo[4,5-c][1,8]naphthyridin-4-one (Compound 44)

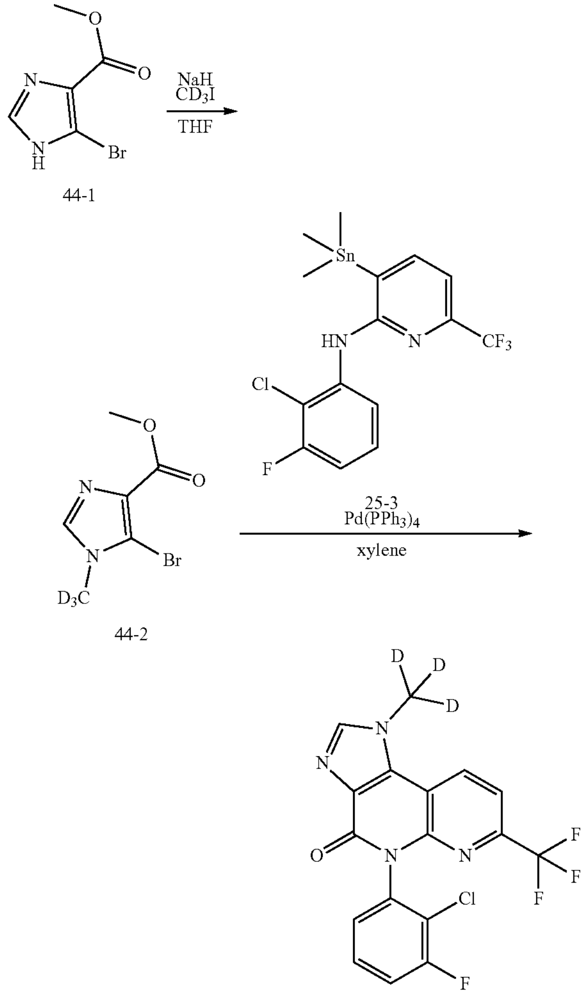

44-1

25-3

44-2

Compound 44

Step 1: synthesis of methyl 5-bromo-1-(methyl-$d_3$)-1H-imidazole-4-formate (Intermediate 44-2)

NaH (117.06 mg, 2.93 mmol, 60% effective content) was added to a solution (5 mL) of intermediate 44-1 (300 mg, 1.46 mmol) in tetrahydrofuran at 0° C., and the mixture was stirred for reaction for 30 min. Deuterated iodomethane (415.41 mg, 2.93 mmol) was added, and the mixture was stirred at 20° C. for 16 h after the addition. After the reaction was completed, methanol (10 mL) was added to quench the reaction. The reaction mixture was concentrated to dryness under reduced pressure. The residue was purified by a silica gel column (ISCO®; 12 g of SepaFlash© silica gel column; eluent: 15-70% ethyl acetate/petroleum ether, gradient @ 40 mL/min) to give the title compound (270 mg).

MS m/z (ESI): 222.0 $[M+H]^+$.

$^1H$ NMR (400 MHz, Chloroform-d) δ=7.46 (s, 1H), 4.03-3.82 (s, 3H).

Step 2: synthesis of 5-(2-chloro-3-fluorophenyl)-1-(methyl-$d_3$)-7-(trifluoromethyl)-1,5-dihydro-4H-imidazo[4,5-c][1,8]naphthyridin-4-one (Compound 44)

Intermediate 44-2 (80 mg, 360.27 μmol) and intermediate 25-3 (163.37 mg, 360.27 μmol) were dissolved in xylene (8 mL), tetrakis(triphenylphosphine)palladium(0) (41.63 mg, 36.03 μmol) was added, and the mixture was stirred at 140° C. for 16 h under nitrogen atmosphere. After the reaction was completed, the mixture was cooled to 20° C. and concentrated to dryness under reduced pressure. The residue was purified by thin-layer chromatography (tetrahydrofuran: dichloromethane= 1:1), and was then purified by preparative high performance liquid chromatography (formic acid condition; column: Waters Xbridge BEH C18 100×25 mm×5 μm; mobile phase: [A: water (0.225% formic acid), B: acetonitrile]; B %: 30%-50%, 14 min) to give the title compound (41.6 mg).

MS m/z (ESI): 400.0 $[M+H]^+$.

$^1H$ NMR (400 MHz, Methanol-$d_4$) δ=8.89 (d, J=8.2 Hz, 1H), 8.26 (s, 1H), 7.79 (d, J=8.2 Hz, 1H), 7.58-7.51 (m, 1H), 7.48-7.42 (m, 1H), 7.36-7.27 (m, 1H).

Example 45. Synthesis of 1-methyl-5-(2-methylpyridin-3-yl)-7-(trifluoromethyl)-1,5-dihydro-4H-imidazo[4,5-c]quinolin-4-one (Compound 45)

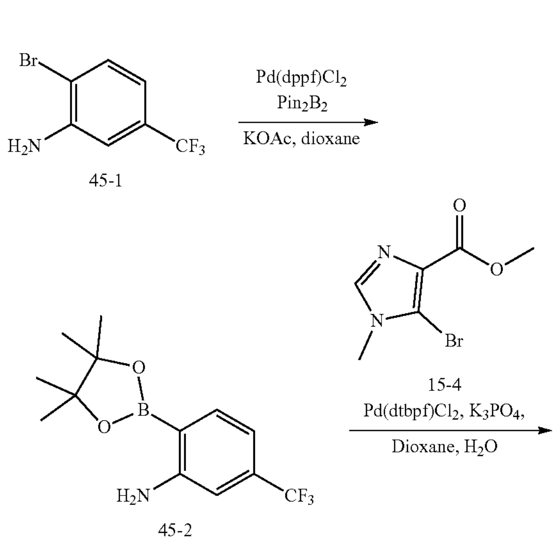

45-1

15-4

45-2

-continued

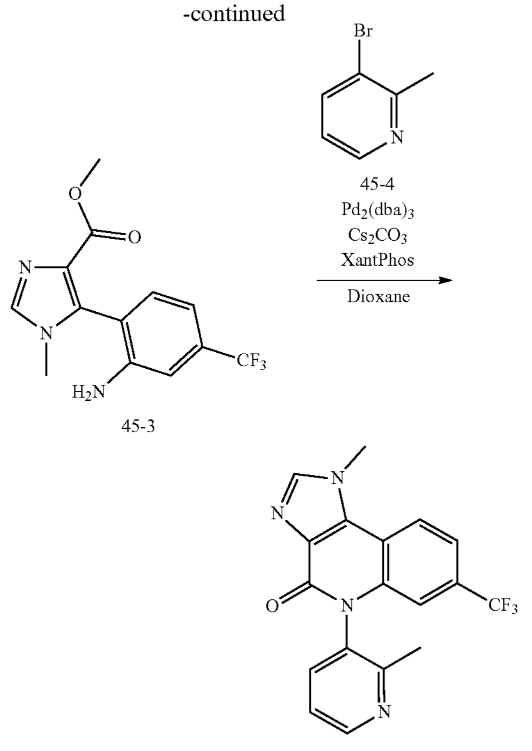

45-3

45-4

Compound 45

Step 1: synthesis of 2-(4,4,5,5-tetramethyl-1,3,2-dioxaborolan-2-yl)-5-(trifluoromethyl)aniline (intermediate 45-2)

Intermediate 45-1 (5 g, 20.83 mmol) and bis(pinacolato) diboron (6.35 g, 25.00 mmol) were dissolved in anhydrous dioxane (50 mL), potassium acetate (4.09 g, 41.66 mmol) and $Pd(dppf)Cl_2$ (1.52 g, 2.08 mmol) were added thereto, and the reaction mixture was stirred at 80° C. for 4 h under nitrogen atmosphere. After the reaction was cooled to room temperature, water (50 mL) and ethyl acetate (50 mL) were added sequentially. The organic phase was washed with water (50 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=10:1) to give the title compound (5.22 g).

MS m/z (ESI): 288.0 $[M+H]^+$.

Step 2: synthesis of methyl 5-(2-amino-4-(trifluoromethyl)phenyl)-1-methyl-1H-imidazole-4-carboxylate (intermediate 45-3)

Intermediate 45-2 (500 mg, 1.74 mmol) and intermediate 15-4 (318 mg, 1.45 mmol) were dissolved in anhydrous dioxane (5 mL), potassium phosphate (616 mg, 2.9 mmol), water (0.5 mL), and $Pd(dtbpf)Cl_2$ (95 mg, 0.1 mmol) were added thereto, and the reaction mixture was stirred at 100° C. for 4 h under nitrogen atmosphere. After the reaction was cooled to room temperature, water (5 mL) and ethyl acetate (5 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was separated and purified by preparative thin-layer chromatography (dichloromethane: methanol=40:1) to give the title compound (200 mg).

MS m/z (ESI): 300.0 $[M+H]^+$.

Step 3: synthesis of 1-methyl-5-(2-methylpyridin-3-yl)-7-(trifluoromethyl)-1,5-dihydro-4H-imidazo[4,5-c]quinolin-4-one (Compound 45)

Intermediate 45-3 (60 mg, 0.2 mmol) and intermediate 45-4 (69 mg, 0.4 mmol) were dissolved in anhydrous dioxane (1 mL), cesium carbonate (196 mg, 0.6 mmol), XantPhos (23 mg, 0.04 mmol), and $Pd_2(dba)_3$ (11 mg, 0.02 mmol) were added thereto, and the reaction mixture was stirred at 100° C. for 12 h under nitrogen atmosphere. After the reaction was cooled to room temperature, the reaction mixture was filtered and concentrated to dryness under reduced pressure, and the residue was purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 55%-75%, 12 min] to give the title compound (8 mg).

MS m/z (ESI): 359.0 $[M+H]^+$.

$^1H$ NMR (400 MHz, DMSO-$d_6$) δ 8.71-8.69 (m, 1H), 8.52 (d, J=8.4 Hz, 1H), 8.31 (s, 1H), 7.84-7.82 (m, 1H), 7.72-7.70 (m, 1H), 7.57-7.54 (m, 1H), 6.67 (s, 1H), 4.29 (s, 3H), 2.11 (s, 3H).

Example 46. 7-chloro-1-methyl-5-(2-methylpyridin-3-yl)-1,5-dihydro-4H-imidazo[4,5-c]quinolin-4-one (Compound 46)

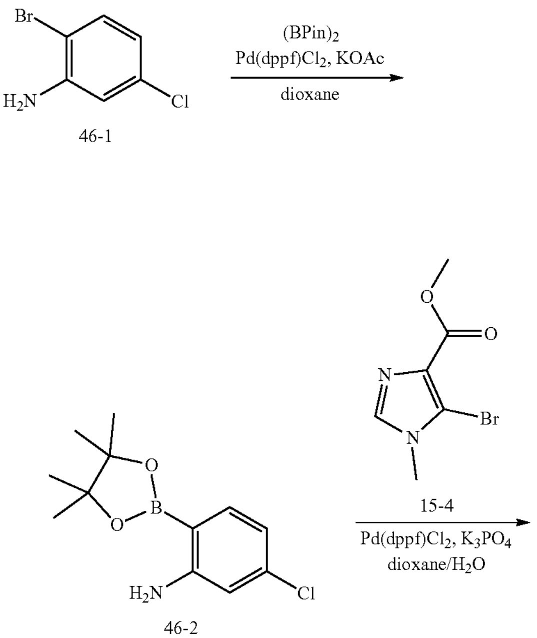

46-1

15-4

46-2

-continued

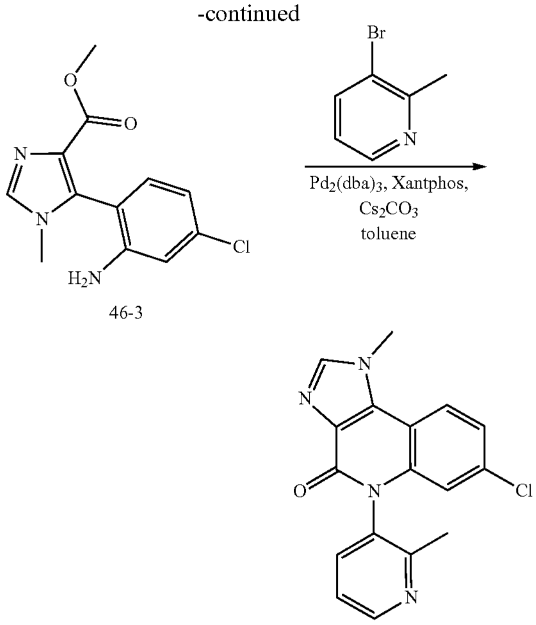

46-3

Compound 46

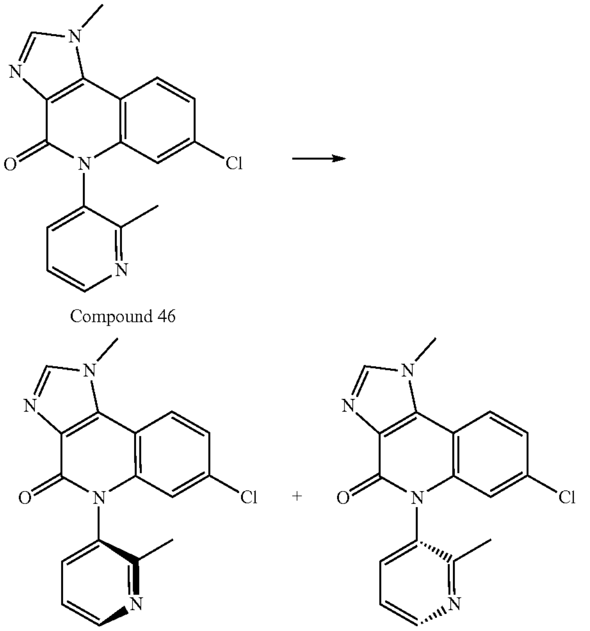

Compound 46

Step 1: synthesis of 5-chloro-2-(4,4,5,5-tetramethyl-1,3,2-dioxaborolan-2-yl)aniline (Intermediate 46-2)

Reactant 46-1 (5 g, 24.22 mmol) was dissolved in anhydrous 1,4-dioxane (50 mL), bis(pinacolato)diboron ($(BPin)_2$) (7.38 g, 29.06 mmol), Pd(dppf)$Cl_2$ (1.77 g, 2.42 mmol), and potassium acetate (4.75 g, 48.43 mmol) were added thereto, and the reaction mixture was stirred at 100° C. for 12 h under nitrogen atmosphere. After the reaction was completed and cooled to room temperature, water (50 mL) and ethyl acetate (100 mL) were added sequentially. The organic phase was washed with water (50 mL×2) and dried over anhydrous sodium sulfate. After the organic phase was filtered, the organic phase was concentrated under reduced pressure, and the residue was purified by column chromatography (petroleum ether:ethyl acetate=100:1) to give the title compound (5 g).

MS m/z (ESI): 254.0 $[M+H]^+$.

Step 2: synthesis of methyl 5-(2-amino-4-chlorophenyl)-1-methyl-1H-imidazole-4-carboxylate (intermediate 46-3)

Intermediate 46-2 (1.75 g, 6.89 mmol) and intermediate 15-4 (1 g, 4.57 mmol) were dissolved in 1,4-dioxane (10 mL) and water (2 mL), Pd(dppf)$Cl_2$ (0.1 g, 0.138 mmol) and $K_3PO_4$ (1.9 g, 8.95 mmol) were added thereto, and the reaction mixture was stirred at 100° C. for 12 h under nitrogen atmosphere. After the reaction was completed and cooled to room temperature, water (50 mL) and ethyl acetate (100 mL) were added sequentially. The mixture was left to stand for liquid separation, and the organic phase was separated. The organic phase was washed with water (50 mL×2) and dried over anhydrous sodium sulfate. After the organic phase was filtered, the filtrate was concentrated under reduced pressure, and the residue was purified by column chromatography (petroleum ether:ethyl acetate=1:1) to give the title compound (0.8 g).

MS m/z (ESI): 266.0 $[M+H]^+$

Step 3: synthesis of 7-chloro-1-methyl-5-(2-methylpyridin-3-yl)-1,5-dihydro-4H-imidazo[4,5-c]quinolin-4-one (Compound 46)

Intermediate 46-3 (150 mg, 0.56 mmol) and 2-methyl-3-bromo-pyridine (144.5 mg, 0.84 mmol) were dissolved in anhydrous toluene (5 mL), and $Pd_2(dba)_3$ (51 mg, 56 μmol), $Cs_2CO_3$ (360 mg, 1.10 mmol), and 4,5-bis(diphenylphosphino)-9,9-dimethylxanthene (Xantphos) (32.7 mg, 56 μmol) were added thereto. The reaction mixture was stirred at 100° C. for 12 h under nitrogen atmosphere. After the reaction was completed and cooled to room temperature, the reaction mixture was filtered, and the filtrate was concentrated to dryness under reduced pressure. The residue was purified by column chromatography (dichloromethane: methanol=20:1) to give a crude product, and was then purified by preparative high performance liquid chromatography [YMC-Actus Triart $C_{18}$ column, 5 μm silica, 30 mm diameter, 150 mm length; a mixture of water (containing 0.05% $NH_4HCO_3$) and acetonitrile with decreasing polarity was used as the eluent, acetonitrile gradient: 40%-70%, 15 min] to give the title compound (21.4 mg).

MS m/z (ESI): 325.0 $[M+H]^+$.

$^1$H NMR (400 MHz, DMSO-$d_6$) δ 8.69-8.67 (m, 1H), 8.31 (d, J=8.7 Hz, 1H), 8.23 (s, 1H), 7.79-7.77 (m, 1H), 7.55-7.52 (m, 1H), 7.45-7.42 (m, 1H), 6.45 (d, J=2.1 Hz, 1H), 4.23 (s, 3H), 2.11 (s, 3H).

Compound 46 (21 mg) was prepared by supercritical fluid chromatography (column: DAICEL CHIRALPAK AD (250 mm×30 mm, 10 μm); mobile phase: A: carbon dioxide; B: ethanol (0.1% ammonia water); B %: 40%) to give Compound 46-P1 (5.2 mg, RT: 1.519 min) and Compound 46-P2 (5.8 mg, RT: 2.025 min).

Compound 46-P1:

$^1$H NMR (400 MHz, Chloroform-d) δ=8.74 (d, J=3.8 Hz, 1H), 8.04 (d, J=8.5 Hz, 1H), 7.87 (s, 1H), 7.58 (d, J=7.8 Hz, 1H), 7.44 (dd, J=4.9, 7.7 Hz, 1H), 7.32 (dd, J=1.9, 8.7 Hz, 1H), 6.63 (d, J=1.8 Hz, 1H), 4.25 (s, 3H), 2.30 (s, 3H).

MS m/z (ESI): 325.1 $[M+H]^+$.

Compound 46-P2:

$^1$H NMR (400 MHz, Chloroform-d) δ=8.74 (d, J=4.0 Hz, 1H), 8.05 (d, J=8.5 Hz, 1H), 7.86 (s, 1H), 7.58 (d, J=7.8 Hz, 1H), 7.44 (dd, J=5.0, 7.8 Hz, 1H), 7.32 (dd, J=1.8, 8.5 Hz, 1H), 6.63 (d, J=1.8 Hz, 1H), 4.25 (s, 3H), 2.30 (s, 3H).

MS m/z (ESI): 325.1 $[M+H]^+$.

Example 47. 7-chloro-1-methyl-5-(2-(trifluoromethyl)pyridin-3-yl)-1,5-dihydro-4H-imidazo[4,5-c]quinolin-4-one (Compound 47)

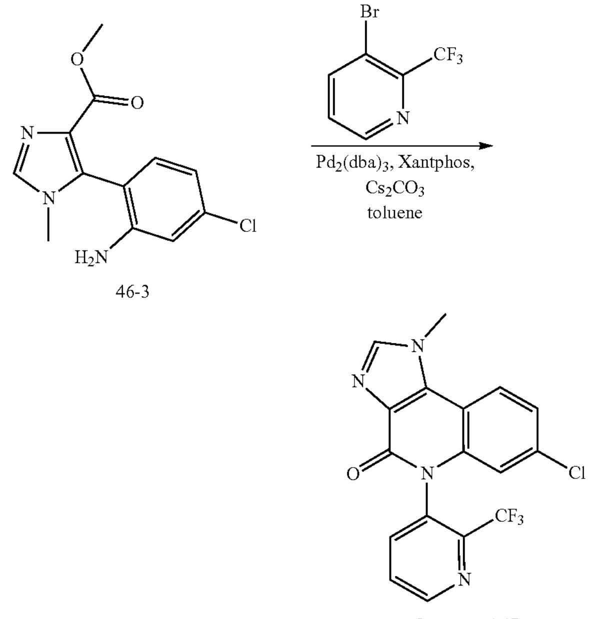

46-3

Compound 47

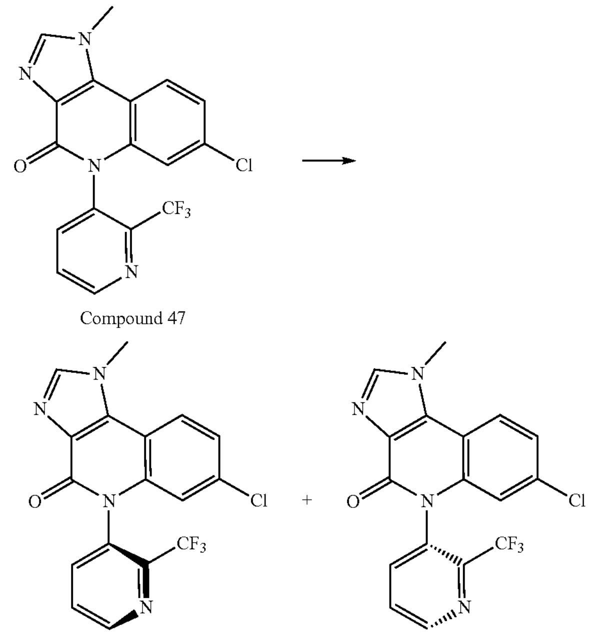

Compound 47

Step 1: synthesis of 7-chloro-1-methyl-5-(2-(trifluoromethyl)pyridin-3-yl)-1,5-dihydro- 4H-imidazo[4,5-c]quinolin-4-one (Compound 47)

Intermediate 46-3 (150 mg, 0.56 mmol) and 2-trifluoromethyl-3-bromo-pyridine (189 mg, 0.84 mmol) were dissolved in anhydrous toluene (5 mL), and $Pd_2(dba)_3$ (51 mg, 56 μmol), $Cs_2CO_3$ (360 mg, 1.10 mmol), and 4,5-bis(diphenylphosphino)-9,9-dimethylxanthene (Xantphos) (32.7 mg, 56 μmol) were added thereto. The reaction mixture was stirred at 100° C. for 12 h under nitrogen atmosphere. After the reaction was completed and cooled to room temperature, the reaction mixture was filtered, and the filtrate was concentrated to dryness under reduced pressure. The residue was purified by column chromatography (dichloromethane: methanol=20:1) to give a crude product, and was then purified by preparative high performance liquid chromatography [YMC-Actus Triart $C_{18}$ column, 5 μm silica, 30 mm diameter, 150 mm length; a mixture of water (containing 0.05% $NH_4HCO_3$) and acetonitrile with decreasing polarity was used as the eluent, acetonitrile gradient: 40%-70%, 15 min] to give the title compound (37.7 mg).

MS m/z (ESI): 379.0 $[M+H]^+$.

$^1$H NMR (400 MHz, DMSO-$d_6$) δ 9.00-8.98 (m, 1H), 8.30 (d, J=8.7 Hz, 1H), 8.23 (s, 1H), 8.21-8.19 (m, 1H), 8.08-8.05 (m, 1H), 7.46-7.43 (m, 1H), 6.55 (d, J=2.0 Hz, 1H), 4.23 (s, 3H).

Compound 47 (35 mg) was prepared by supercritical fluid chromatography (column: DAICEL CHIRALPAK AD (250 mm×30 mm, 10 μm); mobile phase: A: carbon dioxide; B: isopropanol (0.1% ammonia water); B %: 35%; flow rate: 70 mL/min) to give Compound 47-P1 (7.6 mg, RT: 1.385 min) and Compound 47-P2 (10.6 mg, RT: 1.786 min).

Compound 47-P1:

$^1$H NMR (400 MHz, Methanol-$d_4$) δ=8.99 (d, J=4.0 Hz, 1H), 8.36 (d, J=8.8 Hz, 1H), 8.15 (s, 1H), 8.10-8.06 (m, 1H), 8.04-7.99 (m, 1H), 7.47 (dd, J=2.0, 8.8 Hz, 1H), 6.59 (d, J=2.0 Hz, 1H), 4.31 (s, 3H).

MS m/z (ESI): 379.0 $[M+H]^+$.

Compound 47-P2:

$^1$H NMR (400 MHz, Methanol-$d_4$) δ=8.99 (d, J=4.3 Hz, 1H), 8.36 (d, J=8.8 Hz, 1H), 8.15 (s, 1H), 8.10-8.05 (m, 1H), 8.04-7.98 (m, 1H), 7.47 (dd, J=1.9, 8.7 Hz, 1H), 6.59 (d, J=2.0 Hz, 1H), 4.31 (s, 3H).

MS m/z (ESI): 379.0 $[M+H]^+$.

Example 48. 5-(2-cyclopropylpyridin-3-yl)-1-methyl-7-(trifluoromethyl)-1,5-dihydro-4H-imidazo[4,5-c]quinolin-4-one (Compound 48)

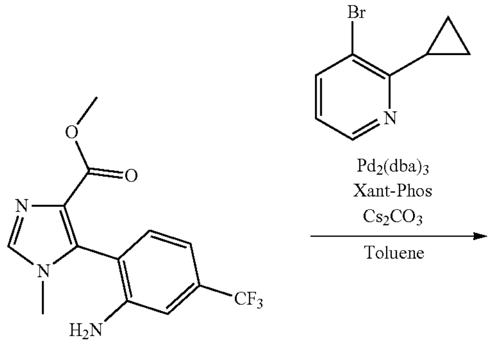

45-3

-continued

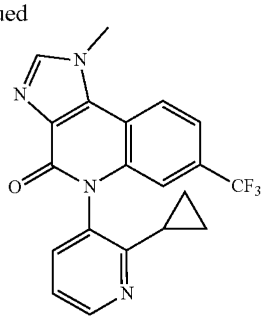

Compound 48

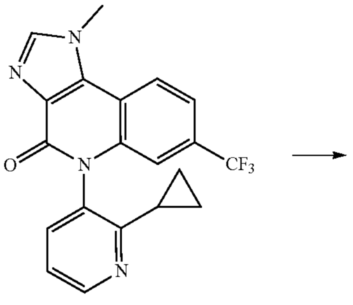

Compound 48

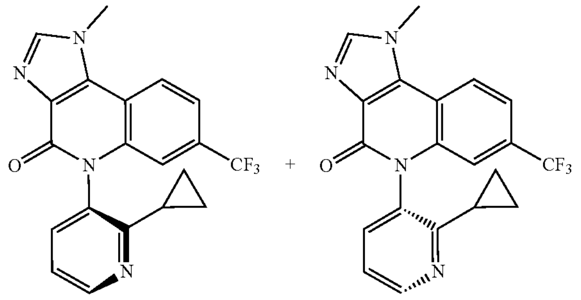

Intermediate 45-3 (250 mg, 0.83 mmol) and 3-bromo-2-cyclopropylpyridine (181 mg, 0.91 mmol) were dissolved in an anhydrous toluene solution (3 mL), cesium carbonate (541 mg, 1.66 mmol), 4,5-bis(diphenylphosphino)-9,9-dimethylxanthene (Xantphos) (96 mg, 0.17 mmol), and $Pd_2(dba)_3$ (76 mg, 0.08 mmol) were added thereto, and the reaction mixture was stirred at 100° C. for 4 h under nitrogen atmosphere. After the reaction was completed and cooled to room temperature, the reaction mixture was filtered, and the filtrate was concentrated to dryness under reduced pressure. The residue was purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 55%-75%, 12 min] to give the title compound (90 mg).

MS m/z (ESI): 385.1 $[M+H]^+$.

$^1$H NMR (400 MHz, DMSO-$d_6$) δ 8.67-8.64 (m, 1H), 8.51 (d, J=8.4 Hz, 1H), 8.31 (s, 1H), 7.80-7.78 (m, 1H), 7.71-7.69 (m, 1H), 7.46-7.43 (m, 1H), 6.71 (s, 1H), 4.28 (s, 3H), 1.50-1.46 (m, 1H), 1.12-1.09 (m, 1H), 0.78-0.74 (m, 2H), 0.62-0.53 (m, 1H).

Compound 48 (90 mg) was prepared by supercritical fluid chromatography (column: DAICEL CHIRALCEL OJ (250 mm×30 mm, 10 μm); mobile phase: A: carbon dioxide; B: ethanol (0.1% ammonia water); B %: 20%; flow rate: 70 mL/min) to give Compound 48-P1 (31.3 mg, RT: 3.257 min) and Compound 48-P2 (33.2 mg, RT: 3.564 min).

Compound 48-P1:

$^1$H NMR (400 MHz, Methanol-$d_4$) δ=8.66 (d, J=4.3 Hz, 1H), 8.57 (d, J=8.5 Hz, 1H), 8.22 (s, 1H), 7.76-7.70 (m, 2H), 7.50-7.40 (m, 1H), 6.91 (s, 1H), 4.36 (s, 3H), 1.60-1.50 (m, 1H), 1.25-1.20 (m, 1H), 0.95-0.90 (m, 1H), 0.84-0.80 (m, 1H), 0.75-0.60 (m, 1H).

MS m/z (ESI): 385.1 $[M+H]^+$.

Compound 48-P2:

$^1$H NMR (400 MHz, Methanol-$d_4$) δ=8.66 (d, J=4.8 Hz, 1H), 8.57 (d, J=8.5 Hz, 1H), 8.23 (s, 1H), 7.77-7.71 (m, 2H), 7.47 (dd, J=4.8, 7.8 Hz, 1H), 6.91 (s, 1H), 4.37 (s, 3H), 1.60-1.52 (m, 1H), 1.26-1.18 (m, 1H), 0.95-0.87 (m, 1H), 0.87-0.79 (m, 1H), 0.72-0.63 (m, 1H).

MS m/z (ESI): 385.1 $[M+H]^+$.

Example 49. 7-chloro-5-(2-cyclopropylpyridin-3-yl)-1-methyl-1,5-dihydro-4H-imidazo[4,5-c]quinolin-4-one (Compound 49)

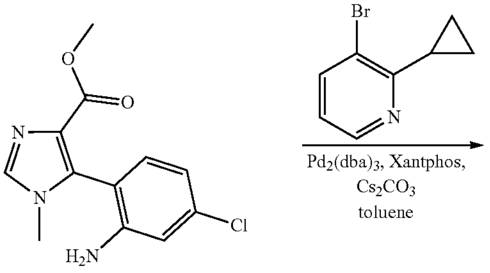

46-3

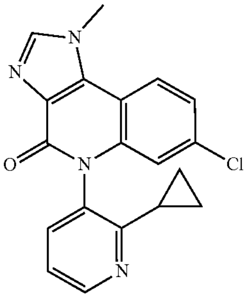

Compound 49

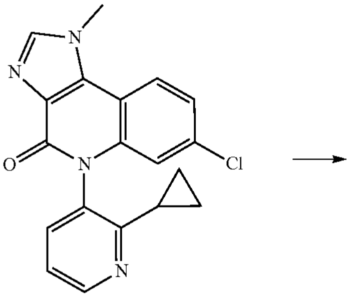

Compound 49

-continued

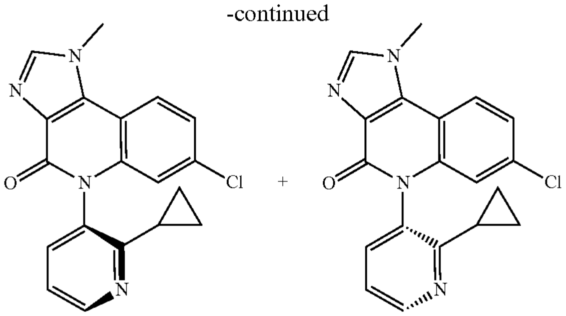

Intermediate 46-3 (150 mg, 0.56 mmol) and 3-bromo-2-cyclopropylpyridine (144.5 mg, 0.73 mmol) were dissolved in anhydrous toluene (5 mL), and $Pd_2(dba)_3$ (51 mg, 56 μmol), $Cs_2CO_3$ (360 mg, 1.10 mmol), and 4,5-bis(diphenylphosphino)-9,9-dimethylxanthene (Xantphos) (32.7 mg, 56 μmol) were added thereto. The reaction mixture was stirred at 100° C. for 12 h under nitrogen atmosphere. After the reaction was cooled to room temperature, the reaction mixture was filtered, and the filtrate was concentrated to dryness under reduced pressure. The residue was purified by column chromatography (dichloromethane:methanol=20:1) to give a crude product, and was then purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 40%-70%, 15 min] to give the title compound (73.3 mg).

MS m/z (ESI): 351.1 $[M+H]^+$.

$^1H$ NMR (400 MHz, DMSO-$d_6$) δ 8.64-8.62 (m, 1H), 8.30 (d, J=8.7 Hz, 1H), 8.23 (s, 1H), 7.75-7.73 (m, 1H), 7.51-7.38 (m, 2H), 6.48 (d, J=2.1 Hz, 1H), 4.23 (s, 3H), 1.53-1.43 (m, 1H), 1.09-0.98 (m, 1H), 0.90-0.72 (m, 2H), 0.69-0.62 (m, 1H).

Compound 49 (73 mg) was prepared by supercritical fluid chromatography (column: (S, S) WHELK-01 250 mm×30 mm, 5 μm; mobile phase: A: carbon dioxide; B: methanol (0.1% ammonia water); B %: 55%) to give Compound 49-P1 (17 mg, RT: 2.385 min) and Compound 49-P2 (21.2 mg, RT: 3.855 min).

Compound 49-P1:

$^1H$ NMR (400 MHz, Methanol-$d_4$) δ=8.65-8.60 (m, 1H), 8.36 (d, J=8.8 Hz, 1H), 8.15 (s, 1H), 7.70 (d, J=7.0 Hz, 1H), 7.50-7.40 (m, 2H), 6.67 (s, 1H), 4.31 (s, 3H), 1.60-1.50 (m, 1H), 1.25-1.10 (m, 1H), 1.05-0.90 (m, 1H), 0.88-0.80 (m, 1H), 0.75-0.70 (m, 1H).

MS m/z (ESI): 351.1 $[M+H]^+$.

Compound 49-P2:

$^1H$ NMR (400 MHz, Methanol-$d_4$) δ=8.65-8.60 (m, 1H), 8.36 (d, J=8.5 Hz, 1H), 8.15 (s, 1H), 7.70 (d, J=7.3 Hz, 1H), 7.50-7.40 (m, 2H), 6.67 (s, 1H), 4.31 (s, 3H), 1.60-1.50 (m, 1H), 1.20-1.10 (m, 1H), 0.99-0.84 (m, 1H), 0.83-0.75 (m, 1H), 0.74-0.68 (m, 1H).

MS m/z (ESI): 351.1 $[M+H]^+$.

Example 50. 5-(2-chlorophenyl)-1-(2-hydroxyethyl)-7-(trifluoromethyl)-1,5-dihydro-4H-imidazo[4,5-c][1,8]naphthyridin-4-one (Compound 50)

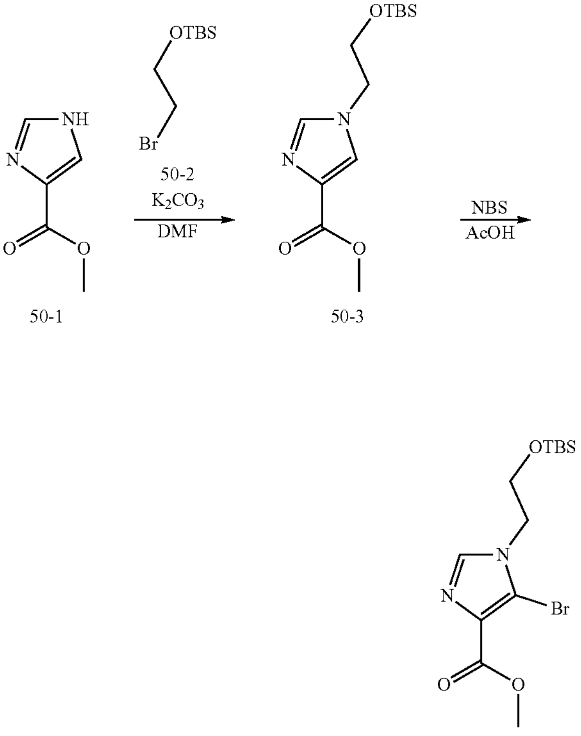

50-1 50-3 50-4

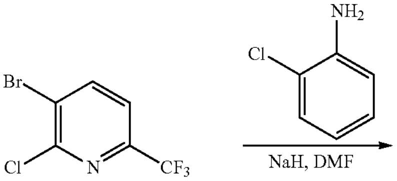

15-1

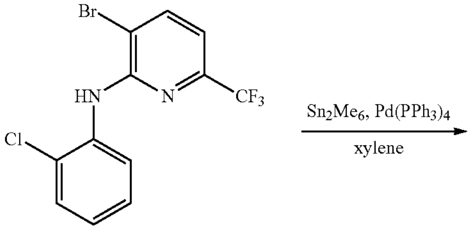

50-5

-continued

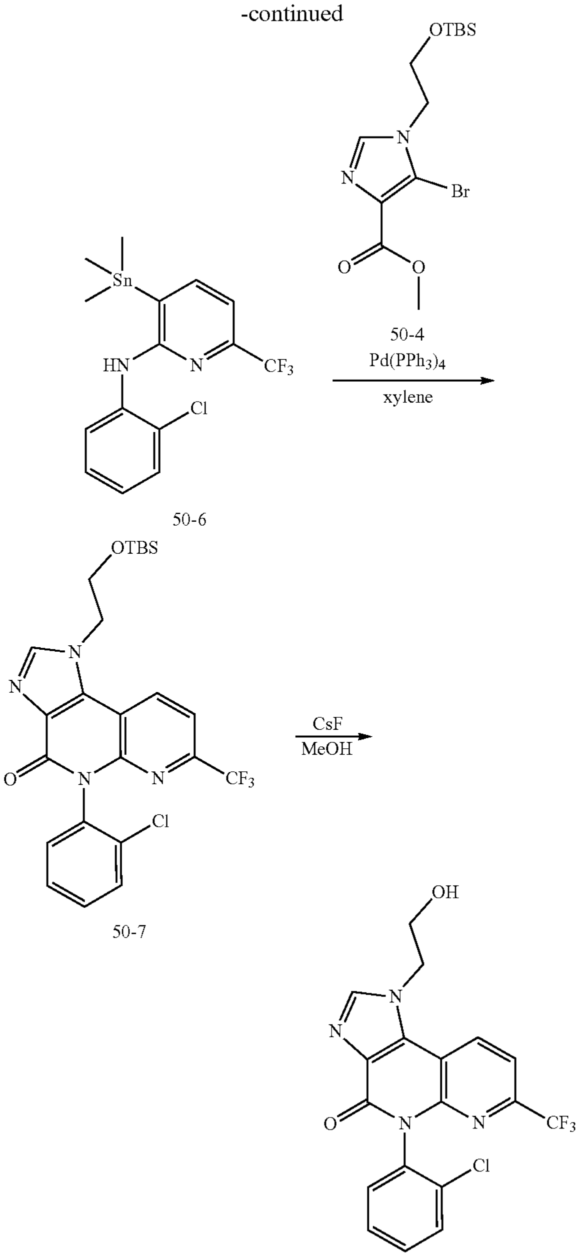

50-4

50-6

50-7

Compound 50

Step 1: synthesis of methyl 1-(2-((tert-butyldimethylsilyl)oxy)ethyl)-1H-imidazole-4-formate (intermediate 50-3)

Intermediate 50-1 (5 g) was dissolved in an anhydrous N,N-dimethylformamide solution (70 mL) at 25° C., potassium carbonate (16.44 g) and intermediate 50-2 (11.38 g) were added thereto, and the reaction mixture was stirred for reaction at 25° C. for 16 h under nitrogen atmosphere. After the reaction was completed, water (200 mL) and ethyl acetate (100 mL) were added sequentially to the reaction mixture. The organic phase was washed with a saturated aqueous sodium chloride solution (200 mL×2), and the washed organic phase was dried over an appropriate amount of anhydrous sodium sulfate. The organic phase was filtered and concentrated under reduced pressure to remove the solvent. The residue was purified by column chromatography (0-50% tetrahydrofuran/petroleum ether, 40 mL/min) to give the title compound (6.5 g).

MS m/z (ESI): =284.9 $[M+H]^+$.

Step 2: synthesis of methyl 5-bromo-1-(2-((tert-butyldimethylsilyl)oxy)ethyl)-1H-imidazole-4-formate (intermediate 50-4)

Intermediate 50-3 (6.5 g) was dissolved in acetic acid (130 mL) at 25° C., N-bromosuccinimide (NBS) (4.07 g) was added thereto, and the reaction mixture was stirred for reaction at 60° C. for 16 h under nitrogen atmosphere. After the reaction was completed, a saturated sodium bicarbonate solution was added to the reaction mixture to adjust the pH to 7. Water (100 mL) and ethyl acetate (200 mL) were added sequentially. The organic phase was washed with water (100 mL×2), and the washed organic phase was dried over an appropriate amount of anhydrous sodium sulfate. The organic phase was filtered and concentrated to dryness under reduced pressure. The residue was purified by column chromatography (0-30% tetrahydrofuran/petroleum ether, 60 mL/min) to give the title compound (1 g).

MS m/z (ESI): =362.9 $[M+H]^+$.

Step 3: synthesis of 3-bromo-N-(2-chlorophenyl)-6-(trifluoromethyl)pyridin-2-amine (Intermediate 50-5)

o-chloroaniline (2.94 g) was dissolved in an N,N-dimethylformamide solution (50 mL), sodium hydride (60%) (1.15 g) was added at 0-5° C., and the reaction mixture was stirred at 0° C. for 0.5 h. Intermediate 15-1 (5 g) was added to the reaction mixture, and the mixture was stirred at room temperature for 12 h. The reaction mixture was slowly poured into a saturated aqueous ammonium chloride solution (50 mL). The mixture was extracted with ethyl acetate (60 mL×2). The organic phases were combined and washed with saturated brine (100 mL), and the washed organic phase was dried over an appropriate amount of anhydrous sodium sulfate and filtered. The filtrate was concentrated to dryness under reduced pressure, and the residue was purified by preparative thin-layer chromatography (silica, petroleum ether:ethyl acetate=10:1) to give the title compound (3.5 g).

MS m/z (ESI): 351.0 $[M+H]^+$.

Step 4: synthesis of N-(2-chlorophenyl)-6-(trifluoromethyl)-3-(trimethylstannyl)pyridin-2-amine (intermediate 50-6)

Intermediate 50-5 (500 mg) and hexamethylditin (700 mg) were dissolved in an anhydrous xylene solution (5 mL), $Pd(PPh_3)_4$ (164 mg) was added thereto, and the reaction mixture was stirred at 120° C. for 1 h under nitrogen atmosphere. After the reaction was cooled to room temperature, water (50 mL) and ethyl acetate (50 mL) were added sequentially. The organic phase was washed with water (50 mL×2), and the washed organic phase was dried over an appropriate amount of anhydrous sodium sulfate. The residue was purified by preparative thin-layer chromatography (silica, petroleum ether:ethyl acetate=100:1) to give the title compound (300 mg).

MS m/z (ESI): 437.0 $[M+H]^+$

Step 5: synthesis of 1-(2-((tert-butyldimethylsilyl)oxy)ethyl)-5-(2-chlorophenyl)-7-(trifluoromethyl)-1,5-dihydro-4H-imidazo[4,5-c][1,8]naphthyridin-4-one (intermediate 50-7)

Intermediate 50-6 (60 mg) was dissolved in a xylene solution (1 mL) at 25° C., a catalyst $Pd(PPh_3)_4$ (19.08 mg) and intermediate 50-4 (71.91 mg) were added thereto, and the reaction mixture was stirred for reaction at 140° C. for 16 h under nitrogen atmosphere. After the reaction was completed and cooled to room temperature, water (10 mL) and ethyl acetate (5 mL) were added sequentially. The organic phase was washed with water (10 mL×2), and the washed organic phase was dried over an appropriate amount of anhydrous sodium sulfate. After the organic phase was filtered, the organic phase was concentrated to dryness under reduced pressure, and the residue was purified by preparative thin-layer chromatography (silica, petroleum ether/tetrahydrofuran=5/1) to give the title compound (60 mg).

MS m/z (ESI): =523.0 $[M+H]^+$.

Step 6: synthesis of 5-(2-chlorophenyl)-1-(2-hydroxyethyl)-7-(trifluoromethyl)-1,5-dihydro-4H-imidazo[4,5-c][1,8]naphthyridin-4-one (Compound 50)

Intermediate 50-7 (50 mg) was dissolved in an anhydrous methanol solution (1 mL) at 20° C., cesium fluoride (145.22 mg) was added to the reaction mixture, and the reaction mixture was stirred at 20° C. for 15 h under nitrogen atmosphere. After the reaction was completed, the mixture was concentrated to dryness under reduced pressure. Water (10 mL) and ethyl acetate (5 mL) were added sequentially. The organic phase was washed with water (10 mL×2), and the washed organic phase was dried over an appropriate amount of anhydrous sodium sulfate. After the organic phase was filtered, the organic phase was concentrated to dryness under reduced pressure, and the residue was purified by high performance liquid chromatography (acidic condition; column: Waters Xbridge BEH C18 100×25 mm×5 μm; mobile phase: A: water (0.225% formic acid), B: acetonitrile; B %: 24%-44%, 12 min) to give the title compound (8.1 mg).

$^1$H NMR (400 MHz, DMSO-$d_6$) δ=8.88 (d, J=8.3 Hz, 1H), 8.33 (s, 1H), 7.80 (d, J=8.3 Hz, 1H), 7.70 (dd, J=3.4, 6.1 Hz, 1H), 7.57-7.53 (m, 2H), 7.52-7.48 (m, 1H), 5.17 (t, J=5.3 Hz, 1H), 4.74 (t, J=5.0 Hz, 2H), 3.93-3.85 (m, 2H).

MS m/z (ESI): =409.0 $[M+H]^+$.

Example 51. 5-(2-chlorophenyl)-7-(trifluoromethyl)oxazolo[5,4-c][1,8]naphthyridin-4 (5H)-one (Compound 51)

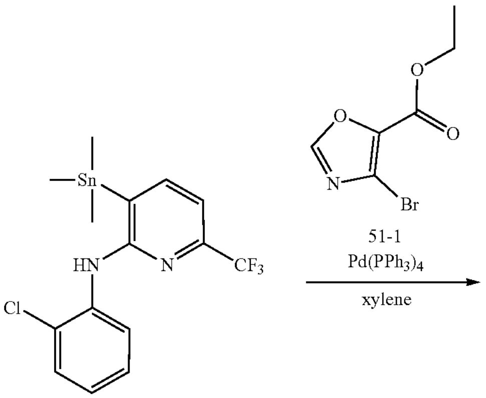

50-6

51-1

-continued

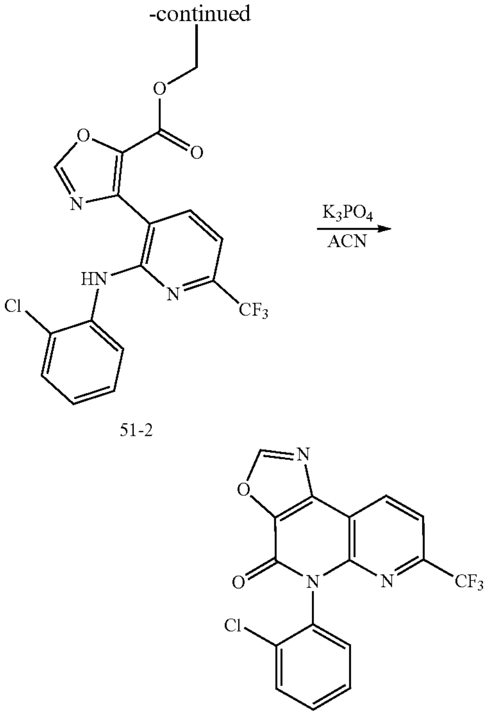

51-2

Compound 51

Step 1: synthesis of ethyl 4-(2-((2-chlorophenyl)amino)-6-(trifluoromethyl)pyridin-3-yl)oxazole-5-carboxylate (intermediate 51-2)

Intermediate 50-6 (500 mg) and intermediate 51-1 (700 mg) were dissolved in an anhydrous xylene solution (5 mL), $Pd(PPh_3)_4$ (53.05 mg) was added thereto, and the reaction mixture was stirred at 140° C. for 4 h under nitrogen atmosphere. After the reaction was cooled to room temperature, water (50 mL) and ethyl acetate (50 mL) were added sequentially. The organic phase was washed with water (50 mL×2), and the washed organic phase was dried over an appropriate amount of anhydrous sodium sulfate. The residue was purified by preparative thin-layer chromatography (silica, petroleum ether:ethyl acetate=3:1) to give the title compound (100 mg).

MS m/z (ESI): 412.0 $[M+H]^+$.

Step 2: synthesis of 5-(2-chlorophenyl)-7-(trifluoromethyl)oxazolo[5,4-c][1,8]naphthyridin-4 (5H)-one (Compound 51)

Intermediate 51-2 (100 mg) was dissolved in an anhydrous acetonitrile solution (2 mL), $K_3PO_4$ (257 mg) was added thereto, and the reaction mixture was stirred at 25° C. for 2 h under nitrogen atmosphere. After the reaction was cooled to room temperature, the reaction mixture was filtered and concentrated to dryness under reduced pressure, and the residue was purified by preparative high-pressure liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 50%-80%, 15 min] to give the title compound (20.0 mg).

MS m/z (ESI): 366.0 $[M+H]^+$.

$^1$H NMR (400 MHz, DMSO-$d_6$) δ 9.27 (s, 1H), 8.88 (d, J=8.0 Hz, 1H), 7.97 (d, J=8.0 Hz, 1H), 7.79-7.70 (m, 1H), 7.63-7.58 (m, 3H).

Example 52. 3-(1-methyl-4-oxo-7-(trifluoromethyl)-1,4-dihydro-5H-imidazo[4,5-c][1,8]naphthyridin-5-yl)benzonitrile (Compound 52)

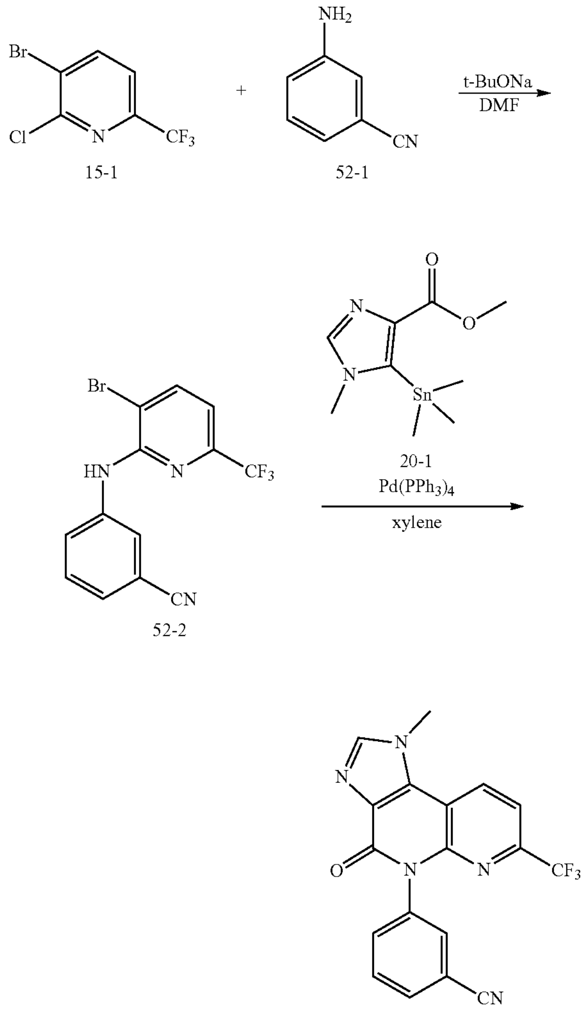

15-1 + 52-1 → 52-2 → Compound 52

Step 1: synthesis of 3-((3-bromo-6-(trifluoromethyl)pyridin-2-yl)amino)benzonitrile (Intermediate 52-2)

Reactant 52-1 (113.40 mg) was dissolved in N,N-dimethylformamide (10 mL), and reactant 15-1 (250 mg) was added. The reaction mixture was stirred for reaction at 60° C. for 12 h. After the reaction was completed, water (5 mL) was added to the reaction mixture. The mixture was extracted with ethyl acetate (10 mL×3 times). The organic layer was washed with saturated brine (10 mL×3 times). The organic phase was concentrated to dryness under reduced pressure, and the residue was purified by column chromatography (petroleum ether:ethyl acetate=1:1) to give the title compound (190 mg).

MS m/z (ESI): =341.9 [M+H]$^+$.

Step 2: synthesis of 3-(1-methyl-4-oxo-7-(trifluoromethyl)-1,4-dihydro-5H-imidazo[4,5-c][1,8]naphthyridin-5-yl)benzonitrile (Compound 52)

Intermediate 52-2 (190 mg) was dissolved in xylene (3 mL), and intermediate 20-1 (168.25 mg) and tetrakis(triphenylphosphine)palladium(0) (64.18 mg) were added. The reaction mixture was warmed to 140° C. and stirred for reaction for 12 h under nitrogen atmosphere. After the reaction was completed, the reaction mixture was concentrated to dryness under reduced pressure, and the residue was purified by preparative high performance liquid chromatography (column: Waters Xbridge BEH C18 100×25 mm×5 μm; mobile phase: [water (0.225% formic acid)-acetonitrile]; B %: 26%-46%, 12 min) to give the title compound (6.1 mg).

MS m/z (ESI): =370.0[M+H]$^+$.

$^1$H NMR (400 MHz, METHANOL-$d_4$) δ=8.90 (d, J=8.1 Hz, 1H), 8.26 (s, 1H), 7.91 (d, J=7.9 Hz, 1H), 7.82-7.75 (m, 3H), 7.69 (d, J=8.0 Hz, 1H), 4.35 (s, 3H).

Example 53. 5-(2-chlorophenyl)-1-(2-(dimethylamino)ethyl)-7-(trifluoromethyl)-1,5-dihydro-4H-imidazo[4,5-c][1,8]naphthyridin-4-one (Compound 53)

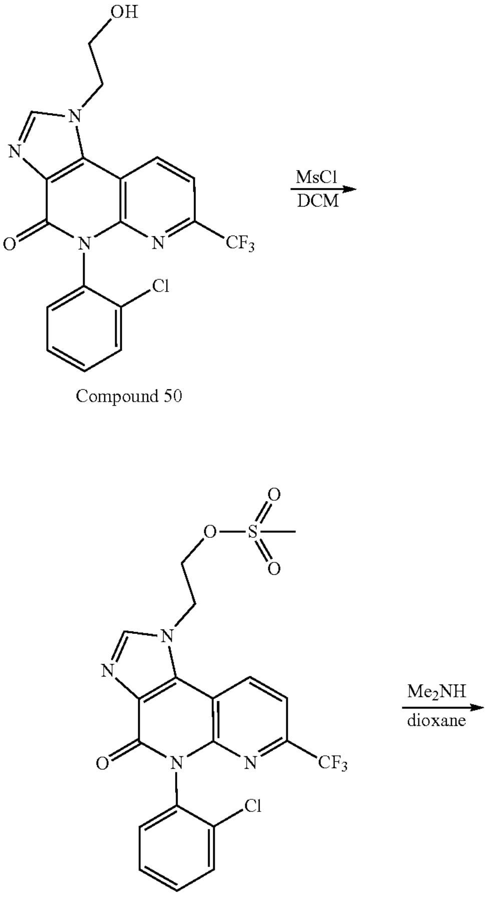

Compound 50 → 53-1

-continued

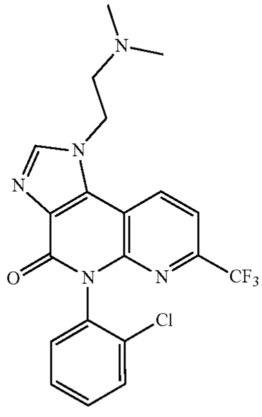

Compound 53

Step 1: synthesis of 2-(5-(2-chlorophenyl)-4-oxo-7-(trifluoromethyl)-4,5-dihydro-1H-imidazo[4,5-c][1,8]naphthyridin-1-yl)ethyl methanesulfonate (intermediate 53-1)

Compound 50 (100 mg) was dissolved in an anhydrous dichloromethane (4 mL) solution at 25° C., triethylamine (49.51 mg) was added thereto, and the reaction system was cooled to 0° C. Methanesulfonyl chloride (56.05 mg) was dissolved in anhydrous dichloromethane (1 mL) and slowly added to the reaction mixture, and the reaction mixture was stirred for reaction at 25° C. for 3 h under nitrogen atmosphere. After the reaction was completed, the organic phase was concentrated to dryness under reduced pressure to give the title compound (108 mg).

MS m/z (ESI): =487.0 $[M+H]^+$.

Step 2: synthesis of 5-(2-chlorophenyl)-1-(2-(dimethylamino)ethyl)-7-(trifluoromethyl)-1,5-dihydro-4H-imidazo[4,5-c][1,8]naphthyridin-4-one (Compound 53)

Intermediate 53-1 (36 mg) was dissolved in an anhydrous dioxane solution (1 mL) at 20° C., and an aqueous dimethylamine solution (416.71 mg) was added to the reaction mixture. The reaction mixture was stirred for reaction at 100° C. for 4 h under nitrogen atmosphere. After the reaction was completed, the organic phase was concentrated to dryness under reduced pressure, and the residue was purified by high performance liquid chromatography (acidic condition; column: Waters Xbridge BEH C18 100×25 mm×5 μm; mobile phase: A: water (0.225% formic acid), B: acetonitrile; B %: 12%-32%, 12 min) to give the title compound (8.8 mg).

$^1$H NMR (400 MHz, METHANOL-$d_4$) δ=8.80 (d, J=8.3 Hz, 1H), 8.38 (s, 1H), 7.80 (d, J=8.3 Hz, 1H), 7.65 (dd, J=1.6, 7.7 Hz, 1H), 7.59-7.47 (m, 2H), 7.35 (dd, J=1.8, 7.5 Hz, 1H), 4.96-4.92 (m, 2H), 3.19 (t, J=6.4 Hz, 2H), 2.58 (s, 6H).

MS m/z (ESI): =436.0 $[M+H]^+$.

Example 54. 5-(2-chlorophenyl)-1-(2-(methylamino)ethyl)-7-(trifluoromethyl)-1,5-dihydro-4H-imidazo[4,5-c][1,8]naphthyridin-4-one (Compound 54)

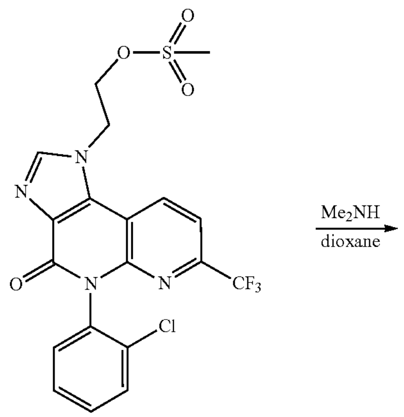

53-1

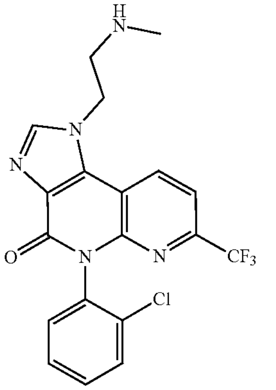

Compound 54

Intermediate 53-1 (36 mg) was dissolved in anhydrous dioxane (1 mL) at 20° C., and an aqueous methylamine solution (114.82 mg) was added to the reaction mixture. The reaction mixture was stirred for reaction at 100° C. for 4 h under nitrogen atmosphere. After the reaction was completed, the organic phase was concentrated to dryness under reduced pressure, and the residue was purified by high performance liquid chromatography (acidic condition; column: Waters Xbridge BEH C18 100×25 mm×5 μm; mobile phase: A: water (0.225% formic acid), B: acetonitrile; B %: 7%-27%, 12 min) to give the title compound (5.3 mg).

$^1$H NMR (400 MHz, METHANOL-$d_4$) δ=8.79 (d, J=8.0 Hz, 1H), 8.55 (s, 1H), 7.84 (d, J=8.3 Hz, 1H), 7.63-7.58 (m, 1H), 7.50 (dt, J=1.4, 7.8 Hz, 1H), 7.35 (dt, J=1.3, 7.7 Hz, 1H), 6.79-6.72 (m, 1H), 5.11 (s, 2H), 3.82-3.62 (m, 2H), 2.83 (s, 3H).

MS m/z (ESI): =422.0 $[M+H]^+$.

Example 55. 1-(2-aminoethyl)-5-(2-chlorophenyl)-7-(trifluoromethyl)-1,5-dihydro-4H-imidazo[4,5-c][1,8]naphthyridin-4-one (Compound 55)

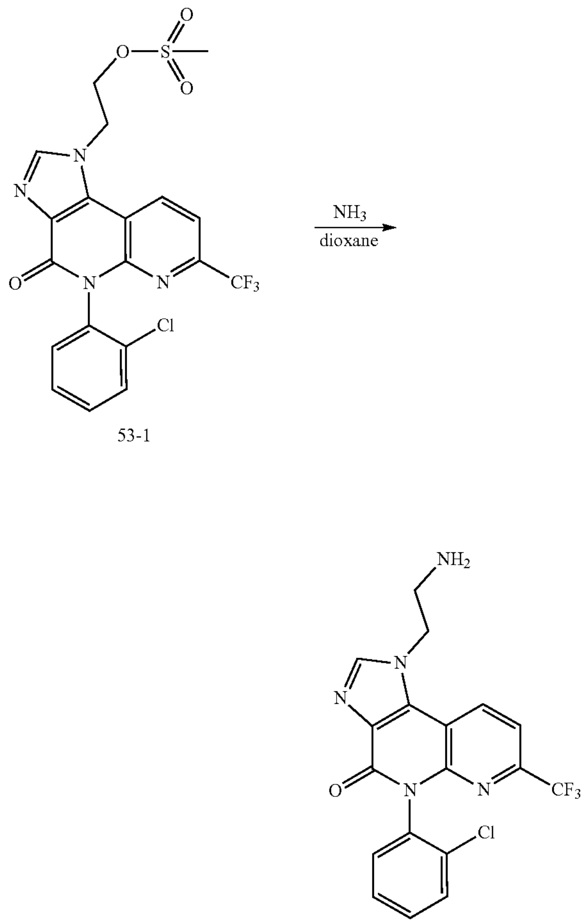

53-1

Compound 55

Intermediate 53-1 (36 mg) was dissolved in an anhydrous dioxane solution (1 mL) at 20° C., and an aqueous ammonia solution (392.64 mg) was added to the reaction mixture. The reaction mixture was stirred for reaction at 100° C. for 4 h under nitrogen atmosphere. After the reaction was completed, the organic phase was concentrated to dryness under reduced pressure, and the residue was purified by high performance liquid chromatography (acidic condition; column: Waters Xbridge BEH C18 100×25 mm×5 μm; mobile phase: A: water (0.225% formic acid), B: acetonitrile; B %: 17%-37%, 12 min) to give the title compound (5.3 mg).

1H NMR (400 MHz, METHANOL-$d_4$) δ=8.78 (d, J=8.3 Hz, 1H), 8.37 (s, 1H), 7.82 (d, J=8.3 Hz, 1H), 7.65-7.60 (m, 1H), 7.52 (dt, J=1.3, 7.8 Hz, 1H), 7.42 (dt, J=1.0, 7.7 Hz, 1H), 6.99 (d, J=6.8 Hz, 1H), 5.09-4.96 (m, 2H), 3.65 (s, 2H).

MS m/z (ESI): =408.0 $[M+H]^+$.

Example 56. 5-(2-chlorophenyl)-1,7-dimethyl-1,5-dihydro-4H-imidazo[4,5-c][1,8]naphthyridin-4-one (Compound 56)

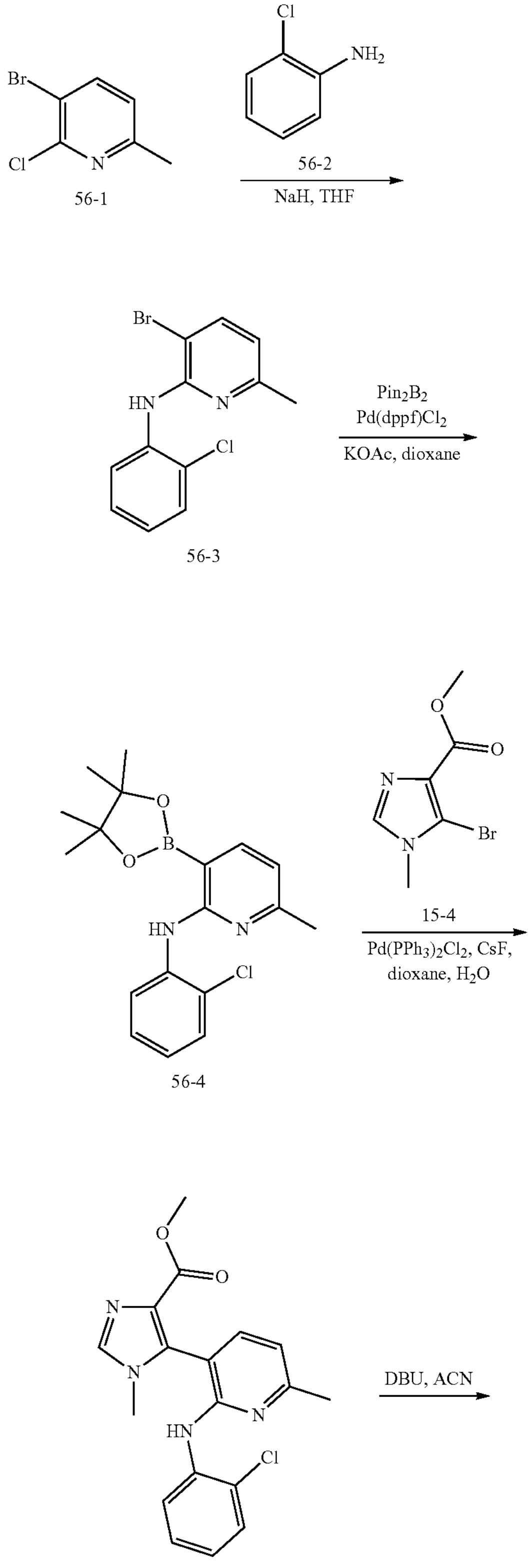

56-1

56-3

56-4

56-5

-continued

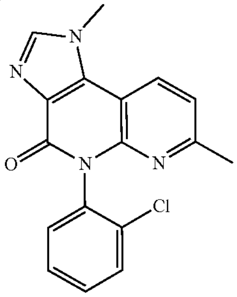

Compound 56

Step 1: synthesis of 3-bromo-N-(2-chlorophenyl)-6-methylpyridin-2-amine (Intermediate 56-3)

Reactant 56-2 (3.7 g) was dissolved in tetrahydrofuran (30 mL), sodium hydride (1.9 g) was added to the reaction mixture at 0° C., and the mixture was stirred at room temperature for 30 min. The reaction mixture was cooled to 0° C., and reactant 56-1 (5 g) was added. The reaction mixture was stirred at 25° C. for 6 h under nitrogen atmosphere. After the reaction was completed and cooled to 0° C., water (100 mL) and ethyl acetate (300 mL) were added sequentially. The organic phase was washed with water (60 mL×2), and the washed organic phase was dried over an appropriate amount of anhydrous sodium sulfate. After the organic phase was filtered, the organic phase was concentrated under reduced pressure to remove the solvent, and the residue was purified by column chromatography (petroleum ether:ethyl acetate=100:1) to give the title compound (6 g).

MS m/z (ESI): 297.2 $[M+H]^+$.

Step 2: synthesis of N-(2-chlorophenyl)-6-methyl-3-(4,4,5,5-tetramethyl-1,3,2-dioxaborolan-2-yl)pyridin-2-amine (intermediate 56-4)

Intermediate 56-3 (3 g) and bis(pinacolato)diboron (5.1 g) were dissolved in 1,4-dioxane (30 mL), and potassium acetate (2.9 g) and Pd(dppf)$Cl_2$ (738 mg) were added thereto. The reaction mixture was stirred at 100° C. for 15 h under nitrogen atmosphere. After the reaction was completed and the reaction mixture was cooled to room temperature, water (200 mL) and ethyl acetate (90 mL) were added sequentially. The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Gemini NX C18 5 μm×10×150 mm; mobile phase: A: 0.05% TFA v/v, B: acetonitrile; B %: 40%-45%, 15 min) to give the title compound (800 mg).

MS m/z (ESI): 345.2$[M+H]^+$.

Step 3: synthesis of methyl 5-(2-((2-chlorophenyl) amino)-6-methylpyridin-3-yl)-1-methyl-1H-imidazole-4-carboxylate (intermediate 56-5)

Intermediate 56-4 (200 mg) and intermediate 15-4 (195 mg) were dissolved in dioxane (2 mL) and water (0.4 mL), cesium fluoride (267 mg) and $Pd(PPh_3)_2Cl_2$ (39 mg) were added thereto, and the reaction mixture was stirred at 100° C. for 16 h under nitrogen atmosphere. After the reaction was completed and cooled to room temperature, water (30 mL) and ethyl acetate (40 mL) were added sequentially. The organic phase was washed with saturated brine (30 mL×2), and the washed organic phase was dried over an appropriate amount of anhydrous sodium sulfate. After the organic phase was filtered, the organic phase was concentrated under reduced pressure to remove the solvent, and the residue was purified by column chromatography (petroleum ether:ethyl acetate=100:1) to give the title compound (70 mg).

MS m/z (ESI): 357.2 $[M+H]^+$.

Step 4: synthesis of 5-(2-chlorophenyl)-1,7-dimethyl-1,5-dihydro-4H-imidazo[4,5-c][1,8]naphthyridin-4-one (Compound 56)

Intermediate 56-5 (70 mg) was dissolved in acetonitrile (2 mL), 1,8-diazabicyclo[5.4.0]undec-7-ene (DBU) (89 mg) was added thereto, and the reaction mixture was stirred at 25° C. for 16 h under nitrogen atmosphere. After the reaction was completed, water (30 mL) and ethyl acetate (40 mL) were added sequentially to the reaction mixture. The organic phase was washed with saturated brine (30 mL×2), and the washed organic phase was dried over an appropriate amount of anhydrous sodium sulfate and concentrated to dryness under reduced pressure. The residue was purified by preparative high performance liquid chromatography [YMC-Actus Triart $C_{18}$ column, 5 μm silica, 30 mm diameter, 150 mm length; a mixture of water (containing 0.05% $NH_4HCO_3$) and acetonitrile with decreasing polarity was used as the eluent, acetonitrile gradient: 40%-75%, 13 min] to give the title compound (4 mg).

MS m/z (ESI): 325.2 $[M+H]^+$.

$^1H$ NMR (400 MHz, Chloroform-d) δ 8.20 (d, J=8.2 Hz, 1H), 7.82 (s, 1H), 7.61-7.54 (m, 1H), 7.48-7.39 (m, 2H), 7.37-7.31 (m, 1H), 7.09 (d, J=8.1 Hz, 1H), 4.19 (s, 3H), 2.41 (s, 3H).

Example 57. 1-methyl-7-(trifluoromethyl)-5-(2-(trifluoromethyl)phenyl)-1,5-dihydro-4H-imidazo[4,5-c][1,8]naphthyridin-4-one (Compound 57)

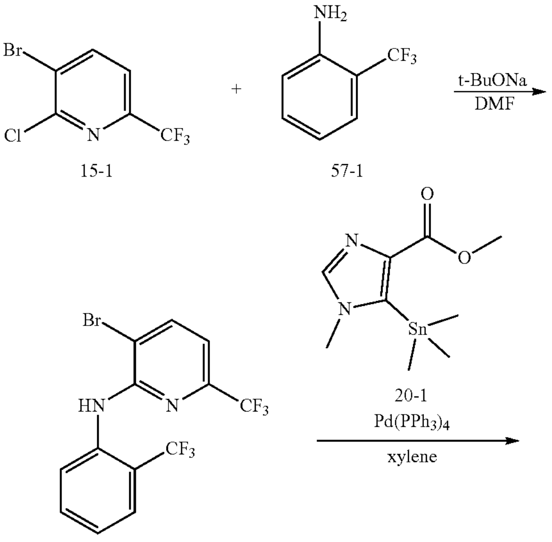

15-1

57-1

20-1

57-2

-continued

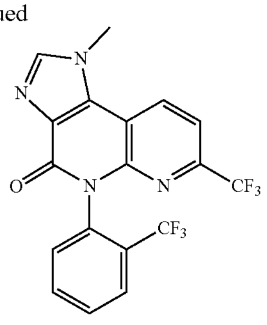

Compound 57

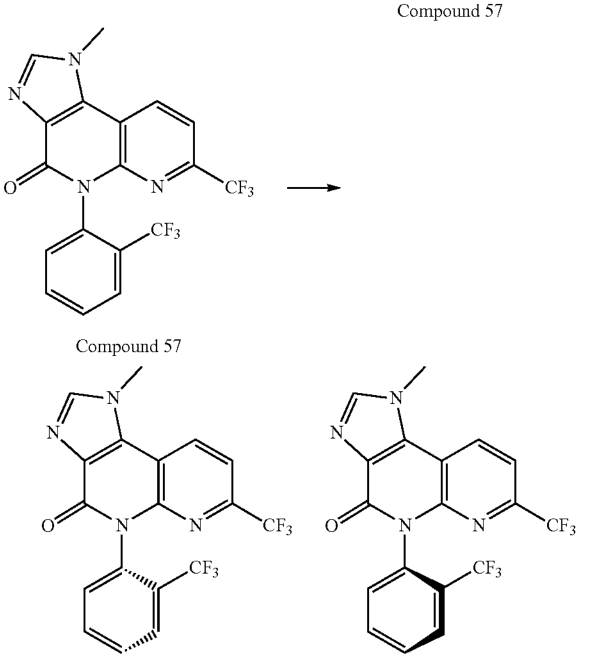

Compound 57

Step 1: synthesis of 3-bromo-6-(trifluoromethyl)-N-[2-(trifluoromethyl)phenyl]pyridin-2-amine (intermediate 57-2)

Intermediate 15-1 (200 mg) and reactant 57-1 (123.73 mg) were dissolved in anhydrous N,N-dimethylformamide (4 mL), sodium tert-butoxide (184.50 mg) was added thereto, and the reaction mixture was stirred at 25° C. for 16 h. After the reaction was completed, water (20 mL) was added to the reaction mixture. The mixture was extracted with ethyl acetate (10 mL×3 times). The organic phases were combined and dried over anhydrous sodium sulfate. After the organic layer was filtered, the organic layer was concentrated to dryness under reduced pressure, and the residue was purified by preparative thin-layer chromatography (petroleum ether:ethyl acetate=10:1) to give the title compound (61.6 mg).

MS m/z (ESI): 384.9 [M+H]$^+$.

Step 2: synthesis of 1-methyl-7-(trifluoromethyl)-5-(2-(trifluoromethyl)phenyl)-1,5-dihydro-4H-imidazo[4,5-c][1,8]naphthyridin-4-one (Compound 57)

Intermediate 57-2 (60 mg) and intermediate 20-1 (47.2 mg) were dissolved in xylene (1 mL), tetrakis(triphenylphosphine)palladium(0) (18.0 mg) was added thereto, and the reaction mixture was stirred at 140° C. for 16 h under nitrogen atmosphere. After the reaction was completed, water (10 mL) was added to the reaction mixture. The mixture was extracted with ethyl acetate (5 mL×3 times). The organic phases were combined and dried over anhydrous sodium sulfate. After the organic layer was filtered, the organic layer was concentrated to dryness under reduced pressure. The residue was purified by preparative high performance liquid chromatography (column: Waters Xbridge BEH C18 100×25 mm×5 μm; mobile phase: A: water (0.225% formic acid v/v), B: acetonitrile; B %: 23%-53%, 12 min), and was then separated by supercritical fluid chromatography (column: DAICEL CHIRALCEL OD-H (250 mm×30 mm, 5 μm); mobile phase: [A: carbon dioxide; B: 0.1% ammonia water/ethanol]; B %: 35%) to give Compound 57-P1 (1.9 mg, RT: 3.805 min) and Compound 57-P2 (1.9 mg, RT: 4.112 min).

Compound 57-P1:

MS m/z (ESI): 413.0 [M+H]$^+$.

$^1$H NMR (400 MHz, Methanol-$d_4$) δ 8.90 (d, J=8.3 Hz, 1H), 8.25 (s, 1H), 7.94 (d, J=7.8 Hz, 1H), 7.89-7.84 (m, 1H), 7.80-7.75 (m, 2H), 7.48 (d, J=7.9 Hz, 1H), 4.35 (s, 3H).

Compound 57-P2:

MS m/z (ESI): 413.0 [M+H]$^+$.

$^1$H NMR (400 MHz, Methanol-$d_4$) δ 8.78 (d, J=8.3 Hz, 1H), 8.14 (s, 1H), 7.82 (d, J=7.8 Hz, 1H), 7.77-7.72 (m, 1H), 7.68-7.61 (m, 2H), 7.36 (d, J=7.9 Hz, 1H), 4.23 (s, 3H).

Example 58. 5-(2-chloro-4-(difluoromethoxy)phenyl)-1-methyl-7-(trifluoromethyl)-1,5-dihydro-4H-imidazo[4,5-c][1,8]naphthyridin-4-one (Compound 58)

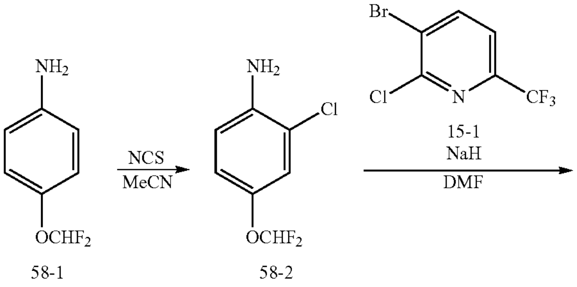

58-1

58-2

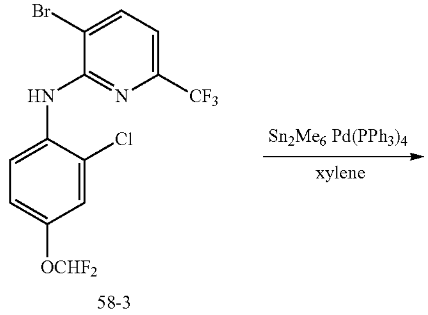

58-3

-continued

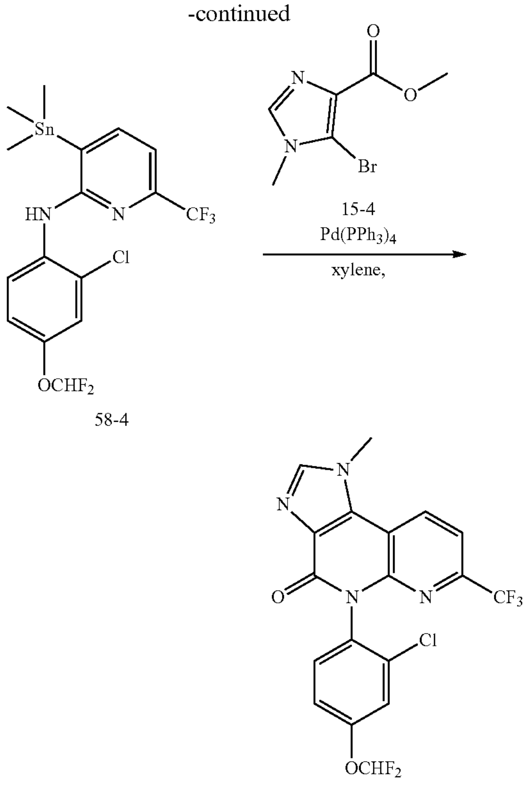

58-4

15-4

Compound 58

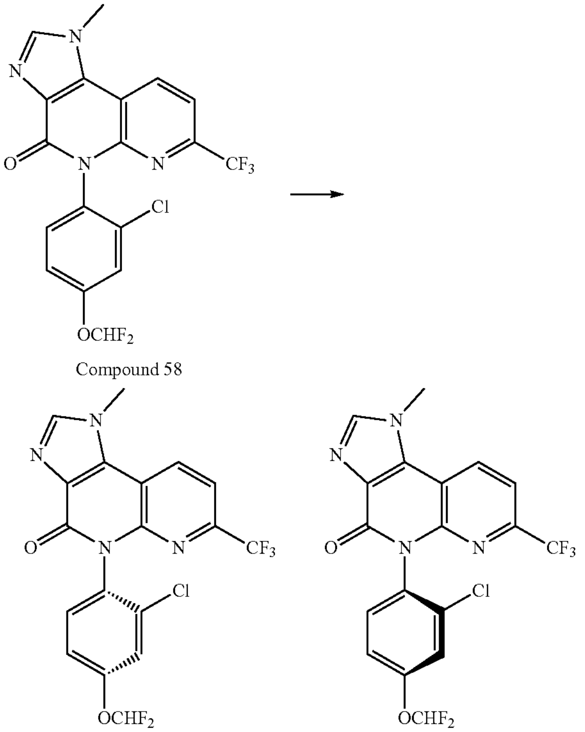

Compound 58

Step 1: synthesis of 2-chloro-4-(difluoromethoxy)aniline (intermediate 58-2)

Reactant 58-1 (1 g) was dissolved in an anhydrous acetonitrile solution (10 mL) at 25° C., N-chlorosuccinimide (839.13 mg) was added thereto, and the reaction mixture was stirred for reaction at 80° C. for 16 h under nitrogen atmosphere. After the reaction was completed, ethyl acetate (20 mL) and water (40 mL) were added to the reaction mixture, and the mixture was washed with a saturated aqueous sodium chloride solution (40 mL×2 times). The organic phases were combined and dried over anhydrous sodium sulfate. After the organic phase was filtered, the organic phase was concentrated to dryness under reduced pressure, and the residue was purified by column chromatography (0-5% ethyl acetate/petroleum ether, 60 mL/min) to give the title compound (830 mg).

MS m/z (ESI): =193.8 $[M+H]^+$.

Step 2: synthesis of 3-bromo-N-(2-chloro-4-(difluoromethoxy)phenyl)-6-(trifluoromethyl)pyridin-2-amine (intermediate 58-3)

Intermediate 58-2 (730 mg) was dissolved in an anhydrous N,N-dimethylformamide solution (9 mL) at 25° C. The mixture was cooled to 0° C., and sodium hydride (301.66 mg) was slowly added thereto. After the mixture was stirred for 30 min, intermediate 15-1 (982.14 mg) was dissolved in an anhydrous N,N-dimethylformamide solution (2 mL) and then added to the reaction system. The reaction mixture was stirred for reaction at 25° C. for 16 h under nitrogen atmosphere. After the reaction was completed, the mixture was cooled to 0° C. Water (5 mL) was added, and ethyl acetate (20 mL) and water (40 mL) were then added to the reaction mixture. The mixture was washed with a saturated aqueous sodium chloride solution (40 mL×2 times). The organic phases were combined and dried over anhydrous sodium sulfate. After the organic phase was filtered, the organic phase was concentrated to dryness under reduced pressure to give the title compound (1.5 g).

MS m/z (ESI): =417 $[M+H]^+$.

Step 3: synthesis of N-(2-chloro-4-(difluoromethoxy)phenyl)-6-(trifluoromethyl)-3-(trimethylstannyl)pyridin-2-amine (intermediate 58-4)

Intermediate 58-3 (300 mg) was dissolved in an anhydrous xylene solution (3 mL) at 20° C., and Pd($PPh_3$)$_4$ (83.02 mg) and hexamethyldistannane (470.78 mg) were added to the reaction mixture. The reaction mixture was stirred for reaction at 140° C. for 16 h under nitrogen atmosphere. After the reaction was completed, the reaction mixture was quenched by adding a saturated cesium fluoride solution (10 mL), and ethyl acetate (10 mL) and water (20 mL) were then added. The mixture was extracted with ethyl acetate (20 mL×2 times). The organic phases were combined and dried over anhydrous sodium sulfate. After the organic phase was filtered, the organic phase was concentrated to dryness under reduced pressure, and the residue was purified by thin-layer chromatography (petroleum ether/ethyl acetate=10/1) to give the title compound (80 mg).

MS m/z (ESI): =503.0 $[M+H]^+$.

Step 4: synthesis of 5-(2-chloro-4-(difluoromethoxy)phenyl)-1-methyl-7-(trifluoromethyl)-1,5-dihydro-4H-imidazo[4,5-c][1,8]naphthyridin-4-one (Compound 58)

Intermediate 58-4 (80 mg) was dissolved in an anhydrous xylene solution (1 mL) at 20° C., and Pd($PPh_3$)$_4$ (18.43 mg) and intermediate 15-4 (34.94 mg, 159.53 μmol) were added to the reaction mixture. The reaction mixture was stirred for reaction at 140° C. for 16 h under nitrogen atmosphere. After the reaction was completed, ethyl acetate (10 mL) and water (20 mL) were added to the reaction mixture, and the mixture was extracted with ethyl acetate (20 mL×2 times). The organic phases were combined and dried over anhydrous sodium sulfate. After the organic phase was filtered, the organic phase was concentrated to dryness under reduced pressure. The residue was purified by high performance liquid chromatography (acidic condition; column: Waters Xbridge BEH C18 100×25 mm×5 μm; mobile phase: A: water (0.225% formic acid), B: acetonitrile; B %: 32%-52%, 12 min), and was then further purified by supercritical fluid chromatography (alkaline condition; column: Phenomenex-Cellulose-2 (250 mm×30 mm, 10 μm); mobile phase: [0.1% ammonia water], B: ethanol; B %: 40%-40%) to give Compound 58-P1 (1.5 mg, RT: 2.495 min) and Compound 58-P2 (1.9 mg, RT: 3.176 min).

Compound 58-P1

$^1$H NMR (400 MHz, METHANOL-$d_4$) δ=8.91 (d, J=8.3 Hz, 1H), 8.26 (s, 1H), 7.81 (d, J=8.3 Hz, 1H), 7.53-7.46 (m, 2H), 7.34 (dd, J=2.5, 8.8 Hz, 1H), 7.24-6.84 (m, 1H), 4.35 (s, 3H).

MS m/z (ESI): =445.0 $[M+H]^+$.

Compound 58-P2

$^1$H NMR (400 MHz, METHANOL-$d_4$) δ=8.91 (d, J=8.3 Hz, 1H), 8.26 (s, 1H), 7.81 (d, J=8.0 Hz, 1H), 7.53-7.46 (m, 2H), 7.34 (dd, J=2.5, 8.8 Hz, 1H), 7.24-6.84 (m, 1H), 4.35 (s, 3H).

MS m/z (ESI): =445.0 $[M+H]^+$.

Example 59. 5-(4-methoxyphenyl)-1-methyl-7-(trifluoromethyl)-1,5-dihydro-4H-imidazo[4,5-c][1,8]naphthyridin-4-one (Compound 59)

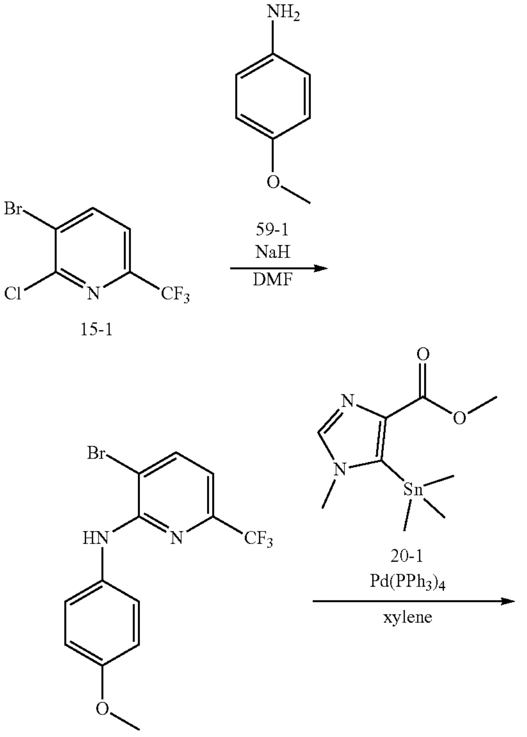

15-1

59-2

-continued

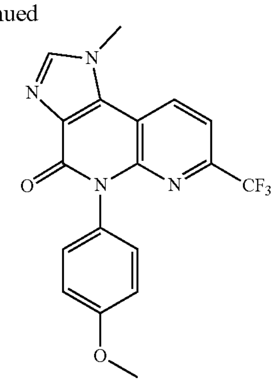

Compound 59

Step 1: synthesis of 3-bromo-N-(4-methoxyphenyl)-6-(trifluoromethyl)pyridin-2-amine (Intermediate 59-2)

Intermediate 59-1 (23.64 mg) was dissolved in an anhydrous N,N-dimethylformamide solution (0.5 mL) at 25° C. The mixture was cooled to 0° C., and sodium hydride (15.36 mg) was slowly added thereto. After the mixture was stirred for 30 min, intermediate 15-1 (500 mg) was dissolved in an anhydrous N,N-dimethylformamide solution (0.5 mL) and then added to the reaction system. The reaction mixture was stirred for reaction at 25° C. for 16 h under nitrogen atmosphere. After the reaction was completed, the reaction mixture was cooled to 0° C. The sodium hydride was quenched with an aqueous solution (1 mL), and ethyl acetate (10 mL) and water (20 mL) were added to the reaction mixture. The mixture was extracted 2 times with a saturated aqueous sodium chloride solution (20 mL). The organic phases were combined and dried over anhydrous sodium sulfate. After the organic layer was filtered, the organic layer was concentrated to dryness under reduced pressure, and the residue was purified by silica gel preparative thin-layer chromatography (petroleum ether/tetrahydrofuran=10/1) to give the title compound (40 mg).

MS m/z (ESI): =346.8 $[M+H]^+$.

Step 2: synthesis of 5-(4-methoxyphenyl)-1-methyl-7-(trifluoromethyl)-1,5-dihydro-4H-imidazo[4,5-c][1,8]naphthyridin-4-one (Compound 59)

Intermediate 59-2 (40 mg) was dissolved in anhydrous xylene (1 mL) at 20° C., and $Pd(PPh_3)_4$ (13.32 mg) and intermediate 20-1 (34.91 mg) were added to the reaction mixture. The reaction mixture was stirred for reaction at 140° C. for 16 h under nitrogen atmosphere. After the reaction was completed, ethyl acetate (10 mL) and water (20 mL) were added to the reaction mixture, and the mixture was extracted with ethyl acetate (20 mL×2 times). The organic phases were combined and dried over anhydrous sodium sulfate. After the organic phase was filtered, the organic phase was concentrated under reduced pressure to remove the solvent, and the residue was purified by high performance liquid chromatography (acidic condition; column: Waters Xbridge BEH C18 100×25 mm×5 μm; mobile phase: A: water (0.225% formic acid), B: acetonitrile; B %: 21%-41%, 12 min) to give the title compound (2.2 mg). 1H NMR (400 MHz, METHANOL-$d_4$) δ=8.87 (d, J=8.3 Hz, 1H), 8.23

(s, 1H), 7.76 (d, J=8.0 Hz, 1H), 7.24-7.16 (m, 2H), 7.15-7.07 (m, 2H), 4.34 (s, 3H), 3.92 (s, 3H).

MS m/z (ESI): =375.0 $[M+H]^+$.

Example 60. 1-methyl-5-(1-methyl-1H-pyrazol-5-yl)-7-(trifluoromethyl)-1,5-dihydro-4H-imidazo[4,5-c][1,8]naphthyridin-4 (5H)-one (Compound 60)

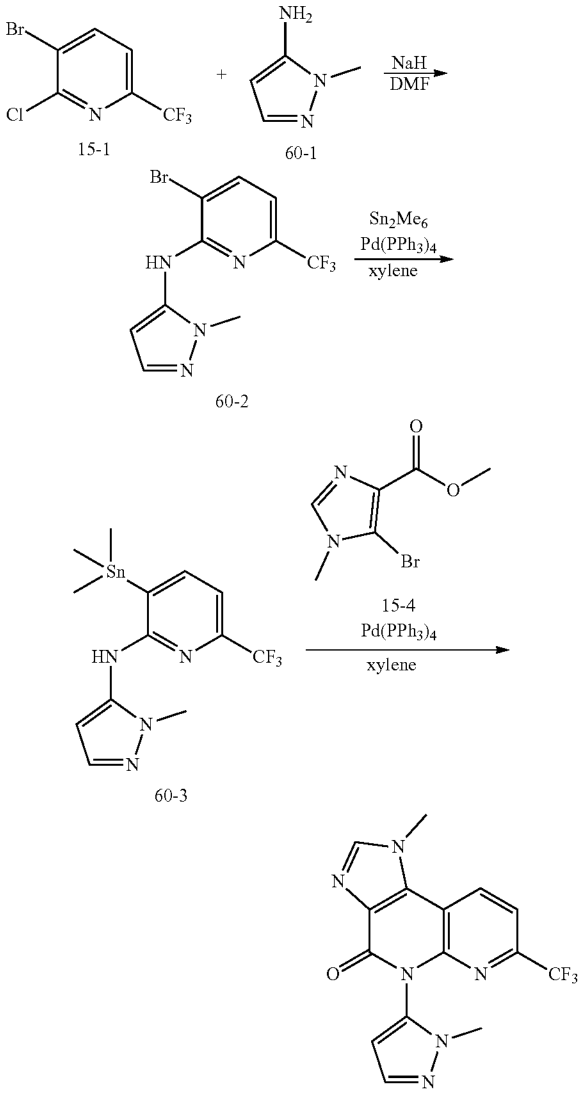

Step 1: synthesis of 3-bromo-N-(1-methyl-1H-pyrazol-5-yl)-6-(trifluoromethyl)pyridin-2-amine (intermediate 60-2)

Intermediate 60-1 (18.65 mg) was dissolved in anhydrous N,N-dimethylformamide (1 mL) at 25° C., sodium hydride (23.04 mg) was added to the reaction mixture after the reaction mixture was cooled to 0° C., and the reaction mixture was stirred at 0° C. for 30 min under nitrogen atmosphere. Intermediate 15-1 (50 mg) was added to the reaction mixture. The reaction mixture was stirred at 20° C. for 16 h under nitrogen atmosphere. After the reaction was completed, the reaction mixture was cooled to 0° C., and water (20 mL) was added. The mixture was extracted with ethyl acetate (10 mL×2 times). The organic phases were combined and dried over anhydrous sodium sulfate. After the organic layer was filtered, the organic layer was concentrated to dryness under reduced pressure, and the residue was purified by preparative thin-layer chromatography (petroleum ether:tetrahydrofuran=1:1) to give the title compound (45 mg).

MS m/z (ESI): =320.8 $[M+H]^+$.

Step 2: synthesis of N-(1-methyl-1H-pyrazol-5-yl)-6-(trifluoromethyl)-3-(trimethylstannyl)pyridin-2-amine (intermediate 60-3)

Intermediate 60-2 (45 mg) was dissolved in anhydrous xylene (1 mL) at 25° C., and $Pd(PPh_3)_4$ (16.19 mg) and hexamethyldistannane (91.83 mg) were added to the reaction mixture. The reaction mixture was stirred for reaction at 140° C. for 16 h under nitrogen atmosphere. After the reaction was completed, a saturated aqueous cesium fluoride solution (10 mL) was added to the reaction mixture. The mixture was extracted with ethyl acetate (10 mL×2 times). The organic phases were combined and dried over anhydrous sodium sulfate. After the organic phase was filtered, the organic phase was concentrated to dryness under reduced pressure, and the residue was purified by preparative thin-layer chromatography (petroleum ether:tetrahydrofuran=1:1) to give the title compound (40 mg).

MS m/z (ESI): =407.1 $[M+H]^+$.

Step 3: synthesis of 1-methyl-5-(1-methyl-1H-pyrazol-5-yl)-7-(trifluoromethyl)-1,5-dihydro-4H-imidazo[4,5-c][1,8]naphthyridin-4 (5H)-one (Compound 60)

Intermediate 60-3 (28 mg) was added to anhydrous xylene (1 mL) at 25° C., $Pd(PPh_3)_4$ (7.99 mg) and intermediate 15-4 (22.71 mg) were added to the reaction mixture, and the reaction mixture was reacted at 140° C. for 16 h under nitrogen atmosphere. After the reaction was completed, the reactant was filtered, and the filtrate was concentrated to dryness under reduced pressure. The residue was purified by preparative high performance liquid chromatography (column: Waters Xbridge BEH C18 100×25 mm×5 μm; mobile phase: [A: water (0.225% formic acid), B: acetonitrile]; B %: 17%-27%, 12 min) to give the title compound (1.1 mg). 1H NMR (400 MHz, METHANOL-$d_4$) δ=8.91 (d, J=8.0 Hz, 1H), 8.27 (s, 1H), 7.85 (d, J=8.3 Hz, 1H), 7.69 (d, J=2.0 Hz, 1H), 6.38 (d, J=2.3 Hz, 1H), 4.35 (s, 3H), 3.60 (s, 3H).

MS m/z (ESI): =349.1 $[M+H]^+$.

Example 61. 5-(2-chlorophenyl)-1-ethyl-7-(trifluoromethyl)-1,5-dihydro-4H-imidazo[4,5-c][1,8]naphthyridin-4-one (Compound 61)

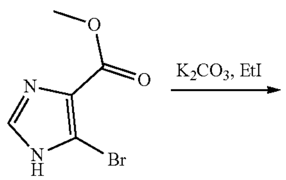

61-1

-continued

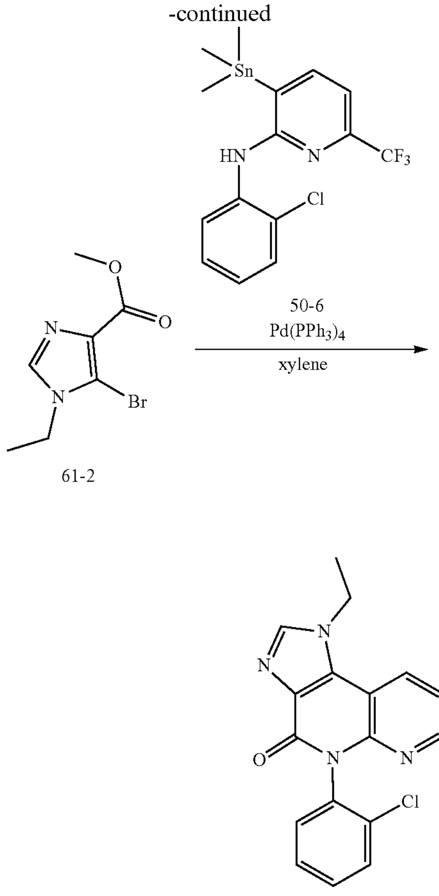

Compound 61

Step 1: synthesis of methyl 5-bromo-1-ethyl-1H-imidazole-4-formate (intermediate 61-2)

Potassium carbonate (606.75 mg) was added to a solution of intermediate 61-1 (300 mg) in N,N-dimethylformamide (4 mL) at 20° C., and the mixture was stirred for reaction for 0.5 h. Iodoethane (273.89 mg) was added, and the reaction mixture was stirred at 50° C. for 16 h. After the reaction was completed, the reaction mixture was filtered to give a filtrate. The filtrate was concentrated to dryness under reduced pressure. The residue was slurried using tetrahydrofuran (10 mL) and filtered again to give a filtrate. The filtrate was concentrated to dryness under reduced pressure. The residue was purified by thin-layer chromatography (tetrahydrofuran: petroleum ether=2:1) to give the title compound (130 mg).

MS m/z (ESI): 233.0 [M+H]$^+$

Step 2: synthesis of 5-(2-chlorophenyl)-1-ethyl-7-(trifluoromethyl)-1,5-dihydro-4H-imidazo[4,5-c][1,8]naphthyridin-4-one (Compound 61)

Intermediate 61-2 (56 mg) and intermediate 50-6 (104.63 mg) were dissolved in xylene (5 mL), tetrakis(triphenylphosphine)palladium(0) (27.77 mg) was added, and the reaction mixture was stirred for reaction at 140° C. for 16 h under nitrogen atmosphere. The reaction mixture was then cooled to 20° C. Potassium tert-butoxide (40.44 mg) was added, and the mixture was reacted at 90° C. for 16 h. After the reaction was completed, the reaction mixture was filtered, and the filtrate was concentrated to dryness under reduced pressure. The residue was purified by thin-layer chromatography (tetrahydrofuran:petroleum ether=3:1), and was then purified by high performance liquid chromatography (formic acid condition; column: Waters Xbridge BEH C18 100×25 mm×5 μm; mobile phase: [A: water (0.225% formic acid), B: acetonitrile]; B %: 28%-48%, 12 min) to give the title compound (1.6 mg).

MS m/z (ESI): 393.0 [M+H]$^+$.

$^1$HNMR (400 MHz, METHANOL-$d_4$) δ=8.79 (d, J=8.3 Hz, 1H), 8.33 (s, 1H), 7.79 (d, J=8.3 Hz, 1H), 7.69-7.61 (m, 1H), 7.58-7.49 (m, 2H), 7.46-7.38 (m, 1H), 4.75 (q, J=7.3 Hz, 2H), 1.67 (t, J=7.3 Hz, 3H).

Example 62. 5-(2,4-dichlorophenyl)-1-methyl-7-(trifluoromethyl)-1,5-dihydro-4H-imidazo[4,5-c][1,8]naphthyridin-4-one (Compound 62)

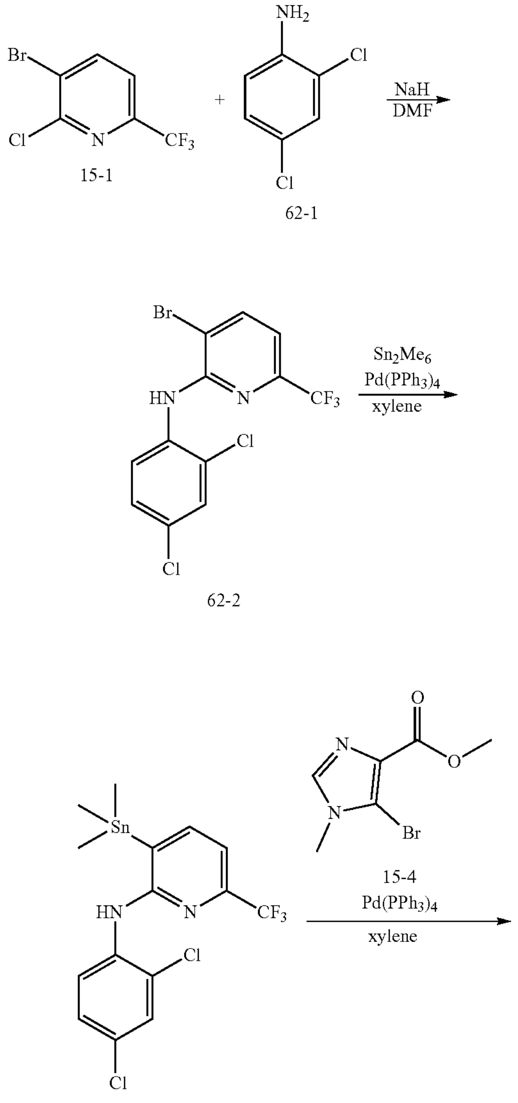

-continued

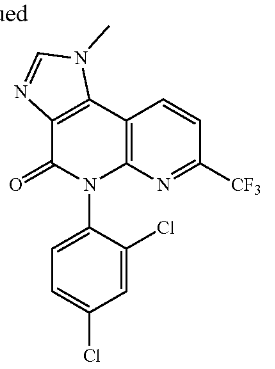

Compound 62

Step 1: synthesis of 3-bromo-N-(2,4-dichlorophenyl)-6-(trifluoromethyl)pyridin-2-amine (intermediate 62-2)

Reactant 62-1 (273.72 mg) was dissolved in N,N-dimethylformamide (6 mL). Sodium hydride (122.86 mg) was added to the reaction mixture at 0° C. under nitrogen atmosphere, and the mixture was stirred for 30 min. A solution of intermediate 15-1 (400 mg) in N,N-dimethylformamide (2 mL) was added to the reaction mixture at 0° C., and the reaction mixture was stirred for reaction at 20° C. for 16 h. After the reaction was completed, the reaction mixture was quenched with water (20 mL). The mixture was extracted with ethyl acetate (10 mL×3 times). The organic phases were combined and dried over anhydrous sodium sulfate. After the organic phase was filtered, the organic phase was concentrated to dryness under reduced pressure, and the residue was purified by column chromatography (ISCO®; 12 g of SepaFlash® Silica Flash column; eluent: 0% ethyl acetate/petroleum ether, gradient @ 40 mL/min) to give the title compound (500 mg).

MS m/z (ESI): 384.8 $[M+H]^+$.

Step 2: synthesis of N-(2,4-dichlorophenyl)-6-(trifluoromethyl)-3-(trimethylstannyl)pyridin-2-amine (intermediate 62-3)

Intermediate 62-2 (300 mg) was dissolved in xylene (3 mL), and $Pd(PPh_3)_4$ (89.81 mg) and hexamethyldistannane (1.02 g) were added at 20° C. The reaction mixture was stirred for reaction at 140° C. for 1 h under nitrogen atmosphere. After the reaction was completed, the reaction mixture was quenched with a saturated aqueous cesium fluoride solution (20 mL). The mixture was extracted with ethyl acetate (20 mL×3 times). The organic phases were combined and dried over anhydrous sodium sulfate. After the organic phase was filtered, the organic phase was concentrated under reduced pressure to remove the solvent, and the residue was purified by silica gel column chromatography (ISCO®; 20 g of SepaFlash® Silica Flash column; petroleum ether @ 40 mL/min) to give the title compound (190 mg).

MS m/z (ESI): 470.9 $[M+H]^+$.

Step 3: synthesis of 5-(2,4-dichlorophenyl)-1-methyl-7-(trifluoromethyl)-1,5-dihydro-4H-imidazo[4,5-c][1,8]naphthyridin-4-one (Compound 62)

Intermediate 62-3 (150 mg) and intermediate 15-4 (104.88 mg) were dissolved in xylene (2 mL), $Pd(PPh_3)_4$ (55.33 mg) was added at 20° C., and the reaction mixture was stirred for reaction at 140° C. for 16 h under nitrogen atmosphere. After the reaction was completed, the reaction mixture was diluted with water (20 mL). The mixture was extracted with ethyl acetate (20 mL×3 times). The organic phases were combined and dried over anhydrous sodium sulfate. After the organic phase was filtered, the organic phase was concentrated under reduced pressure to remove the solvent, and the residue was purified by preparative thin-layer chromatography (petroleum ether:tetrahydrofuran=10:1). The residue was then further purified by high performance liquid chromatography (column: YMC-Actus Triart C18 150×30 mm×5 μm; mobile phase: [A: water (0.05% ammonia water v/v), B: acetonitrile]; B %: 45%-65%, 11 min) to give the title compound (10.2 mg).

$^1H$ NMR (400 MHz, DMSO-$d_6$) δ=8.88 (d, J=8.0 Hz, 1H), 8.35 (s, 1H), 7.92 (d, J=2.3 Hz, 1H), 7.86 (d, J=8.0 Hz, 1H), 7.68-7.63 (m, 1H), 7.61-7.55 (m, 1H), 4.28 (s, 3H).

MS m/z (ESI): 412.9 $[M+H]^+$.

Example 63. 5-(3-fluorophenyl)-1-methyl-7-(trifluoromethyl)-1,5-dihydro-4H-imidazo[4,5-c][1,8]naphthyridin-4-one (Compound 63)

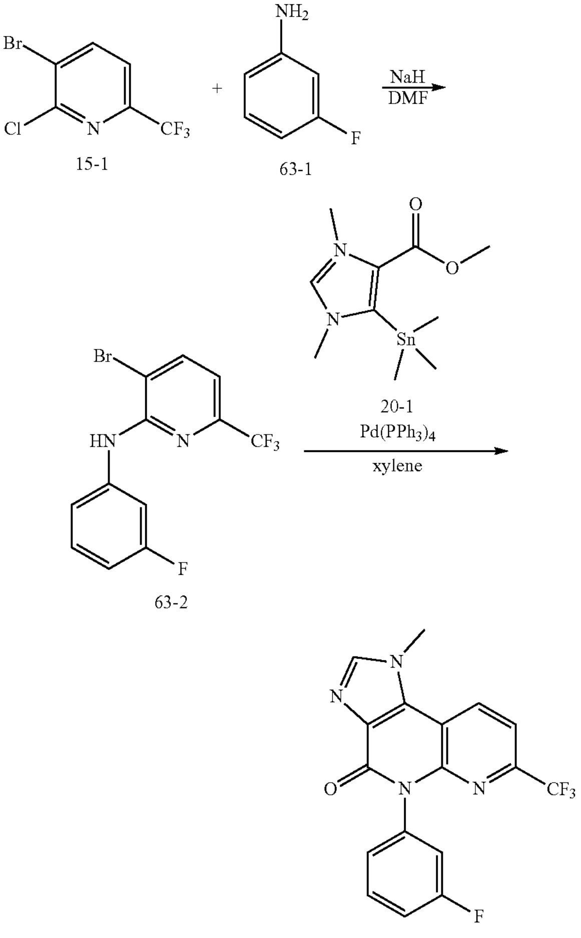

Compound 63

Step 1: synthesis of 3-bromo-N-(3-fluorophenyl)-6-(trifluoromethyl)pyridin-2-amine (Intermediate 63-2)

Reactant 63-1 (128.00 mg) was dissolved in N,N-dimethylformamide (3 mL). Sodium hydride (69.11 mg) was added to the reaction mixture at 0° C. under nitrogen atmosphere, and the mixture was stirred for 30 min. Intermediate 15-1 (300 mg) was added to the reaction mixture at 0° C., and the reaction mixture was stirred for reaction at 20° C. for 16 h. After the reaction was completed, the reaction mixture was quenched with water (10 mL), and the mixture was extracted with ethyl acetate (20 mL×3 times). The organic phase was concentrated under reduced pressure, and the residue was purified by column chromatography (ISCO®; 20 g of Sepa-Flash© Silica Flash column; petroleum ether @ 60 mL/min) to give the title compound (117 mg).

MS m/z (ESI): 334.8 $[M+H]^+$.

Step 2: synthesis of 5-(3-fluorophenyl)-1-methyl-7-(trifluoromethyl)-1,5-dihydro-4H-imidazo[4,5-c][1,8]naphthyridin-4-one (Compound 63)

Intermediate 63-2 (100 mg) and intermediate 20-1 (120.54 mg) were dissolved in xylene (8 mL), $Pd(PPh_3)_4$ (34.48 mg) was added at 20° C., and the reaction mixture was stirred for reaction at 140° C. for 16 h under nitrogen atmosphere. The reaction mixture was concentrated under reduced pressure, and the residue was purified by preparative thin-layer chromatography (dichloromethane:methanol=10:1). The residue was then further purified by high performance liquid chromatography (column: YMC-Actus Triart C18 150×30 mm×5 μm; mobile phase: [A: water (0.225% formic acid v/v), B: acetonitrile]; B %: 38%-58%, 11 min) to give the title compound (8.7 mg).

$^1H$ NMR (400 MHz, DMSO-$d_6$) δ=8.84 (d, J=8.1 Hz, 1H), 8.33 (s, 1H), 7.82 (d, J=8.2 Hz, 1H), 7.59 (dt, J=6.5, 8.1 Hz, 1H), 7.35 (dt, J=1.8, 8.6 Hz, 1H), 7.28 (td, J=2.1, 9.8 Hz, 1H), 7.18 (dd, J=0.9, 7.8 Hz, 1H), 4.27 (s, 3H).

MS m/z (ESI): 363.1 $[M+H]^+$.

Example 64. 1-methyl-5-(pyridin-3-yl)-7-(trifluoromethyl)-1,5-dihydro-4H-imidazo[4,5-c][1,8]naphthyridin-4-one (Compound 64)

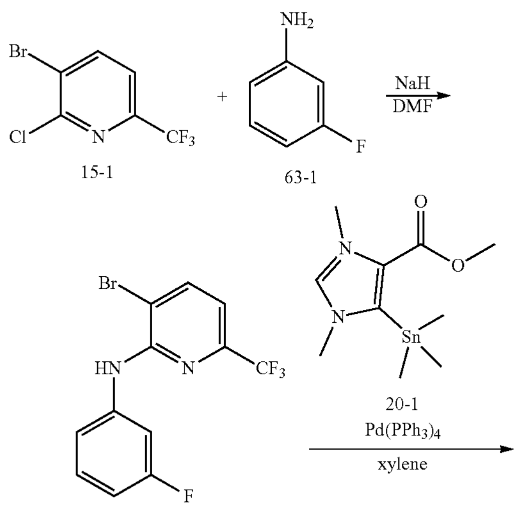

63-2

-continued

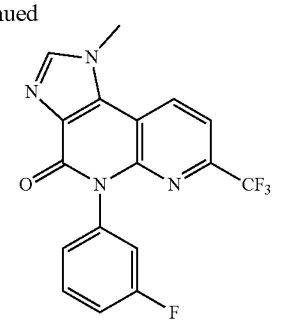

Compound 63

Step 1: synthesis of 3-bromo-N-(pyridin-3-yl)-6-(trifluoromethyl)pyridin-2-amine+ (Intermediate 64-2)

Potassium tert-butoxide (538.61 mg) was added to a solution of intermediate 15-1 (500 mg) and intermediate 64-1 (180.7 mg) in N,N-dimethylformamide (10 mL). The reaction mixture was stirred at 25° C. for 16 h. After the reaction was completed, water (200 mL) was added to the reaction mixture. The mixture was extracted with ethyl acetate (100 mL×3 times). The organic phases were combined and dried over anhydrous sodium sulfate. After the organic phase was filtered, the organic phase was concentrated under reduced pressure to remove the solvent, and the residue was purified by silica gel column chromatography (petroleum ether:ethyl acetate=1:0 to 10:1) to give the title compound (380.7 mg).

MS m/z (ESI): =317.9 $[M+H]^+$.

Step 2: synthesis of N-(pyridin-3-yl)-6-(trifluoromethyl)-3-(trimethylstannyl)pyridin-2-amine (intermediate 64-3)

Intermediate 64-2 (380 mg) was dissolved in xylene (4 mL), and hexamethyldistannane (782.79 mg) and tetrakis(triphenylphosphine)palladium(0) (138.05 mg) were added. The reaction mixture was stirred for reaction at 140° C. for 4 h under nitrogen atmosphere. After the reaction was completed, a saturated potassium fluoride solution (5 mL) was added to the reaction mixture. The mixture was extracted with ethyl acetate (5 mL×3 times). The organic phase was concentrated to dryness under reduced pressure, and the residue was purified by preparative thin-layer chromatography (petroleum ether:ethyl acetate=3:1) to give the title compound (50 mg).

MS m/z (ESI): =403.9$[M+H]^+$.

Step 3: synthesis of 1-methyl-5-(pyridin-3-yl)-7-(trifluoromethyl)-1,5-dihydro-4H-imidazo[4,5-c][1,8]naphthyridin-4-one (Compound 64)

Intermediate 64-3 (50 mg) was dissolved in xylene (2 mL), and intermediate 15-4 (27.24 mg) and tetrakis(triphenylphosphine)palladium(0) (14.37 mg) were added. The reaction mixture was stirred for reaction at 140° C. for 12 h under nitrogen atmosphere. After the reaction was completed, the reaction mixture was concentrated to dryness under reduced pressure, and the residue was purified by preparative high performance liquid chromatography (column: Waters Xbridge BEH C18 100×25 mm×5 μm; mobile phase: [A: water (0.225% formic acid), B: acetonitrile]; B %: 9%-29%, 12 min) to give the title compound (16.6 mg).

MS m/z (ESI): =346.0[M+H]$^+$.

$^1$H NMR (400 MHz, METHANOL-$d_4$) δ=8.91 (d, J=8.3 Hz, 1H), 8.70 (dd, J=1.5, 5.0 Hz, 1H), 8.56 (d, J=2.0 Hz, 1H), 8.26 (s, 1H), 7.94-7.89 (m, 1H), 7.83-7.77 (m, 1H), 7.71 (dd, J=4.9, 8.1 Hz, 1H), 4.36 (s, 3H).

Example 65. 5-(2-chloro-3-fluorophenyl)-1-methyl-7-(trifluoromethyl)-1,5-dihydro-4H-imidazo[4',5':4,5]pyrido[2,3-d]pyrimidin-4-one (Compound 65)

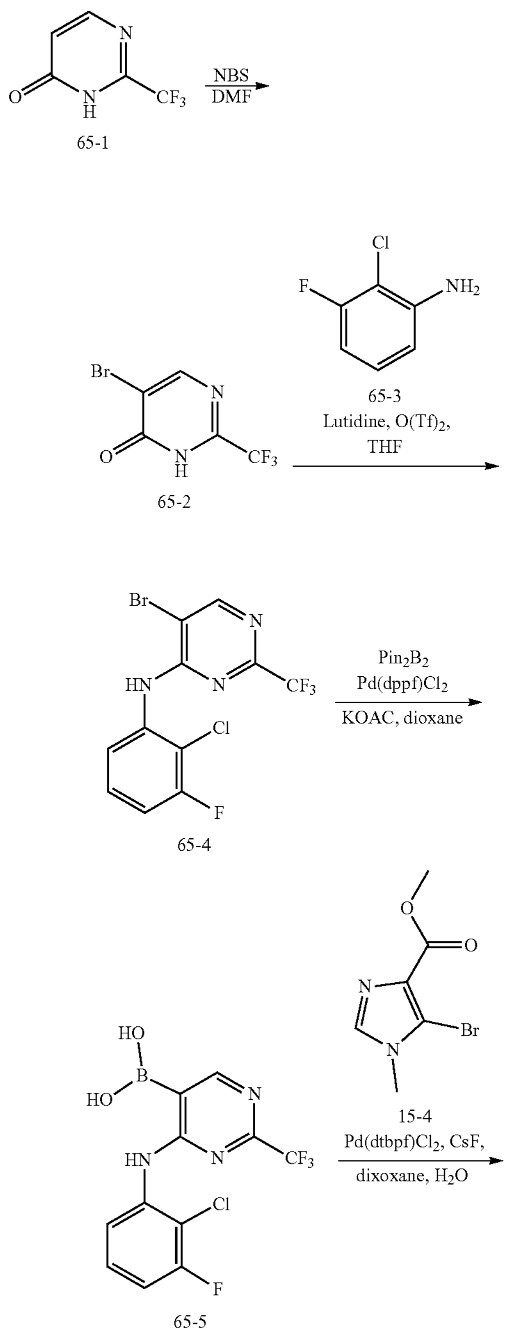

-continued

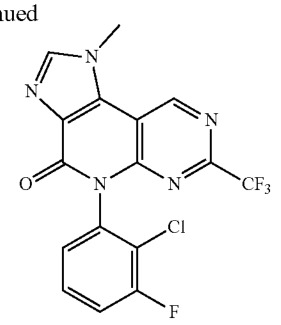

Compound 65

Step 1: synthesis of 5-bromo-2-(trifluoromethyl) pyrimidin-4 (3H)-one (intermediate 65-2)

Intermediate 65-1 (5 g) was dissolved in N,N-dimethylformamide (50 mL), and N-bromosuccinimide (6.5 g) was then added to the reaction mixture. The reaction mixture was stirred at 50° C. for 18 h. After the reaction mixture was cooled to room temperature, water (60 mL) and ethyl acetate (80 mL) were added sequentially. The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (petroleum ether:ethyl acetate=10:1) to give the title compound (5 g).

MS m/z (ESI): 243.2 [M+H]$^+$

Step 2: synthesis of 5-bromo-N-(2-chloro-3-fluorophenyl)-2-(trifluoromethyl)pyrimidin-4-amine (intermediate 65-4)

Intermediate 65-2 (500 mg) and 2,6-dimethylpyridine (330 mg) were dissolved in anhydrous tetrahydrofuran (5 mL), trifluoromethanesulfonic anhydride (697 mg) was added dropwise thereto at −78° C., and the mixture was stirred at 0° C. for 2 h. Intermediate 65-3 (896 mg) was then added to the reaction mixture. The reaction mixture was stirred at 70° C. for 3 h. $H_2O$ (20 mL) and ethyl acetate (20 mL×3) were added sequentially to the reaction mixture. The organic phase was washed with saturated brine (30 mL×2), and the washed organic phase was dried over an appropriate amount of anhydrous sodium sulfate. The residue was purified by preparative thin-layer chromatography (silica, petroleum ether:ethyl acetate=100:0-50:50) to give the title compound (270 mg).

MS m/z (ESI): 370.2 [M+H]$^+$

Step 3: synthesis of (4-((2-chloro-3-fluorophenyl) amino)-2-(trifluoromethyl)pyrimidin-5-yl)boronic acid (intermediate 65-5)

Intermediate 65-4 (300 mg) and bis(pinacolato)diboron (278 mg) were dissolved in 1,4-dioxane (3 mL), potassium acetate (211 mg) and Pd(dppf)$Cl_2$ (46 mg) were added thereto, and the reaction mixture was stirred at 100° C. for 15 h under nitrogen atmosphere. After the reaction mixture was cooled to room temperature, water (40 mL) and ethyl acetate (80 mL) were added sequentially. The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (dichloromethane: methanol=10:1) to give the title compound (200 mg).

MS m/z (ESI): 336.1 $[M+H]^+$

Step 4: synthesis of 5-(2-chloro-3-fluorophenyl)-1-methyl-7-(trifluoromethyl)-1,5-dihydro-4H-imidazo[4',5':4,5]pyrido[2,3-d]pyrimidin-4-one (Compound 65)

Intermediate 65-5 (200 mg) and intermediate 15-4 (195 mg) were dissolved in dioxane (2 mL) and water (0.4 mL), cesium fluoride (267 mg) and $Pd(dtbpf)Cl_2$ (39 mg) were added thereto, and the reaction mixture was stirred at 100° C. for 16 h under nitrogen atmosphere. After the reaction was cooled to room temperature, water (30 mL) and ethyl acetate (40 mL) were added sequentially. The organic phase was washed with saturated brine (30 mL×2), and the washed organic phase was dried over an appropriate amount of anhydrous sodium sulfate and concentrated under reduced pressure. The residue was purified by preparative high performance liquid chromatography (column: Gemini NX C18 5 μm×10×150 mm; mobile phase: A: 0.05% TFA v/v, B: acetonitrile; B %: 40%-45%, 12 min) to give the title compound (13 mg).

MS m/z (ESI): 398.1 $[M+H]^+$.

$^1H$ NMR (400 MHz, DMSO-$d_6$) δ 9.76 (s, 1H), 8.42 (s, 1H), 7.69-7.60 (m, 2H), 7.47 (d, J=7.3 Hz, 1H), 4.32 (s, 3H).

Example 66. 5-(2-chloro-3-fluorophenyl)-1-methyl-7-(trifluoromethyl)-1,5-dihydro-4H-imidazo[4,5-c]quinolin-4-one (Compound 66)

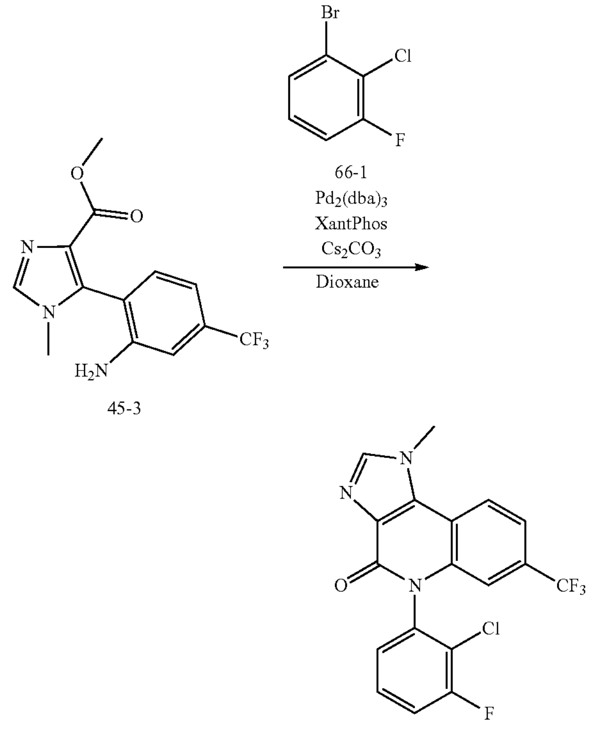

66-1

45-3

Compound 66

Intermediate 45-3 (50 mg) and intermediate 66-1 (70 mg) were dissolved in an anhydrous dioxane solution (1 mL), and cesium carbonate (163 mg), XantPhos (19 mg), and $Pd_2(dba)_3$ (10 mg) were added. The reaction mixture was stirred at 100° C. for 12 h under nitrogen atmosphere. After the reaction was cooled to room temperature, the reaction mixture was filtered, and the filtrate was concentrated to dryness under reduced pressure. The concentrated residue was purified by preparative high performance liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 55%-75%, 12 min] to give the title compound (2 mg).

MS m/z (ESI): 396.0 $[M+H]^+$.

$^1H$ NMR (400 MHz, Chloroform-d) δ 8.21 (d, J=8.4 Hz, 1H), 7.89 (s, 1H), 7.57-7.50 (m, 2H), 7.43-7.41 (m, 1H), 7.26-7.21 (m, 1H), 6.88 (s, 1H), 4.28 (s, 3H).

Example 67. 5-(2-ethylpyridin-3-yl)-1-methyl-7-(trifluoromethyl)-1,5-dihydro-4H-imidazo[4,5-c][1,8]naphthyridin-4-one (Compound 67)

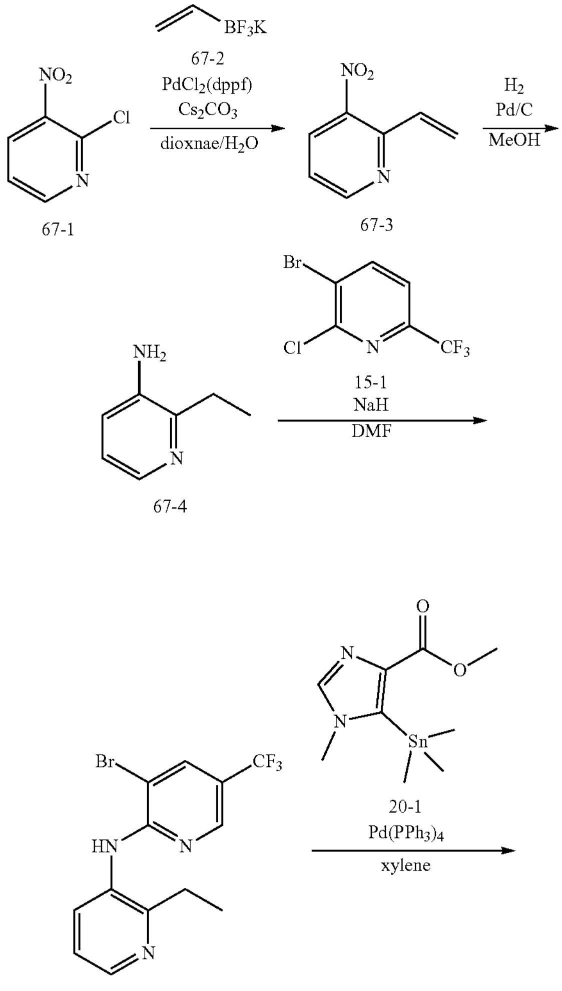

67-2

67-1

67-3

15-1

67-4

20-1

67-5

-continued

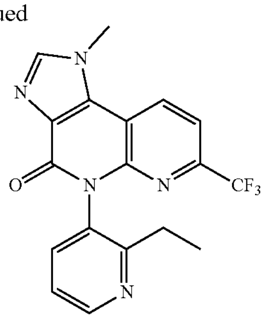

Compound 67

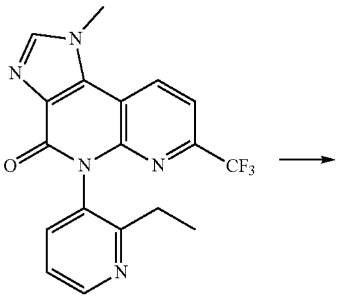

Compound 67

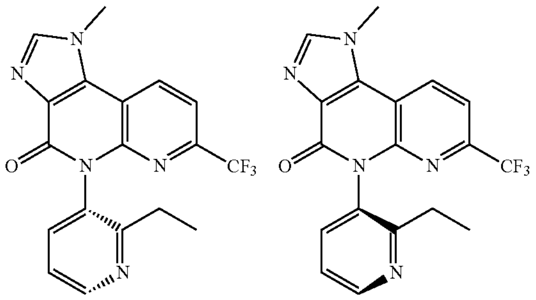

Step 1: synthesis of 3-nitro-2-vinyl-pyridine (intermediate 67-3)

Intermediate 67-1 (2.5 g) was added to dioxane (50 mL) and water (16 mL) under nitrogen atmosphere. Intermediate 67-2 (4.22 g), $PdCl_2$(dppf) (10.62 mg), and cesium carbonate (10.28 g) were added to the reaction mixture. The reaction mixture was stirred for reaction at 90° C. for 16 h under nitrogen atmosphere. After the reaction was completed, water (40 mL) was added to the reaction mixture. The mixture was extracted with ethyl acetate (40 mL×3 times). The organic phases were combined and dried over anhydrous sodium sulfate. After the organic phase was filtered, the organic phase was concentrated under reduced pressure to remove the solvent, and the residue was purified by flash column chromatography (ISCO©; 20 g of Sepa-Flash© Silica Flash chromatographic column; eluent: 0-12% ethyl acetate/petroleum ether, gradient @ 80 mL/min) to give the title compound (1.98 g).

MS m/z (ESI): 150.9 $[M+H]^+$.

Step 2: synthesis of 2-ethylpyridin-3-amine (intermediate 67-4)

Intermediate 67-3 (140.49 mg) was dissolved in anhydrous methanol (50 mL) under nitrogen atmosphere, wet palladium on carbon (300 mg) was added to the reaction mixture, and the reaction mixture was stirred at 45° C. for 16 h under nitrogen atmosphere. After the reaction was completed, the reaction mixture was filtered, and the filtrate was concentrated under reduced pressure to remove the solvent to give the title compound (1.22 g).

MS m/z (ESI): 123.2 $[M+H]^+$.

Step 3: synthesis of 3-bromo-N-(2-ethylpyridin-3-yl)-6-(trifluoromethyl)pyridin-2-amine (intermediate 67-5)

Intermediate 67-4 (140.49 mg) was dissolved in anhydrous N,N-dimethylformamide (3 mL) under nitrogen atmosphere, sodium hydride (69.00 mg) was added to the reaction mixture after the reaction mixture was cooled to 0° C., and the reaction mixture was stirred at 0° C. for 30 min. Intermediate 15-1 (300 mg) was dissolved in anhydrous N,N-dimethylformamide (2 mL) and added to the reaction mixture. The reaction mixture was stirred at 25° C. for 16 h under nitrogen atmosphere. After the reaction was completed, water (10 mL) was added to the reaction mixture. The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by a flash silica gel column (ISCO®; 12 g of SepaFlash© Silica Flash chromatographic column; eluent: 0-13% ethyl acetate/petroleum ether, gradient @ 40 mL/min) to give the title compound (31.8 mg).

MS m/z (ESI): 345.9 $[M+H]^+$.

Step 4: synthesis of 5-(2-ethylpyridin-3-yl)-1-methyl-7-(trifluoromethyl)-1,5-dihydro-4H-imidazo[4,5-c][1,8]naphthyridin-4-one (Compound 67)

Intermediate 67-5 (31.8 mg) was added to anhydrous xylene (1 mL) under nitrogen atmosphere, and tetrakis (triphenylphosphine)palladium(0) (10.62 mg) and intermediate 20-1 (27.83 mg) were added to the reaction mixture. Subsequently, the reaction mixture was stirred at 140° C. for 16 h under nitrogen atmosphere. After the reaction was completed, water (10 mL) was added to the reaction mixture. The mixture was extracted with ethyl acetate (10 mL×3 times). The organic phases were combined and dried over anhydrous sodium sulfate. The organic phase was filtered and concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 11%-41%, 12 min) to give the title compound (7 mg). The compound was lyophilized to remove the solvent, and the residue was purified by preparative supercritical fluid chromatography (column: DAICEL CHIRALPAK AD (250 mm×30 mm, 10 μm); mobile phase: [A: supercritical carbon dioxide, B: ethanol (0.1% ammonia water)]; B %: 25%-25%) to give Compound 67-P1 (2.03 mg, RT: 4.35 min) and Compound 67-P2 (2.02 mg, RT: 5.01 min).

Compound 67-P1

MS m/z (ESI): 374.1 $[M+H]^+$.

$^1H$ NMR (400 MHz, METHANOL-$d_4$) δ 8.93 (d, J=8.0 Hz, 1H), 8.66 (d, J=3.5 Hz, 1H), 8.28 (s, 1H), 7.81 (d, J=8.3 Hz, 1H), 7.72 (d, J=8.0 Hz, 1H), 7.52 (dd, J=4.9, 7.9 Hz, 1H), 4.36 (s, 3H), 2.48 (q, J=7.5 Hz, 2H), 1.08 (t, J=7.5 Hz, 3H).

Compound 67-P2

MS m/z (ESI): 374.1 [M+H]$^+$.

$^1$H NMR (400 MHz, METHANOL-$d_4$) δ 8.93 (d, J=8.3 Hz, 1H), 8.66 (dd, J=1.5, 5.0 Hz, 1H), 8.28 (s, 1H), 7.81 (d, J=8.3 Hz, 1H), 7.72 (dd, J=1.5, 7.8 Hz, 1H), 7.52 (dd, J=4.9, 7.9 Hz, 1H), 4.36 (s, 3H), 2.48 (q, J=7.7 Hz, 2H), 1.08 (t, J=7.5 Hz, 3H).

Example 68. 5-(2-methoxypyridin-3-yl)-1-methyl-7-(trifluoromethyl)-1,5-dihydro-4H-imidazo[4,5-c][1,8]naphthyridin-4-one (Compound 68)

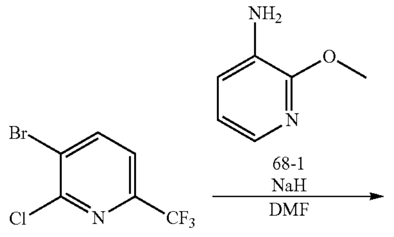

15-1

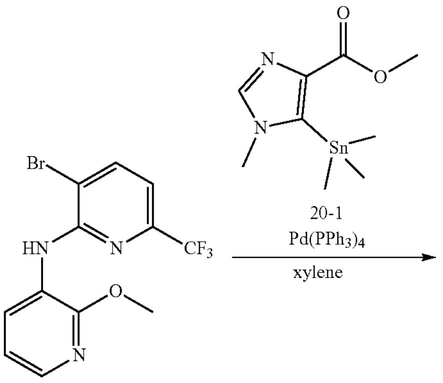

68-2

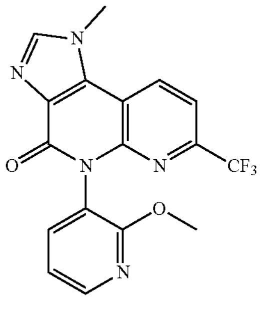

Compound 68

Step 1: synthesis of 3-bromo-N-(2-methoxypyridin-3-yl)-6-(trifluoromethyl)pyridin-2-amine (intermediate 68-2)

Intermediate 68-1 (238.33 mg) was dissolved in anhydrous N,N-dimethylformamide (5 mL) under nitrogen atmosphere, sodium hydride (115.19 mg) was added to the reaction mixture after the reaction mixture was cooled to 0° C., and the reaction mixture was stirred at 0° C. for 30 min. Intermediate 15-1 (500 mg) was dissolved in anhydrous N,N-dimethylformamide (3 mL) and added to the reaction mixture. The reaction mixture was stirred at 25° C. for 16 h under nitrogen atmosphere. After the reaction was completed, water (10 mL) was added to the reaction mixture. The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by a flash silica gel column (ISCO©; 12 g of SepaFlash© Silica Flash chromatographic column; eluent: 0-5% ethyl acetate/petroleum ether, gradient @ 40 mL/min) to give the title compound (231.4 mg).

MS m/z (ESI): 347.9 [M+H]$^+$.

Step 2: synthesis of 5-(2-methoxypyridin-3-yl)-1-methyl-7-(trifluoromethyl)-1,5-dihydro-4H-imidazo[4,5-c][1,8]naphthyridin-4-one (Compound 68)

Intermediate 68-2 (231.4 mg) was added to anhydrous xylene (7 mL) under nitrogen atmosphere, and tetrakis(triphenylphosphine)palladium(0) (76.81 mg) and intermediate 20-1 (201.37 mg) were added to the reaction mixture. The reaction mixture was stirred at 140° C. for 16 h under nitrogen atmosphere. After the reaction was completed, the reaction mixture was filtered and concentrated under reduced pressure to remove the solvent. The residue was purified by thin-layer chromatography (petroleum ether: ethyl acetate=10:1) to give a crude product (20 mg). The crude product was added to anhydrous xylene (7 mL), potassium tert-butoxide (30 mg) was added to the reaction mixture, and the reaction mixture was stirred at 100° C. for 2 h. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 23%-43%, 12 min) to give the title compound (6.3 mg).

MS m/z (ESI): 376.1 [M+H]$^+$.

$^1$H NMR (400 MHz, METHANOL-$d_4$) δ 8.89 (d, J=8.1 Hz, 1H), 8.32 (dd, J=1.7, 5.1 Hz, 1H), 8.25 (s, 1H), 7.78 (d, J=8.3 Hz, 1H), 7.73 (dd, J=1.8, 7.5 Hz, 1H), 7.20 (dd, J=5.1, 7.4 Hz, 1H), 4.35 (s, 3H), 3.81 (s, 3H).

Example 69. 5-(5-(difluoromethoxy)pyridin-2-yl)-1-methyl-7-(trifluoromethyl)-1,5-dihydro-4H-imidazo[4,5-c][1,8]naphthyridin-4-one (Compound 69)

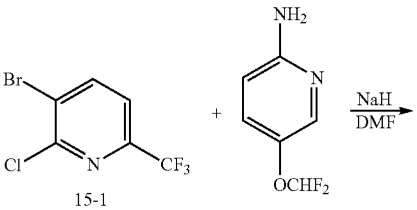

15-1

69-1

-continued

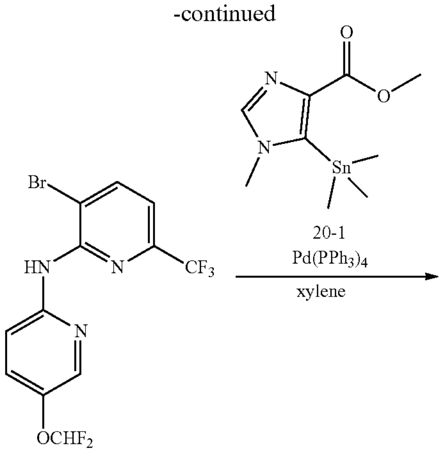

69-2

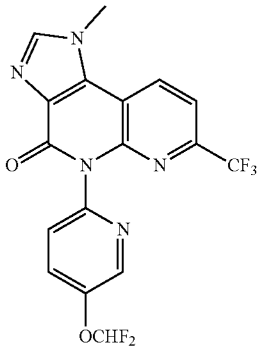

Compound 69

Step 1: synthesis of 3-bromo-N-(5-(difluoromethoxy)pyridin-2-yl)-6-(trifluoromethyl)pyridin-2-amine (intermediate 69-2)

Reactant 69-1 (245.93 mg) was dissolved in N,N-dimethylformamide (10 mL), sodium hydride (92.14 mg) was added at 0° C., and the mixture was stirred for 30 min. Intermediate 15-1 (400 mg) was added at 0° C. The reaction mixture was stirred for reaction at 20° C. for 16 h under nitrogen atmosphere. After the reaction was completed, the reaction mixture was quenched with water (20 mL), and the mixture was extracted with ethyl acetate (20 mL×3 times). The organic phase was concentrated under reduced pressure, and the residue was purified by column chromatography (ISCO©; 12 g of SepaFlash© Silica Flash column; eluent: 0-5% ethyl acetate/petroleum ether, gradient @ 40 mL/min) to give the title compound (400 mg).

MS m/z (ESI): 383.8 $[M+H]^+$.

Step 2: synthesis of 5-(5-(difluoromethoxy)pyridin-2-yl)-1-methyl-7-(trifluoromethyl)-1,5-dihydro-4H-imidazo[4,5-c][1,8]naphthyridin-4-one (Compound 69)

Intermediate 69-2 (100 mg) and intermediate 20-1 (119.50 mg) were dissolved in xylene (5 mL), $Pd(PPh_3)_4$ (30.08 mg) was added at 20° C., and the reaction mixture was stirred for reaction at 140° C. for 16 h under nitrogen atmosphere. After the reaction was completed, the reaction mixture was concentrated under reduced pressure, and the residue was purified by preparative thin-layer chromatography (dichloromethane:methanol=10:1). The residue was then further purified by high performance liquid chromatography (column: Phenomenex C18 150×30 mm×5 μm; mobile phase: [A: water (ammonia water+ammonium bicarbonate), B: acetonitrile]; B %: 35%-55%, 2 min) to give the title compound (46.3 mg).

$^1H$ NMR (400 MHz, DMSO-$d_6$) δ=8.86 (d, J=8.2 Hz, 1H), 8.58 (d, J=2.7 Hz, 1H), 8.35 (s, 1H), 7.95 (dd, J=2.8, 8.6 Hz, 1H), 7.83 (d, J=8.2 Hz, 1H), 7.63 (d, J=8.7 Hz, 1H), 7.50 (t, J=73.2 Hz, 1H), 4.27 (s, 3H).

MS m/z (ESI): 412.1 $[M+H]^+$.

Example 70. 5-(3-fluoro-2-methoxyphenyl)-1-methyl-7-(trifluoromethyl)-1,5-dihydro-4H-imidazo[4,5-c][1,8]naphthyridin-4-one (Compound 70)

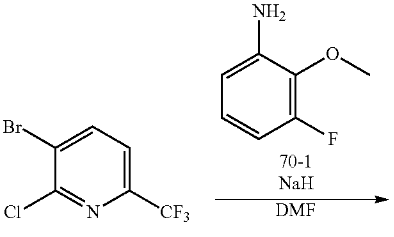

15-1

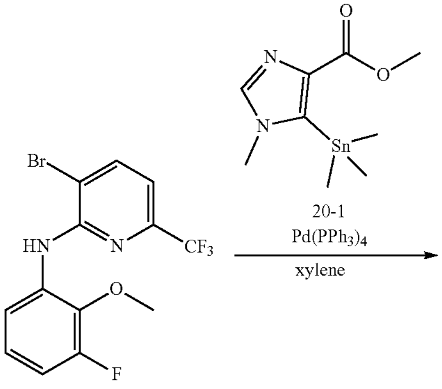

70-2

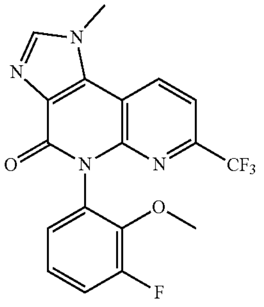

Compound 70

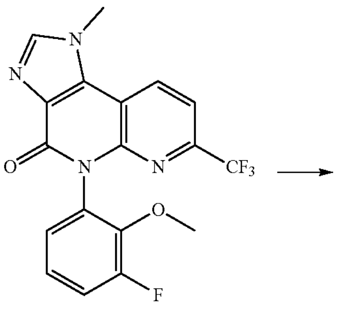

Compound 70

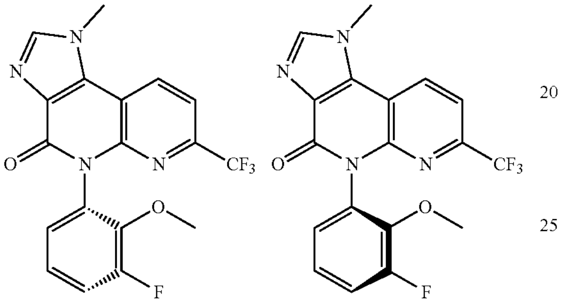

Step 1: synthesis of 3-bromo-N-(3-fluoro-2-methoxyphenyl)-6-(trifluoromethyl)pyridin-2-amine (intermediate 70-2)

Intermediate 70-1 (270.97 mg) was dissolved in anhydrous N,N-dimethylformamide (5 mL) under nitrogen atmosphere, sodium hydride (115.19 mg, 60% effective content) was added to the reaction mixture after the reaction mixture was cooled to 0° C., and the reaction mixture was stirred at 0° C. for 30 min. Intermediate 15-1 (500 mg) was dissolved in anhydrous N,N-dimethylformamide (3 mL) and added to the reaction mixture. The reaction mixture was stirred at 25° C. for 16 h under nitrogen atmosphere. After the reaction was completed, water (10 mL) was added to the reaction mixture. The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by a flash silica gel column (ISCO®; 12 g of SepaFlash© Silica Flash chromatographic column; eluent: 0-5% ethyl acetate/petroleum ether, gradient @ 40 mL/min) to give the title compound (231.4 mg).

MS m/z (ESI): 365.0 $[M+H]^+$.

Step 2: synthesis of 5-(3-fluoro-2-methoxyphenyl)-1-methyl-7-(trifluoromethyl)-1,5-dihydro-4H-imidazo[4,5-c][1,8]naphthyridin-4-one (Compound 70)

Intermediate 70-2 (100 mg) was added to anhydrous xylene (7 mL) under nitrogen atmosphere, and tetrakis (triphenylphosphine)palladium(0) (41.96 mg) and intermediate 20-1 (110.00 mg) were added to the reaction mixture. The reaction mixture was stirred at 140° C. for 16 h under nitrogen atmosphere. After the reaction was completed, the reaction mixture was filtered and concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 24%-44%, 12 min), and was then purified by preparative supercritical fluid chromatography (column: DAICEL CHIRALCEL OD-H (250 mm×30 mm, 5 μm); mobile phase: [A: supercritical carbon dioxide, B: ethanol (0.1% ammonia water)]; B %: 40%-40%) to give Compound 70-P1 (3.5 mg, RT: 5.883 min) and Compound 70-P2 (3.8 mg, RT: 6.298 min).

Compound 70-P1

MS m/z (ESI): 393.1 $[M+H]^+$.

$^1$H NMR (400 MHz, METHANOL-$d_4$) δ 8.89 (d, J=8.1 Hz, 1H), 8.26 (s, 1H), 7.79 (d, J=8.3 Hz, 1H), 7.37-7.33 (m, 1H), 7.26 (dt, J=5.5, 8.1 Hz, 1H), 7.10 (d, J=7.9 Hz, 1H), 4.35 (s, 3H), 3.72 (d, J=1.9 Hz, 3H).

Compound 70-P2

MS m/z (ESI): 393.1 $[M+H]^+$.

$^1$H NMR (400 MHz, METHANOL-$d_4$) δ 8.77 (d, J=8.1 Hz, 1H), 8.13 (s, 1H), 7.67 (d, J=8.3 Hz, 1H), 7.30-7.22 (m, 1H), 7.13 (dt, J=5.3, 8.2 Hz, 1H), 6.98 (d, J=7.9 Hz, 1H), 4.23 (s, 3H), 3.60 (d, J=1.9 Hz, 3H).

Example 71. 5-[4-(difluoromethoxy)-3-fluorophenyl]-1-methyl-7-(trifluoromethyl)-1,5-dihydro-4H-imidazo[4,5-c][1,8]naphthyridin-4-one (Compound 71)

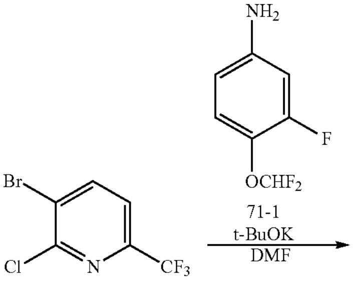

15-1

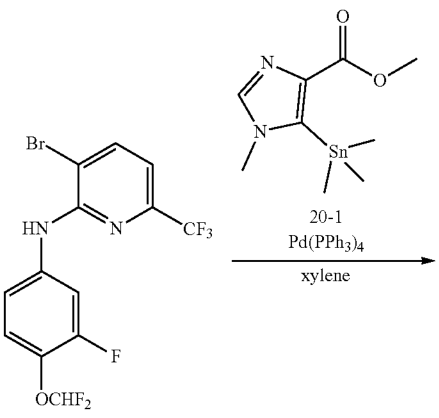

71-2

-continued

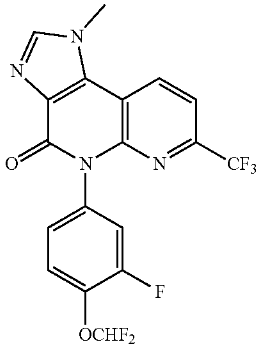

Compound 71

Step 1: synthesis of 3-bromo-N-[4-(difluoromethoxy)-3-fluorophenyl]-6-(trifluoromethyl)pyridin-2-amine (intermediate 71-2)

Intermediate 15-1 (300 mg) and intermediate 71-1 (203.69 mg) were dissolved in anhydrous N,N-dimethylformamide (5 mL), and potassium tert-butoxide (322.60 mg) was added to the reaction mixture. The reaction mixture was stirred at 25° C. for 16 h. After the reaction was completed, water (20 mL) was added to the reaction mixture. The mixture was extracted with ethyl acetate (10 mL×3 times). The organic phases were combined and dried over anhydrous sodium sulfate. After the organic phase was filtered, the organic phase was concentrated under reduced pressure to remove the solvent, and the residue was purified by a flash silica gel column (ISCO©; 12 g of SepaFlash© Silica Flash chromatographic column; eluent: 0-10% ethyl acetate/petroleum ether, gradient @ 40 mL/min) to give the title compound (218.9 mg).

MS m/z (ESI): 401.0 $[M+H]^+$.

Step 2: synthesis of 5-[4-(difluoromethoxy)-3-fluorophenyl]-1-methyl-7-(trifluoromethyl)-1,5-dihydro-4H-imidazo[4,5-c][1,8]naphthyridin-4-one (Compound 71)

Intermediate 71-2 (100 mg) was added to anhydrous xylene (4 mL) under nitrogen atmosphere, and tetrakis(triphenylphosphine)palladium(0) (28.81 mg) and intermediate 20-1 (75.53 mg) were added to the reaction mixture. Subsequently, the reaction mixture was stirred at 140° C. for 16 h under nitrogen atmosphere. After the reaction was completed, the reaction mixture was filtered and concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 31%-51%, 14 min) to give the title compound (25.8 mg).

MS m/z (ESI): 429.1 $[M+H]^+$.

$^1H$ NMR (400 MHz, METHANOL-$d_4$) δ 8.89 (d, J=8.3 Hz, 1H), 8.25 (s, 1H), 7.79 (d, J=8.3 Hz, 1H), 7.51 (t, J=8.5 Hz, 1H), 7.34 (dd, J=2.3, 10.9 Hz, 1H), 7.21 (s, 1H), 7.00 (t, J=70.4 Hz, 1H), 4.35 (s, 3H).

Example 72. 1-(methyl-$d_3$)-5-(2-methylpyridin-3-yl)-7-(trifluoromethyl)-1,5-dihydro-4H-imidazo[4,5-c][1,8]naphthyridin-4-one (Compound 72)

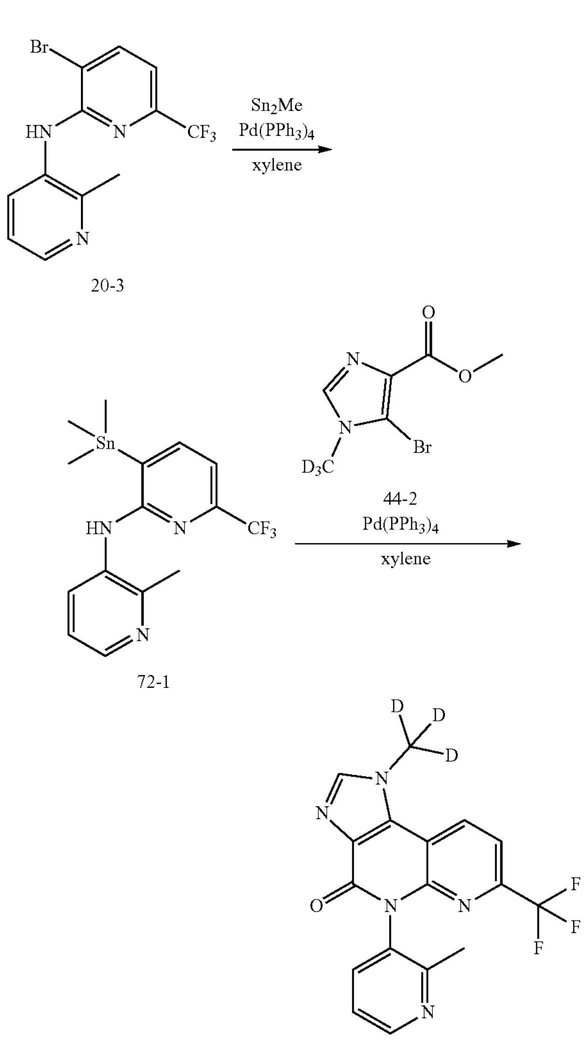

Compound 72

Step 1: synthesis of N-(2-methylpyridin-3-yl)-6-(trifluoromethyl)-3-(trimethylstannyl)pyridin-2-amine Intermediate 20-3 (300 mg) was dissolved in xylene (8 mL), and hexamethyldistannane (591.88 mg) and tetrakis(triphenylphosphine)palladium(0) (104.38 mg) were added. The mixture was sealed and heated to 140° C. for reaction for 1 h under nitrogen atmosphere. After the reaction was completed, the mixture was cooled to 20° C., quenched with a potassium fluoride solution (20 mL), and extracted with ethyl acetate (10 mL). The organic phase was concentrated to dryness under reduced pressure, and the residue was purified by a silica gel column (ISCO©; 12 g of SepaFlash© silica gel column; eluent: 10-35% ethyl acetate/petroleum ether, gradient @ 30 mL/min) to give the title compound (130 mg).

MS m/z (ESI): 417.9 $[M+H]^+$.

Step 2: synthesis of 1-(methyl-$d_3$)-5-(2-methylpyridin-3-yl)-7-(trifluoromethyl)-1,5-dihydro-4H-imidazo[4,5-c][1,8]naphthyridin-4-one (Compound 72)

Intermediate 72-1 (130 mg) and intermediate 44-2 (69.39 mg) were dissolved in xylene (5 mL), tetrakis(triphenylphosphine)palladium(0) (36.11 mg) was added, and the reaction mixture was stirred for reaction at 140° C. for 16 h under nitrogen atmosphere. After the reaction was completed, the mixture was concentrated to dryness under reduced pressure. The residue was purified by thin-layer chromatography (tetrahydrofuran:dichloromethane=1:1), and was then purified by preparative high performance liquid chromatography (formic acid condition; column: Waters Xbridge BEH C18 100×25 mm×5 μm; mobile phase: [A: water (0.225% formic acid), B: acetonitrile]; B %: 4%-34%, 12 min) to give the title compound (22.3 mg).

MS m/z (ESI): 363.0 $[M+H]^+$.

$^1H$ NMR (400 MHz, METHANOL-$d_4$) δ=8.91 (d, J=8.3 Hz, 1H), 8.58 (d, J=3.8 Hz, 1H), 8.25 (s, 1H), 7.80 (d, J=8.3 Hz, 1H), 7.76-7.70 (m, 1H), 7.50 (dd, J=5.0, 7.8 Hz, 1H), 2.19 (s, 3H).

Example 73. 2-chloro-3-(1-methyl-4-oxo-7-(trifluoromethyl)-1,4-dihydro-5H-imidazo[4,5-c][1,8]naphthyridin-5-yl)benzonitrile (Compound 73)

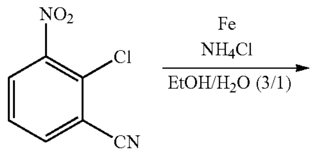

73-1

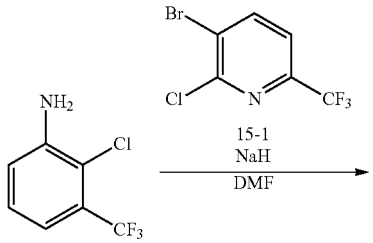

73-2

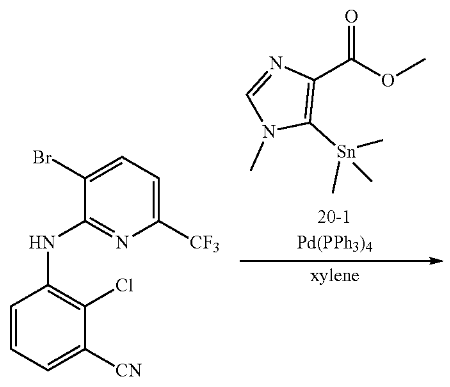

73-3

-continued

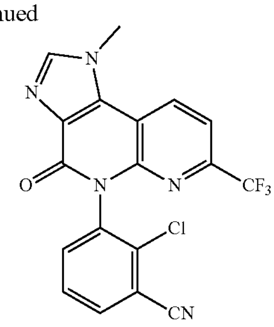

Compound 73

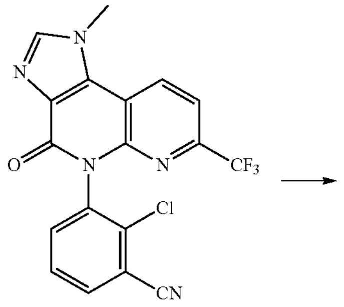

Compound 73

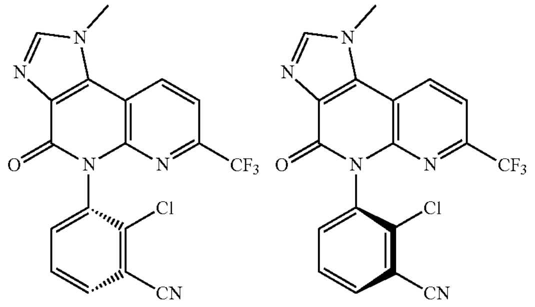

Step 1: synthesis of 3-amino-2-chlorobenzonitrile (intermediate 73-2)

Intermediate 73-1 (500 mg) was dissolved in anhydrous ethanol (9 mL) and water (3 mL) at 25° C., and iron powder (458.84 mg) and ammonium chloride (732.50 mg) were added to the reaction mixture. The reaction mixture was stirred at 70° C. for 16 h under nitrogen atmosphere. After the reaction was completed, the reaction mixture was cooled to 25° C., and water (50 mL) was added. The mixture was extracted with ethyl acetate (50 mL×2 times). The organic phases were combined and dried over anhydrous sodium sulfate. After the organic phase was filtered, the organic phase was concentrated under reduced pressure to remove the solvent to give the title compound (375 mg).

MS m/z (ESI): =153.1 $[M+H]^+$.

Step 2: synthesis of 3-((3-bromo-6-(trifluoromethyl)pyridin-2-yl)amino)-2-chlorobenzonitrile (intermediate 73-3)

Intermediate 73-2 (256.03 mg) was dissolved in an N,N-dimethylformamide solution (5 mL) at 25° C., and sodium hydride (117.96 mg, 60% effective content) was added to the reactant after the reactant was cooled to 0° C. The reaction mixture was stirred at 0° C. for 0.5 h under nitrogen atmosphere, and intermediate 15-1 (150 mg) was added to the reactant. After the reaction was completed, water (200 mL) was added to the reaction mixture. The mixture was extracted with ethyl acetate (100 mL×2 times). The organic phases were combined and dried over anhydrous sodium sulfate. After the organic phase was filtered, the organic phase was concentrated under reduced pressure to remove the solvent to give the title compound (120 mg).

MS m/z (ESI): =375.7 $[M+H]^+$.

Step 3: synthesis of 2-chloro-3-(1-methyl-4-oxo-7-(trifluoromethyl)-1,4-dihydro-5H-imidazo[4,5-c][1,8]naphthyridin-5-yl)benzonitrile (Compound 73)

Intermediate 73-3 (120 mg) was added to anhydrous xylene (5 mL) at 25° C., tetrakis(triphenylphosphine)palladium(0) (36.82 mg) and intermediate 20-1 (144.81 mg) were added to the reaction mixture, and the reaction mixture was reacted at 140° C. for 16 h under nitrogen atmosphere. After the reaction was completed, the reactants were filtered, and the mixture was concentrated under reduced pressure to remove the solvent. The residue was purified by preparative high performance liquid chromatography (column: Waters Xbridge BEH C18 100×25 mm×5 μm; mobile phase: [water (0.225%) formic acid-acetonitrile]; B %: 25%-45%, 12 min) to give the title compound (65 mg).

Compound 73 was further purified by preparative supercritical fluid chromatography (column: DAICEL CHIRALCEL OJ (250 mm×30 mm, 10 μm); mobile phase: A: carbon dioxide, B: ethanol (0.1% ammonia water)) to give Compound 73-P1 (13.3 mg, RT: 3.105 min) and Compound 73-P2 (11 mg, RT: 3.557 min).

Compound 73-P1

MS m/z (ESI): =404.0 $[M+H]^+$.

$^1$H NMR (400 MHz, METHANOL-$d_4$) δ=8.93 (d, J=8.0 Hz, 1H), 8.28 (s, 1H), 8.03 (dd, J=1.5, 7.8 Hz, 1H), 7.86-7.80 (m, 2H), 7.77-7.71 (m, 1H), 4.36 (s, 3H).

MS m/z (ESI): =404.0 $[M+H]^+$.

Compound 73-P2

$^1$H NMR (400 MHz, METHANOL-$d_4$) δ=8.93 (d, J=8.3 Hz, 1H), 8.28 (s, 1H), 8.03 (dd, J=1.6, 7.7 Hz, 1H), 7.85-7.79 (m, 2H), 7.77-7.69 (m, 1H), 4.36 (s, 3H).

Example 74. 1-((1-methyl-1H-pyrazol-4-yl)methyl)-5-(2-methylpyridin-3-yl)-7-(trifluoromethyl)-1,5-dihydro-4H-imidazo[4,5-c][1,8]naphthyridin-4-one (Compound 74)

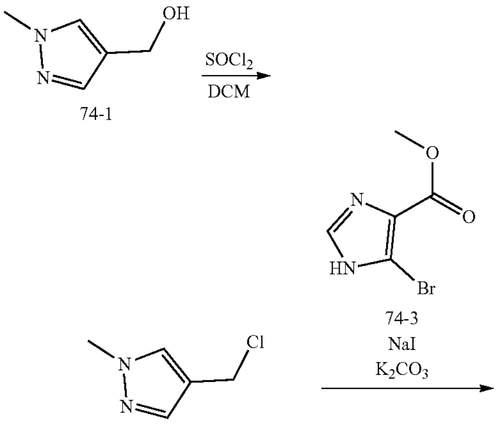

74-1
74-3
74-2

-continued

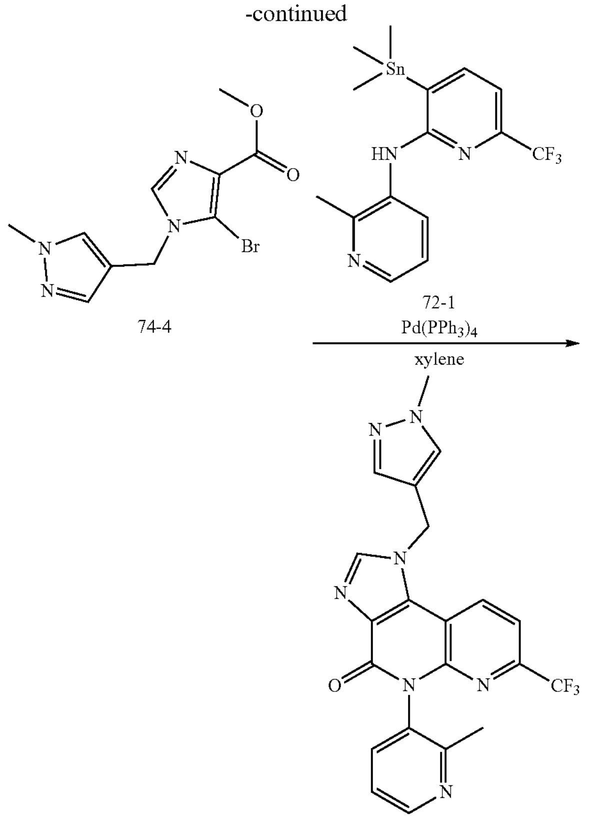

74-4
72-1
Compound 74

Step 1: synthesis of 4-(chloromethyl)-1-methyl-1H-pyrazole (intermediate 74-2)

Reactant 74-1 (2 g) was dissolved in dichloromethane (23 mL), thionyl chloride (3.18 g) was added at 0° C., and the reaction mixture was stirred for reaction at 25° C. for 16 h under nitrogen atmosphere. After the reaction was completed, the reaction mixture was concentrated under reduced pressure to give the title compound (crude product, 3.02 g).

$^1$H NMR (400 MHz, DMSO-$d_6$) δ=7.79 (s, 1H), 7.48 (s, 1H), 4.68 (s, 2H), 3.81 (s, 3H)

Step 2: synthesis of methyl 5-bromo-1-((1-methyl-1H-pyrazol-4-yl)methyl)-1H-imidazole-4-formate (intermediate 74-4)

Intermediate 74-2 (300 mg) and intermediate 74-3 (471.01 mg) were dissolved in acetonitrile (10 mL), sodium iodide (344.39 mg) and potassium carbonate (952.60 mg) were added at 25° C., and the reaction mixture was stirred for reaction at 80° C. for 24 h. After the reaction was completed, the reaction mixture was diluted with water (20 mL). The mixture was extracted with ethyl acetate (20 mL×3 times). The organic phase was concentrated under reduced pressure, and the residue was purified by preparative thin-layer chromatography (dichloromethane:methanol=10:1) to give the title compound (201 mg).

$^1$H NMR (400 MHz, DMSO-$d_6$) δ NMR (400 MHz, DMSO-48 (s, 1H), 4.68 (s, 2H), 3.81 (s, 3H) 3.79 (s, 3H), 3.75 (s, 3H).

MS m/z (ESI): =299.0 $[M+H]^+$.

Step 3: synthesis of 1-((1-methyl-1H-pyrazol-4-yl) methyl)-5-(2-methylpyridin-3-yl)-7-(trifluoromethyl)-1,5-dihydro-4H-imidazo[4,5-c][1,8]naphthyridin-4-one (Compound 74)

Intermediate 74-4 (100 mg) and intermediate 72-1 (139.08 mg) were dissolved in xylene (5 mL), and tetrakis (triphenylphosphine)palladium(0) (38.63 mg) was added at 25° C. under nitrogen atmosphere. The reaction mixture was stirred for reaction at 140° C. for 16 h under nitrogen atmosphere. After the reaction was completed, the reaction mixture was concentrated under reduced pressure. The residue was purified by preparative thin-layer chromatography (dichloromethane:methanol=10:1), and was then further purified by high performance liquid chromatography (column: $C_{18}$-1 150×30 mm×5 μm; mobile phase: [A: water (ammonia water+ammonium bicarbonate), B: acetonitrile]; B %: 25%-45%, 2 min) to give the title compound (29.4 mg).

$^1$H NMR (400 MHz, DMSO-$d_6$) δ=8.77 (d, J=8.2 Hz, 1H), 8.56 (dd, J=J=1.4, 4.8 Hz, 1H), 8.49 (s, 1H), 7.81 (d, J=8.3 Hz, 1H), 7.75 (s, 1H), 7.70 (dd, J=1.4, 7.9 Hz, 1H), 7.50 (s, 1H), 7.43 (dd, J=4.8, 7.9 Hz, 1H), 5.79 (s, 2H), 3.77 (s, 3H), 2.09 (s, 3H).

MS m/z (ESI): =440.2 [M+H]$^+$.

Example 75. 1-methyl-5-(2-methylpyridin-3-yl)-7-(trifluoromethyl)-1,5-dihydro-4H-imidazo[4',5':4,5] pyrido[2,3-d]pyrimidin-4-one (Compound 75)

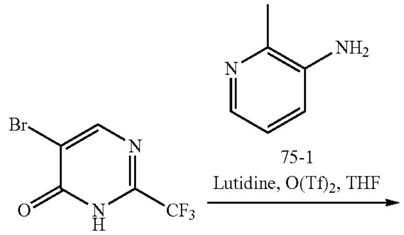

65-2

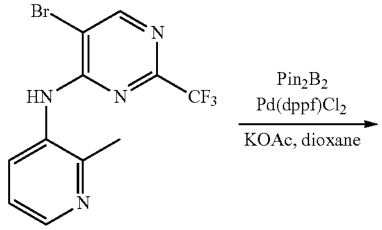

75-2

-continued

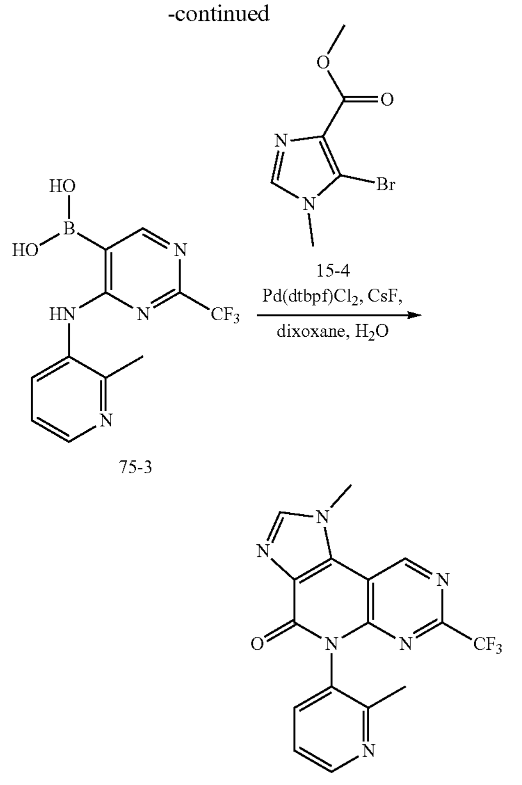

75-3

Compound 75

Step 1: synthesis of 5-bromo-N-(2-methylpyridin-3-yl)-2-(trifluoromethyl)pyrimidin-4-amine (intermediate 75-2)

Intermediate 65-2 (500 mg) and 2,6-dimethylpyridine (330 mg) were dissolved in anhydrous tetrahydrofuran (5 mL), trifluoromethanesulfonic anhydride (697 mg) was added dropwise thereto at −78° C., and the mixture was reacted at 0° C. for 2 h. Intermediate 75-1 (667 mg) was then added to the reaction mixture. The reaction mixture was stirred at 70° C. for 3 h. $H_2O$ (20 mL) and ethyl acetate (20 mL×3) were added sequentially to the reaction mixture. The organic phase was washed with saturated brine (30 mL×2), and the washed organic phase was dried over an appropriate amount of anhydrous sodium sulfate. The residue was purified by preparative thin-layer chromatography (petroleum ether:ethyl acetate=100:0-50:50) to give the title compound (230 mg).

MS m/z (ESI): 333.2 [M+H]$^+$.

Step 2: synthesis of (4-((2-methylpyridin-3-yl) amino)-2-(trifluoromethyl)pyrimidin-5-yl)boronic acid (intermediate 75-3)

Intermediate 75-2 (220 mg) and bis(pinacolato)diboron (252 mg) were dissolved in 1,4-dioxane (3 mL). Potassium acetate (194 mg) and Pd(dppf)$Cl_2$ (42 mg) were added thereto. The reaction mixture was stirred at 100° C. for 15 h under nitrogen atmosphere. After the reaction mixture was cooled to room temperature, water (40 mL) and ethyl acetate (80 mL) were added sequentially.

The organic phase was washed with water (30 mL×2), and the washed organic phase was dried over an appropriate amount of anhydrous sodium sulfate. After the organic phase was filtered, the organic phase was concentrated under reduced pressure to remove the solvent, and the residue was purified by preparative thin-layer chromatography (dichloromethane:methanol=10:1) to give the title compound (160 mg).

MS m/z (ESI): 299.1 [M+H]$^+$.

Step 3: synthesis of 1-methyl-5-(2-methylpyridin-3-yl)-7-(trifluoromethyl)-1,5-dihydro-4H-imidazo[4',5':4,5]pyrido[2,3-d]pyrimidin-4-one (Compound 75)

Intermediate 75-3 (160 mg) and intermediate 15-4 (175 mg) were dissolved in dioxane (2 mL) and water (0.4 mL). Cesium fluoride (156 mg) and Pd(dtbpf)$Cl_2$ (39 mg) were added thereto, and the reaction mixture was stirred at 100° C. for 16 h under nitrogen atmosphere. After the reaction was cooled to room temperature, water (30 mL) and ethyl acetate (40 mL) were added sequentially. The organic phase was washed with saturated brine (30 mL×2), and the washed organic phase was dried over an appropriate amount of anhydrous sodium sulfate and concentrated under reduced pressure. The residue was purified by preparative high performance liquid chromatography (column: Gemini NX C18 5 μm×10×150 mm; mobile phase: A: 0.05% TFA v/v, B: acetonitrile; B %: 40%-45%, 12 min) to give the title compound (15 mg).

MS m/z (ESI): 361.1 [M+H]$^+$.

$^1$H NMR (400 MHz, DMSO-$d_6$) δ 9.75 (s, 1H), 8.63-8.57 (m, 1H), 8.41 (s, 1H), 7.76 (d, J=7.8 Hz, 1H), 7.46 (s, 1H), 4.31 (s, 3H), 2.12 (s, 3H).

Example 76. 1-methyl-5-(pyrimidin-5-yl)-7-(trifluoromethyl)-1,5-dihydro-4H-imidazo[4,5-c][1,8]naphthyridin-4-one (Compound 76)

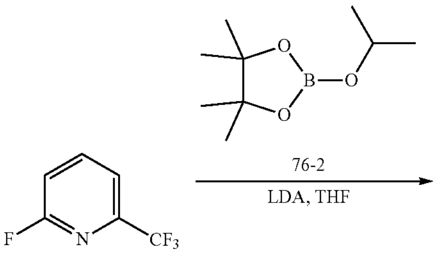

76-2

76-1

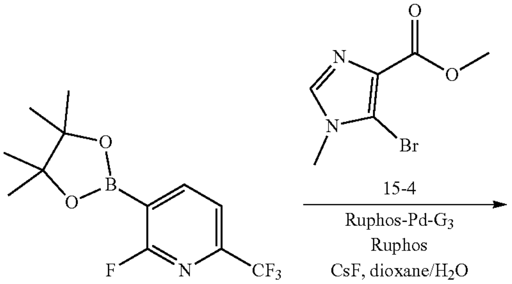

15-4

76-3

-continued

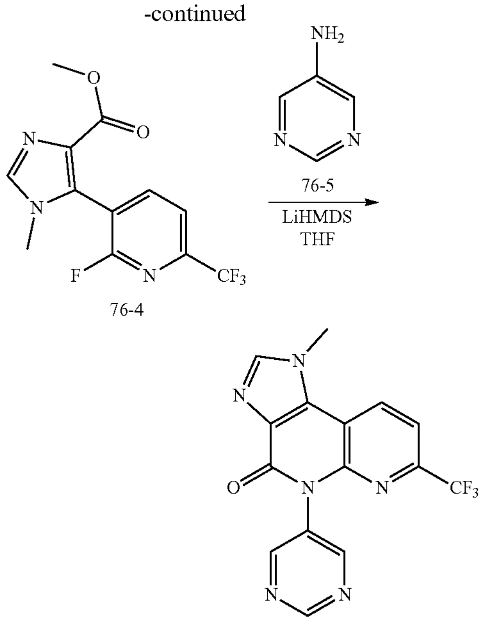

76-5

76-4

Compound 76

Step 1: synthesis of 2-fluoro-3-(4,4,5,5-tetramethyl-1,3,2-dioxaborolan-2-yl)-6-(trifluoromethyl)pyridine (intermediate 76-3)

Intermediate 76-1 (100 g) was dissolved in THF (1000 mL). Intermediate 76-2 (124 g) was added to the reaction mixture. The reaction mixture was stirred at −78° C. for 10 min under nitrogen atmosphere. Lithium diisopropylamide (318 mL) was added in batches, and the reaction mixture was stirred at 25° C. for 4 h. The reaction mixture was cooled to 0° C., and an aqueous HCl solution was added to adjust the pH of the reaction mixture to 4. The mixture was then extracted with ethyl acetate (1500 mL×2). The combined organic phases were washed with brine (300 mL×2), and the washed organic phases were dried over anhydrous $Na_2SO_4$, filtered, concentrated under reduced pressure, and distilled under reduced pressure (90° C.) to give the title compound (130 g).

MS m/z (ESI): 292.1 [M+H]$^+$.

Step 2: synthesis of methyl 5-(2-fluoro-6-(trifluoromethyl)pyridin-3-yl)-1-methyl-1H-imidazole-4-carboxylate (intermediate 76-4)

Intermediate 15-4 (29.0 g) and intermediate 76-3 (58 g) were dissolved in 1,4-dioxane (250 mL) and water (25 mL). Cesium fluoride (60.25 g), Ruphos (6.2 g), and Ruphos Pd G3 (11.10 g) were added, and the reaction mixture was stirred at 100° C. for 4 h under nitrogen atmosphere. After the reaction mixture was cooled to room temperature, 290 mL of 6 M $K_2CO_3$aqueous solution was added. The mixture was stirred at 25° C. for 0.5 h and extracted with ethyl acetate (300 mL×2). The combined organic phases were washed with brine (300 mL×2), and the washed organic phases were dried over anhydrous $Na_2SO_4$, filtered, concentrated under reduced pressure, and purified by preparative thin-layer chromatography (silica, dichloromethane:methanol=20:1) to give the title compound (22.3 g).

MS m/z (ESI): 304.1 [M+H]$^+$.

Step 3: synthesis of 1-methyl-5-(pyrimidin-5-yl)-7-(trifluoromethyl)-1,5-dihydro-4H-imidazo[4,5-c][1,8]naphthyridin-4-one (Compound 76)

Intermediate 76-4 (100 mg) and intermediate 76-5 (31 mg) were dissolved in anhydrous tetrahydrofuran (2 mL). Lithium bis(trimethylsilyl)amide (LiHMDS) (1 mL, 1.0N) was added dropwise thereto at 0° C., and the mixture was stirred at 25° C. for 1 h after the addition. After the reaction was completed, a saturated aqueous ammonium chloride solution (8 mL) and ethyl acetate (8 mL×3) were added sequentially to the reaction mixture. The organic phase was washed with water (8 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Gemini NX C18 5 μm×10×150 mm; mobile phase: A: water (0.225% formic acid v/v), B: acetonitrile; B %: 30%-50%) to give the title compound (6 mg).

MS m/z (ESI): 347.0 $[M+H]^+$.

$^1H$ NMR (400 MHz, DMSO-$d_6$) δ 9.32 (s, 1H), 8.95 (s, 2H), 8.91 (d, J=8.2 Hz, 1H), 8.38 (s, 1H), 7.89 (d, J=8.2 Hz, 1H), 4.30 (s, 3H).

Example 77. Synthesis of 1-methyl-5-(pyrazin-2-yl)-7-(trifluoromethyl)-1,5-dihydro- 4H-imidazo[4,5-c][1,8]naphthyridin-4-one (Compound 77)

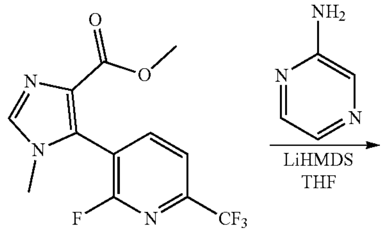

76-4

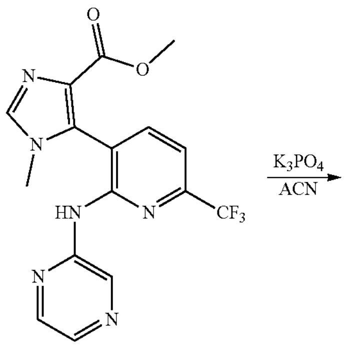

77-1

-continued

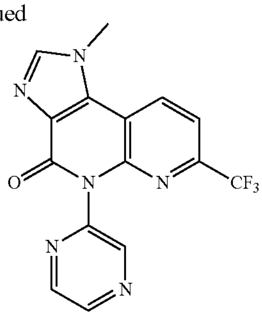

Compound 77

Step 1: synthesis of methyl 1-methyl-5-(2-(pyrazin-2-ylamino)-6-(trifluoromethyl)pyridin-3-yl)-1H-imidazole-4-carboxylate (intermediate 77-1)

Intermediate 76-4 (100 mg) and 2-aminopyrazine (31 mg) were dissolved in anhydrous tetrahydrofuran (2 mL). Lithium bis(trimethylsilyl)amide (1 mL) was added dropwise thereto at 0° C., and the mixture was stirred at 25° C. for 1 h after the addition. After the reaction was completed, a saturated aqueous ammonium chloride solution (8 mL) and ethyl acetate (8 mL×3) were added sequentially. The organic phase was washed with water (8 mL×2), and the washed organic phase was dried over an appropriate amount of anhydrous sodium sulfate. After the organic phase was filtered, the organic phase was concentrated under reduced pressure to remove the solvent. The residue was purified by flash column chromatography (ISCO®; 20 g of SepaFlash© Silica Flash chromatographic column; gradient 0-5% methanol/dichloromethane 80 mL/min) to give the title compound (60.0 mg).

MS m/z (ESI): 379.0 $[M+H]^+$

Step 2: synthesis of 1-methyl-5-(pyrazin-2-yl)-7-(trifluoromethyl)-1,5-dihydro-4H-imidazo[4,5-c][1,8]naphthyridin-4-one (Compound 77)

Intermediate 77-2 (100 mg) was dissolved in anhydrous acetonitrile (3 mL). Potassium phosphate (100 mg) was added, and the mixture was stirred at 80° C. for 4 h. After the reaction was completed, a saturated aqueous ammonium chloride solution (8 mL) and ethyl acetate (8 mL×3) were added sequentially. The organic phase was washed with water (8 mL×2), and the washed organic phase was dried over an appropriate amount of anhydrous sodium sulfate. After the organic phase was filtered, the organic phase was concentrated under reduced pressure to remove the solvent. The residue was purified by preparative high performance liquid chromatography (column: Waters Xbridge BEH C18 100×25 mm×5 μm; mobile phase: [A: water (0.225% formic acid), B: acetonitrile]; B %: 33%-50%, 12 min) to give the title compound (23.5 mg).

MS m/z (ESI): 347.0 $[M+H]^+$.

$^1H$ NMR (400 MHz, DMSO-$d_6$) δ 8.93-8.81 (m, 4H) 8.38 (s, 1H), 7.88 (d, J=8.2 Hz, 1H), 4.30 (s, 3H).

Example 78. 5-(2,3-difluorophenyl)-1-methyl-7-(trifluoromethyl)-1,5-dihydro-4H-imidazo[4,5-c][1,8]naphthyridin-4-one (Compound 78)

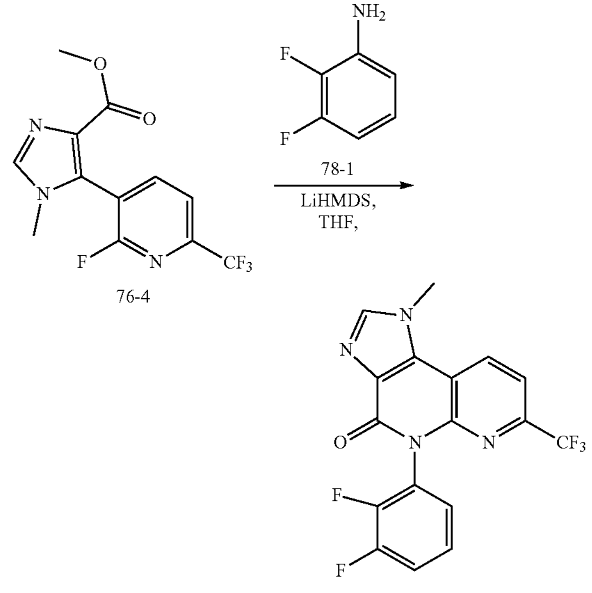

76-4

78-1

Compound 78

Intermediate 76-4 (50 mg) and intermediate 78-1 (22 mg, 0.17 mmol) were dissolved in tetrahydrofuran (1 mL), and the reaction mixture was stirred at 0° C. for 10 min under nitrogen atmosphere. Lithium bis(trimethylsilyl)amide (0.34 mL) was added to the reaction mixture. The reaction mixture was stirred at 24° C. for 2 h. The reaction mixture was cooled to 0° C. 5 mL $H_2O$ was added to quench the reaction. Water (15 mL) and ethyl acetate (30 mL) were added sequentially. The organic phase was washed with saturated brine (30 mL×2), and the washed organic phase was dried over an appropriate amount of anhydrous sodium sulfate and concentrated under reduced pressure to give 50 mg crude product. The crude product was purified by preparative high performance liquid chromatography (column: Gemini NX C18 5 μm×10×150 mm; mobile phase: A: 0.05% TFA v/v, B: acetonitrile; B %: 40%-45%, 12 min) to give the title compound (5 mg).

MS m/z (ESI): 381.2 $[M+H]^+$.

$^1H$ NMR (400 MHz, DMSO-$d_6$) δ 8.88 (d, J=8.2 Hz, 1H), 8.36 (s, 1H), 7.88 (d, J=8.2 Hz, 1H), 7.70-7.58 (m, 1H), 7.47-7.30 (m, 2H), 4.27 (s, 3H).

Example 79. 1-methyl-5-(4-methylpyrimidin-5-yl)-7-(trifluoromethyl)-1,5-dihydro-4H-imidazo[4,5-c][1,8]naphthyridin-4-one (Compound 79)

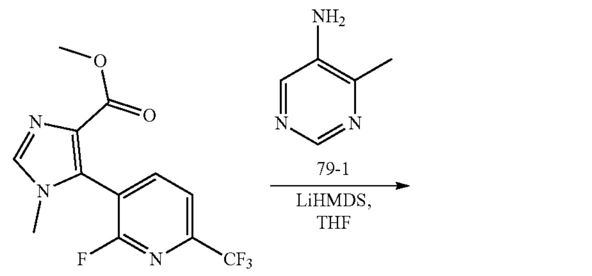

76-4

79-1

-continued

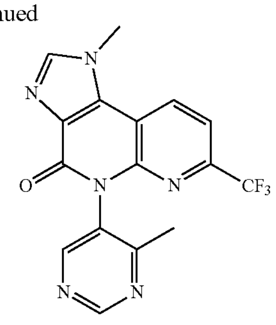

Compound 79

Step 1: synthesis of 1-methyl-5-(4-methylpyrimidin-5-yl)-7-(trifluoromethyl)-1,5-dihydro-4H-imidazo[4,5-c][1,8]naphthyridin-4-one (Compound 79)

Intermediate 76-4 (80 mg) and intermediate 79-1 (29 g) were dissolved in tetrahydrofuran (2 mL). A lithium bis(trimethylsilyl)amide solution (1 mol/L in THF, 0.4 mL) was added dropwise thereto at 0° C., and the reaction mixture was stirred at 0° C. for 3 h. The reaction mixture was concentrated under reduced pressure to remove the solvent, and the residue was purified by preparative high performance liquid chromatography (column: Gemini NX C18 5 μm×10×150 mm; mobile phase: A: water (0.225% formic acid v/v), B: acetonitrile; B %: 40%-60%, 12 min) to give the title compound (31 mg).

MS m/z (ESI): 361.1 $[M+H]^+$.

$^1H$ NMR (400 MHz, DMSO-$d_6$) δ 9.17 (s, 1H), 8.91 (d, J=8.2 Hz, 1H), 8.74 (s, 1H), 8.38 (s, 1H), 7.89 (d, J=8.2 Hz, 1H), 4.29 (s, 3H), 2.15 (s, 3H).

Example 80. 5-(2-chloro-3-ethynylphenyl)-1-methyl-7-(trifluoromethyl)-1,5-dihydro-4H-imidazo[4,5-c][1,8]naphthyridin-4-one (Compound 80)

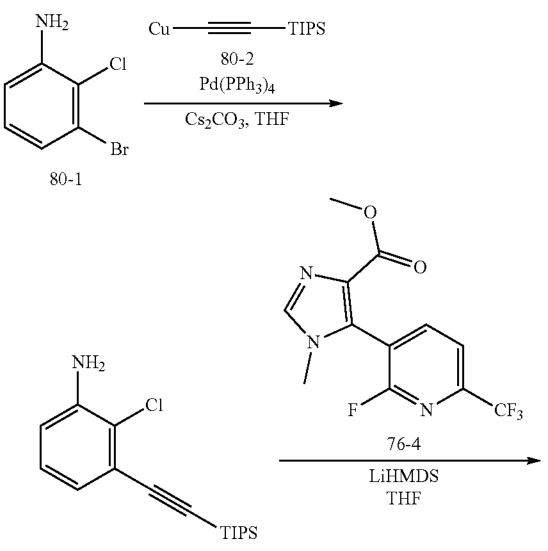

80-1

80-2

80-3

76-4

-continued

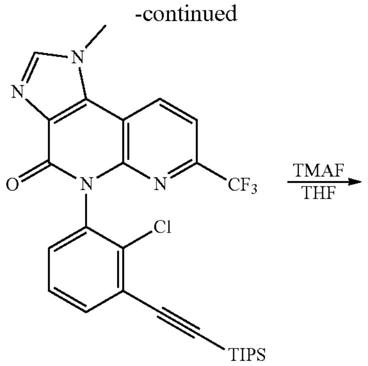

80-4

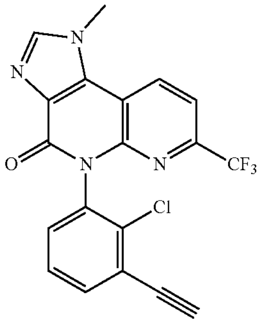

Compound 80

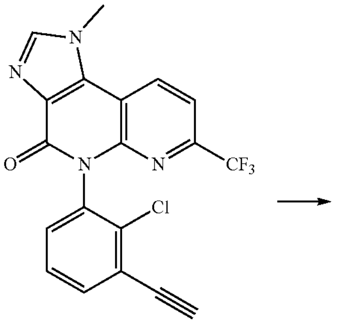

Compound 80

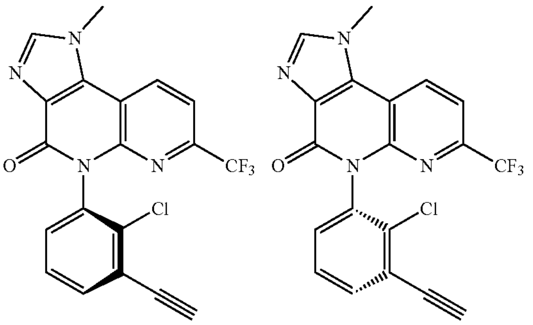

Step 1: Synthesis of 2-chloro-3-((triisopropylsilyl)ethynyl)aniline (intermediate 80-3)

Intermediate 80-1 (316 mg), intermediate 80-2 (562 mg), tetrakis(triphenylphosphine)palladium(0) (707 mg), and cesium carbonate (998 mg) were dissolved in anhydrous tetrahydrofuran (8 mL), and the mixture was reacted at 60° C. for 10 h. A saturated aqueous ammonium chloride solution (20 mL) and ethyl acetate (20 mL×2) were added sequentially to the reaction mixture. The organic phase was washed with saturated brine (20 mL×2), and the washed organic phase was dried over an appropriate amount of anhydrous sodium sulfate and concentrated under reduced pressure to remove the solvent. The residue was purified by preparative thin-layer chromatography (silica, petroleum ether:ethyl acetate=4:1) to give the title compound (174 mg).

MS m/z (ESI): 308.1 $[M+H]^+$.

Step 2: synthesis of 5-(2-chloro-3-((triisopropylsilyl)ethynyl)phenyl)-1-methyl-7-(trifluoromethyl)-1,5-dihydro-4H-imidazo[4,5-c][1,8]naphthyridin-4-one (intermediate 80-4)

Intermediate 80-3 (125 mg) and intermediate 76-4 (152 mg) were dissolved in anhydrous tetrahydrofuran (4 mL). A solution of lithium bis(trimethylsilyl)amide in THF (1 mol/L, 0.8 mL) was added dropwise thereto at 0° C., and the reaction mixture was stirred at 0° C. for 2 h. The reaction mixture was concentrated under reduced pressure to remove the solvent, and the residue was purified by preparative thin-layer chromatography (silica, dichloromethane:methanol=20:1) to give the title compound (165 mg).

MS m/z (ESI): 558.9 $[M+H]^+$.

Step 3: synthesis of 5-(2-chloro-3-ethynylphenyl)-1-methyl-7-(trifluoromethyl)-1,5-dihydro-4H-imidazo[4,5-c][1,8]naphthyridin-4-one (Compound 80)

Intermediate 80-4 (160 mg, 0.3 mmol) and tetramethylammonium fluoride (56 mg, 0.6 mmol) were dissolved in tetrahydrofuran (2 mL), and the mixture was reacted at 25° C. for 5 h. The reaction mixture was washed with water (15 mL) and extracted with ethyl acetate (10 mL×2). The organic phase was dried over an appropriate amount of anhydrous sodium sulfate and concentrated under reduced pressure to remove the solvent, and the residue was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (32 mg).

MS m/z (ESI): 403.0 $[M+H]^+$.

$^1$H NMR (400 MHz, DMSO-$d_6$) δ 8.87 (d, J=8.2 Hz, 1H), 8.35 (s, 1H), 7.85 (d, J=8.2 Hz, 1H), 7.78-7.76 (m, 1H), 7.63-7.48 (m, 2H), 4.67 (s, 1H), 4.28 (s, 3H).

Compound 80 (46.5 mg) was separated and prepared by supercritical fluid chromatography (column: DAICEL CHIRALPAK AD-H (250 mm×30 mm, 5 μm); mobile phase: A: carbon dioxide; B: ethanol (0.1% ammonia water); B %: 45%; flow rate: 70 mL/min) to give compound 80-P1 (6.4 mg, RT: 1.499 min) and compound 80-P2 (9.1 mg, RT: 1.893 min).

Compound 80-P1:

$^1$H NMR (400 MHz, METHANOL-$d_4$) δ=8.93-8.87 (m, 1H), 8.25 (s, 1H), 7.79 (d, J=8.3 Hz, 1H), 7.76-7.71 (m, 1H), 7.55-7.48 (m, 1H), 7.48-7.43 (m, 1H), 4.35 (s, 3H), 3.94 (s, 1H).

MS m/z (ESI): 403.1$[M+H]^+$.

Compound 80-P2:

$^1$H NMR (400 MHz, METHANOL-$d_4$) δ=8.90 (d, J=8.3 Hz, 1H), 8.25 (s, 1H), 7.79 (d, J=8.3 Hz, 1H), 7.76-7.70 (m, 1H), 7.54-7.49 (m, 1H), 7.49-7.43 (m, 1H), 4.35 (s, 3H), 3.94 (s, 1H).

MS m/z (ESI): 403.0 $[M+H]^+$.

Example 81. 5-(2-cyclopropylpyridin-3-yl)-7-(trifluoromethyl)oxazolo[4,5-c][1,8]naphthyridin-4(5H)-one (Compound 81)

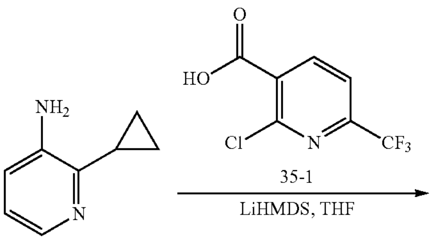

42-4

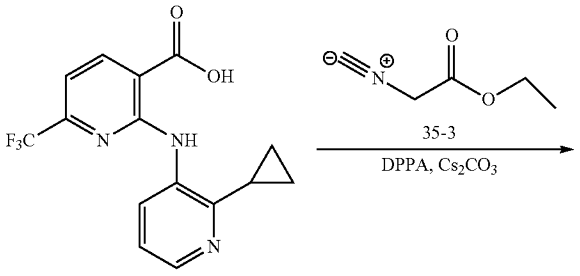

81-1

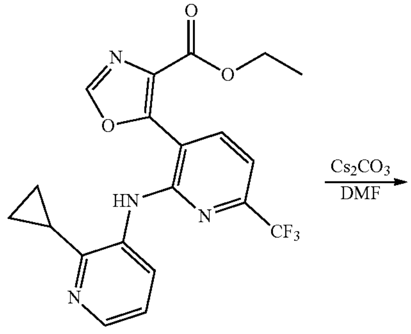

81-2

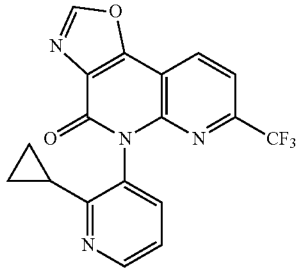

Compound 81

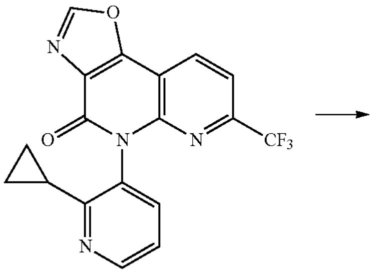

Compound 81

-continued

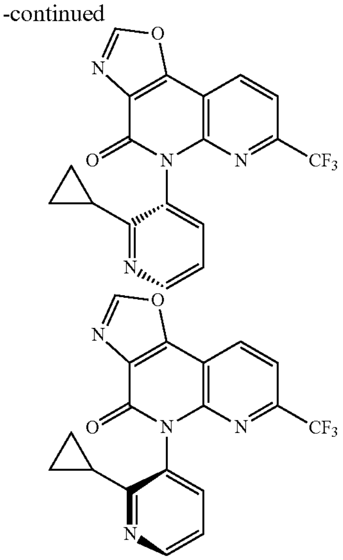

Step 1: synthesis of 2-((2-cyclopropylpyridin-3-yl)amino)-6-(trifluoromethyl)pyridine-3-carboxylic acid (intermediate 81-1)

Intermediate 35-1 (300 mg) was dissolved in anhydrous tetrahydrofuran (4 mL). LiHMDS (1 M, 5.0 mL) was added dropwise thereto at −78° C. The mixture was reacted at −78° C. for 1 h, and intermediate 42-4 (323 mg) was added to the reaction mixture. The reaction system was warmed to room temperature and reacted for 3 h. A saturated aqueous ammonium chloride solution (10 mL) and ethyl acetate (20 mL×3) were added sequentially to the reaction mixture. The organic phase was washed with water (20 mL×2), and the washed organic phase was dried over an appropriate amount of anhydrous sodium sulfate. After the organic phase was filtered, the filtrate was concentrated under reduced pressure to give the title compound (220 mg).

MS m/z (ESI): 324.2 $[M+H]^+$.

Step 2: synthesis of ethyl 5-(2-((2-cyclopropylpyridin-3-yl)amino)-6-(trifluoromethyl)pyridin-3-yl)oxazole-4-carboxylate (intermediate 81-2)

Intermediate 81-1 (100 mg) and cesium carbonate (228 mg) were dissolved in N,N-dimethylformamide (1 mL). Diphenylphosphoryl azide (DPPA) (192 mg) was added thereto at 0° C., and the mixture was reacted at room temperature for 1 h after the addition. Intermediate 35-3 (40 mg) was added at 0° C., and the reaction mixture was stirred at 25° C. for 2 h after the addition. Water (5 mL) and ethyl acetate (5 mL×3) were added sequentially to the reaction mixture. The organic phase was washed with saturated brine (5 mL×2). The washed organic phase was dried over an appropriate amount of anhydrous sodium sulfate and concentrated to dryness under reduced pressure, and the residue was purified by preparative thin-layer chromatography (silica, petroleum ether:ethyl acetate=100:0 to 50:50) to give the title compound (70 mg).

MS m/z (ESI): 419.2 $[M+H]^+$.

Step 3: synthesis of 5-(2-cyclopropylpyridin-3-yl)-7-(trifluoromethyl)oxazolo[4,5-c][1,8]naphthyridin-4(5H)-one (Compound 81)

Intermediate 81-2 (70 mg) and cesium carbonate (149 mg) were dissolved in N,N-dimethylformamide (1 mL), and the mixture was reacted at 70° C. for 2 h. The reaction mixture was filtered, and the filtrate was concentrated to dryness under reduced pressure. The residue was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (15 mg).

MS m/z (ESI): 373.2 $[M+H]^+$.

$^1$H NMR (400 MHz, DMSO-$d_6$) δ 9.04 (s, 1H), 8.74 (d, J=8.0 Hz, 1H), 8.56-8.53 (m, 1H), 7.86 (d, J=8.1 Hz, 1H), 7.73-7.68 (m, 1H), 7.32-7.24 (m, 1H), 1.61-1.50 (m, 1H), 1.03-0.92 (m, 1H), 0.75-0.57 (m, 2H), 0.55-0.43 (m, 1H).

Compound 81 (13 mg) was separated and prepared by supercritical fluid chromatography (column: (s,s) WHELK-01 (250 mm×30 mm, 5 μm); mobile phase: A: carbon dioxide; B: ethanol (0.1% ammonia water); B %: 50%; flow rate: 70 mL/min) to give compound 81-P1 (3.2 mg, RT: 1.570 min) and compound 81-P2 (4.9 mg, RT: 2.675 min).

Compound 81-P1

$^1$H NMR (400 MHz, METHANOL-$d_4$) δ=8.80 (s, 1H), 8.77 (d, J=8.0 Hz, 1H), 8.56 (dd, J=1.5, 5.0 Hz, 1H), 7.87 (d, J=8.0 Hz, 1H), 7.70 (dd, J=1.6, 7.9 Hz, 1H), 7.39 (dd, J=4.9, 7.9 Hz, 1H), 1.66-1.58 (m, 1H), 1.17-1.09 (m, 1H), 0.94-0.86 (m, 1H), 0.83-0.75 (m, 1H), 0.68-0.59 (m, 1H).

MS m/z (ESI): 373.1 $[M+H]^+$.

Compound 81-P2

$^1$H NMR (400 MHz, METHANOL-$d_4$) δ=8.80 (s, 1H), 8.77 (d, J=8.0 Hz, 1H), 8.56 (dd, J=1.5, 4.8 Hz, 1H), 7.87 (d, J=8.0 Hz, 1H), 7.70 (dd, J=1.5, 8.0 Hz, 1H), 7.39 (dd, J=4.9, 7.9 Hz, 1H), 1.66-1.57 (m, 1H), 1.18-1.09 (m, 1H), 0.93-0.88 (m, 1H), 0.83-0.75 (m, 1H), 0.68-0.60 (m, 1H).

MS m/z (ESI): 373.1 $[M+H]^+$.

Example 82. 5-(2-methylpyridin-3-yl)-7-(trifluoromethyl)oxazolo[4,5-c]quinolin-4 (5H)-one (Compound 82)

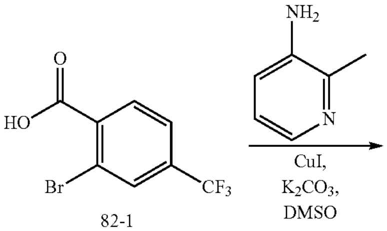

82-1

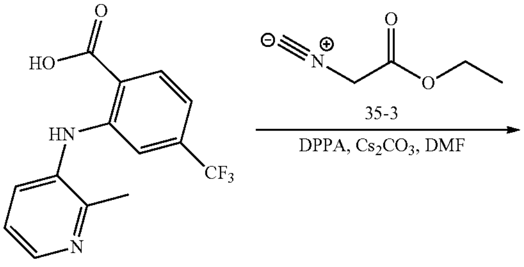

82-2

-continued

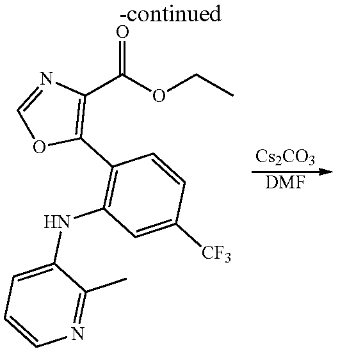

82-3

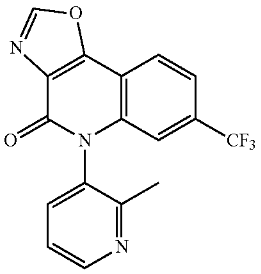

Compound 82

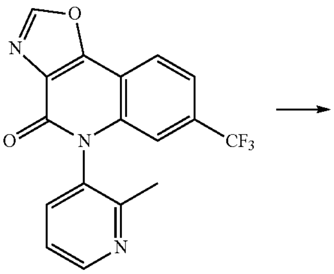

Compound 82

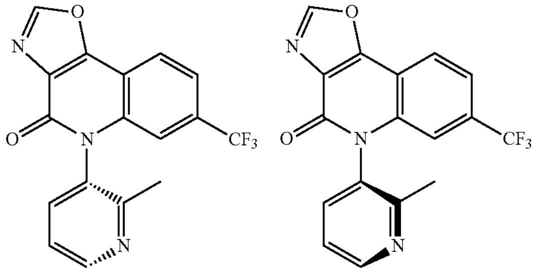

Step 1: synthesis of 2-((2-methylpyridin-3-yl)amino)-4-(trifluoromethyl)benzoic acid (Intermediate 82-2)

Intermediate 82-1 (6 g) and 2-methylpyridin-3-amine (3.62 g) were dissolved in anhydrous dimethylsulfoxide (30 mL). Cuprous iodide (1.70 g), N,N-dimethylglycine (811 mg), and potassium carbonate (6.16 g) were added thereto, and the mixture was stirred at 100° C. for 12 h after the addition. After the reaction was completed and the mixture was filtered, the organic phase was purified by preparative high performance liquid chromatography (column: Waters Xbridge BEH C18 100×25 mm×5 μm; mobile phase: [A: water (0.225% formic acid), B: acetonitrile]; B %: 23%-66%, 25 min) to give the title compound (2 g).

MS m/z (ESI): 297.0 $[M+H]^+$.

Step 2: synthesis of ethyl 5-(2-((2-methylpyridin-3-yl)amino)-4(trifluoromethyl)phenyl)oxazole-4-carboxylate (intermediate 82-3)

Intermediate 82-2 (200 mg, 675.12 μmol) was dissolved in anhydrous N,N-dimethylformamide (5 mL). Cesium carbonate (658 mg, 2.03 mmol) and diphenylphosphoryl azide (DPPA) (371 mg, 1.35 mmol) were added at 0° C., and the reaction mixture was stirred at 0° C. for 0.5 h. Intermediate 35-3 (152 mg, 1.35 mmol) was added to the reaction mixture, and the reaction mixture was stirred at 25° C. for 1 h. After the reaction was completed, water (10 mL) and ethyl acetate (10 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Waters Xbridge BEH C18 100×25 mm×5 μm; mobile phase: [A: water (0.225% formic acid), B: acetonitrile]; B %: 23%-50%, 12 min) to give the title compound (100 mg).

MS m/z (ESI): 392. 0 $[M+H]^+$.

Step 3: synthesis of 5-(2-methylpyridin-3-yl)-7-(trifluoromethyl)oxazolo[4,5-c]quinolin-4 (5H)-one (Compound 82)

Intermediate 82-3 (90 mg, 230 μmol) was dissolved in anhydrous N,N-dimethylformamide (5 mL). Cesium carbonate (228 mg, 0.69 mmol) was added thereto, and the reaction mixture was stirred at 60° C. for 2 h. After the reaction was completed, water (10 mL) and ethyl acetate (10 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Waters Xbridge BEH C18 100×25 mm×5 μm; mobile phase: [A: water (0.225% formic acid), B: acetonitrile]; B %: 23%-50%, 12 min) to give the title compound (10 mg).

MS m/z (ESI): 346.0 $[M+H]^+$.

$^1$H NMR (400 MHz, Chloroform-d) δ 9.07 (s, 1H), 8.73-8.71 (m, 1H), 8.36 (d, J=8.2 Hz, 1H), 7.88-7.86 (m, 1H), 7.81-7.78 (m, 1H), 7.58-7.55 (m, 1H), 6.72 (s, 1H), 2.16 (s, 3H).

Compound 82 (64.6 mg) was separated and prepared by supercritical fluid chromatography (column: DAICEL CHIRALPAK AD (250 mm×30 mm, 10 μm); mobile phase: A: carbon dioxide; B: ethanol (0.1% ammonia water); B %: 25%-25%; flow rate: 70 mL/min) to give compound 82-P1 (20.8 mg, RT: 3.206 min) and compound 82-P2 (18.7 mg, RT: 4.274 min).

Compound 82-P1

$^1$H NMR (400 MHz, METHANOL-$d_4$) δ=8.77 (s, 1H), 8.75 (dd, J=1.4, 4.9 Hz, 1H), 8.39 (d, J=8.0 Hz, 1H), 7.88 (dd, J=1.3, 8.0 Hz, 1H), 7.79 (d, J=8.3 Hz, 1H), 7.64 (dd, J=4.9, 7.9 Hz, 1H), 6.88 (s, 1H), 2.26 (s, 3H).

MS m/z (ESI): 346.1 $[M+H]^+$.

Compound 82-P2

$^1$H NMR (400 MHz, METHANOL-$d_4$) δ=8.77 (s, 1H), 8.75 (dd, J=1.5, 4.8 Hz, 1H), 8.40 (d, J=8.3 Hz, 1H), 7.89 (dd, J=1.4, 7.9 Hz, 1H), 7.82-7.76 (m, 1H), 7.64 (dd, J=4.9, 7.9 Hz, 1H), 6.88 (s, 1H), 2.26 (s, 3H).

MS m/z (ESI): 346.1 $[M+H]^+$.

Example 83. 7-chloro-5-(2-methylpyridin-3-yl)oxazolo[4,5-c]quinolin-4 (5H)-one (Compound 83)

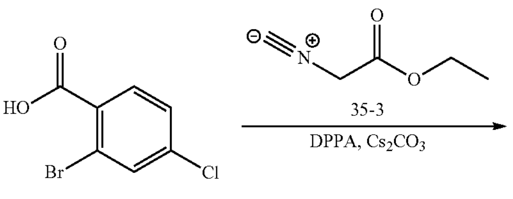

83-1

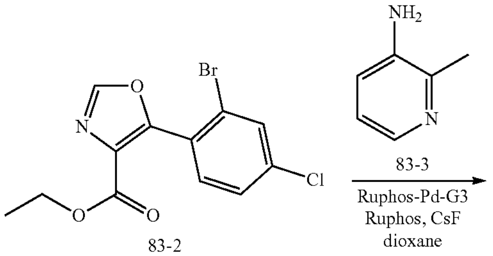

83-2

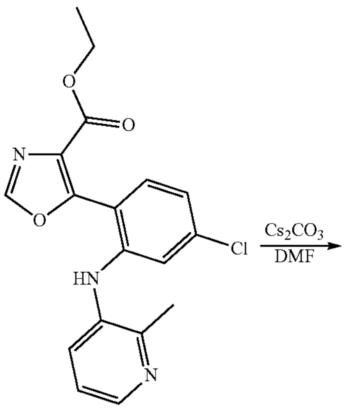

83-4

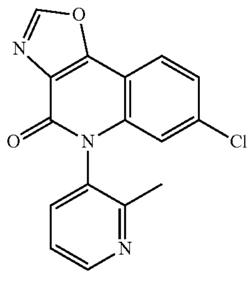

Compound 83

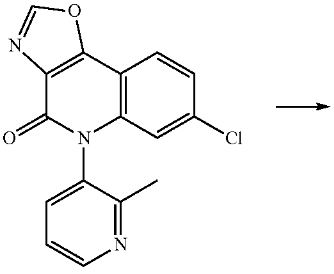

Compound 83

-continued

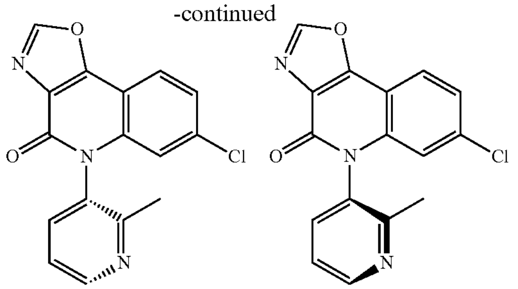

Step 1: synthesis of ethyl 5-(2-bromo-4-chlorophenyl)oxazole-4-carboxylate (Intermediate 83-2)

Intermediate 83-1 (5.0 g) and cesium carbonate (13.8 g) were dissolved in N,N-dimethylformamide (42 mL). DPPA (10.3 g) was added thereto at 0° C., and the mixture was reacted at room temperature for 1 h. Intermediate 35-3 (2.4 g) was added at 0° C., and the reaction mixture was stirred at 25° C. for 2 h. Water (60 mL) and ethyl acetate (70 mL×3) were added sequentially to the reaction mixture. The organic phase was washed with saturated brine (60 mL×2). The washed organic phase was dried over an appropriate amount of anhydrous sodium sulfate and purified by preparative thin-layer chromatography (petroleum ether:ethyl acetate=4:1) to give the title compound (1.8 g).

MS m/z (ESI): 329.9 $[M+H]^+$.

Step 2: synthesis of ethyl 5-(4-chloro-2-((2-methylpyridin-3-yl)amino)phenyl)oxazole-4-carboxylate (intermediate 83-4)

Intermediate 83-2 (200.0 mg) and intermediate 83-3 (78.5 mg) were dissolved in 1,4-dioxane (2 mL). RuPhos-Pd-G3 (50.7 mg), RuPhos (28.2 mg), and cesium fluoride (183.8 mg) were added thereto, and the mixture was reacted at 100° C. for 15 h under nitrogen atmosphere. The reaction mixture was concentrated under reduced pressure to remove the solvent, and the residue was purified by preparative thin-layer chromatography (dichloromethane:methanol=20:1) to give the title compound (150 mg).

MS m/z (ESI): 358.1 $[M+H]^+$.

Step 3: synthesis of 7-chloro-5-(2-methylpyridin-3-yl)oxazolo[4,5-c]quinolin-4 (5H)-one (Compound 83)

Intermediate 83-3 (150 mg) and cesium carbonate (410 mg) were dissolved in N,N-dimethylformamide (5 mL), and the mixture was reacted at 60° C. for 3 h. The reaction mixture was filtered, and the residue was purified by preparative high performance liquid chromatography (column: Gemini NX C18 5 μm×10×150 mm; mobile phase: A: water (0.225% formic acid v/v), B: acetonitrile; B %: 30%-50%, 11 min) to give the title compound (33 mg).

MS m/z (ESI): 312.0 $[M+H]^+$.

$^1$H NMR (400 MHz, DMSO-$d_6$) δ 8.99 (s, 1H), 8.71-8.70 (m, 1H), 8.16 (d, J=8.5 Hz, 1H), 7.85-7.82 (m, 1H), 7.58-7.50 (m, 2H), 6.54 (s, 1H), 2.16 (s, 3H).

Compound 83 (21 mg) was separated and prepared by supercritical fluid chromatography (column: DAICEL CHIRALPAK AD (250 mm×30 mm, 10 μm); mobile phase: A: carbon dioxide; B: ethanol (0.1% ammonia water); B %: 35%-35%; flow rate: 70 mL/min) to give compound 83-P1 (5.9 mg, RT: 4.609 min) and compound 83-P2 (5.5 mg, RT: 6.014 min).

Compound 83-P1

$^1$H NMR (400 MHz, METHANOL-$d_4$) δ=8.72 (dd, J=1.4, 4.9 Hz, 1H), 8.68 (s, 1H), 8.17 (d, J=8.5 Hz, 1H), 7.84 (dd, J=1.3, 8.0 Hz, 1H), 7.62 (dd, J=4.9, 7.9 Hz, 1H), 7.52 (dd, J=1.8, 8.5 Hz, 1H), 6.68 (d, J=1.8 Hz, 1H), 2.26 (s, 3H).

MS m/z (ESI): 312.1 $[M+H]^+$.

Compound 83-P2

$^1$H NMR (400 MHz, METHANOL-$d_4$) δ=8.72 (dd, J=1.3, 5.0 Hz, 1H), 8.68 (s, 1H), 8.17 (d, J=8.5 Hz, 1H), 7.84 (dd, J=1.3, 8.0 Hz, 1H), 7.62 (dd, J=5.0, 8.0 Hz, 1H), 7.52 (dd, J=1.8, 8.5 Hz, 1H), 6.68 (d, J=1.8 Hz, 1H), 2.26 (s, 3H).

MS m/z (ESI): 312.1 $[M+H]^+$.

Example 84. 1-methyl-7-(trifluoromethyl)-5-(2-trifluoromethylpyridin-3-yl)-1,5-dihydro-4H-imidazo[4,5-c]quinolin-4-one (Compound 84)

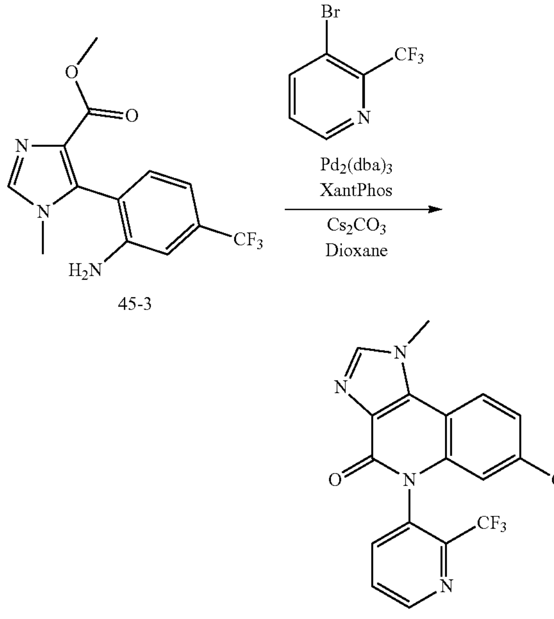

45-3

Compound 84

Intermediate 45-3 (150 mg) and 2-trifluoromethyl-3-bromopyridine (136 mg) were dissolved in anhydrous dioxane solution (2 mL). Cesium carbonate (327 mg), XantPhos (58 mg), and $Pd_2(dba)_3$ (46 mg) were added thereto, and the reaction mixture was stirred at 100° C. for 12 h under nitrogen atmosphere. After the reaction was cooled to room temperature, the reaction mixture was filtered and concentrated to dryness under reduced pressure. The residue was purified by preparative liquid chromatography [YMC-Actus Triart C18 column, 5 μm silica, 30 mm diameter, 150 mm length; a mixture of water (containing 0.05% $NH_4HCO_3$) and acetonitrile with decreasing polarity was used as the eluent, acetonitrile gradient: 55%-75%, 12 min] to give the title compound (7 mg).

MS m/z (ESI): 413.0 $[M+H]^+$.

$^1$H NMR (400 MHz, DMSO-$d_6$) δ 9.04-9.02 (m, 1H), 8.51 (d, J=8.4 Hz, 1H), 8.32 (s, 1H), 8.26 (d, J=1.4 Hz, 1H), 8.11-8.08 (m, 1H), 7.73-7.71 (m, 1H), 6.67 (s, 1H), 4.29 (s, 3H).

Example 85. 5-(2-cyclopropylpyridin-3-yl)-7-(trifluoromethyl)oxazolo[4,5-c]quinolin-4 (5H)-one (Compound 85)

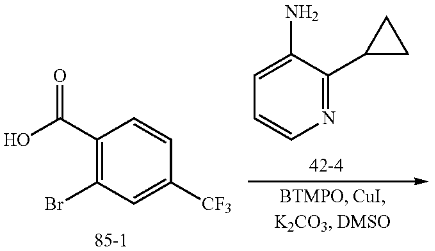

85-1

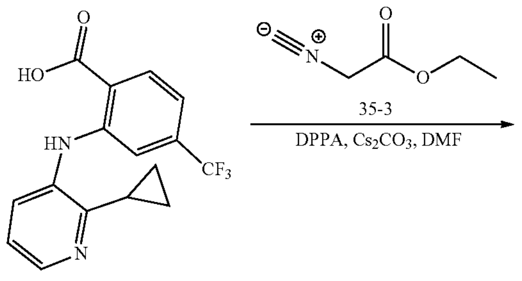

85-2

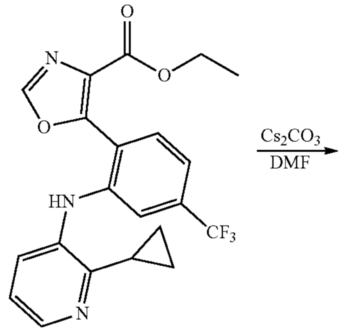

85-3

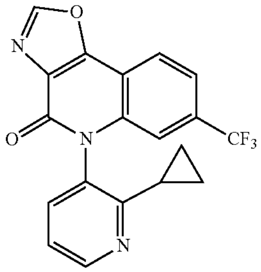

Compound 85

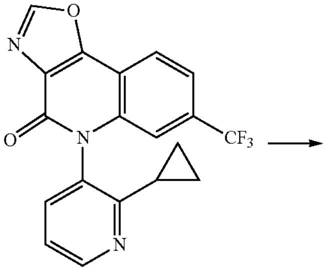

-continued

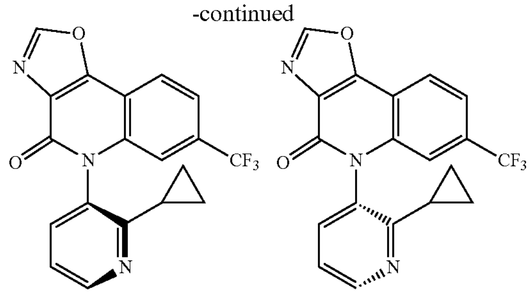

Step 1: synthesis of 2-((2-cyclopropylpyridin-3-yl) amino)-4-(trifluoromethyl)benzoic acid (intermediate 85-2)

Intermediate 85-1 (1.3 g) and intermediate 42-4 (518 mg) were dissolved in anhydrous dimethylsulfoxide (20 mL). Cuprous iodide (368 mg), N,N'-bis(2,4,6-trimethoxyphenyl) ethanediamide (BTMPO) (811 mg), and potassium carbonate (2.0 g) were added, and the mixture was stirred at 100° C. for 12 h. After the reaction was completed, the reaction mixture was filtered, and the filtrate was purified by preparative high performance liquid chromatography (column: Waters Xbridge BEH C18 100×25 mm×5 μm; mobile phase: [A: water (0.225% formic acid), B: acetonitrile]; B %: 23%-66%, 25 min) to give the title compound (500 mg). MS m/z (ESI): 323.0 $[M+H]^+$.

Step 2: synthesis of ethyl 5-(2-((2-cyclopropylpyridin-3-yl)amino)-4-(trifluoromethyl)phenyl)oxazole-4-carboxylate (intermediate 85-3)

Intermediate 85-2 (50 mg, 155.14 μmol) was dissolved in anhydrous N,N-dimethylformamide (5 mL). Cesium carbonate (151 mg) and diphenylphosphoryl azide (75 mg) were added at 0° C. The reaction mixture was stirred at 0° C. for 0.5 h. Intermediate 35-3 (35.10 mg) was added to the reaction mixture, and the reaction mixture was stirred at 25° C. for 1 h. After the reaction was completed, water (10 mL) and ethyl acetate (10 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Waters Xbridge BEH C18 100×25 mm×5 μm; mobile phase: [A: water (0.225% formic acid), B: acetonitrile]; B %: 23%-50%, 12 min) to give the title compound (38 mg).

MS m/z (ESI): 418. 0 $[M+H]^+$.

Step 3: synthesis of 5-(2-cyclopropylpyridin-3-yl)-7-(trifluoromethyl)oxazolo[4,5-c]quinolin-4 (5H)-one (Compound 85)

Intermediate 85-3 (20 mg) was dissolved in anhydrous N,N-dimethylformamide (5 mL). Cesium carbonate (46 mg) was added, and the reaction mixture was stirred at 60° C. for 2 h. After the reaction was completed, water (10 mL) and ethyl acetate (10 mL) were added sequentially. The organic phase was washed with water (5 mL×2), and the washed organic phase was dried over an appropriate amount of anhydrous sodium sulfate. After the organic phase was filtered, the organic phase was concentrated under reduced pressure to remove the solvent, and the residue was purified by preparative high performance liquid chromatography (column: Waters Xbridge BEH C18 100×25 mm×5 μm; mobile phase: [A: water (0.225% formic acid), B: acetonitrile]; B %: 23%-50%, 12 min) to give the title compound (10 mg).

MS m/z (ESI): 372. 0 $[M+H]^+$.

$^1$H NMR (400 MHz, DMSO-$d_6$) δ 9.05 (s, 1H), 8.68-8.65 (m, 1H), 8.35 (d, J=8.2 Hz, 1H), 7.90-7.72 (m, 2H), 7.48-7.46 (m, 1H), 6.75 (s, 1H), 1.64-1.60 (m, 1H), 1.15-1.10 (m, 1H), 0.80-0.78 (m, 2H), 0.77-0.75 (m, 1H).

Compound 85 (133.8 mg) was separated and prepared by supercritical fluid chromatography (column: DAICEL CHIRALCEL OJ (250 mm×30 mm, 10 μm); mobile phase: A: carbon dioxide; B: ethanol (0.1% ammonia water); B %: 20%-20%; flow rate: 70 mL/min) to give compound 85-P1 (46.8 mg, RT: 1.870 min) and compound 85-P2 (49 mg, RT: 2.094 min).

Compound 85-P1:

$^1$H NMR (400 MHz, METHANOL-$d_4$) δ=8.76 (s, 1H), 8.71-8.66 (m, 1H), 8.38 (d, J=8.3 Hz, 1H), 7.78 (d, J=7.8 Hz, 2H), 7.48 (dd, J=4.8, 7.8 Hz, 1H), 6.94 (s, 1H), 1.66-1.57 (m, 1H), 1.27-1.19 (m, 1H), 0.98-0.91 (m, 1H), 0.90-0.82 (m, 1H), 0.76-0.67 (m, 1H).

MS m/z (ESI): 372. 1 $[M+H]^+$.

Compound 85-P2:

$^1$H NMR (400 MHz, METHANOL-$d_4$) δ=8.76 (s, 1H), 8.71-8.65 (m, 1H), 8.38 (d, J=8.3 Hz, 1H), 7.78 (d, J=8.0 Hz, 2H), 7.48 (dd, J=4.8, 7.8 Hz, 1H), 6.94 (s, 1H), 1.65-1.57 (m, 1H), 1.27-1.19 (m, 1H), 0.98-0.91 (m, 1H), 0.90-0.83 (m, 1H), 0.75-0.67 (m, 1H).

MS m/z (ESI): 372. 1 $[M+H]^+$.

Example 86. 7-trifluoromethyl-5-(2-trifluoromethylpyridin-3-yl)oxazolo[4,5-c][1,8]naphthyridin-4(5H)-one (Compound 86)

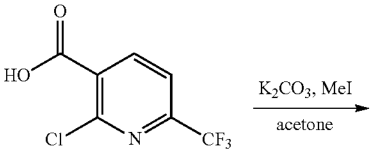

35-1

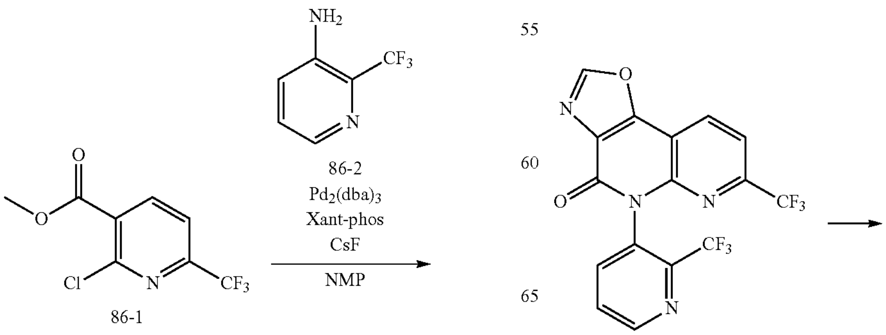

86-1

-continued

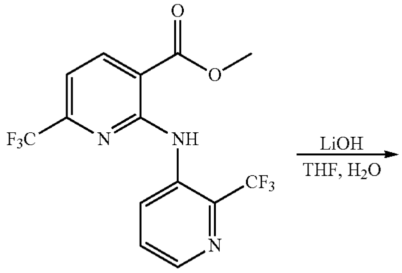

86-3

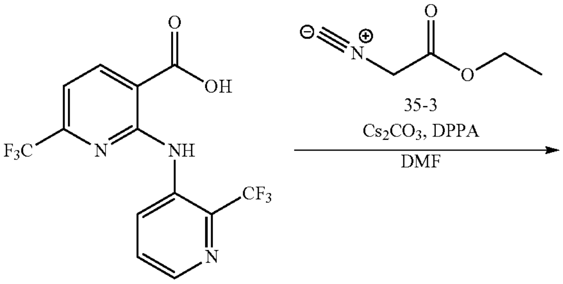

86-4

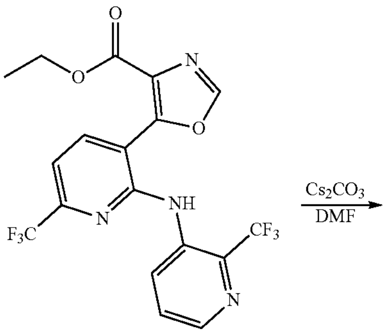

86-5

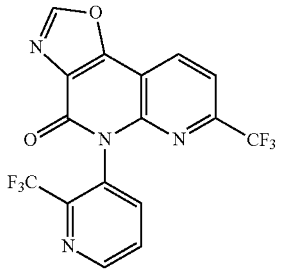

Compound 86

-continued

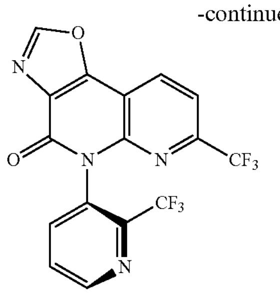

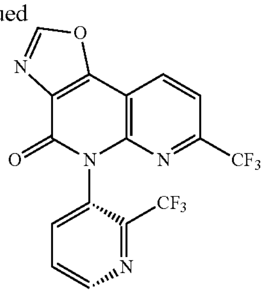

Step 1: synthesis of methyl 2-chloro-6-trifluoromethylpyridine-3-carboxylate (Intermediate 86-1)

Intermediate 35-1 (2 g) and potassium carbonate (3.68 g) were added to acetone (15 mL). Iodomethane (1.89 g) was added dropwise under nitrogen atmosphere, and the mixture was reacted at 35° C. for 16 h. The reaction mixture was poured into 10 mL water, and the mixture was extracted with ethyl acetate (10 mL×3). The organic layers were combined, washed with saturated brine (20 mL×2), and dried over anhydrous sodium sulfate. After the organic layer was filtered, the filtrate was concentrated under reduced pressure, and the residue was purified by column chromatography (petroleum ether:ethyl acetate=10:1) to give the title compound (2 g).

MS m/z (ESI): 240.0 $[M+H]^+$.

Step 2: synthesis of methyl 6-trifluoromethyl-2-((2-trifluoromethylpyridin-3-yl)amino)pyridine-3-carboxylate (intermediate 86-3)

Intermediate 86-1 (2.06 g), intermediate 86-2 (2.09 g), $Pd_2(dba)_3$ (787.37 mg), Xantphos (497.53 mg), and cesium fluoride (2.61 g) were added to N-methyl-2-pyrrolidone (15 mL). After the reaction mixture was stirred at 100° C. for 3 h under nitrogen atmosphere, the reaction mixture was cooled and poured into water, and the mixture was extracted with ethyl acetate (20 mL×3). The organic layers were combined, washed with water (30 mL×2), washed with saturated brine (30 mL), and dried over anhydrous sodium sulfate. After the organic layer was filtered, the filtrate was concentrated under reduced pressure, and the residue was purified by column chromatography (petroleum ether:ethyl acetate=10:1) to give the title compound (2.82 g).

MS m/z (ESI): 366.0 $[M+H]^+$.

Step 3: synthesis of 6-trifluoromethyl-2-((2-trifluoromethylpyridin-3-yl)amino)pyridine-3-carboxylic acid (intermediate 86-4)

Intermediate 86-3 (2 g) was dissolved in tetrahydrofuran (15 mL), and a lithium hydroxide (655.75 mg) aqueous solution (15 mL) was added. After the mixture was reacted at room temperature for 1 h, the reaction mixture was poured into water and the pH was adjusted to 5 with 6 M hydrochloric acid. The mixture was extracted with ethyl acetate (20 mL×3). The organic layers were combined, washed with water (20 mL×2), washed with saturated brine (20 mL), and dried over anhydrous sodium sulfate. After the organic layer was filtered, the filtrate was concentrated under reduced pressure, and the residue was purified by reversed-phase column chromatography (acetonitrile:water=1:4) to give the title compound (0.98 g).

MS m/z (ESI): 352.0 $[M+H]^+$.

Step 4: synthesis of ethyl 5-(6-trifluoromethyl-2-((2-(trifluoromethyl)pyridin-3-yl)amino)pyridin-3-yl)oxazole-4-carboxylate (intermediate 86-5)

Intermediate 86-4 (500 mg) and cesium carbonate (927.72 mg) were added to DMF (5 mL). DPPA (783.59 mg) was added dropwise at 0° C. under nitrogen atmosphere. Intermediate 35-3 (161.04 mg, 1.42 mmol) was added after the mixture was reacted at room temperature for 1 h. The mixture was reacted at room temperature for 16 h. The reaction mixture was poured into water. The mixture was extracted with ethyl acetate (10 mL×3). The organic layers were combined, washed with water (10 mL×2), washed with saturated brine (10 mL), and dried over anhydrous sodium sulfate. After the organic layer was filtered, the filtrate was concentrated under reduced pressure, and the residue was purified by column chromatography (petroleum ether:ethyl acetate=5:1) to give the title compound (493 mg).

MS m/z (ESI): 447.0 $[M+H]^+$.

Step 5: synthesis of 7-trifluoromethyl-5-(2-trifluoromethylpyridin-3-yl)oxazolo[4,5-c][1,8]naphthyridin-4 (5H)-one (Compound 86)

Intermediate 86-5 (300 mg) and cesium carbonate (657.04 mg) were added to DMF (3 mL). After the mixture was reacted at room temperature for 2 h, the reaction mixture was poured into water. The mixture was extracted with ethyl acetate (10 mL×3). The organic layers were combined, washed with water (10 mL×2), washed with saturated brine (10 mL), dried over anhydrous sodium sulfate, and filtered to remove desiccant. The filtrate was concentrated under reduced pressure, and the residue was purified by preparative high performance liquid chromatography (column: Gemini NX C18 3.5 μm×4.6×100 mm; mobile phase: A: 0.05% TFA v/v, B: acetonitrile; B %: 40%-45%, 8 min) to give the title compound (160 mg).

MS m/z (ESI): 401.0 $[M+H]^+$.

$^1$H NMR (400 MHz, DMSO-$d_6$) δ 9.15 (1H, s), 8.95 (1H, d, J=4.0 Hz), 8.85 (1H, d, J=8.0 Hz), 8.19 (1H, d, J=7.7 Hz), 8.04-8.01 (1H, m), 7.97 (1H, d, J=8.1 Hz).

Compound 86 (160 mg) was separated and prepared by supercritical fluid chromatography (column: (s,s) WHELK-01 (250 mm×30 mm, 5 μm); mobile phase: A: carbon dioxide; B: ethanol (0.1% ammonia water); B %: 35%-35%; flow rate: 80 mL/min) to give compound 86-P1 (64.2 mg, RT: 3.345 min) and compound 86-P2 (62.9 mg, RT: 4.149 min).

Compound 86-P1:

$^1$H NMR (400 MHz, METHANOL-$d_4$) δ=8.92 (d, J=4.0 Hz, 1H), 8.81 (s, 1H), 8.79 (d, J=8.0 Hz, 1H), 8.07 (d, J=8.0 Hz, 1H), 7.94 (dd, J=4.7, 7.9 Hz, 1H), 7.89 (d, J=8.0 Hz, 1H)

MS m/z (ESI): 401.0 $[M+H]^+$.

Compound 86-P2:

$^1$H NMR (400 MHz, METHANOL-$d_4$) δ=8.80 (d, J=4.3 Hz, 1H), 8.69 (s, 1H), 8.67 (d, J=8.1 Hz, 1H), 7.95 (d, J=7.9 Hz, 1H), 7.82 (dd, J=4.8, 8.1 Hz, 1H), 7.77 (d, J=8.0 Hz, 1H)

MS m/z (ESI): 401.0 $[M+H]^+$.

Example 87. 7-chloro-5-(2-cyclopropylpyridin-3-yl)-1-difluoromethyl-1,5-dihydro-4H-imidazo[4,5-c]quinolin-4-one (Compound 87)

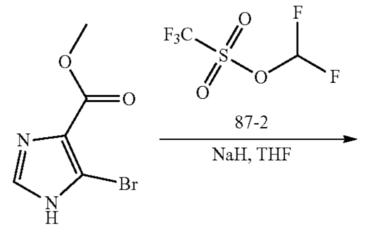

87-1

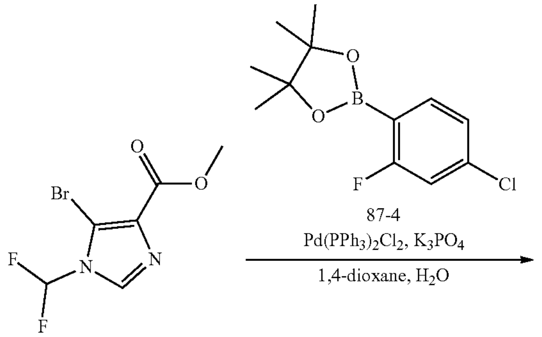

87-3

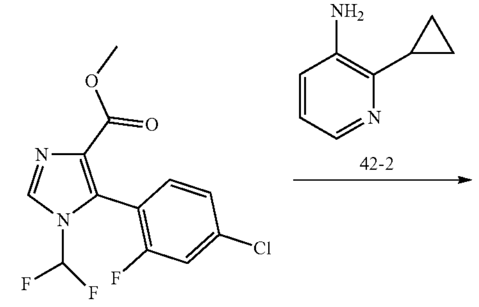

87-5

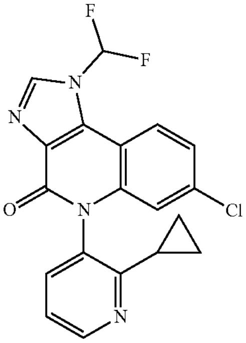

Compound 87

-continued

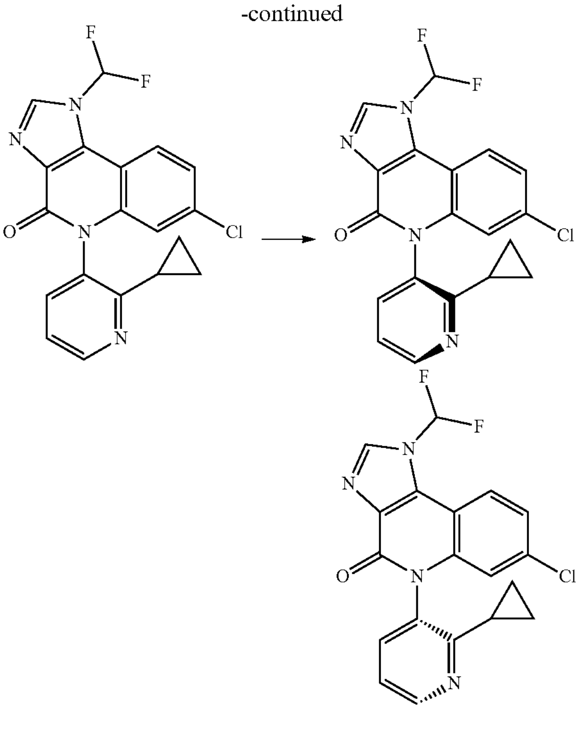

Step 1: synthesis of methyl 5-bromo-1-(difluoromethyl)-1H-imidazole-4-carboxylate (Intermediate 87-3)

Reactant 87-1 (1 g) was dissolved in THF (10 mL) under nitrogen atmosphere. NaH (234.14 mg) was added, and the mixture was stirred at room temperature for 10 min. Reactant 87-2 (1.17 g) was then added, and the mixture was stirred at room temperature for 16 h. The reaction mixture was slowly added to 20 mL saturated aqueous ammonium chloride solution, and the mixture was extracted with ethyl acetate (30 mL×2). The organic phase was washed with 50 mL saturated brine. The washed organic phase was dried over an appropriate amount of anhydrous sodium sulfate, concentrated and purified by column chromatography (petroleum ether/ethyl acetate=3/1) to give the title compound (600 mg).

MS m/z (ESI): 254.9 $[M+H]^+$.

Step 2: synthesis of methyl 5-(4-chloro-2-fluorophenyl)-1-(difluoromethyl)-1H-imidazole-4-carboxylate (intermediate 87-5)

Intermediate 87-3 (250 mg), intermediate 87-4 (301.75 mg), $K_3PO_4$ (624.27 mg), and $Pd(PPh_3)_2Cl_2$ (68.81 mg) were added to a reaction flask. 1,4-dioxane (1.25 mL) and $H_2O$ (0.25 mL) were added, and the mixture was reacted at 80° C. for 4 h under nitrogen atmosphere. After the reaction was cooled to room temperature, 10 mL water was added. The mixture was extracted with ethyl acetate (10 mL×3), and the combined organic phases were washed with saturated brine (20 mL), dried over anhydrous sodium sulfate, concentrated under reduced pressure, and purified by column chromatography (petroleum ether/ethyl acetate=3/1) to give the title compound (200 mg).

MS m/z (ESI): 305.0 $[M+H]^+$.

Step 3: synthesis of 7-chloro-5-(2-cyclopropylpyridin-3-yl)-1-difluoromethyl-1,5-dihydro-4H-imidazo [4,5-c]quinolin-4-one (Compound 87)

Intermediate 87-5 (100 mg) and intermediate 42-2 (41.84 mg) were added to THF (1 mL) under nitrogen atmosphere. The mixture was cooled to −40° C. LiHMDS (1 M, 820.61 μL) was slowly added dropwise. The mixture was stirred for 30 min, slowly warmed to 25° C., and continuously stirred for 10 h. 10 mL water was added to the system. The mixture was extracted with ethyl acetate (10 mL×2). After liquid separation, the organic phase was washed once with a saturated aqueous NaCl solution. After liquid separation, the organic phase was dried over anhydrous magnesium sulfate, filtered, concentrated under reduced pressure, and purified by column chromatography (petroleum ether/ethyl acetate=3/1) to give the title compound (38.8 mg).

MS m/z (ESI): 387.1 $[M+H]^+$.

$^1$H NMR (400 MHz, DMSO-$d_6$) δ 8.68 (s, 1H), 8.64 (dd, J=1.6 Hz, 4.8 Hz, 1H), 8.38 (t, J=58 Hz, 1H), 8.15 (d, J=8.8 Hz, 1H), 7.79 (dd, J=1.6 Hz, 6.4 Hz, 1H), 7.54 (dd, J=2.4 Hz, 6.4 Hz, 1H), 7.44 (dd, J=4.8 Hz, 8.0 Hz, 1H), 6.54 (d, 2.0 Hz, 1H), 1.62-1.52 (m, 1H), 1.09-1.00 (m, 1H), 0.90-0.82 (m, 1H), 0.82-0.73 (m, 1H), 0.72-0.63 (m, 1H).

Compound 87 (38.8 mg) was separated and prepared by supercritical fluid chromatography (column: (s,s) WHELK-01 (250 mm×30 mm, 5 μm); mobile phase: A: carbon dioxide; B: ethanol (0.1% ammonia water); B %: 40%-40%; flow rate: 80 mL/min) to give compound 87-P1 (12.1 mg, RT: 1.783 min) and compound 87-P2 (10.1 mg, RT: 2.604 min).

Compound 87-P1:

$^1$H NMR (400 MHz, METHANOL-$d_4$) δ=8.67 (dd, J=1.5, 4.8 Hz, 1H), 8.57 (s, 1H), 8.31 (d, J=6.8 Hz, 1H), 8.18 (t, J=58.0 Hz, 1H), 7.74 (dd, J=1.6, 7.9 Hz, 1H), 7.52-7.44 (m, 2H), 6.74-6.71 (m, 1H), 1.64-1.55 (m, 1H), 1.22-1.14 (m, 1H), 1.04-0.96 (m, 1H), 0.91-0.82 (m, 1H), 0.80-0.71 (m, 1H)

MS m/z (ESI): 387.0 $[M+H]^+$.

Compound 87-P2:

$^1$H NMR (400 MHz, METHANOL-$d_4$) δ=8.66 (dd, J=1.5, 4.8 Hz, 1H), 8.57 (s, 1H), 8.31 (d, J=6.8 Hz, 1H), 8.18 (t, J=58.0 Hz, 1H), 7.74 (dd, J=1.5, 7.8 Hz, 1H), 7.53-7.43 (m, 2H), 6.74-6.71 (m, 1H), 1.64-1.55 (m, 1H), 1.22-1.15 (m, 1H), 1.04-0.96 (m, 1H), 0.90-0.82 (m, 1H), 0.79-0.71 (m, 1H)

MS m/z (ESI): 387.0 $[M+H]^+$.

Biological Activity and Related Properties Test Example

Test Example 1. Biochemical Test

The brief introduction of the test principle: L-methionine and ATP can be converted into SAM, inorganic phosphate, and inorganic diphosphate under the catalysis of MAT2A enzymes. The content of inorganic phosphate in the sample can be quantitatively determined by adding a developer such as ammonium molybdate or the like to the enzymatic reaction mixture, thereby reflecting the enzymatic activity of MAT2A.

Reference: The experiment referred to the method disclosed in patent WO2018045071.

Material: MAT2A screening kits were purchased from BPS bioscience (U.S.); 384-well plates were purchased from Corning Company (U.S.).

1. MAT2A protein (Pharmaron Beijing Co., Ltd.);
2. L-methionine (Sigma #M9625-5G)
3. ATP (Sigma #A7699-1G)
4. KCl (Sigma #60142-500ML-F)
5. Tris (Sigma #T2663-1L)
6. $MgCl_2$ (Sigma #M1028)
7. EDTA (Invitrogen #AM9260G)
8. BSA (Sangon Biotech #A500023-0100)
9. PiColorLock (abcam #ab270004)

Detection method: In the experimental group, the test compound was dissolved in DMSO, diluted to a final concentration of 10 μM using Echo, and diluted 3-fold. 80 nL of the dilution was transferred to a 384-well plate.

The experimental buffer (50 mM Tris, 50 mM KCl, 15 mM $MgCl_2$, 100 μM EDTA, 0.005% BSA) was prepared. The MAT2A protein was diluted with the experimental buffer (at final concentration of 4 Vg/mL). 40 μL of 2×MAT2A solution was added to the 384-well plate. The plate was centrifuged at 1000 rpm for 1 min and incubated at room temperature for 120 min.

L-methionine and ATP (the final concentration of L-methionine was 200 JIM and the final concentration of ATP was 400 μM) were diluted with the experimental buffer. 40 μL of 2×L-methionine and ATP solution was added to initiate the reaction. The plate was centrifuged at 1000 rpm for 1 min and incubated at room temperature for 90 min.

The PiColorLock™ reaction catalyst was mixed with the PiColorLock™ buffer at a ratio of 1:100 according to the instructions. 20 μL was added to each well, and the plate was shaken for 30 s. 8 μL stabilizing reagent was added, and the plate was shaken for 30 s. The signal values were measured after 30 min of incubation at room temperature.

A negative control group and a positive control group were respectively used as Bottom and Top. The negative control group was not added with MAT2A protein, and other operations were consistent with those of the experimental group. The positive control group was not added with the test compound, only added with DMSO in the same volume, and other operations were consistent with those of the experimental group.

Data Analysis:

The % Compound inhibition was calculated and fitted to give the $IC_{50}$ of the compound.

% Compound inhibition=1-100%×(Signal−Bottom)/(Top−Bottom).

Signal referred to the signal value of the experimental group, Bottom referred to the average signal value of the negative control group, and Top referred to the average signal value of the positive control group.

Experimental Results:

Under the condition of this experiment, the inhibitory effect of the test compound on MAT2A can be expressed as the $IC_{50}$ of the inhibition on the phosphate production level during the enzymatic reaction. The MAT2A inhibitory activity of the test compound is shown in Table 1.

TABLE 1

| Compound | MAT2A inhibitory Activity $IC_{50}$ (nM) | MAT2A inhibitory Activity $IC_{50}$ (nM) |
|---|---|---|
| Compound 1 | ++++ | 31.9 |
| Compound 2 | ++++ | 69.3 |
| Compound 4 | ++++ | 69.6 |
| Compound 5 | ++++ | 41.6 |
| Compound 6 | ++++ | 50.1 |
| Compound 7 | +++ | 128.1 |
| Compound 8 | ++++ | 64.4 |
| Compound 9 | ++++ | 29.6 |
| Compound 10 | ++++ | 33.0 |
| Compound 11 | ++++ | 56.6 |
| Compound 12 | +++ | 102.5 |

TABLE 1-continued

| Compound | MAT2A inhibitory Activity $IC_{50}$ (nM) | MAT2A inhibitory Activity $IC_{50}$ (nM) |
|---|---|---|
| Compound 13 | +++ | 122.4 |
| Compound 14 | ++++ | 46.4 |
| Compound 15 | ++++ | 38.5 |
| Compound 16 | +++ | 122.1 |
| Compound 18 | +++ | 441.5 |
| Compound 19 | ++++ | 51.4 |
| Compound 20 | ++++ | 54.9 |
| Compound 20-P1 | ++++ | 20.5 |
| Compound 21 | ++++ | 64.9 |
| Compound 22 | +++ | 127.9 |
| Compound 23 | ++++ | 78.8 |
| Compound 25 | ++++ | 48.0 |
| Compound 25-P2 | ++++ | 20.6 |
| Compound 26 | +++ | 135.2 |
| Compound 27 | ++ | 819.1 |
| Compound 28 | +++ | 165.4 |
| Compound 31 | +++ | 159.0 |
| Compound 32 | +++ | 119.4 |
| Compound 33 | ++++ | 67.6 |
| Compound 34 | ++++ | 73.1 |
| Compound 35 | ++++ | 49.0 |
| Compound 36 | ++++ | 52.6 |
| Compound 37 | ++++ | 48.3 |
| Compound 38 | ++++ | 82.0 |
| Compound 39 | ++++ | 60.4 |
| Compound 40 | ++++ | 43.0 |
| Compound 41 | ++++ | 56.8 |
| Compound 41-P2 | ++++ | 22.3 |
| Compound 42 | ++++ | 47.0 |
| Compound 42-P2 | ++++ | 20.3 |
| Compound 43-P2 | ++++ | 28.2 |
| Compound 44 | ++++ | 49.5 |
| Compound 45 | ++++ | 47.0 |
| Compound 46 | ++++ | 48.5 |
| Compound 46-P2 | ++++ | 19.8 |
| Compound 47 | ++++ | 50.2 |
| Compound 47-P2 | ++++ | 23.3 |
| Compound 48 | ++++ | 36.0 |
| Compound 48-P2 | ++++ | 21.4 |
| Compound 49 | ++++ | 28.1 |
| Compound 49-P2 | ++++ | 18.7 |
| Compound 50 | +++ | 112.8 |
| Compound 51 | +++ | 181.6 |
| Compound 52 | ++++ | 47.2 |
| Compound 53 | +++ | 314.0 |
| Compound 54 | ++ | 530.4 |
| Compound 55 | +++ | 296.3 |
| Compound 56 | ++++ | 73.7 |
| Compound 57-P2 | ++++ | 42.0 |
| Compound 58-P2 | ++++ | 90.8 |
| Compound 59 | +++ | 251.6 |
| Compound 60 | +++ | 112.8 |
| Compound 61 | +++ | 102.1 |
| Compound 62 | +++ | 250.6 |
| Compound 63 | ++++ | 48.1 |
| Compound 64 | ++++ | 54.3 |
| Compound 65 | ++++ | 78.3 |
| Compound 66 | ++++ | 47.3 |
| Compound 67-P2 | ++++ | 41.4 |
| Compound 68 | ++++ | 53.5 |
| Compound 69 | +++ | 281.6 |
| Compound 70-P2 | ++++ | 37.9 |
| Compound 71 | ++ | 978.2 |
| Compound 72 | ++++ | 52.1 |
| Compound 73-P2 | ++++ | 27.3 |
| Compound 74 | +++ | 140.3 |
| Compound 75 | ++++ | 71.7 |
| Compound 76 | +++ | 201.2 |
| Compound 77 | +++ | 337.2 |
| Compound 78 | ++++ | 80.2 |
| Compound 79 | +++ | 101.7 |
| Compound 80-P2 | ++++ | 32.5 |
| Compound 81 | ++++ | 52.3 |
| Compound 81-P2 | ++++ | 36.2 |
| Compound 82-P2 | ++++ | 23.1 |
| Compound 83 | ++++ | 54.7 |
| Compound 83-P2 | ++++ | 23.1 |
| Compound 84 | ++++ | 53.4 |
| Compound 85-P2 | ++++ | 33.6 |
| Compound 86-P2 | ++++ | 25.0 |
| Compound 87-P2 | ++++ | 38.7 |

In the above table, the symbols used to indicate the inhibitory activity represent the following meanings:
"++++" indicates that the test compound has an $IC_{50}$ range of <100 nM for enzyme inhibitory activity.
"+++" indicates that the test compound has an $IC_{50}$ range of 100-500 nM for enzyme inhibitory activity.
"++" indicates that the test compound has an $IC_{50}$ range of 500-1000 nM for enzyme inhibitory activity.

Test Example 2. Determination of Intracellular SAM Level

The brief introduction of the test principle: After the test MAT2A inhibitor was incubated with cancer cells for a period of time, the cells were lysed with a stop reagent to quench the activity of the MAT2A enzyme. The catalytic product SAM of MAT2A in the cell lysate was quantitatively determined by LC-MS/MS, and thus the activity of MAT2A in the cell was reflected.

Reference: The experiment referred to the method disclosed in patent WO2018045071.

Material and cell: HCT116 $MTAP^{-/-}$ cells were purchased from KYinno; fetal bovine serum, McCoy's 5a culture medium, and penicillin-streptomycin were purchased from Gibco Company (U.S.), and 96-well plates were purchased from Corning Company (U.S.).

Cell culture: HCT116 $MTAP^{-/-}$ cells were cultured with a McCoy's 5a medium containing 10% fetal bovine serum+1% penicillin-streptomycin at 37° C. with 5% $CO_2$. Cells at logarithmic growth phase were available for the experiment.

LC-MS/MS detection: The effect of the compound on the SAM production level in HCT116 $MTAP^{-/-}$ cell strains was detected by LC-MS/MS. The cells were adjusted to a concentration of 50000 cells per well, seeded on a 96-well plate, and incubated overnight at 37° C. with 5% $CO_2$. In the experimental group, the test compound was dissolved in DMSO, diluted sequentially with DMSO and a culture medium, and transferred to a cell plate at a final concentration of 10 μM, 3-fold dilution. The cells were continuously cultured at 37° C. with 5% $CO_2$ for 6 h. The supernatant was pipetted off. After the cells were washed once with PBS, glacial acetic acid was added to lyse the cells. After the lysate was processed, the SAM concentration was determined by LC-MS/MS analysis.

A negative control group and a positive control group were respectively used as Bottom and Top. The negative control group was added with 10 μM positive compound (compound 072 of Example 51 of patent WO2021139775A1) in the same volume, and other operations were consistent with those of the experimental group. The positive control group was not added with the test compound, only added with DMSO in the same volume, and other operations were consistent with those of the experimental group.

Data Analysis:

The % Compound inhibition was calculated and fitted to give the $IC_{50}$ of the compound.

% Compound inhibition=1−100%×(Signal−Bottom)/(Top−Bottom)

Signal referred to the signal value of the experimental group, Bottom referred to the average signal value of the negative control group, and Top referred to the average signal value of the positive control group.

Experimental Results:

The results in Table 2 show that the compound of the present application inhibits intracellular SAM production at a nanomolar level and shows strong MAT2A inhibitory activity.

TABLE 2

| Compound | SAM production inhibitory activity $IC_{50}$ (nM) |
|---|---|
| Compound 1 | 3.8 |
| Compound 2 | 7.4 |
| Compound 20 | 3.0 |
| Compound 20-P1 | 1.6 |
| Compound 25 | 4.4 |
| Compound 25-P2 | 2.8 |
| Compound 36 | 5.6 |
| Compound 37 | 8.8 |
| Compound 41-P2 | 4.6 |
| Compound 49-P2 | 1.9 |

Test Example 3. Cell Proliferation Inhibition Test of Human Colon Cancer HCT116 WT Cells and HCT116 MTAP-1-Cells The brief introduction of the test principle: After the test MAT2A inhibitor was incubated with cancer cells for a period of time, the effect of the test compound on cell proliferation was measured using a cell proliferation count method based on the ATP content.

Reference: The experiment referred to the method disclosed in patent WO2018045071.

Material and cell: HCT116 WT cells and HCT116 $MTAP^{-/-}$ cells were purchased from KYinno; fetal bovine serum, McCoy's 5a culture medium, and penicillin-streptomycin were purchased from Gibco Company (U.S.), 96-well plates were purchased from Corning Company (U.S.), and the Cell-Titer Glo reagent was purchased from Promega Company (U.S.).

Cell culture: HCT116 WT cells and HCT116 $MTAP^{-/-}$ cells were cultured with a McCoy's 5a medium containing 10% fetal bovine serum+1% penicillin-streptomycin at 37° C. with 5% $CO_2$.

Cells at logarithmic growth phase were available for the experiment.

Cell proliferation activity test: The Cell-Titer Glo reagent was used to test the compound for inhibitory activity on proliferation of both HCT116 WT and HCT116 $MTAP^{-/-}$ cell strains. The cells were adjusted to a concentration of 400 cells per well, seeded on a 96-well plate, and incubated overnight at 37° C. with 5% $CO_2$.

In the experimental group, the test compound was diluted sequentially with DMSO and a culture medium, and transferred to a cell plate at a final concentration of 10 μM, 3-fold dilution. The cells were continuously cultured at 37° C. with 5% $CO_2$ for 6 days. The Cell-Titer Glo reagent was added and the cell activity was measured.

A negative control group and a positive control group were respectively used as Bottom and Top. The negative control group was not added with cells, only added with the culture medium in the same volume, and other operations were consistent with those of the experimental group. The positive control group was not added with the test compound, only added with DMSO in the same volume, and other operations were consistent with those of the experimental group.

Data Analysis:

The % Compound inhibition was calculated and fitted to give the $IC_{50}$ of the compound.

% Compound inhibition=1-100%×(Signal−Bottom)/(Top−Bottom).

Signal referred to the signal value of the experimental group, Bottom referred to the average signal value of the negative control group, and Top referred to the average signal value of the positive control group.

HCT116 $MTAP^{-/-}$ cells are cells not expressing MTAP protein obtained by site-directed knockout of wild type HCT116 (HCT116 WT) cells by gene knockout. Synthetic lethality will occur due to MAT2A inhibition and the deletion of MTAP, thereby causing tumor cell death. The activity and selectivity of the MAT2A inhibitor can be evaluated by testing the antiproliferative activity of the MAT2A inhibitor on human colon cancer HCT116 $MTAP^{-/-}$ cells and human colon cancer HCT116 WT.

Experimental Results:

Under the condition of this experiment, the test compound shows strong proliferation inhibition activity on human colon cancer HCT116 $MTAP^{-/-}$ cells, and shows better selectivity compared with the human colon cancer HCT116 WT cells. The corresponding anti-cell proliferation activity of the test compound is shown in Table 3.

TABLE 3

| Compound | HCT116 $MTAP^{-/-}$ Antiproliferative activity $IC_{50}$ (nM) | HCT116 WT Antiproliferative activity $IC_{50}$ (nM) |
|---|---|---|
| Compound 1 | 115.1 | 816.5 |
| Compound 2 | 529.2 | 4772.4 |
| Compound 5 | 273.6 | >10000 |
| Compound 6 | 288.5 | 1112.2 |
| Compound 9 | 425.6 | 4185.0 |
| Compound 20 | 76.52 | 474.2 |
| Compound 20-P1 | 33.0 | 236.7 |
| Compound 25 | 154.7 | 663.2 |
| Compound 25-P2 | 70.5 | 383.9 |
| Compound 35 | 237.5 | 1214.9 |
| Compound 36 | 81.5 | 9968.8 |
| Compound 37 | 168.6 | 9061.6 |
| Compound 38 | 130.5 | 604.8 |
| Compound 39 | 106.3 | 626.4 |
| Compound 40 | 119.5 | 414.0 |
| Compound 41 | 164.3 | 7864.5 |
| Compound 41-P2 | 80.1 | 3815.7 |
| Compound 42 | 244.3 | 2201.8 |
| Compound 42-P2 | 44.2 | 1316.9 |
| Compound 43-P2 | 79.0 | 355.3 |
| Compound 44 | 71.5 | 666.8 |
| Compound 45 | 134.2 | 901.8 |
| Compound 46 | 87.0 | 473.4 |
| Compound 46-P2 | 33.0 | 214.5 |
| Compound 47 | 231.9 | >10000 |
| Compound 47-P2 | 129.8 | 8334.1 |
| Compound 48-P2 | 90.9 | >10000 |
| Compound 49 | 87.9 | 1618.2 |
| Compound 49-P2 | 34.4 | 487.7 |
| Compound 64 | 398.4 | 1053.6 |
| Compound 65 | 188.0 | 858.7 |
| Compound 68 | 394.2 | >10000 |
| Compound 70-P2 | 489.9 | 7939.8 |
| Compound 72 | 191.0 | 970.3 |
| Compound 73-P2 | 193.7 | 2213.0 |
| Compound 81 | 186.2 | 1944.1 |
| Compound 81-P2 | 110.9 | 1341.0 |
| Compound 82-P2 | 50.2 | 271.0 |
| Compound 83-P2 | 54.3 | 202.8 |

Test Example 4. Determination of Metabolic Stability of Compound of the Present Application in Liver Microsomes The metabolic stability of the compound of the present application in liver microsomes was determined using the following method.

I. Experimental Materials and Instruments

1. Human liver microsome (Corning 452117), beagle dog liver microsome (XENOTECH D1000), SD rat liver microsome (XENOTECH R1000), and CD-i mouse liver microsome (XENOTECH M1000)
2. $Na_2HPO_4$ (Tianjin Guangfu Fine Chemical Research Institute 20180130)
3. $KH_2PO_4$ (Tianjin Guangfu Fine Chemical Research Institute 20180920)
4. $MgCl_2$ (Tianjin Guangfu Fine Chemical Research Institute 20191216)
5. NADPH (Solarbio 1216C022)
6. Positive control compound verapamil (Sigma MKBV4993V)
7. AB Sciex API4000 liquid chromatography-mass spectrometry system II. Procedures 1. Preparation of 100 mMV phosphate-buffered saline (PBS): 7.098 g $Na_2HPO_4$ was weighed. 500 mL pure water was added. The mixture was dissolved by sonication to give solution A. 3.400 g $KH_2PO_4$ was weighed. 250 mL pure water was added. The mixture was dissolved by sonication to give solution B. The solution A was placed in a stirrer, and the solution B was slowly added until the pH reached 7.4, so that the 100 mM PBS buffer was prepared.

2. Preparation of Reaction System

The reaction system was prepared as follows:

| Reagent | Stock solution concentration | Volume | Final concentration |
|---|---|---|---|
| Liver microsome | 20 mg/mL | 10 μL | 0.5 mg/mL |
| Phosphate-buffered saline | 100 mM | 346 μL | 100 mM |

3. The reaction system was pre-incubated in a 37° C. water bath for 10 min. 40 μL of 10 mM NADPH solution (NADPH was dissolved by 100 mM phosphate-buffered saline) was added to the reaction system with a final concentration of NADPH being 1 mM. A negative control was made by replacing the NADPH solution with 40 μL phosphate-buffered saline. The negative control was used to exclude the effect of chemical stability of the compound itself.

4. The reaction was initiated by adding 4 μL of 100 μM of the compound of the present application and verapamil, the positive control compound, to the reaction system with a final concentration of the compound being 1 μM.

5. After being uniformly mixed in a vortex oscillator, 50 μL incubation sample was respectively taken out at 0.5, 15, 30, 45, and 60 min, and the reaction was stopped by 200 μL glacial acetonitrile containing an internal standard. The sample was centrifuged at 3220 g for 45 min. 90 μL of the supernatant was transferred to a feeding plate after the centrifugation was completed, and 90 μL ultrapure water was added. The mixture was well mixed for LC-MS/MS analysis.

All data were calculated by Microsoft Excel software. The peak area was detected through an extracted ion chromatogram. The in vitro half-life ($t_{1/2}$) of the compound was determined by linear fitting of the natural logarithm of compound elimination percentage over time.

In vitro half-life ($t_{1/2}$) was calculated by the slope:

$$\text{in vitro } t_{1/2}=0.693/k$$

The in vitro intrinsic clearance (in μL/min/mg protein) was calculated using the following formula:

$$\text{in vitro } CL_{int}=k\times\text{volume of incubation (μL)/amount of proteins (mg)}$$

$CL_{int}$ was intrinsic clearance; k was an elimination rate constant; volume of incubation was the incubation volume (μL); amount of proteins was the amount of protein (mg)

The compound of the present application all show good metabolic stability in liver microsomes, and the corresponding stability in liver microsomes of the test compound is shown in Table 4.

TABLE 4

| Compound | Human liver microsome stability $t_{1/2}$ (min) | Mouse liver microsome stability $t_{1/2}$ (min) |
|---|---|---|
| Compound 20 | >300 | >300 |
| Compound 25 | >300 | 286.5 |
| Compound 25-P2 | >300 | >300 |
| Compound 39 | NA | >300 |
| Compound 40 | >300 | >300 |
| Compound 41-P2 | >300 | >300 |
| Compound 42-P2 | 255.6 | 111.8 |
| Compound 45 | >300 | >300 |
| Compound 48-P2 | >300 | >300 |
| Compound 49-P2 | 226.8 | >300 |
| Compound 81-P2 | >300 | NA |

NA represents untested.

Test Example 5. Determination of Membrane Permeability and Transport Properties of Compound of the Present Application The membrane permeability and transport properties of the compound of the present application were determined using the following method.

I. Experimental Materials and Instruments

1. Caco-2 cells (ATCC)
2. HEPES (Solarbio 804D049), penicillin/streptomycin (Solarbio 20200109), and PBS (Solarbio 20200620)
3. Fetal Bovine Serum (FBS) (Sigma WXBD0055V), lucifer yellow (Sigma MKCJ3738), and $NaHCO_3$ (Sigma SLBZ4647)
4. Hank's balanced salt solution (HBSS) (Gibco 2085528), non-essential amino acid (NEAA) (Gibco 2211548), and Trypsin/EDTA (Gibco 2120732)
5. High glucose DMEM (Corning 20319014)
6. HTS Transwell-96 Well Permeable (Corning, 3391)
7. Resistance detector (Millipore, Millicell® ERS-2)
8. Cellometer® Vision (Nexcelom Bioscience)
9. Infinite 200 PRO microplate reader (Tecan, Infinite M200PRO)
10. Positive control compound metoprolol (Sinopharm 100084-201403), erythromycin (MCE 84550), and cimetidine (Sinopharm 100158-201406)
11. ABI QTrap 5500 liquid chromatography-mass spectrometry system II. Procedures 1. Caco-2 Cell Culture 1) Preparation of transport buffer (HBSS containing 25 mM HEPES, pH 7.4): 5.958 g HEPES and 0.35 g $NaHCO_3$ were accurately weighed and dissolved in 900 mL pure water. 100 mL of 10× HBSS was then added and stirred well. The pH was adjusted to 7.4, and the mixture was filtered.

2) Preparation of Caco-2 cell culture medium: FBS, penicillin/streptomycin, kanamycin, and NEAA was added to a high glucose DMEM (containing L-glutamine) culture medium to prepare a cell culture medium containing 10% FBS, 100 units penicillin/0.1 mg/mL streptomycin, 0.6 μg/mL kanamycin, and 1×NEAA.

3) Cells were cultured with a T-75 flask at 37° C. with 5% $CO_2$ in an incubator. The culture medium was discarded when cell density reached 80-90%. The cells were rinsed with 5 mL PBS. 1.5 mL Trypsin/EDTA was added. The mixture was incubated at 37° C. for 5-10 min in an incubator until the cells shed like quicksand. Finally the Trypsin/EDTA was neutralized with a FBS-containing culture medium.

4) The cell suspension was centrifuged at 120 g for 10 min, and the supernatant was discarded.

5) The cells were resuspended in a cell culture medium. The cell suspension was adjusted to a density of $6.86\times10^5$ cells/mL.

2. Caco-2 Cell Inoculation 1) 50 μL of culture medium was added to the Transwell chamber per well. 25 mL of culture medium was added to the lower chamber, and the chamber was preheated at 37° C. for 1 h with 5% $CO_2$ in an incubator.

2) 50 μL of the cell suspension was added to the preheated Transwell chamber per well at a final density of $2.4\times10^5$ cells/cm$^2$.

3) The cells were cultured for 14-18 days. The culture medium was replaced every other day, and the culture medium was replaced within 48 h after the initial inoculation. The culture medium had to be replaced the day before the experiment.

3. Evaluation of Integrity of Monolayer Cell Membrane

1) The cells fused and differentiated after 14 days of culture and were ready for a transport experiment.

2) The resistance of the monolayer membrane was measured using a resistance detector. The resistance of each well was recorded.

3) After the measurement, the Transwell culture plate was re-incubated.

4) The TEER value was calculated:

TEER value=TEER measurement value (Ω)×membrane area (cm$^2$)

The resistance of the monolayer cell membrane<230Ω cm$^2$ indicates that a monolayer cell membrane is poorly dense and can not be used for experiment.

4. Transport Experiment

1) A 10 mM stock solution of the compound of the present application or the positive control compound was diluted with DMSO to give a 2 mM stock solution. The 2 mM stock solution was then diluted with the transport buffer to give a 10 μM working solution of the compound of the present application or the positive control compound.

2) The Caco-2 cell plate was taken out from the incubator, washed twice with the pre-heated transport buffer, and incubated at 37° C. in an incubator for 30 min.

3) To determine the transport rate of the compound from the apical end to the basal end (A→B), 108 μL of the working solution of the compound was added to the Transwell chamber (apical end), while 8 μL of the sample was immediately taken from the apical end to 72 μL of the transport buffer. 240 μL of a stop solution containing an internal standard was added to stop the transport to be an initial apical end sample. At the same time, 300 μL of the transport buffer was added to the receiving end (basal end). The sample in the experiment was in duplicate.

4) To determine the transport rate of the compound from the basal end to the apical end (B→A), 308 μL of the working solution of the compound was added to the basal end, while 8 μL of the sample was immediately taken from the basal end to 72 μL of the transport buffer. 240 μL of a stop solution containing an internal standard was added to stop the transport to be an initial basal end sample. At the same time, 100 μL of the transport buffer was added to the Transwell chamber (apical end). The sample in the experiment was in duplicate.

5) The cell culture plate was incubated at 37° C. with $CO_2$ in an incubator for 2 h.

6) After the transport experiment was completed, 8 μL of the sample was taken from the administration end (i.e., the apical end in the A→B direction and the basal end in the B→A direction) to 72 μL of the transport buffer. 240 μL of a stop solution containing an internal standard was then added to stop the transport. 80 μL of the sample was taken from the receiving end (i.e., the basal end in the A→B direction and the apical end in the B→A direction) to 240 μL of a stop solution containing an internal standard. The mixture was vortexed at 1000 rpm for 10 min and centrifuged at 3220 g for 30 min. 100 μL of the supernatant was transferred to a feeding plate, and 100 μL of ultrapure water was added. The mixture was well mixed for LC-MS/MS analysis.

7) Fluorescence values were measured after the transport experiment was completed. A 10 mM lucifer yellow stock solution was prepared with water and then diluted to 100 μM with the transport buffer. 100 μL of the lucifer yellow solution was added to the Transwell chamber (apical end). 300 μL of the transport buffer was added to the basal end. The chamber was incubated at 37° C. with $CO_2$ in an incubator for 30 min. 80 μL solution was taken from the apical end and the basal end to a 96-well plate, and the fluorescence value of the cells was measured by a microplate reader at an excitation wavelength of 485 nm and an emission wavelength of 530 nm (to detect integrity of the membrane).

The fluorescence value of Caco-2 cell monolayer membrane was calculated by the following formula:

$$LY\ \text{Leakage}=\{I_{acceptor}\times0.3/(I_{acceptor}\times0.3+I_{donor}\times0.1)\}\times100\%$$

$I_{acceptor}$ referred to the fluorescence density of the receiving end (0.3 mL), and $I_{donor}$ referred to the fluorescence density of the administration end (0.1 mL). LY>1.0% indicates that a monolayer cell membrane is poorly dense and the corresponding results will be excluded from the evaluation.

The peak areas of the compound on the administration end and the receiving end were measured, and the apparent permeability coefficient ($P_{app}$, in cm/s) and the Efflux ratio (efflux ratio) of the compound were calculated:

$$P_{app}=\{V_A\times[\text{drug}]_{acceptor}/(\text{Area}\times\text{incubation time}\times[\text{drug}]_{initial\ donor}\}$$

$V_A$ was the volume of the receiving end solution (A→B was 0.3 mL, and B→A was 0.1 mL). Area was the area of the membrane of the Transwell 96-well plate (0.143 $cm^2$). Incubation time was the time for incubation (in s). $[drug]_{acceptor}$ was the concentration of the drug at the receiving end. $[drug]_{initial\ donor}$ was the initial concentration of the drug at the administration end.

$$\text{Efflux Ratio} = \frac{P_{app(B-A)}}{P_{app(A-B)}}$$

$P_{app(B-A)}$ represented the apparent permeability coefficient from the basal end to the apical end; $P_{app(A-B)}$ represented the apparent permeability coefficient from the apical end to the basal end.

Test Example 6. Determination of Plasma Protein Binding Rate of Compound of the Present Application The protein binding rates of the compound of the present application in plasma of 5 species (humans, monkeys, dogs, rats, and mice) were determined using the following method.

I. Experimental Materials and Instruments

1. Human plasma (BioIVT), monkey plasma (ADME-plasma-pooled monkey-05212020), beagle dog plasma (BioIVT), SD rat plasma (BioIVT), and CD-1 mouse plasma (BioIVT)
2. $Na_2HPO_4$ (Sigma 55136-500G)
3. $NaH_2PO_4$ (Sigma 53139-500G)
4. NaCl (Sigma S5886-IKG)
5. 96-well equilibrium dialysis plate (HTDialysis LLC, Gales Ferry, CT, HTD96B) and equilibrium dialysis membrane (MWCO 12-14K, 1101)
6. Positive control compound warfarin
7. ABI QTrap 5500 liquid chromatography-mass spectrometry system II. Procedures 1. Preparation of a buffer with a concentration of 100 mM sodium phosphate and 150 mM NaCl: an alkaline solution with a concentration of 14.2 g/L $Na_2HPO_4$ and 8.77 g/L NaCl was prepared with ultrapure water, an acidic solution with a concentration of 12.0 g/L $NaH_2PO_4$ and 8.77 g/L NaCl was prepared with ultrapure water, and then the alkaline solution was titrated with the acidic solution until the pH was 7.4 to prepare a buffer with a concentration of 100 mM sodium phosphate and 150 mM NaCl.
2. Preparation of a dialysis membrane: the dialysis membrane was soaked in ultrapure water for 60 min to separate the membrane into two pieces, then soaked with 20% ethanol for 20 min, and finally soaked with dialysis buffer for 20 min.
3. Preparation of plasma: the frozen plasma was quickly thawed at room temperature and then centrifuged at 3,220 g at 4° C. for 10 min to remove clots, and the supernatant was collected to a new centrifuge tube. The pH of the plasma was measured and recorded. The plasma with pH 7-8 was used.
4. Preparation of a plasma sample containing the compound: A 10 mM stock solution of the compound of the present application or the positive control compound was diluted with DMSO to give a 200 μM working solution. 3 μL of 200 μM of the compound working solution was added to 597 μL of human, monkey, dog, rat, or mouse plasma to give a plasma sample with a final concentration of 1 μM.
5. Equilibrium dialysis procedures: a dialysis device was assembled according to the instructions. 120 μL of the plasma sample containing 1 μM of the compound was added to one side of the dialysis membrane, and a dialysate (phosphate buffer) in the same volume was added to the other side. The sample in the experiment was in duplicate. The dialysis plate was sealed with a film, placed in an incubation device, and incubated at approximately 100 rpm at 37° C. with 5% $CO_2$ for 6 h. After the incubation was completed, the film was removed, and 50 μL of the sample was pipetted from the buffer side and the plasma side of each well to different wells of a new plate. 50 μL of blank plasma was added to the phosphate buffer sample. A blank phosphate buffer in the same volume was added to the plasma sample, and then 300 μL of acetonitrile containing an internal standard was added to precipitate the protein. The mixture was vortexed for 5 min and centrifuged at 3220 g at 4° C. for 30 min. 100 μL of the supernatant was transferred to a feeding plate, and 100 μL of ultrapure water was added. The mixture was well mixed for LC-MS/MS analysis.

The peak areas of the compound on the buffer side and the plasma side were measured. The plasma protein binding rate of the compound was calculated by the following formula:

% Free rate=(ratio of compound peak area to internal standard peak $area_{buffer\ side}$/ratio of compound peak area to internal standard peak $area_p$lasma side)×100%

% Binding rate=100%−% Free rate

Test Example 7. Inhibitory Effect of Compound of the Present Application on Enzymatic Activity of CYP2C9, CYP2D6, and CYP3A4

The inhibition of CYP2C9, CYP2D6, and CYP3A4 activity by the compound of the present application was determined using the following method.

I. Experimental Materials and Instruments

1. Human liver microsome (Corning 452117)
2. NADPH (Solarbio 705Y021)
3. Positive substrates diclofenac (Sigma SLBV3438), dextromethorphan (TRC 3-EDO-175- 1), and midazolam (Cerilliant FE01161704)
4. Positive inhibitors sulfaphenazole (D. Ehrenstorfer GmbH 109012), quinidine (TCI WEODL-RE), and ketoconazole (Sigma 100M1091V)
5. AB Sciex Triple Quad 5500 liquid chromatography-mass spectrometry system II. Procedures 1. Preparation of 100 mM phosphate-buffered saline (PBS): 7.098 g $Na_2HPO_4$ was weighed. 500 mL pure water was added. The mixture was dissolved by sonication to give solution A. 3.400 g $KH_2PO_4$ was weighed. 250 mL pure water was added. The mixture was dissolved by sonication to give solution B. The solution A was placed in a stirrer, and the solution B was slowly added until the pH reached 7.4, so that the 100 mM PBS buffer was prepared.

2. A 10 mM NADPH solution was prepared with a 100 mM PBS buffer. A 10 mM stock solution of the compound of the present application was diluted with DMSO to give a compound working solution at a concentration of 200× (6000, 2000, 600, 200, 60, 20, and 0 μM). The positive inhibitor stock solution was diluted with DMSO to give a positive inhibitor working solution at a concentration of 200×(sulfaphenazole, 1000, 300, 100, 30, 10, 3, and 0 μM;

quinidine/ketoconazole, 100, 30, 10, 3, 1, 0.3, and 0 μM). Substrate working solutions (120 μM diclofenac, 400 μM dextromethorphan, and 200 μM midazolam) at a concentration of 200× were prepared with water, acetonitrile, or acetonitrile/methanol.

3. 2 μL of 20 mg/mL liver microsome solution, 1 μL of substrate working solution, 1 μL of compound working solution, and 176 μL of PBS buffer were taken, mixed well, and placed in a 37° C. water bath for pre-incubation for 15 min. 1 μL of sulfaphenazole, quinidine, or ketoconazole working solution was added to the positive control group instead of the compound working solution. At the same time, 10 mM NADPH solution was placed together in the 37° C. water bath for pre-incubation for 15 min. After 15 min, 20 μL of NADPH was added to each well to initiate the reaction. The mixture was incubated at 37° C. for 5 min (CYP2C9), 20 min (CYP2D6), or 5 min (CYP3A4). All incubated samples were in duplicate. After incubation for the corresponding period of time, 400 μL of icy methanol containing internal standard was added to all samples to stop the reaction. The mixture was vortexed, mixed well, and centrifuged for 40 min at 4° C. at 3220 g. 100 μL of the supernatant was transferred to a feeding plate after the centrifugation was completed, and 100 μL ultrapure water was added. The mixture was well mixed for LC-MS/MS analysis.

The reduction of metabolite production in the treatment groups versus the control group was compared by the peak area ratios of the sample to the internal standard, and the $IC_{50}$ value was calculated using Excel XLfit 5.3.1.3.

Percentages of remaining activity were calculated according to the following formula:

$$\text{Remaining activity \%} = \text{peak area ratio of metabolite to internal standard}_{test\ sample} / \text{peak area ratio of metabolite to internal standard}_{blank\ solvent} \times 100\%.$$

Drug-drug interaction (DDI) refers to the physical or chemical changes caused by no less than 2 drugs, as well as changes in efficacy due to such changes. Interpretation of the drug-drug interaction can provide better pharmaceutical services for patients, promote reasonable medication, and avoid adverse reactions to the maximum extent. The drug-drug interaction is dominated by metabolic interactions which are primarily associated with CYP450 enzymes involved in drug metabolism. The results in Table 7 show that the compounds of the present application have a weak inhibitory effect on CYP450, indicating that the compounds of the present application have a lower potential risk of developing DDI.

TABLE 7

| Compound | CYP2C9 inhibition $IC_{50}$ (μM) | CYP2D6 inhibition $IC_{50}$ (μM) | CYP3A4 inhibition $IC_{50}$ (μM) |
|---|---|---|---|
| Compound 20 | >30 | >30 | >30 |
| Compound 25 | >30 | >30 | >30 |
| Compound 25-P2 | >30 | >30 | >30 |
| Compound 39 | >30 | >30 | >30 |
| Compound 40 | >30 | >30 | >30 |
| Compound 41-P2 | >30 | 18.2 | >30 |
| Compound 42-P2 | >30 | >30 | >30 |
| Compound 45 | >30 | >30 | >30 |
| Compound 48-P2 | >30 | >30 | >30 |
| Compound 49-P2 | >30 | >30 | >30 |
| Compound 81-P2 | >30 | >30 | >30 |

Test Example 8. Assay for hERG Inhibitory Activity of Compound of Present Application The inhibition of hERG activity by the compounds of the present application was determined using the following method.

I. Experimental Materials and Instruments

1. Dialyzed fetal bovine serum Shanghai Bohan Biotechnology Co., Ltd (BS-0005-500)
2. DMEM culture medium Thermo Fisher Scientific (China) Co., Ltd. (10569)
3. HEPES Thermo Fisher Scientific (China) Co., Ltd. (15630080)
4. Trypsin Thermo Fisher Scientific (China) Co., Ltd. (2192509)
5. Penicillin-streptomycin solution Thermo Fisher Scientific (China) Co., Ltd. (15140-122)
6. MEM non-essential amino acid solution Thermo Fisher Scientific (China) Co., Ltd. (11140)
7. Geneticin (G418) Thermo Fisher Scientific (China) Co., Ltd. (11811031)
8. Blasticidin Thermo Fisher Scientific (China) Co., Ltd. (R21001)
9. PolylysineThermo Fisher Scientific (China) Co., Ltd. (P4832)
10. Dofetilide Beijing Express Technology Co., Ltd. (D525700)
11. Doxycycline Sigma-Aldrich (Shanghai) Trading Co., Ltd. (D9891)
12. Carbon dioxide incubator Thermo Fisher Scientific (China) Co., Ltd. (371)
13. Puller Sutter Company, U.S. (P-97)
14. Micromanipulator Siskiyou Company, U.S. (MC1000e)
15. Micromanipulator Sutter Company, U.S. (ROE-200; MP285)
16. Amplifier HEKA Company, Germany (EPC10)
17. Microscope Olympus (China) Co., Ltd. (IX51/71/73)
18. Perfusion system ALA Company, U.S. (VM8 gravity administration system)

II. Culture of Cell Lines and Cells

HEK293 cells (Cat. No: K1236) stably expressing hERG ion channel were purchased from Invitrogen. The cells were cultured in a culture medium containing 85% DMEM, 10% dialyzed fetal bovine serum, 0.1 mM non-essential amino acid solution, 100 U/mL penicillin-streptomycin solution, 25 mM HEPES, 5 μg/mL blasticidin, and 400 μg/mL geneticin. When the cell density increased to 40-80% of the bottom area of the culture dish, the cells were digested with trypsin and subcultured thrice every week. Before the experiment, the cells were cultured at a density of $5\times10^5$ in 6-cm culture dishes, induced for 48 h with 1 μg/mL doxycycline, and then digested and inoculated on a slide for the subsequent manual patch-clamp experiment.

III. Preparation of Solutions

1) Extracellular fluid: 132 mM sodium chloride, 4 mM potassium chloride, 3 mM calcium chloride, 0.5 mM magnesium chloride, 11.1 mM glucose, and 10 mM HEPES (adjusted to pH 7.35 with sodium hydroxide).
2) Intracellular fluid: 140 mM potassium chloride, 2 mM magnesium chloride, 10 mM EGTA, 5 mM ATP-magnesium salt, and 10 mM HEPES (adjusted to pH 7.35 with potassium hydroxide).

Note: the osmotic pressure of the solutions was controlled at 280-300 mOsmol/kg. The solutions were filtered and stored at 4° C. before use. The ATP-magnesium salt was prepared into a 100 mM stock solution, subpackaged, and stored in a −20° C. refrigerator. On the day of the experiment, a certain amount of the stock solution was added into the intracellular fluid right before use.

IV. Procedures

1) The slides carrying HEK293 cells in the culture dish were placed in the perfusion chamber of the micromanipulation stage.
2) Appropriate cells were placed in the center of the field of view under an Olympus IX51, IX71, or IX73 inverted microscope. The tip of the glass electrode was found using a 10× objective lens and placed in the center of the field of view. The electrode was then moved down using a micromanipulator while the electrode was slowly brought into proximity to the cell using the coarse adjustment.
3) When the electrode was in close proximity to the cell, the lens was switched to a 40× objective lens for observation. The micromanipulator was used for fine adjustment to make the electrode approach the surface of the cell gradually.
4) Negative pressure was applied to form a seal with a resistance higher than 1 GΩ between the electrode tip and the cell membrane.
5) The instantaneous capacitance current Cfast was compensated under the voltage clamp mode. Then negative pressure was repeatedly applied to the membrane for rupture, and finally, a whole-cell recording mode was formed.
6) The slow capacitive current Cslow, the cell membrane capacitance (Cm), and the input membrane resistance (Ra) were compensated under a membrane potential clamp at −60 mV.
7) After the cells were stabilized, the clamp voltage was changed to −90 mV, the sampling frequency was set at 20 kHz, and the filtration frequency was 10 kHz. The detection condition of the drain current was that the clamp voltage was changed to −80 mV, and the time course was 500 ms.
8) The hERG current test method was as follows: a 4.8-second depolarization command voltage was applied to depolarize the membrane potential from −80 mV to +30 mV, and then a 5.2-second repolarization voltage was instantaneously applied to reduce the membrane potential to −50 mV to remove channel inactivation, thus allowing the observation of the hERG tail current. The peak value of the tail current was the magnitude of the hERG current.
9) The hERG current used to detect the test compound was recorded continuously for 120 seconds prior to dosing to assess the stability of hERG current production by the test cells. Only stable cells within the acceptance range of the evaluation criteria were used in the subsequent compound detection.

Assay of the test compound for inhibition of hERG current: The hERG current measured in the extracellular fluid containing 0.1% DMSO was used as the baseline of the assay. The solution containing the test compound was perfused around the cells sequentially in an ascending order of concentration after the hERG current remained stable for at least 5 minutes. After the completion of each perfusion, a suspension of about 5 minutes was set to allow the compound to act sufficiently on the cells and the hERG current was recorded simultaneously. The last 5 hERG current values were recorded after the recorded current tended to stabilize, and the average value thereof was taken as the final current value at the specific concentration. After the compound was tested, 150 nM dofetilide was added to the same cell to completely inhibit the current as a positive control for the cell.

Meanwhile, the positive compound dofetilide was synchronously detected by the same patch-clamp system before and after the test compound experiment was finished, so that the reliability and the sensitivity of the whole detection system were ensured.

V. Data Analysis The data was output by PatchMaster software and analyzed as follows:

1) After a blank solvent or a compound gradient solution was perfused, 5 continuous current values were obtained after stabilization, and the average values were calculated and were respectively used as the tail current magnitude$_{blank}$ and the tail current magnitude$_{compound}$d.
2) The current inhibition percentages were calculated by the following formula.

$$\text{Tail current inhibition rate} = \left(1 - \frac{\text{tail current magnitude}_{compound} - \text{tail current magnitude}_{positive\ drug}}{\text{tail current magnitude}_{blank} - \text{tail current magnitude}_{positive\ drug}}\right) \times 100$$

3) The dose-response curve was fitted by Graphpad Prism 8.0 software and the $IC_{50}$ value was calculated.

The compounds of the present application have no obvious inhibitory effect on the hERG potassium channel, which suggests that the compound has a low risk of cardiotoxicity due to the inhibition of hERG potassium channel. The hERG potassium channel inhibitory activity of the test compounds is shown in Table 8.

TABLE 8

| Compound | $IC_{50}$ (nM) |
|---|---|
| Compound 20 | >30 |
| Compound 25 | >30 |
| Compound 25-P2 | >30 |
| Compound 39 | >30 |
| Compound 40 | >30 |
| Compound 41-P2 | >30 |
| Compound 42-P2 | >30 |
| Compound 45 | >30 |
| Compound 48-P2 | >30 |
| Compound 49-P2 | >30 |
| Compound 81-P2 | >30 |

Test Example 9. Determination of Pharmacokinetics of Compounds of Present Application The pharmacokinetics of the compounds of the present application were determined in mice using the following method.

I. Materials:

Balb/c Nude mice, purchased from Beijing Vital River Laboratory Animal Technology Co., Ltd.

NMP (N-methyl-2-pyrrolidone), Solutol® HS 15 (polyoxyethylenated 12-hydroxystearic acid), and Vitamin E TPGS (D-α-tocopherol-polyethylene glycol 1000 succinate), purchased from Sigma.

Acetonitrile, purchased from Merck (USA).

II. Vehicle Preparation:

10% aqueous VE TPGS solution: 1 g of VE TPGS was dissolved in purified water, and the volume was brought to 10 mL.

5% NMP+10% Solutol® HS 15+85% water: 0.5 mL of NMP was measured using a pipette, 1 g of Solutol® HS 15 was weighed, and the volume was brought to 10 mL with water.

III. Procedures:

6 female Balb/c Nude mice (20-30 g, 4-6 weeks) were randomized into 2 groups of 3. Group 1 was administered with 1 mpk (1 mg/kg) test compound by injection at the tail vein (IV), and the vehicle was 5% NMP+10% Solutol® HS 15+85% water. Group 2 was administered with 1 or 3 mpk test compound by oral administration (PO) (see the table below for specific doses), and the vehicle was 5% NMP+10% Solutol® HS 15+85% water or 10% Vitamin E TPGS aqueous solution. Before the experiment, all animals were given free access to food and water. Blood samples of the mice in each group were collected intravenously pre-dose and at 0.083 h (only the intravenous injection group), 0.25 h, 0.5 h, 1 h, 2 h, 4 h, 6 h, 8 h, and 24 h post-dose. The whole blood samples were collected in $K_2$EDTA vacutainers, and the plasma samples were prepared by 5 min of centrifugation (4000 rpm, 4° C.).

10 μL of mouse plasma was added to 150 μL acetonitrile solvent (containing an internal standard) to precipitate the protein. The mixture was vortexed for 0.5 min and centrifuged (14000 rpm) for 5 min. The supernatant was diluted 2-fold with water containing 0.1% (v/v) FA and quantitatively detected on an LC-MS/MS system (AB Sciex Triple Quad 6500+). When the concentration of the sample was measured, quality control samples were also analyzed and a Balb/c Nude mouse plasma standard curve was plotted. For 10× diluted samples, 2 μL of the sample was added to 18 μL of blank plasma. The mixture was vortexed for 0.5 min. Then 300 μL of acetonitrile solvent (containing an internal standard) was added to precipitate the protein. The other steps were the same as those in undiluted samples.

The compounds of the present application feature stable metabolism in mice, good absorption, high oral bioavailability, and good pharmacokinetics. The corresponding mouse pharmacokinetics of the compounds of the present application are specified in Tables 9-1 and 9-2.

TABLE 9-1

| | PK parameters | Compound 25 | Compound 25-P2 | Compound 41-P2 |
|---|---|---|---|---|
| PO | Dose (mg/kg) | 1# | 3* | 1# |
| | $AUC_{0-24}$ (h*ng/mL) | 5845 | 30282 | 10455 |
| | F (%) | About 100% | About 100% | About 100% |

TABLE 9-2

| | PK parameters | Compound 42-P2 | Compound 48-P2 | Compound 49-P2 |
|---|---|---|---|---|
| PO | Dose (mg/kg) | 1# | 1# | 1# |
| | $AUC_{0-24}$ (h*ng/ml) | 10511 | 24437 | 11276 |
| | F (%) | About 100% | About 100% | 89.6% |

#represents that the oral vehicle formulation was 5% NMP + 10% Solutol ® HS 15 + 85% water.

*represents that the oral vehicle formulation was 10% VE TPGS aqueous solution.

The invention claimed is:

1. A compound of formula (I) or a pharmaceutically acceptable salt thereof:

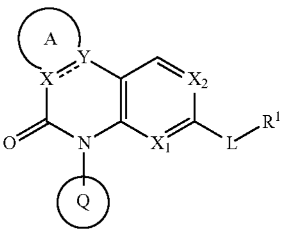

(I)

wherein,

L is selected from a chemical bond and O;

$R^1$ is selected from halogen and the following groups optionally substituted with $R^{1a}$: $C_1$-$C_{10}$ alkyl, $C_3$-$C_{10}$ cycloalkyl, and 3- to 10-membered heterocyclyl;

$X_1$ and $X_2$ are both CH, and ring A is selected from the following groups optionally substituted with $R^2$: pyrazolyl, imidazolyl, oxazolyl, isoxazolyl, triazolyl,

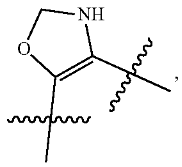
,
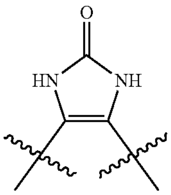
,
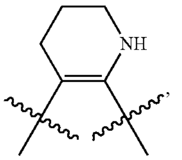
,
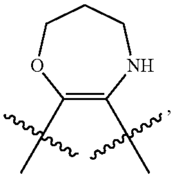
,
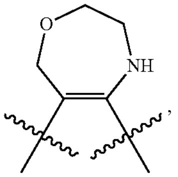
,
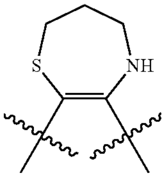
,
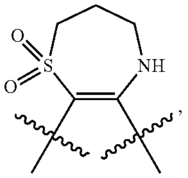
,
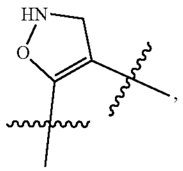
,
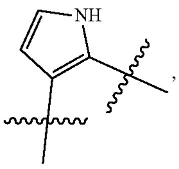
and
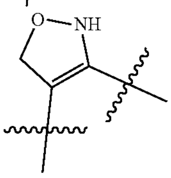
;

X and Y are ring atoms of ring A, and are each independently selected from a C atom and an N atom; X and Y are connected by a single bond when at least one of X and Y is selected from an N atom; X and Y are connected by a single bond or a double bond when X and Y are both selected from a C atom;

$R^2$ is selected from halogen, =O, OH, CN, and the following groups optionally substituted with $R^{2a}$: $NH_2$, $C_1$-$C_{10}$ alkyl, $C_3$-$C_{10}$ cycloalkyl, 3- to 10-membered heterocyclyl, $C_1$-$C_{10}$ alkoxy, $C_3$-$C_{10}$ cycloalkyloxy, and 3- to 10-membered heterocyclyloxy;

ring Q is selected from $C_6$-$C_{10}$ aryl and 5- to 10-membered heteroaryl, and the $C_6$-$C_{10}$ aryl or the 5- to 10-membered heteroaryl is optionally substituted with $R^3$;

$R^3$ is selected from halogen, =O, OH, CN, $NO_2$, and the following groups optionally substituted with $R^{3a}$: SH, $NH_2$, $C_2$-$C_{10}$ alkenyl, $C_2$-$C_{10}$ alkynyl, $C_1$-$C_{10}$ alkyl, $C_3$-$C_{10}$ cycloalkyl, 3- to 10-membered heterocyclyl, $C_1$-$C_{10}$ alkoxy, $C_3$-$C_{10}$ cycloalkyloxy, and 3- to 10-membered heterocyclyloxy;

$R^{1a}$, $R^{2a}$, and $R^{3a}$ are each independently selected from a deuterium atom, F, Cl, Br, I, OH, CN, =O, and the following groups optionally substituted with $R^b$: $NH_2$, $C_1$-$C_6$ alkyl, $C_3$-$C_6$ cycloalkyl, 4- to 7-membered heterocyclyl, 5- to 6-membered heteroaryl, $C_1$-$C_6$ alkoxy, $C_3$-$C_6$ cycloalkyloxy, and 4- to 7-membered heterocyclyloxy; and $R^b$ is each independently selected from F, Cl, Br, I, OH, CN, =O, $NH_2$, SH, $C_1$-$C_6$ alkyl, $C_3$-$C_6$ cycloalkyl, and 4- to 7-membered heterocyclyl.

2. The compound of formula (I) or the pharmaceutically acceptable salt thereof according to claim 1, wherein $R^1$ is selected from halogen and the following groups optionally substituted with $R^{1a}$: $C_1$-$C_3$ alkyl, $C_3$-$C_6$ cycloalkyl, and 4- to 7-membered heterocyclyl; and/or $R^{1a}$ is each independently selected from F, Cl, Br, I, OH, CN, =O, and the following groups optionally substituted with $R^b$: $NH_2$, $C_1$-$C_6$ alkyl, $C_3$-$C_6$ cycloalkyl, 4- to 7-membered heterocyclyl, and $C_1$-$C_6$ alkoxy; or $R^1$ is selected from halogen and the following groups optionally substituted with $R^{1a}$: $C_1$-$C_3$ alkyl and 4- to 7-membered heterocyclyl; and/or $R^{1a}$ is each independently selected from F, Cl, Br, and I; or $R^1$ is selected from halogen and the following groups optionally substituted with $R^{1a}$: methyl, ethyl, and oxetanyl; and/or $R^{1a}$ is each independently selected from F, Cl, Br, and I.

3. The compound of formula (I) or the pharmaceutically acceptable salt thereof according to claim 1 wherein the structural unit

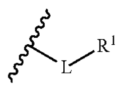

is selected from $C_1$, $CH_3$, $CF_3$, $OCH_2CH_3$ and

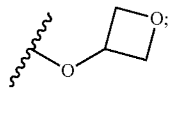 [SMILES: *OC1COC1]

or the structural unit

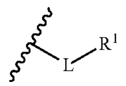

is selected from $C_1$, $CH_3$, $CF_3$, and $OCH_2CH_3$.

4. The compound of formula (I) or the pharmaceutically acceptable salt thereof according to claim 1, wherein X and Y are both C, and are connected by a single bond or a double bond; or one of X and Y is C and the other is N, and X and Y are connected by a single bond.

5. The compound of formula (I) or the pharmaceutically acceptable salt thereof according to claim 1, wherein $R^2$ is selected from =O and the following groups optionally substituted with $R^{2a}$: $NH_2$, $C_1$-$C_6$ alkyl, $C_3$-$C_6$ cycloalkyl, and $C_1$-$C_6$ alkoxy, and the $R^{2a}$ is selected from a deuterium atom, F, Cl, Br, I, $C_1$-$C_3$ alkyl, $NH_2$ optionally substituted with $C_1$-$C_3$ alkyl, and 5- to 6-membered heteroaryl optionally substituted with $C_1$-$C_3$ alkyl; or $R^2$ is selected from =O, methyl, ethyl, $CD_3$, $CH_2CH_2N(CH_3)_2$, $CH_2CH_2OH$, $CH_2CH_2NH(CH_3)$, $CH_2CH_2NH_2$, $OCH_3$, $NHCH_3$, $CHF_2$, $CF_3$, cyclopropyl, and

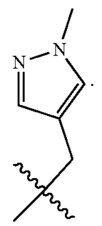 [SMILES: *Cc1cnn(C)c1]

6. The compound of formula (I) or the pharmaceutically acceptable salt thereof according to claim 1, wherein ring Q is selected from phenyl, pyridinyl, pyrazolyl, pyrimidinyl, and pyrazinyl, and the phenyl, the pyridinyl, the pyrazolyl, the pyrimidinyl, or the pyrazinyl is optionally substituted with $R^3$.

7. The compound of formula (I) or the pharmaceutically acceptable salt thereof according to claim 1, wherein $R^3$ is selected from halogen, =O, OH, CN, and the following groups optionally substituted with $R^{3a}$: SH, $C_2$-$C_3$ alkynyl, $C_1$-$C_6$ alkyl, $C_3$-$C_6$ cycloalkyl, $C_1$-$C_6$ alkoxy, and $C_3$-$C_6$ cycloalkyloxy; and $R^{3a}$ is selected from halogen, CN, and $C_1$-$C_3$ alkyl; or $R^3$ is selected from halogen, CN, $C_3$-$C_6$ cycloalkyl, $C_2$-$C_3$ alkynyl, $C_1$-$C_6$ alkyl optionally substituted with halogen, and $C_1$-$C_6$ alkoxy optionally substituted with halogen; or $R^3$ is selected from F, Cl, Br, CN, SH, isopropyl, cyclopropyl, methyl, ethyl, trifluoromethyl, ethynyl, $OCHF_2$, methoxy, and methylthio.

8. The compound of formula (I) or the pharmaceutically acceptable salt thereof according to claim 1, wherein ring Q is selected from phenyl, pyridinyl, pyrazolyl, pyrimidinyl, and pyrazinyl, and the phenyl, the pyridinyl, the pyrazolyl, the pyrimidinyl, or the pyrazinyl is optionally substituted with $R^3$; $R^3$ is each independently selected from halogen, CN, $C_3$-$C_6$ cycloalkyl, $C_2$-$C_3$ alkynyl, $C_1$-$C_6$ alkyl optionally substituted with halogen, and $C_1$-$C_6$ alkoxy optionally substituted with halogen; or ring Q is selected from phenyl, pyridinyl, pyrazolyl, pyrimidinyl, or pyrazinyl, and the phenyl, the pyridinyl, the pyrazolyl, the pyrimidinyl, or the pyrazinyl is optionally substituted with $R^3$; $R^3$ is each independently selected from F, Cl, Br, CN, isopropyl, cyclopropyl, methyl, ethyl, trifluoromethyl, ethynyl, $OCHF_2$, and methoxy; or ring Q is selected from

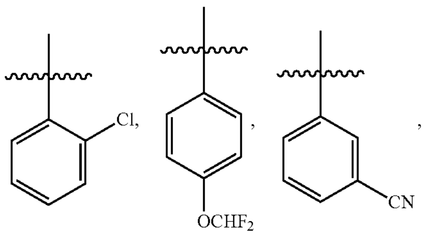
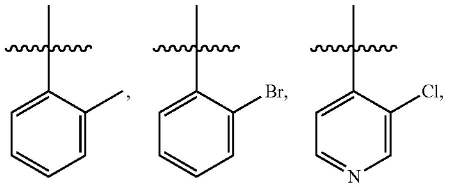
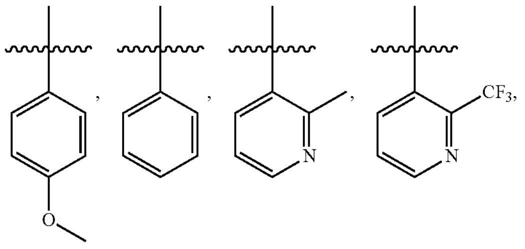
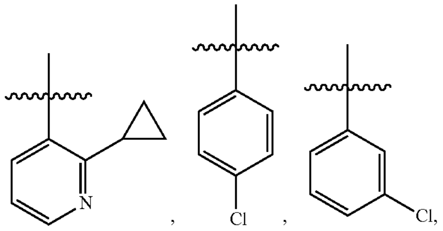
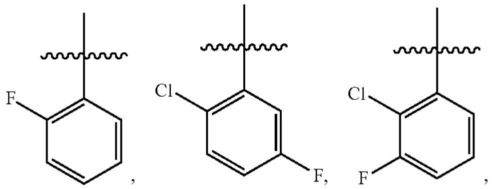
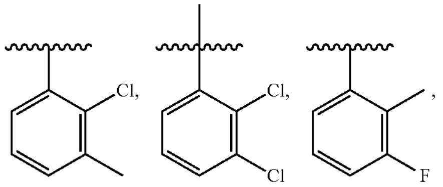
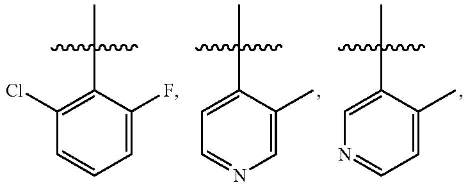
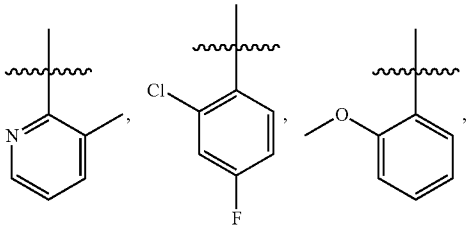
-continued
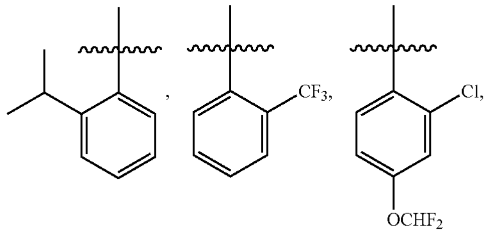
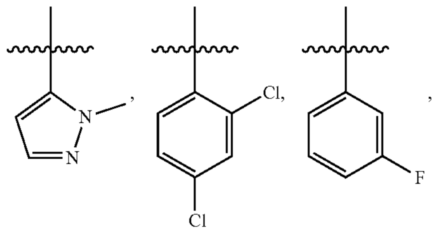
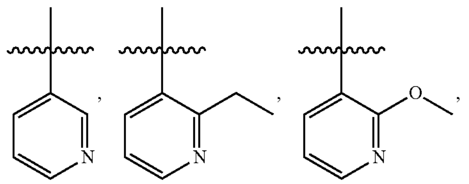
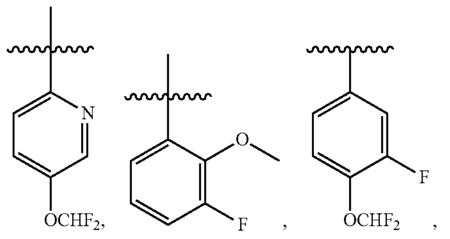
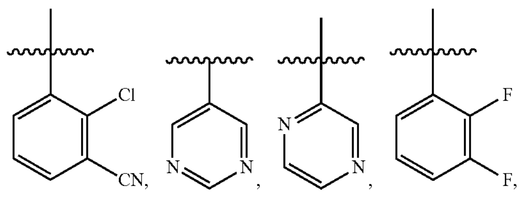
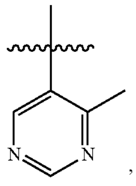
, and
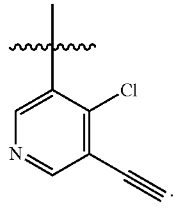
9. The compound of formula (I) or the pharmaceutically acceptable salt thereof according to claim 1, wherein the compound of formula (I) or the pharmaceutically acceptable salt thereof is a compound of formula (Ia) or a pharmaceutically acceptable salt thereof:

(Ia)
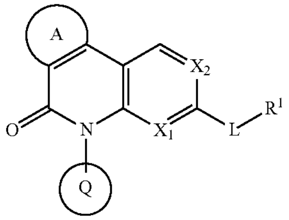
wherein ring A, ring Q, $X_1$, $X_2$, L, and $R^1$ are as defined in claim 1.
10. A compound or a pharmaceutically acceptable salt thereof, wherein the compound is selected from one of the following structures:
1
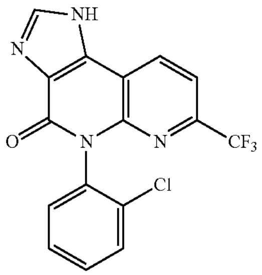
2
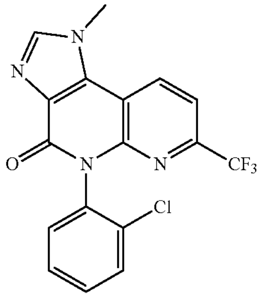
3
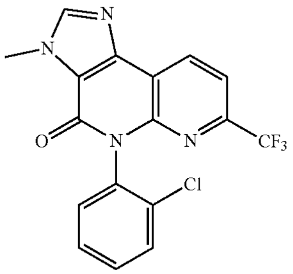
4
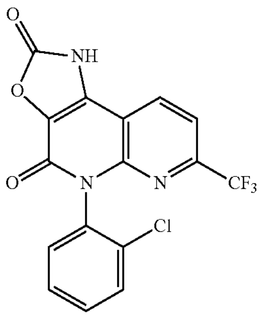
-continued
5
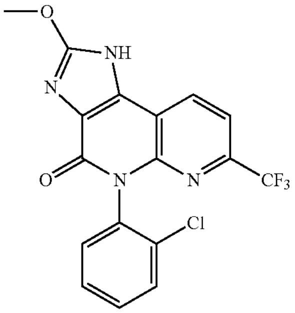
6
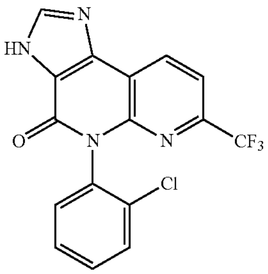
7
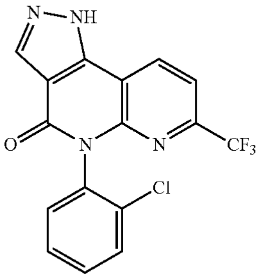
8
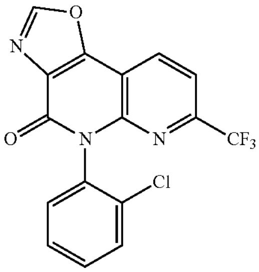
9
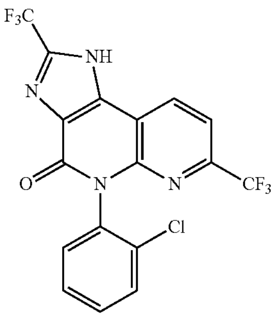

-continued
10
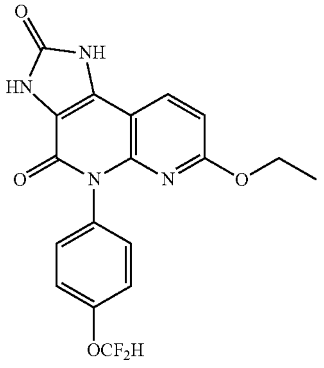
11
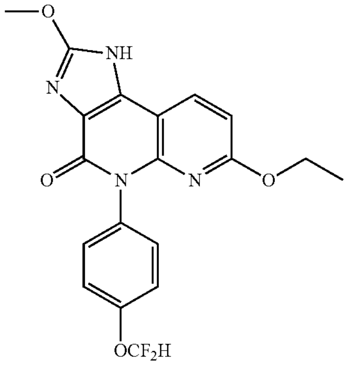
12
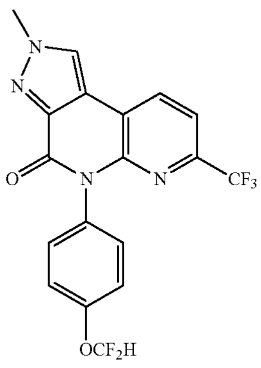
13
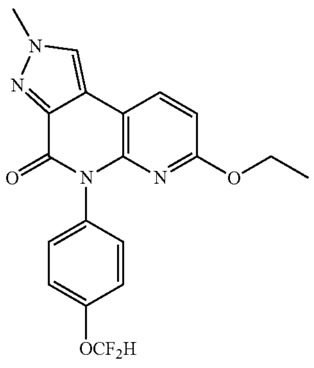
-continued
14
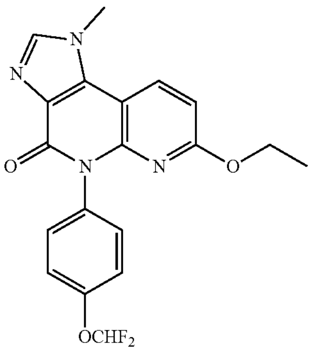
15
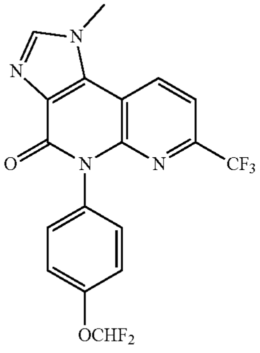
16
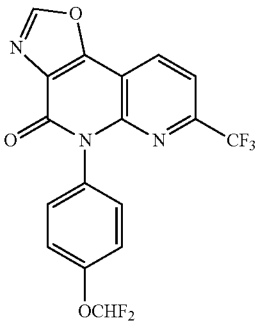
17
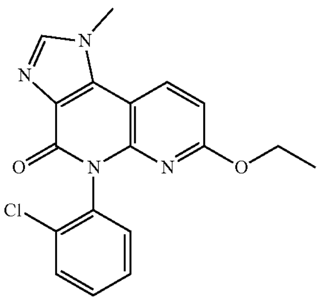

-continued
18
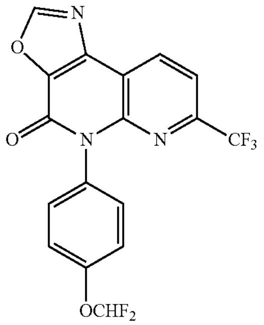
19
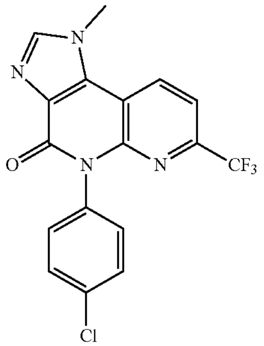
20
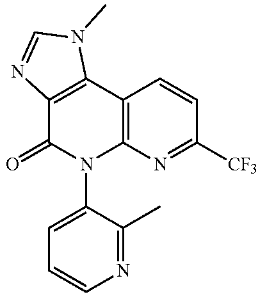
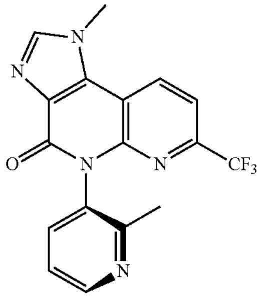
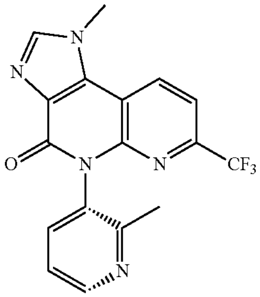
21
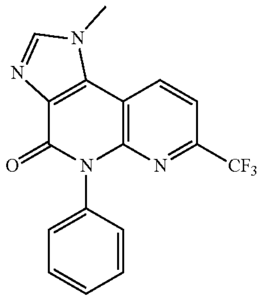
-continued
22
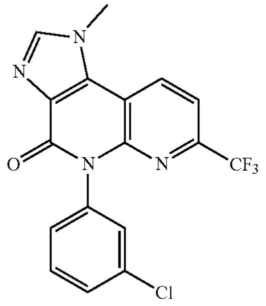
23
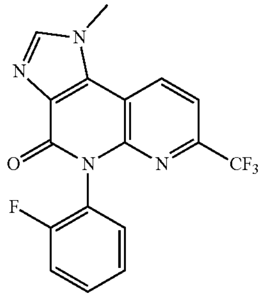
24
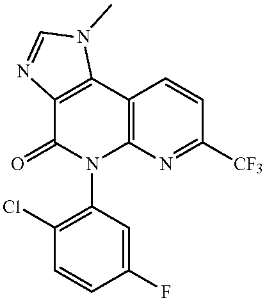
25
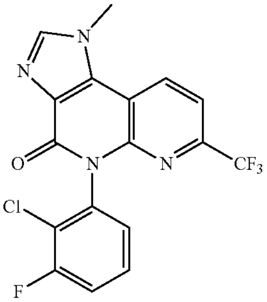
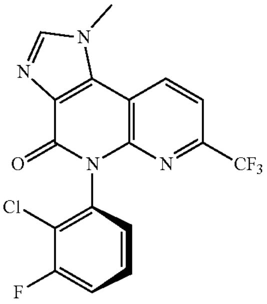

-continued
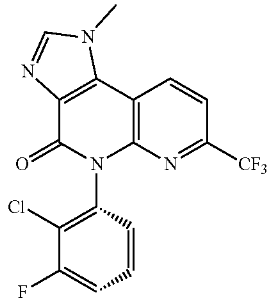
26
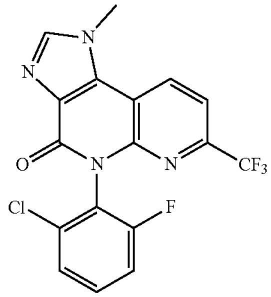
27
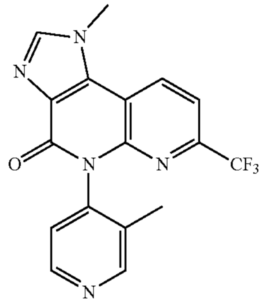
28
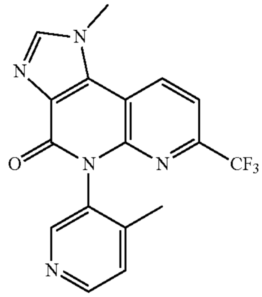
29
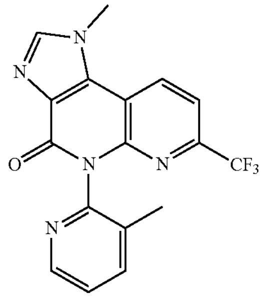
-continued
30
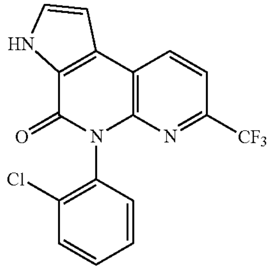
31
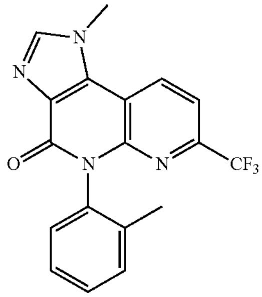
32
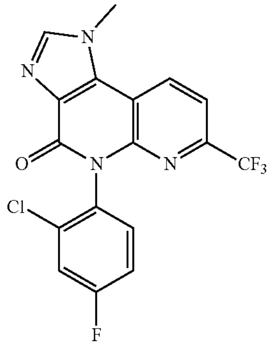
33
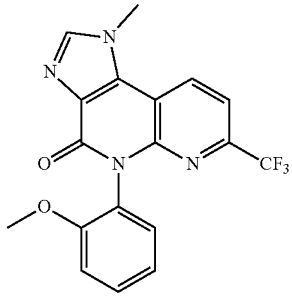
34
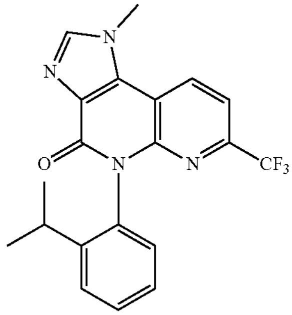

-continued
35
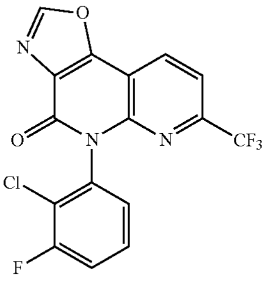
36
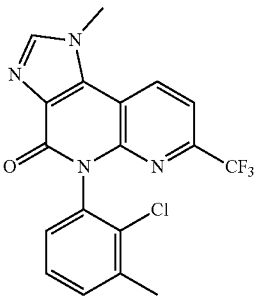
37
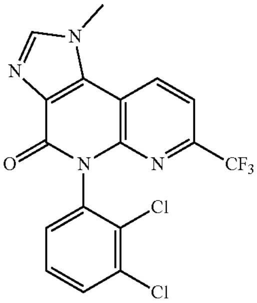
38
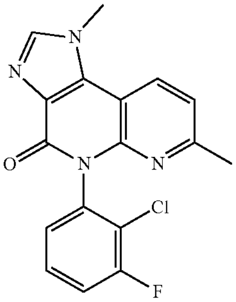
39
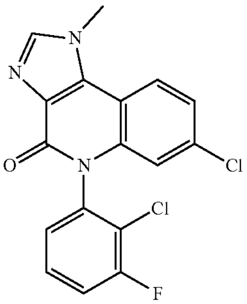
-continued
40
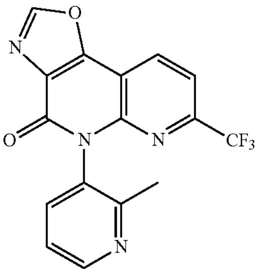
41
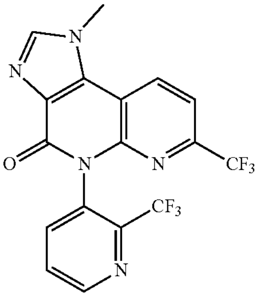
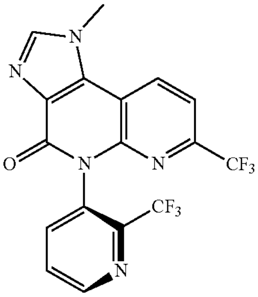
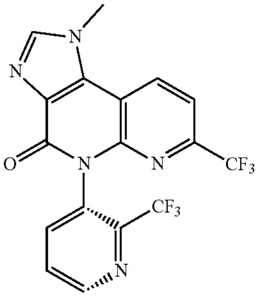
42
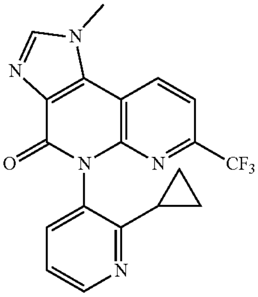
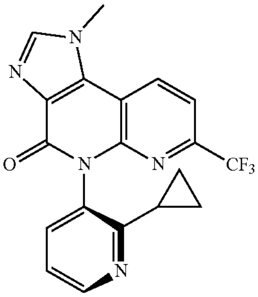
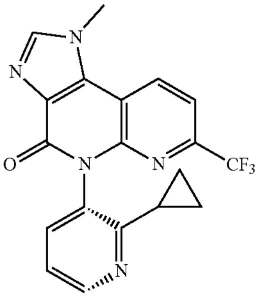

-continued
43
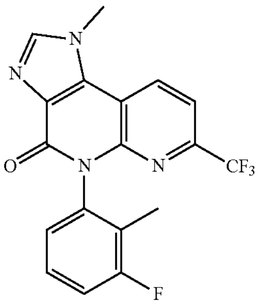
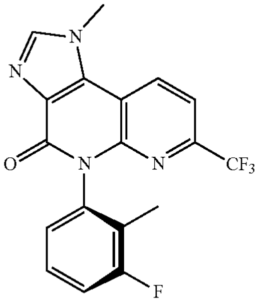
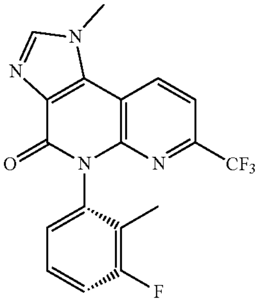
44
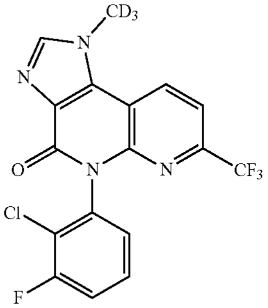
45
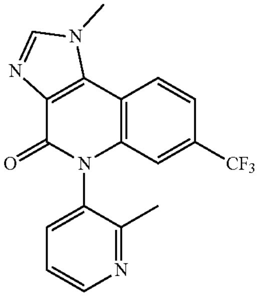
46
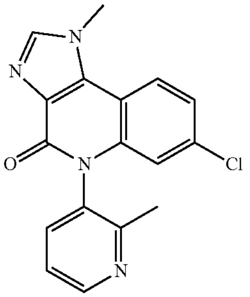
-continued
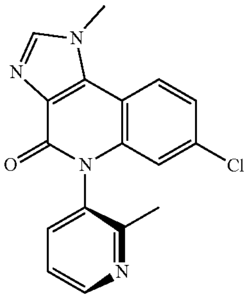
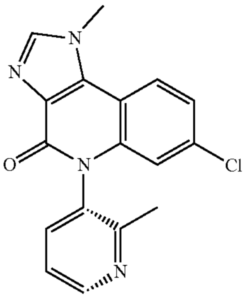
47
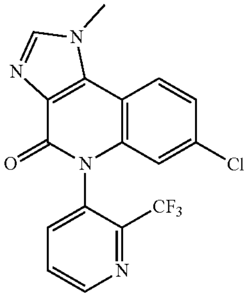
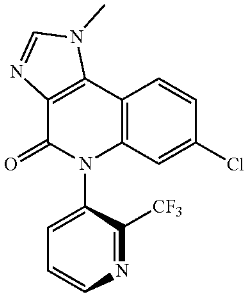
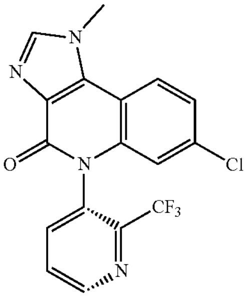
48
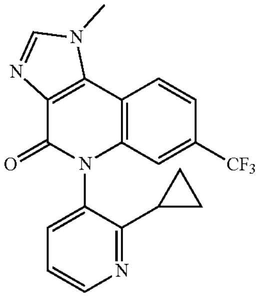
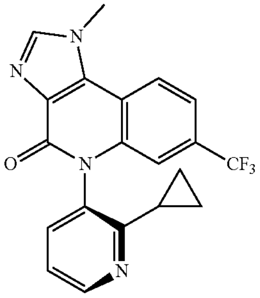
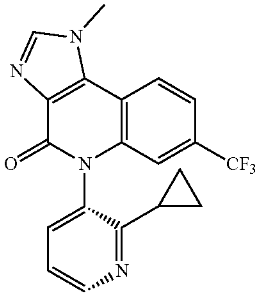

-continued
49
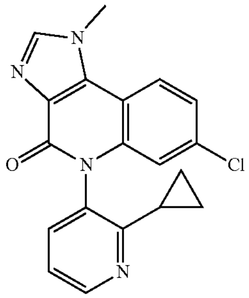
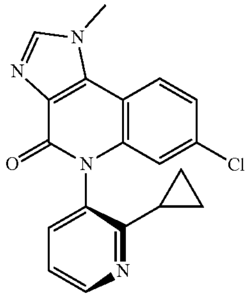
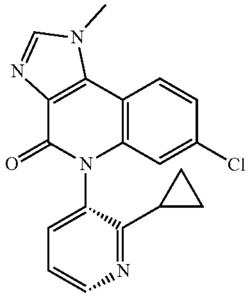
50
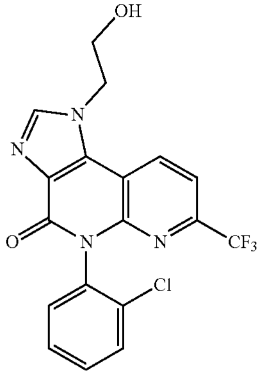
51
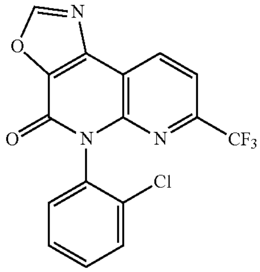
52
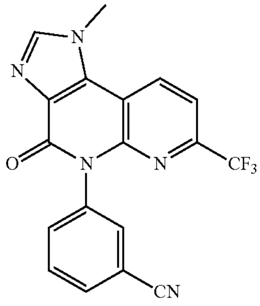
-continued
53
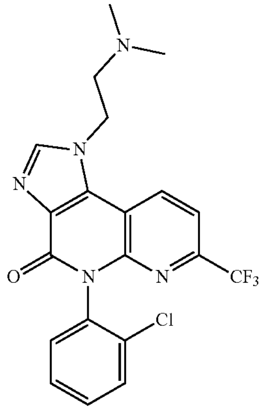
54
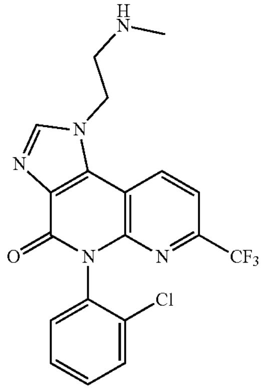
55
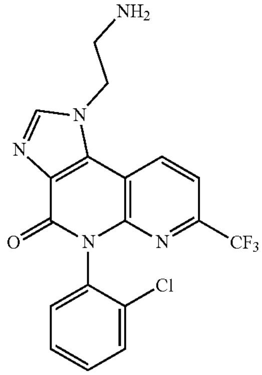
56
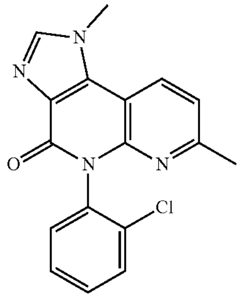

-continued
57
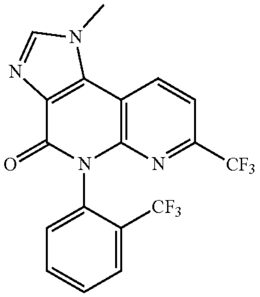
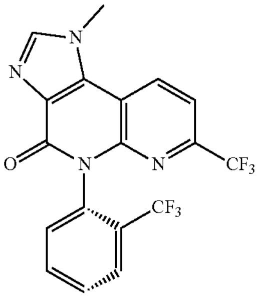
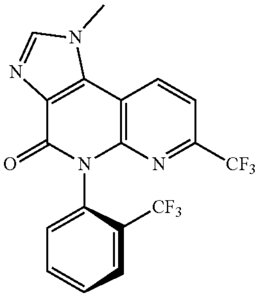
58
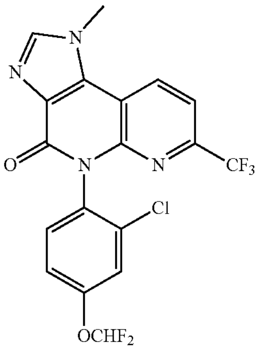
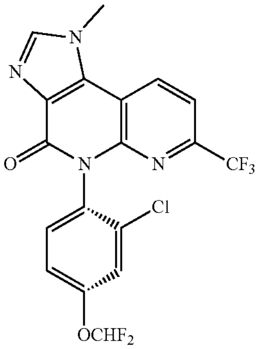
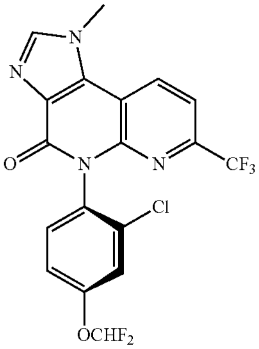
59
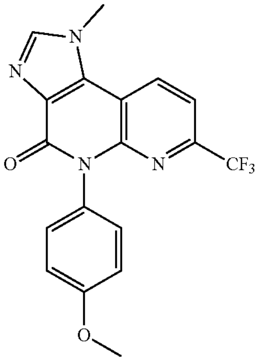
-continued
60
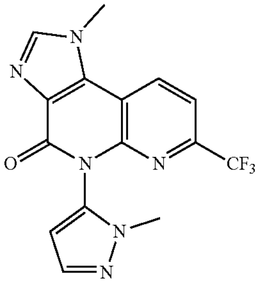
61
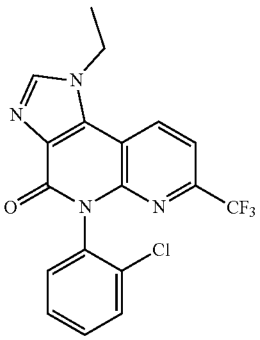
62
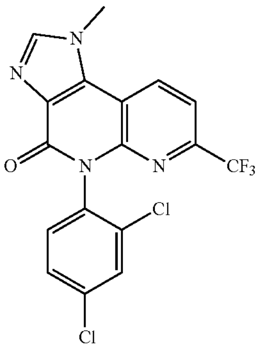
63
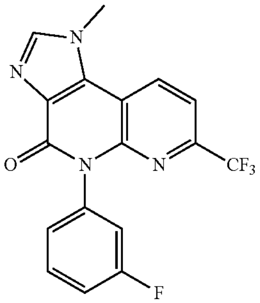
64
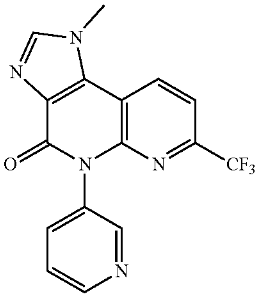

-continued
65
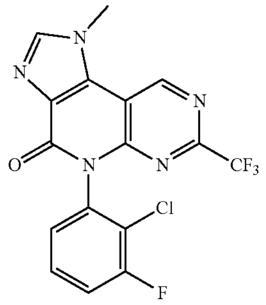
66
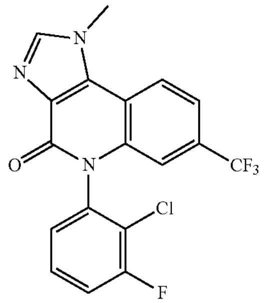
67
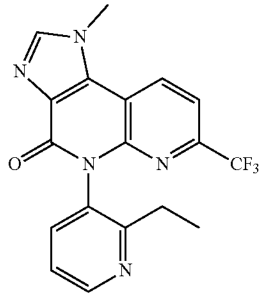
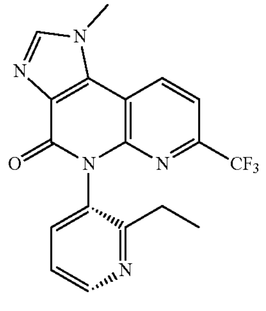
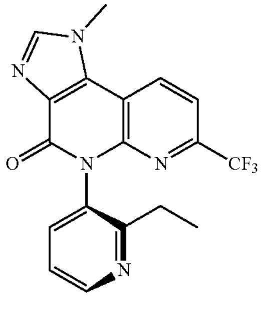
68
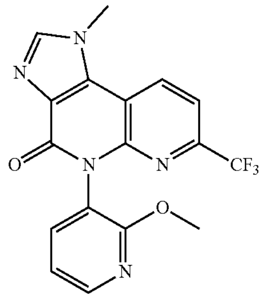
-continued
69
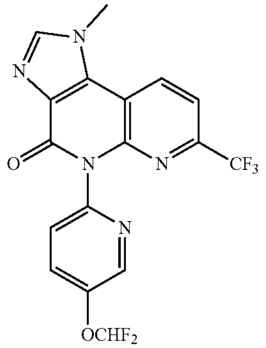
70
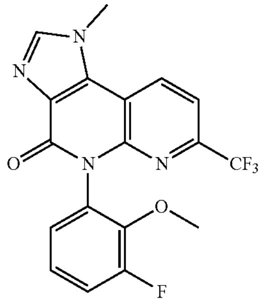
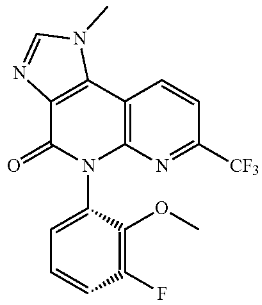
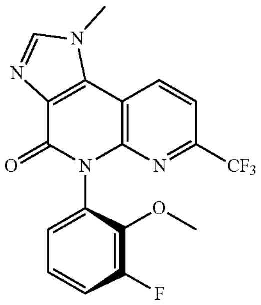
71
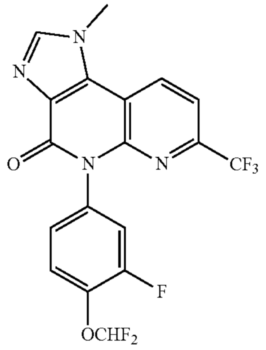
72
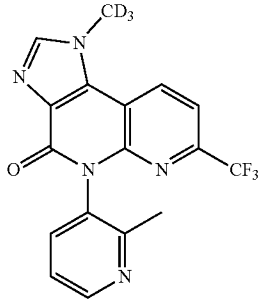

-continued
73
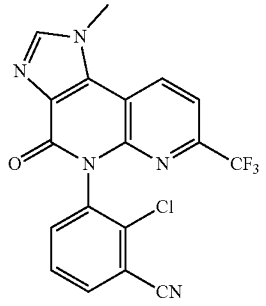
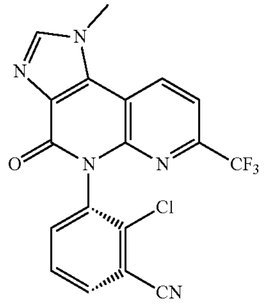
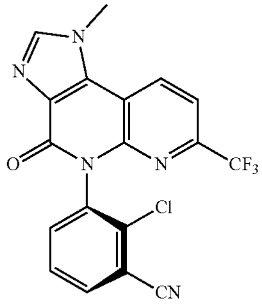
74
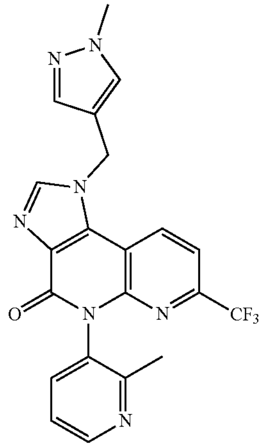
75
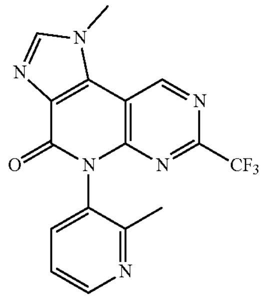
76
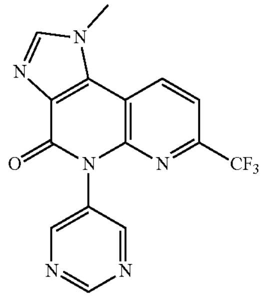
-continued
77
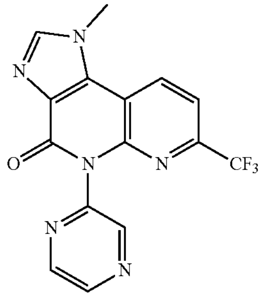
78
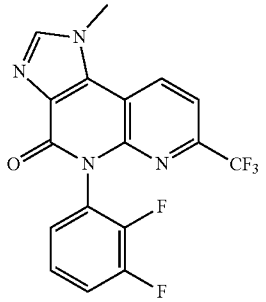
79
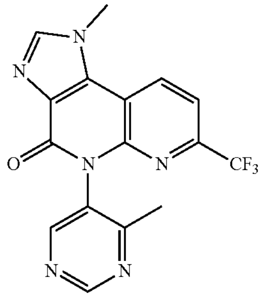
80
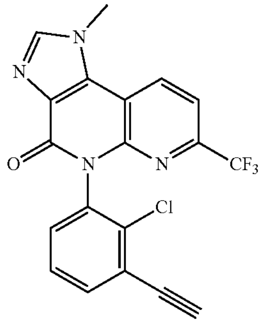
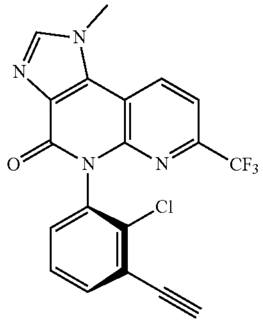
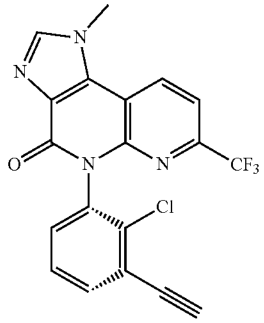

81
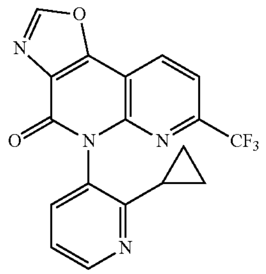
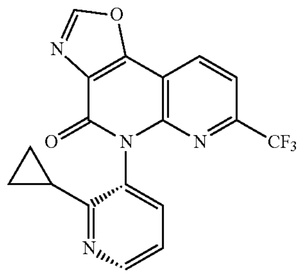
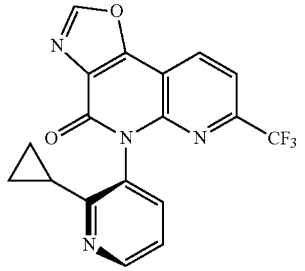
82
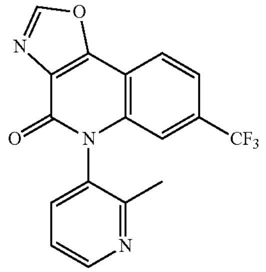
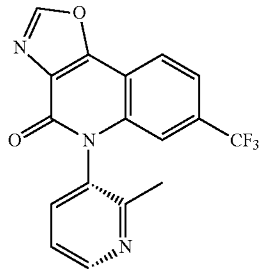
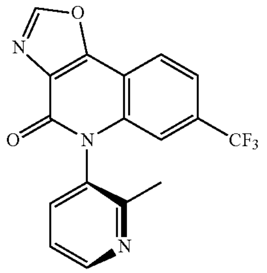
83
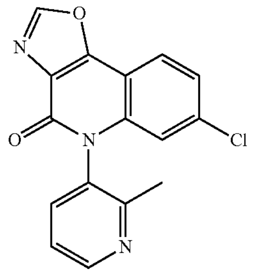
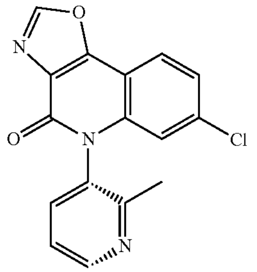
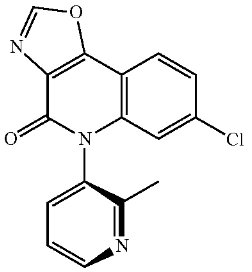
84
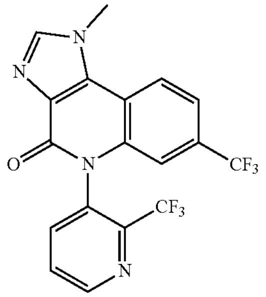
85
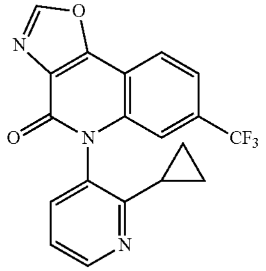
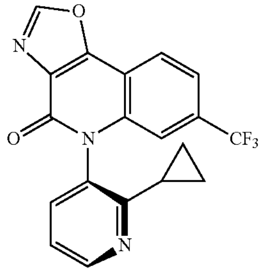
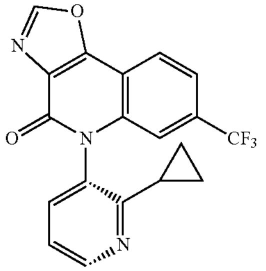
86
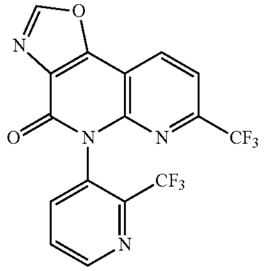
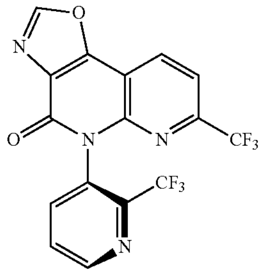
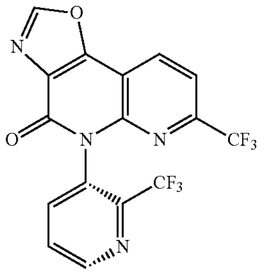

-continued
87
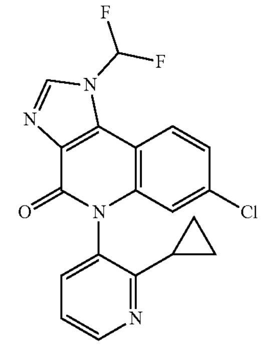
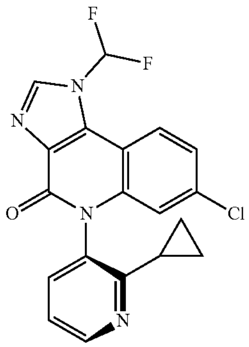
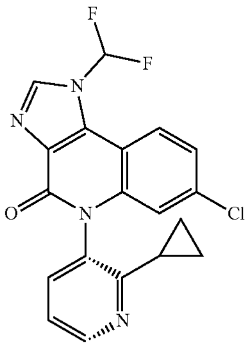
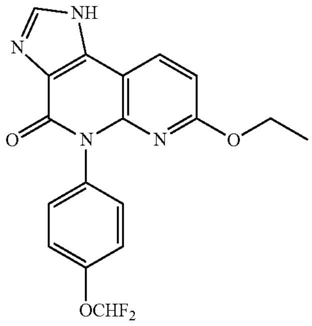
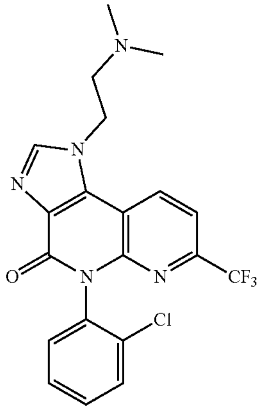
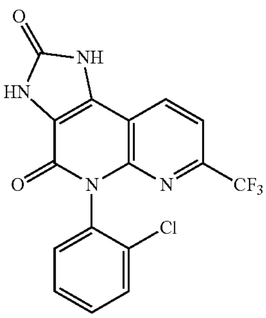
-continued
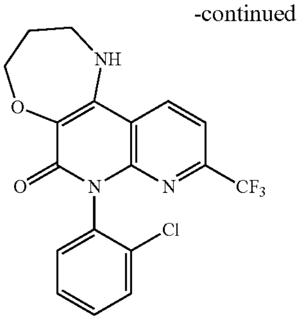
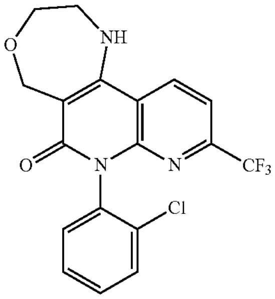
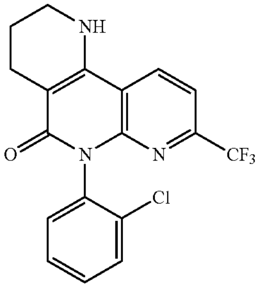
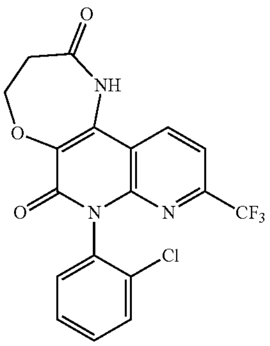
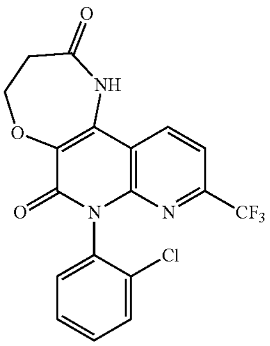

-continued
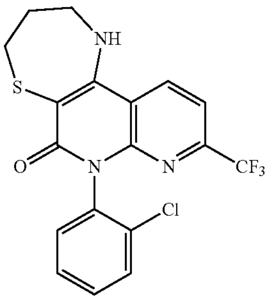
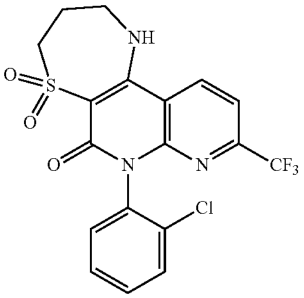
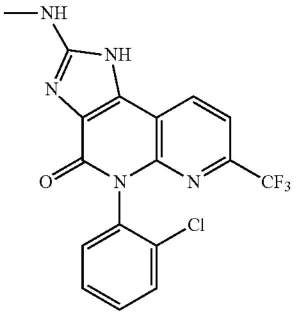
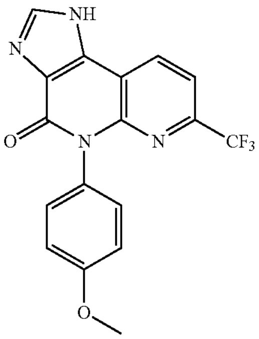
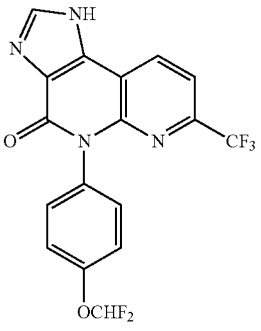
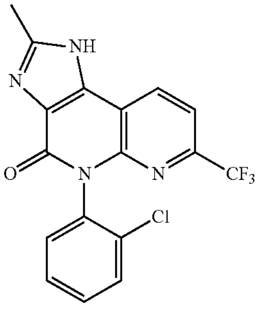
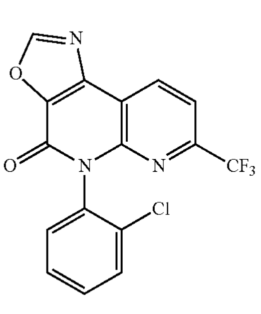
-continued
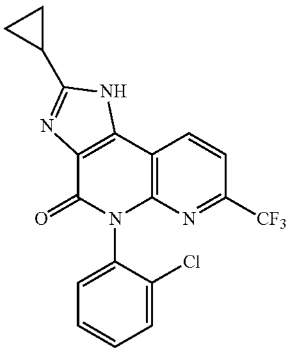
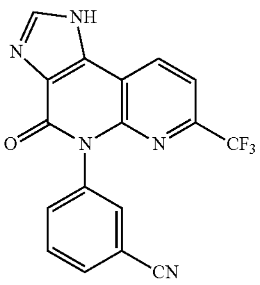
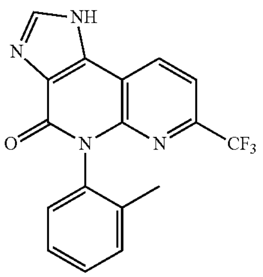
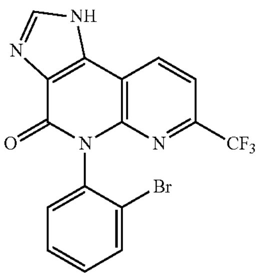
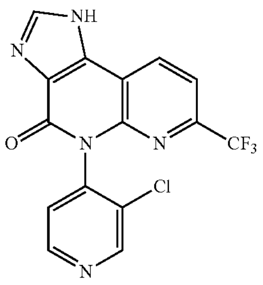
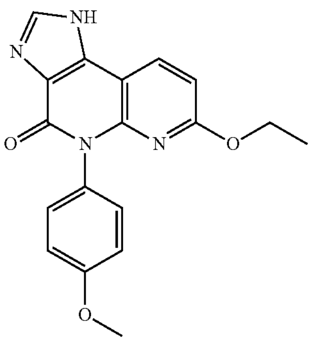
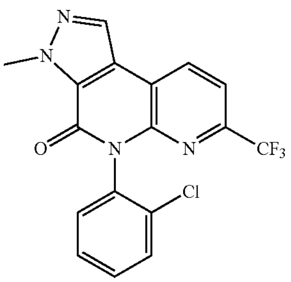

-continued
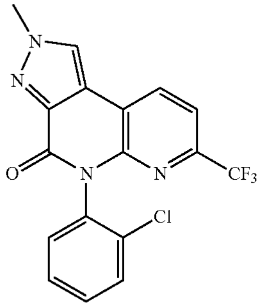
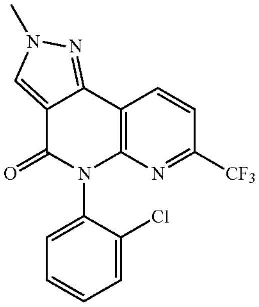
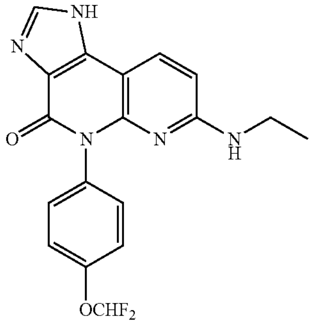
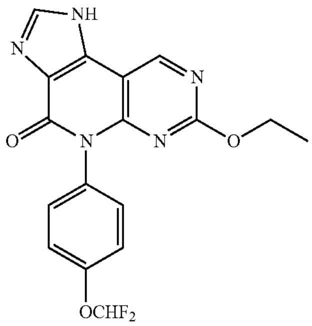
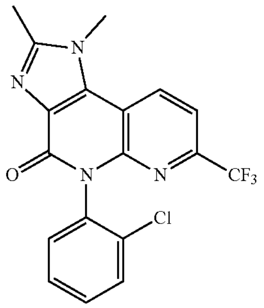
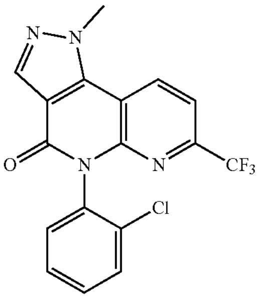
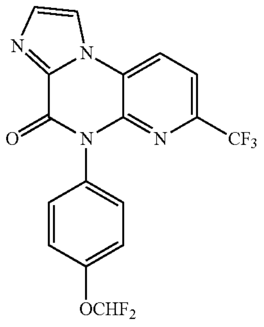
-continued
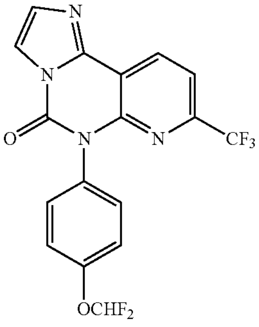
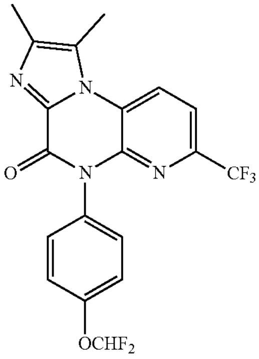
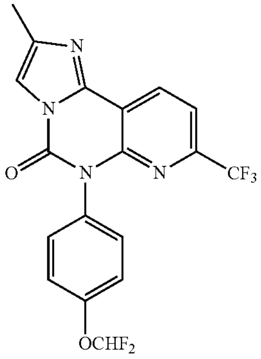
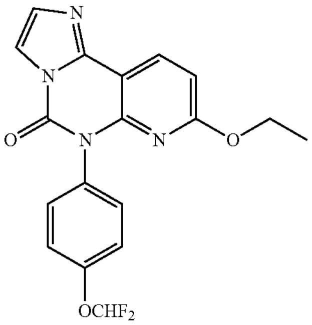
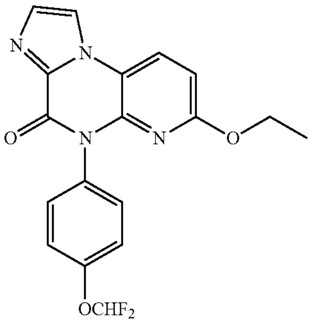
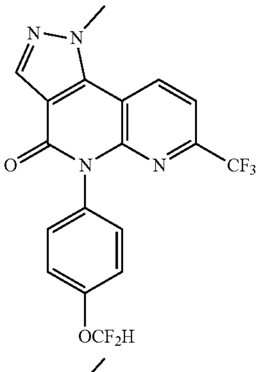
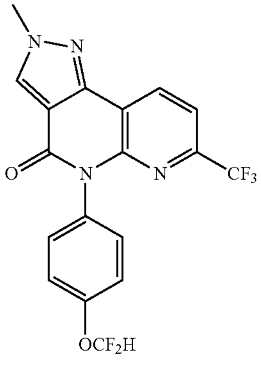
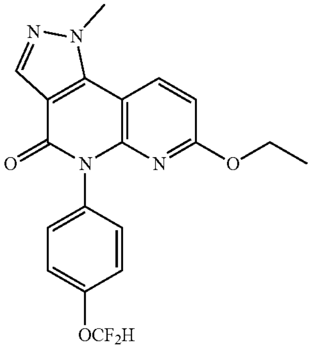

-continued
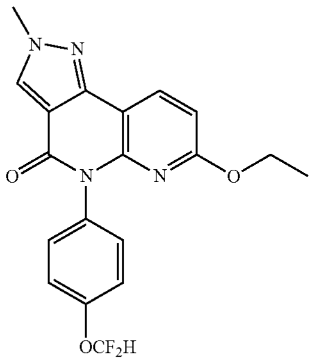
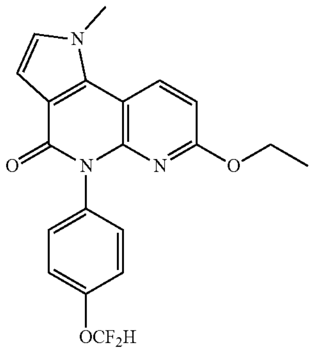
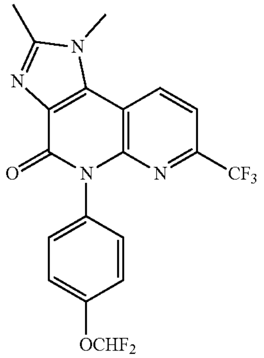
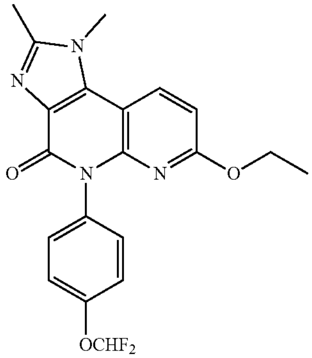
-continued
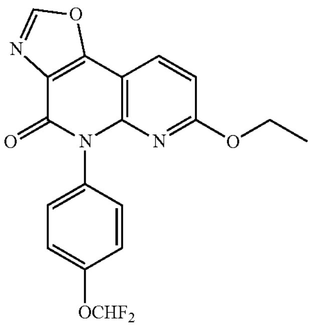
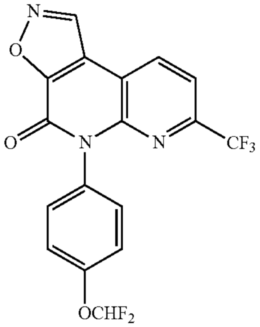
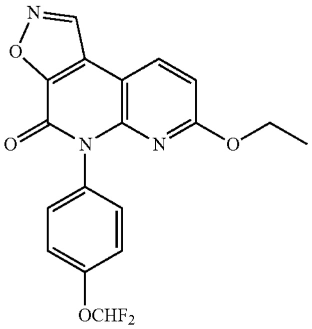
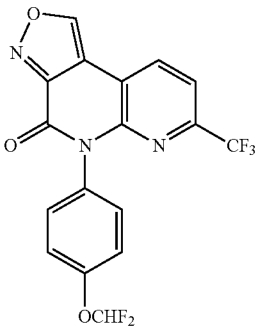
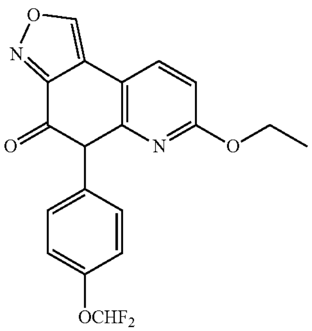

-continued

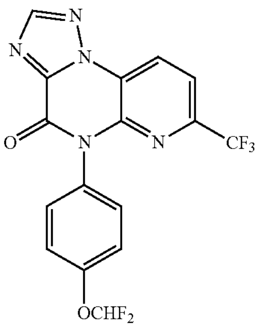

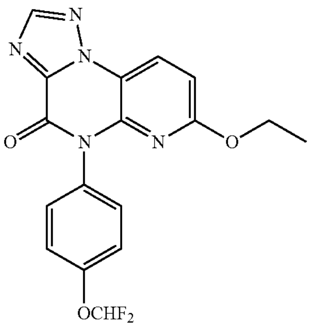

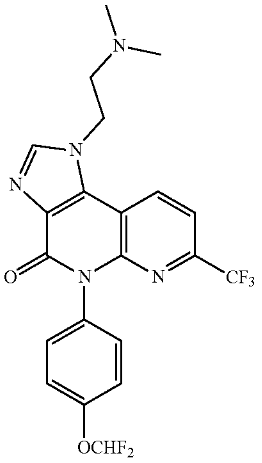

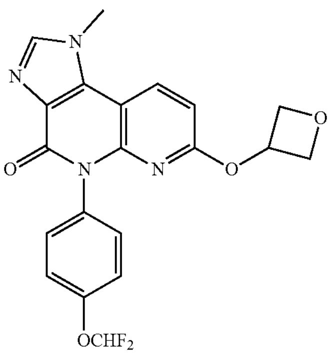

-continued

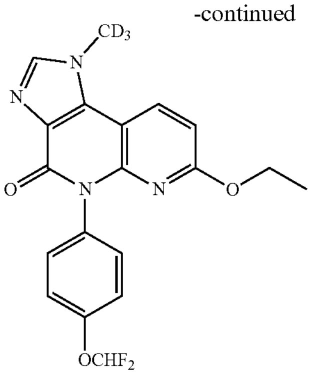

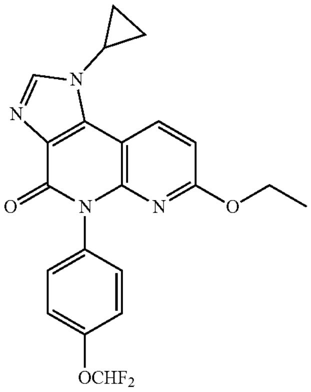

and

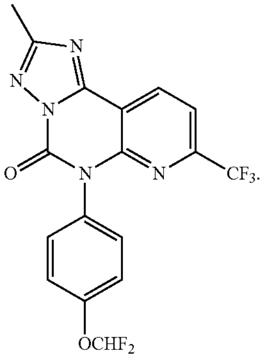 [SMILES: Cc1nc2c3ccc(C(F)(F)F)nc3n(-c3ccc(OC(F)F)cc3)c(=O)n2n1]

11. A pharmaceutical composition, comprising the compound or the pharmaceutically acceptable salt thereof according to claim 1 and a pharmaceutically acceptable excipient.

12. A method for treating a tumor with reduced or absent MTAP activity, comprising administering the compound or the pharmaceutically acceptable salt thereof according to claim 1 to a subject in need thereof.

13. A pharmaceutical composition, comprising the compound or the pharmaceutically acceptable salt thereof according to claim 10 and a pharmaceutically acceptable excipient.

14. A method for treating a tumor with reduced or absent MTAP activity, comprising administering the compound or the pharmaceutically acceptable salt thereof according to claim 13 to a subject in need thereof.

15. A method for treating a tumor with reduced or absent MTAP activity, comprising administering the pharmaceutical composition according to claim 11 to a subject in need thereof.

16. A method for treating a tumor with reduced or absent MTAP activity, comprising administering the pharmaceutical composition according to claim 13 to a subject in need thereof.

17. The compound of formula (I) or the pharmaceutically acceptable salt thereof according to claim 1, wherein ring A is selected from the following groups optionally substituted with $R^2$:
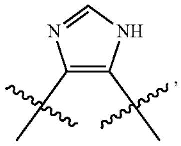, 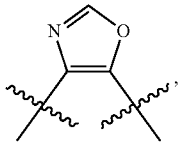, 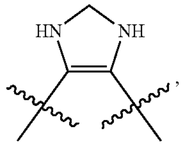,
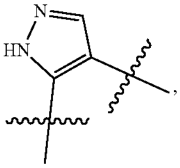, 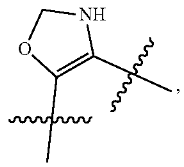,
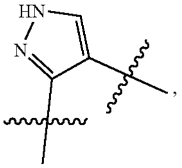, and 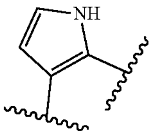;
or
ring A is selected from
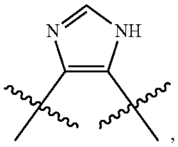, 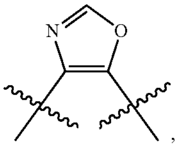,
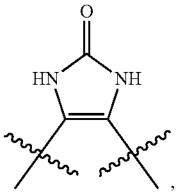, 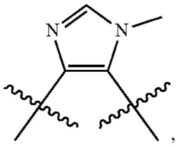,
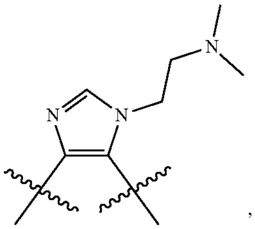, 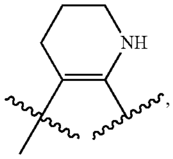,
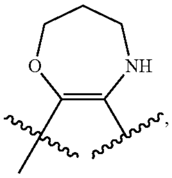, 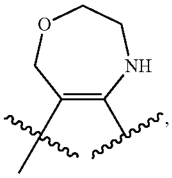,
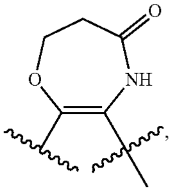, 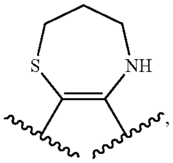,
-continued
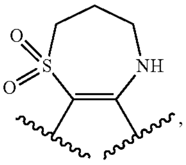, 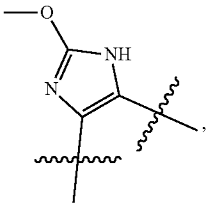,
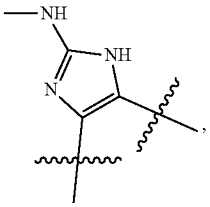, 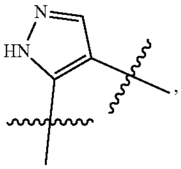,
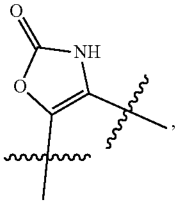, 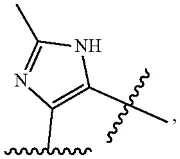,
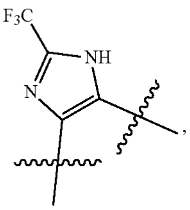, 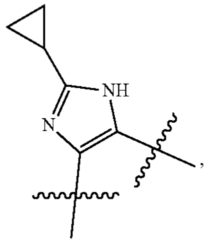,
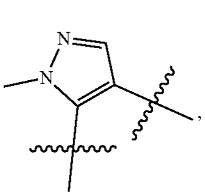, 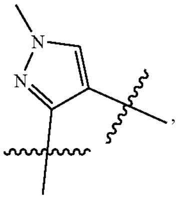,
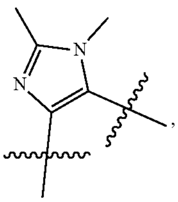, 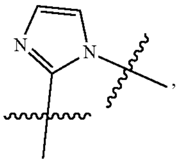, 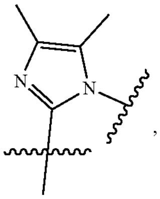,
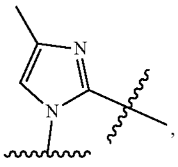,
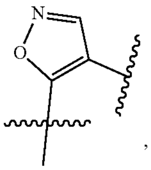, 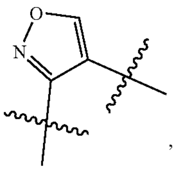, 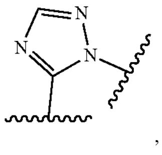, -continued
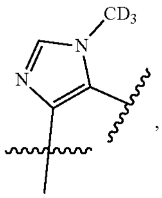
,
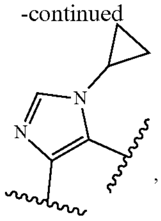
,
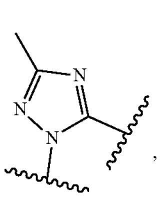
,
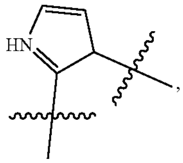
,
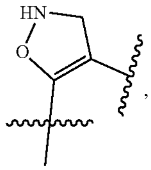
,
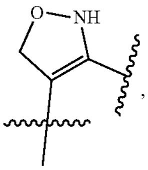
,
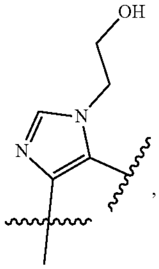
,
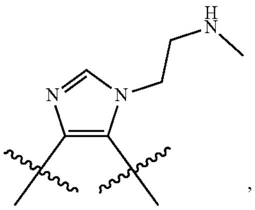
,
-continued
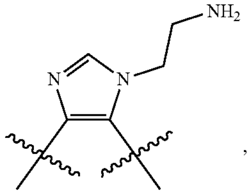
,
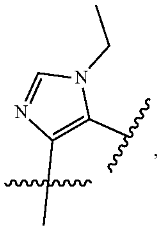
,
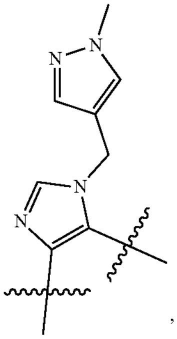
, and
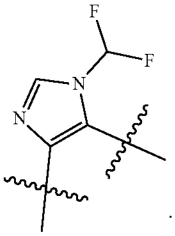
.
* * * * *